United States Patent
Kaufman et al.

(10) Patent No.: US 11,510,680 B2
(45) Date of Patent: Nov. 29, 2022

(54) ENDOVASCULAR COIL WITH MULTIPLE SECTIONS

(71) Applicant: RAPID MEDICAL LTD., Yokneam (IL)

(72) Inventors: Eyal Kaufman, Kibbutz Ein Harod (IL); Matan Gedulter, Givat Ela (IL); Ronen Eckhouse, Shimshit (IL)

(73) Assignee: RAPID MEDICAL LTD., Yokneam (IL)

( * ) Notice: Subject to any disclaimer, the term of this patent is extended or adjusted under 35 U.S.C. 154(b) by 0 days.

(21) Appl. No.: 17/456,187

(22) Filed: Nov. 23, 2021

(65) Prior Publication Data

US 2022/0151635 A1    May 19, 2022

Related U.S. Application Data

(63) Continuation of application No. PCT/IB2021/000825, filed on Nov. 19, 2021.
(Continued)

(51) Int. Cl.
*A61B 17/12* (2006.01)
*A61L 31/02* (2006.01)
(Continued)

(52) U.S. Cl.
CPC ...... *A61B 17/1214* (2013.01); *A61B 17/1204* (2013.01); *A61B 17/12036* (2013.01);
(Continued)

(58) Field of Classification Search
CPC ........ A61B 17/12145; A61B 17/12113; A61B 17/12022; A61B 17/12027;
(Continued)

(56) References Cited

U.S. PATENT DOCUMENTS

| 4,166,468 A | 9/1979 | Haynie |
| 4,540,404 A | 9/1985 | Wolvek |

(Continued)

OTHER PUBLICATIONS

International Search Report and Written Opinion of the International Searching Authority dated Apr. 12, 2022, by the U.S. Patent and Trademark Office in International Application No. PCT/IB2021/000825 (14 pages).

*Primary Examiner* — Kelly J Bekker
*Assistant Examiner* — Mikail A Mannan
(74) *Attorney, Agent, or Firm* — Finnegan, Henderson, Farabow, Garrett & Dunner LLP

(57) ABSTRACT

Consistent with disclosed embodiments, systems, devices, methods, and computer readable media for filling a hollow body structure may be provided. In some implementations, an endovascular instrument for filling a hollow body structure may be provided and may include an elongated member configured to exhibit differing coiling properties along a length thereof. The elongated member may include a first region configured to bend within the hollow body structure to form a stabilizing frame. The elongated member may also include a second region located proximal to the first region and configured to bend, after formation of the frame, substantially within the frame, thereby forming a curved mass substantially within the frame. The first region and the second region may be interconnected. The embodiments may further include at least one structural property that differs between the first region and the second region.

19 Claims, 42 Drawing Sheets

Related U.S. Application Data

(60) Provisional application No. 63/116,105, filed on Nov. 19, 2020, provisional application No. 63/221,254, filed on Jul. 13, 2021, provisional application No. 63/260,522, filed on Aug. 24, 2021.

(51) Int. Cl.
*A61B 17/00* (2006.01)
*A61B 90/00* (2016.01)
*A61F 2/70* (2006.01)

(52) U.S. Cl.
CPC .. *A61B 17/12113* (2013.01); *A61B 17/12145* (2013.01); *A61L 31/022* (2013.01); *A61B 90/39* (2016.02); *A61B 2017/00022* (2013.01); *A61B 2017/00084* (2013.01); *A61B 2017/00115* (2013.01); *A61B 2017/00557* (2013.01); *A61B 2017/1205* (2013.01); *A61B 2017/1209* (2013.01); *A61B 2017/12054* (2013.01); *A61B 2017/12081* (2013.01); *A61F 2002/704* (2013.01)

(58) Field of Classification Search
CPC ........ A61B 17/12031; A61B 17/12036; A61B 17/1204; A61B 17/12045; A61B 17/12099; A61B 17/12172; A61B 17/12109; A61B 17/1214; A61B 90/39; A61L 31/022
USPC .......................................................... 606/200
See application file for complete search history.

(56) References Cited

U.S. PATENT DOCUMENTS

| | | |
|---|---|---|
| 4,594,996 A | 6/1986 | Ibrahim |
| 4,932,959 A | 6/1990 | Horzewski |
| 5,161,773 A | 11/1992 | Tower |
| 5,295,994 A | 3/1994 | Bonutti |
| 5,360,403 A | 11/1994 | Mische |
| 5,628,754 A | 5/1997 | Shevlin |
| 5,749,891 A * | 5/1998 | Ken ................. A61B 17/12113 606/191 |
| 5,785,715 A | 7/1998 | Schatz |
| 5,860,966 A | 1/1999 | Tower |
| 5,868,753 A | 2/1999 | Schatz |
| 5,871,474 A | 2/1999 | Hermann |
| 5,941,888 A | 8/1999 | Wallace |
| 6,106,531 A | 8/2000 | Schatz |
| 6,159,206 A | 12/2000 | Ogawa |
| 6,171,299 B1 | 1/2001 | Bonutti |
| 6,447,489 B1 | 9/2002 | Peterson |
| 6,569,181 B1 | 5/2003 | Burns |
| 6,585,748 B1 | 7/2003 | Jeffree |
| 7,311,719 B2 | 12/2007 | Bonutti |
| 8,231,551 B2 | 7/2012 | Griffin et al. |
| 8,252,013 B2 | 8/2012 | Leibowitz |
| 8,790,363 B2 * | 7/2014 | Ferrera ............ A61B 17/12022 606/191 |
| 9,149,173 B2 | 10/2015 | Scopton |
| 10,118,025 B2 | 11/2018 | Doi |
| 10,441,746 B2 | 10/2019 | Besselink |
| 11,129,964 B2 | 9/2021 | Banerjee |
| 11,154,692 B2 | 10/2021 | Friedman et al. |
| 2002/0151926 A1 * | 10/2002 | Wallace ............ A61B 17/12145 606/200 |
| 2002/0160034 A1 | 10/2002 | Levesque |
| 2003/0181939 A1 | 9/2003 | Bonutti |
| 2004/0204701 A1 | 10/2004 | Cox |
| 2005/0059934 A1 | 3/2005 | Wenchell |
| 2005/0107823 A1 * | 5/2005 | Leone ............... A61B 17/12118 606/200 |
| 2006/0241671 A1 | 10/2006 | Greenhalgh |
| 2006/0241686 A1 * | 10/2006 | Ferrera ............ A61B 17/12022 606/200 |
| 2008/0086196 A1 | 4/2008 | Truckai |
| 2009/0177261 A1 | 7/2009 | Teoh |
| 2010/0063572 A1 | 3/2010 | Teoh |
| 2010/0204684 A1 | 8/2010 | Garrison |
| 2011/0118776 A1 * | 5/2011 | Chen ................. A61B 17/12022 606/200 |
| 2014/0031858 A1 * | 1/2014 | Bhagchandani ............................ A61B 17/12109 606/200 |
| 2015/0182226 A1 | 7/2015 | Teoh |
| 2015/0289879 A1 | 10/2015 | Bowman |
| 2017/0367579 A1 | 12/2017 | Reiner |
| 2019/0046156 A1 | 2/2019 | De Cicco |
| 2021/0085928 A1 | 3/2021 | Friedman et al. |
| 2022/0110710 A1 | 4/2022 | Rangwala |
| 2022/0117555 A1 | 4/2022 | Zarbatany |

\* cited by examiner

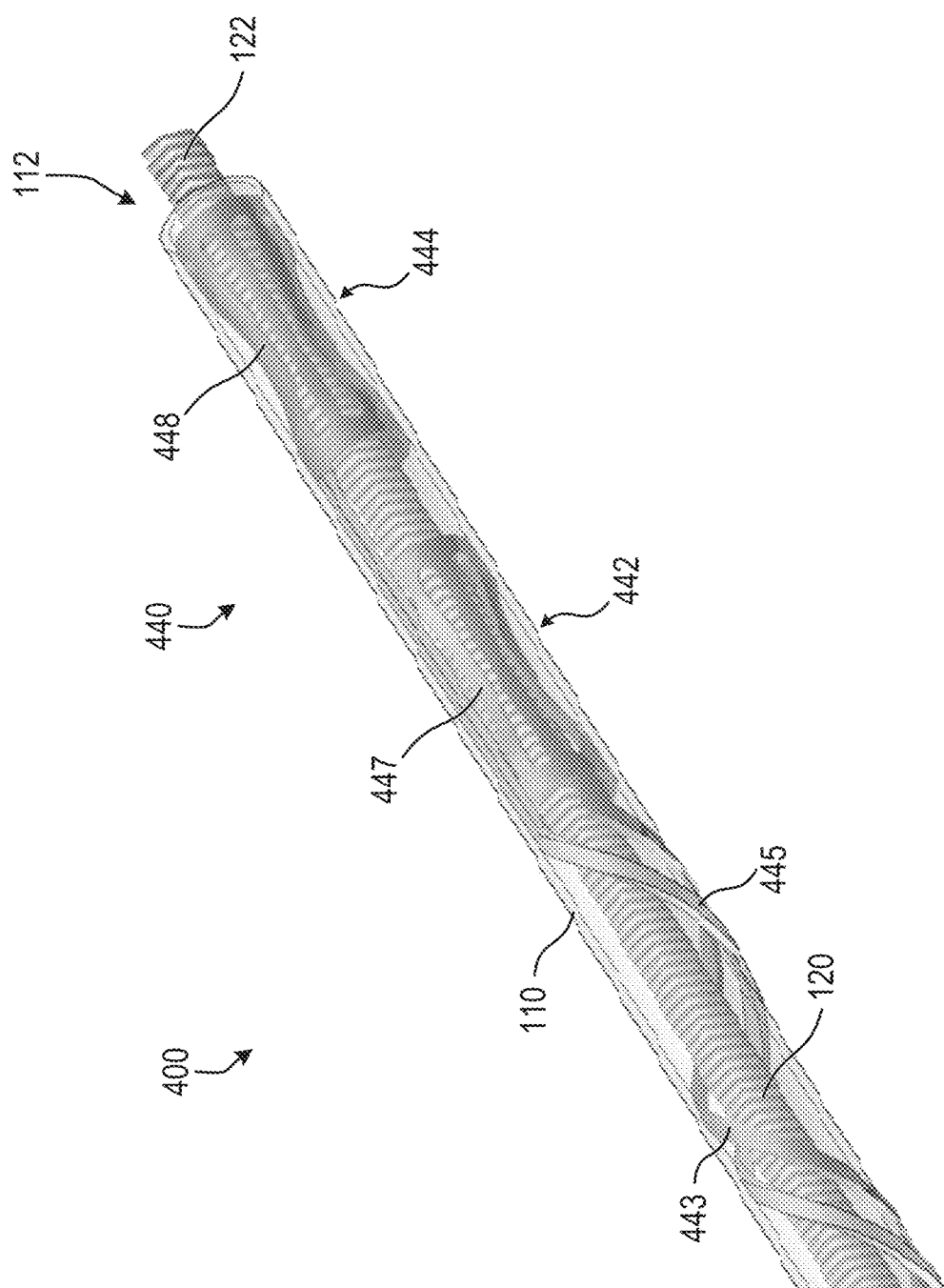

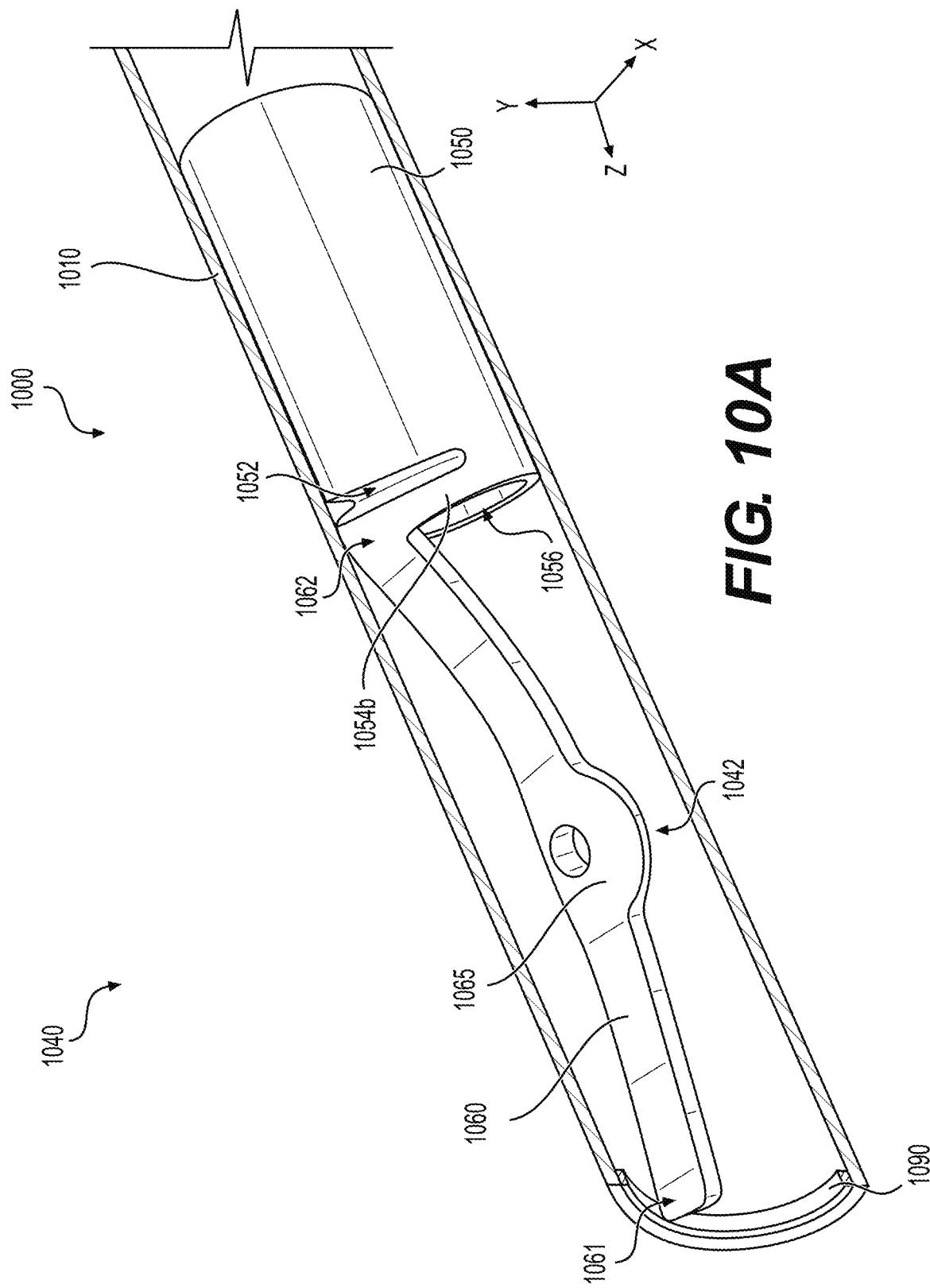

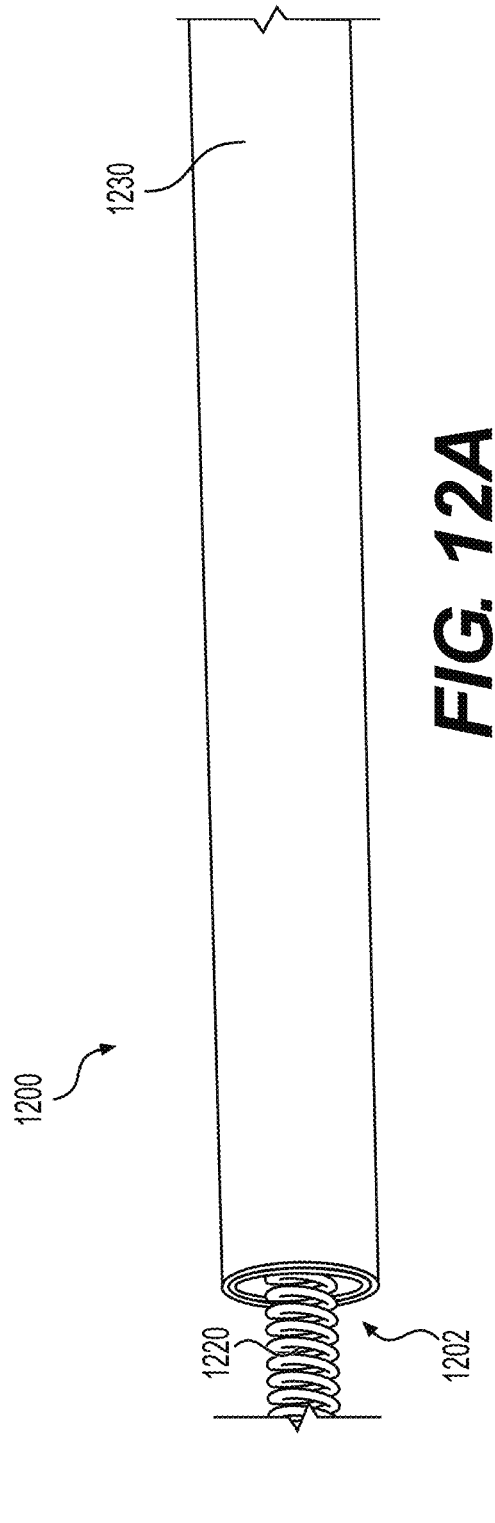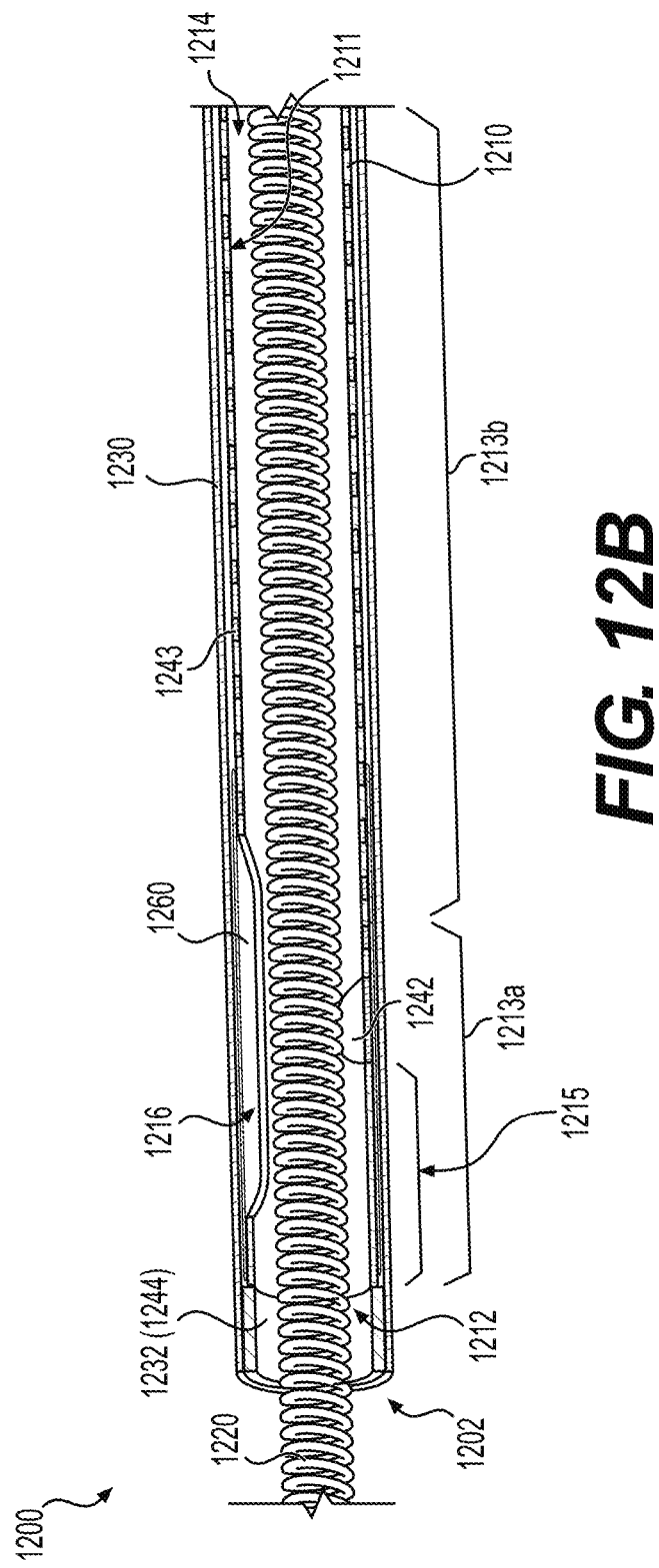
FIG. 12A
FIG. 12B

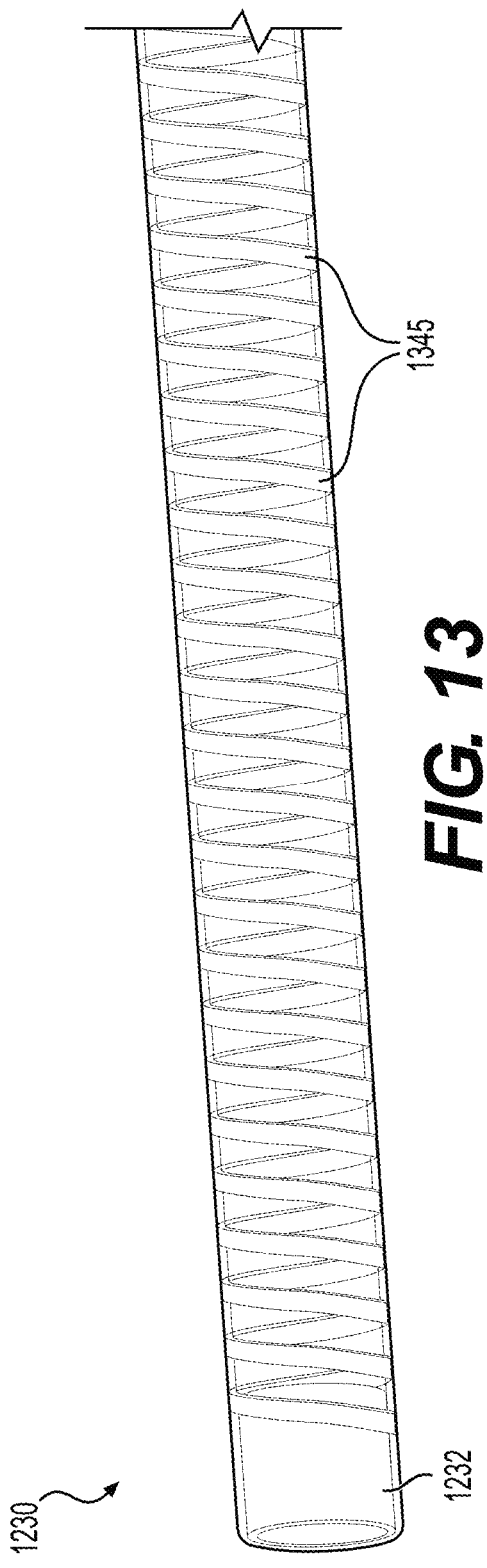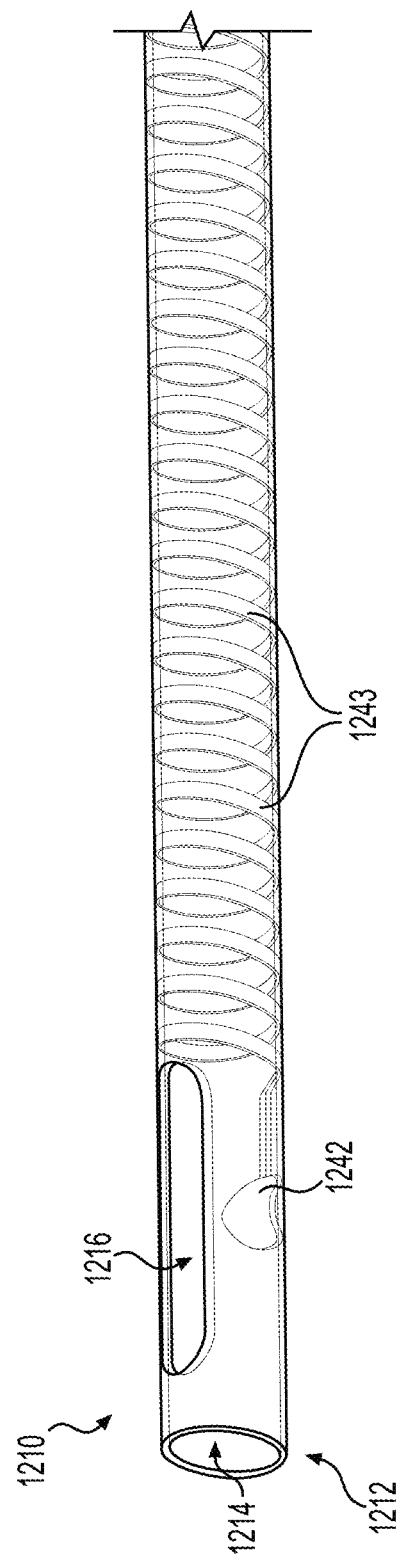

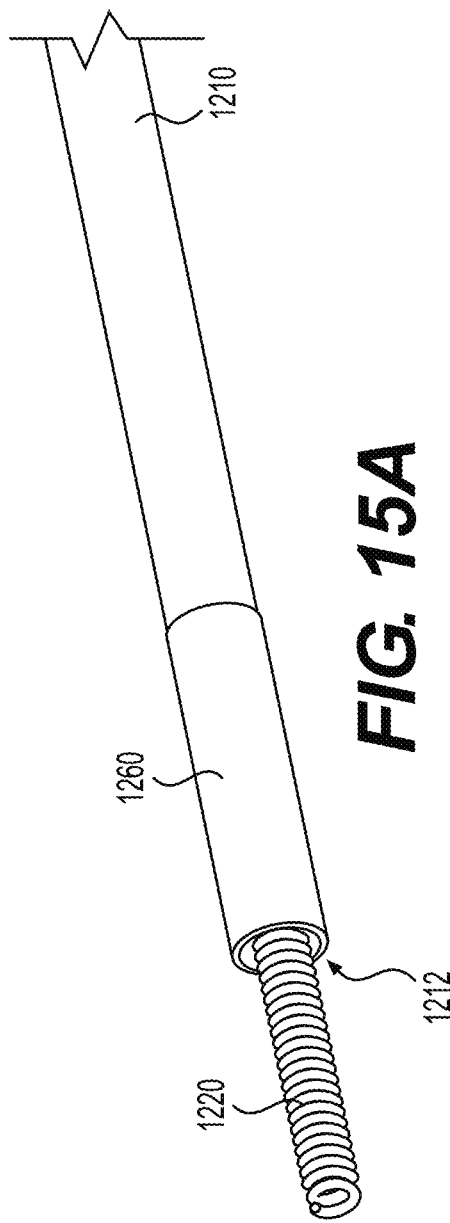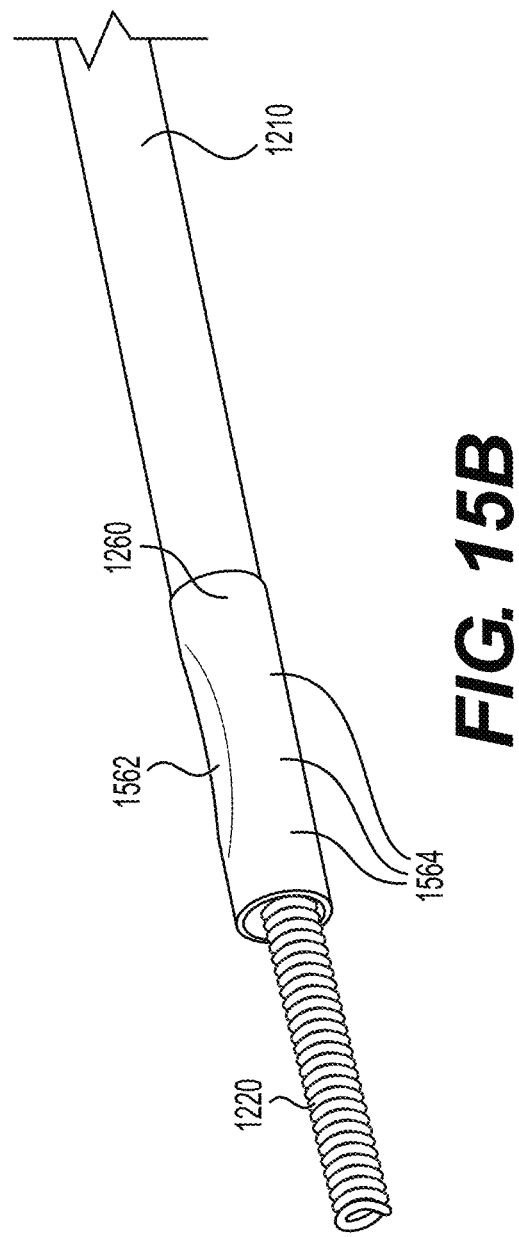

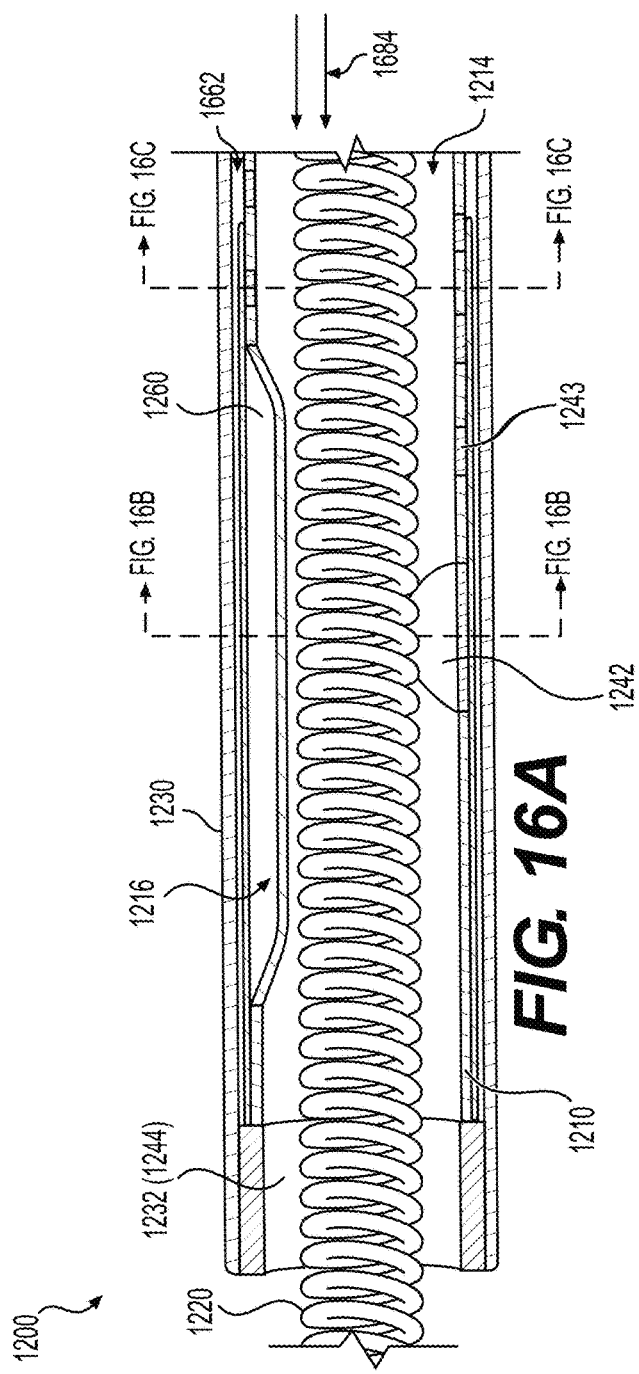
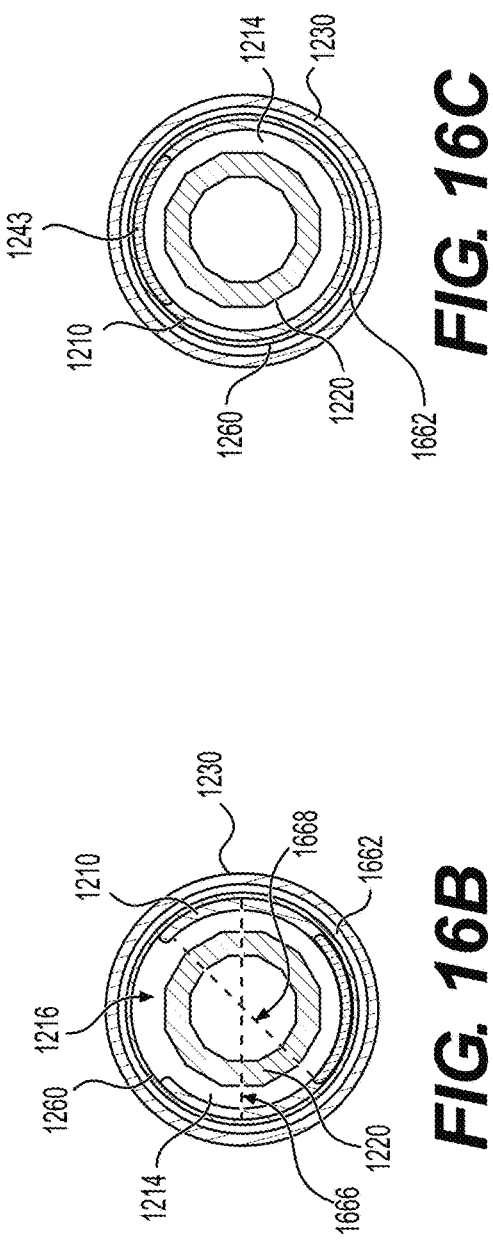
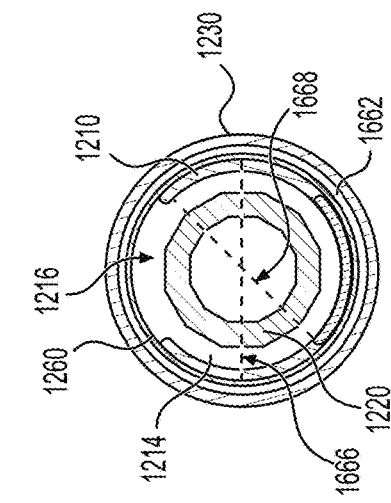

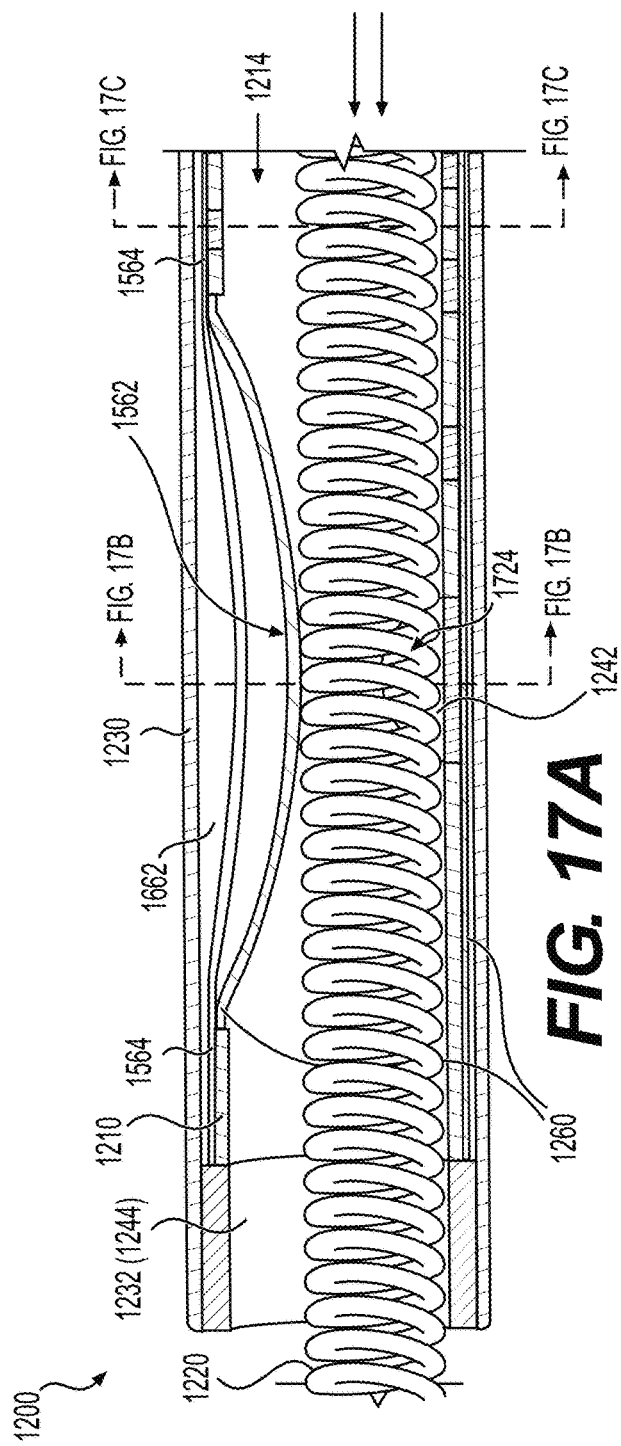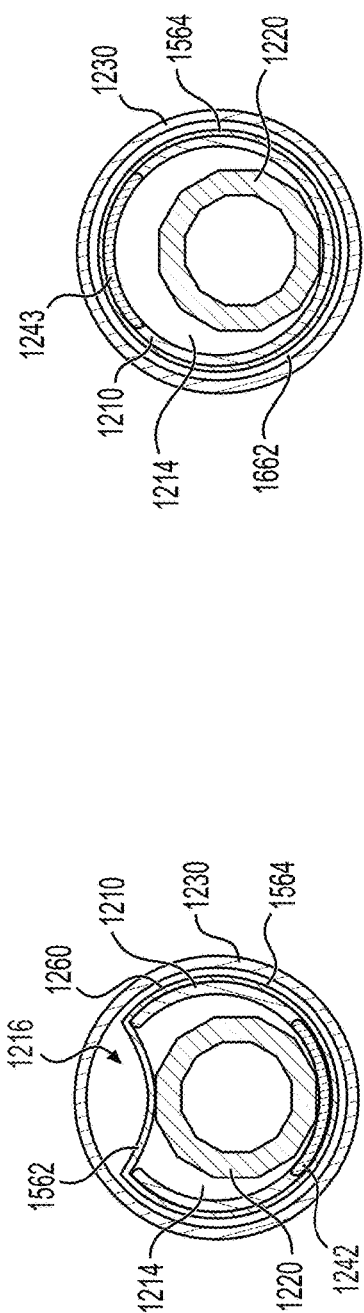

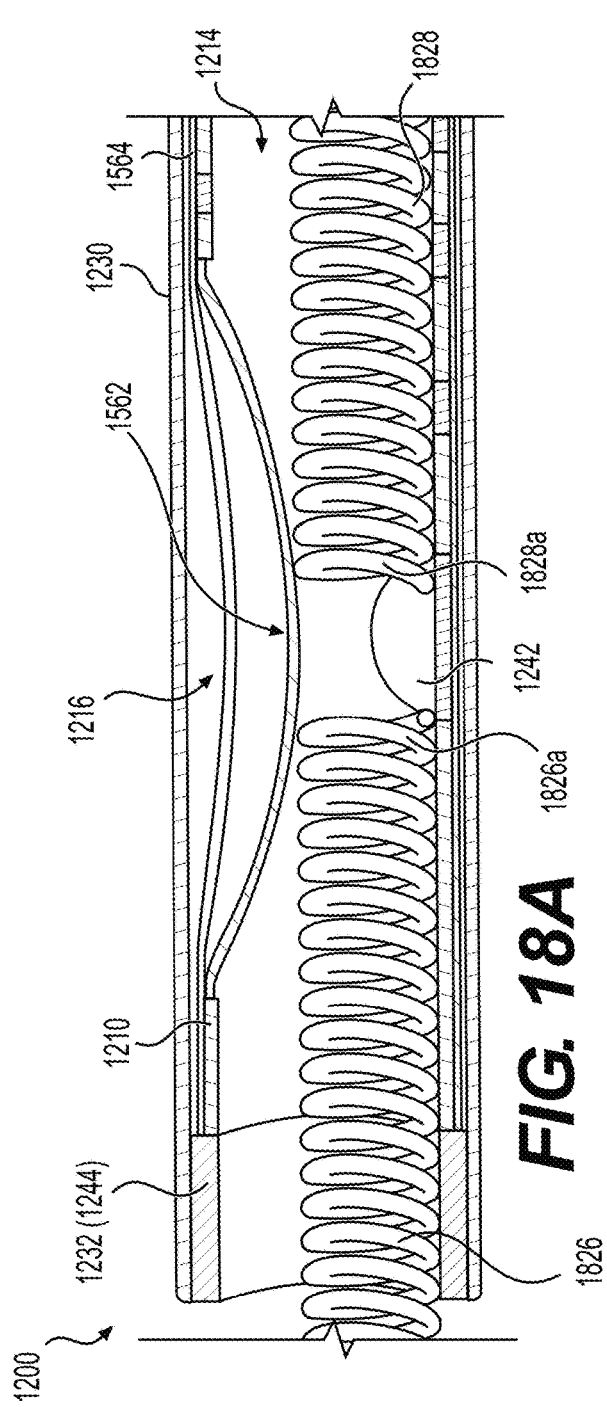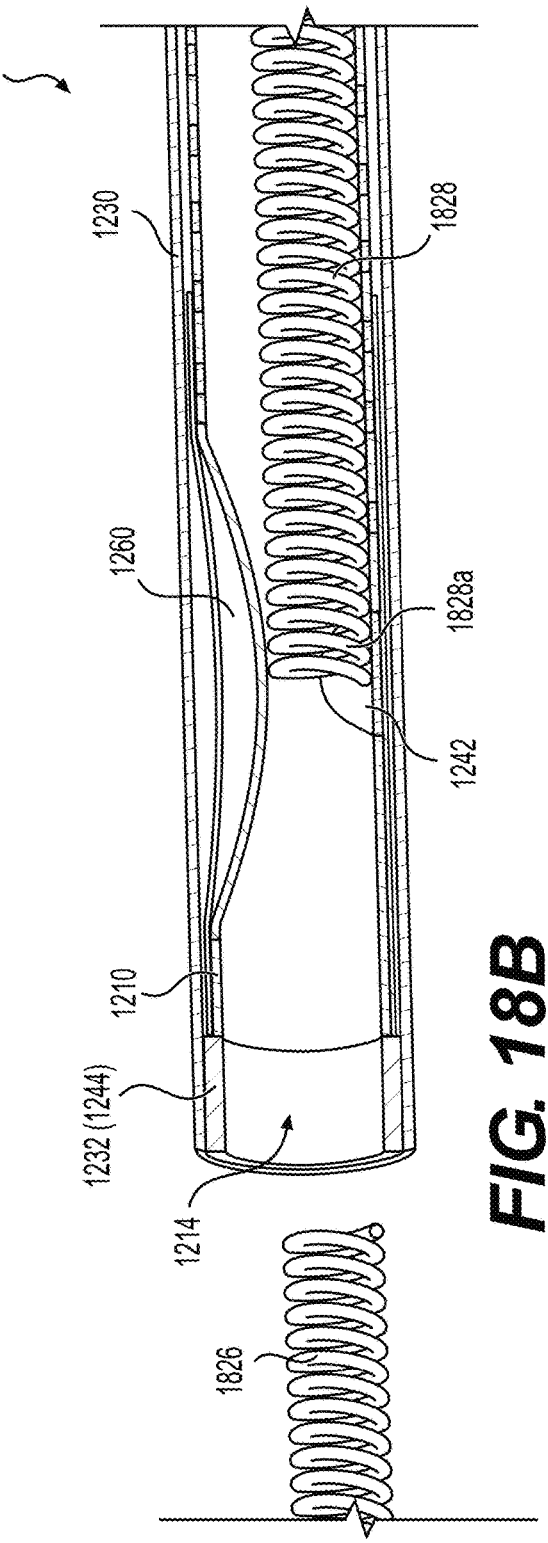

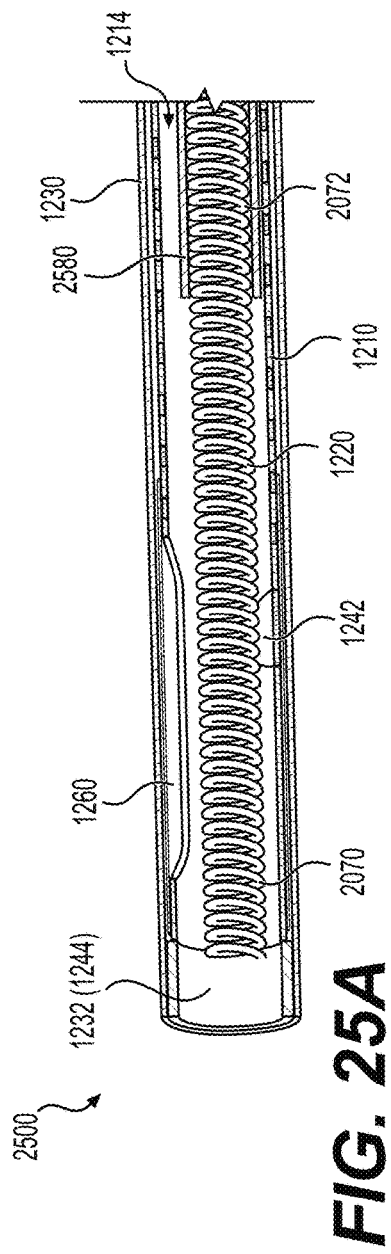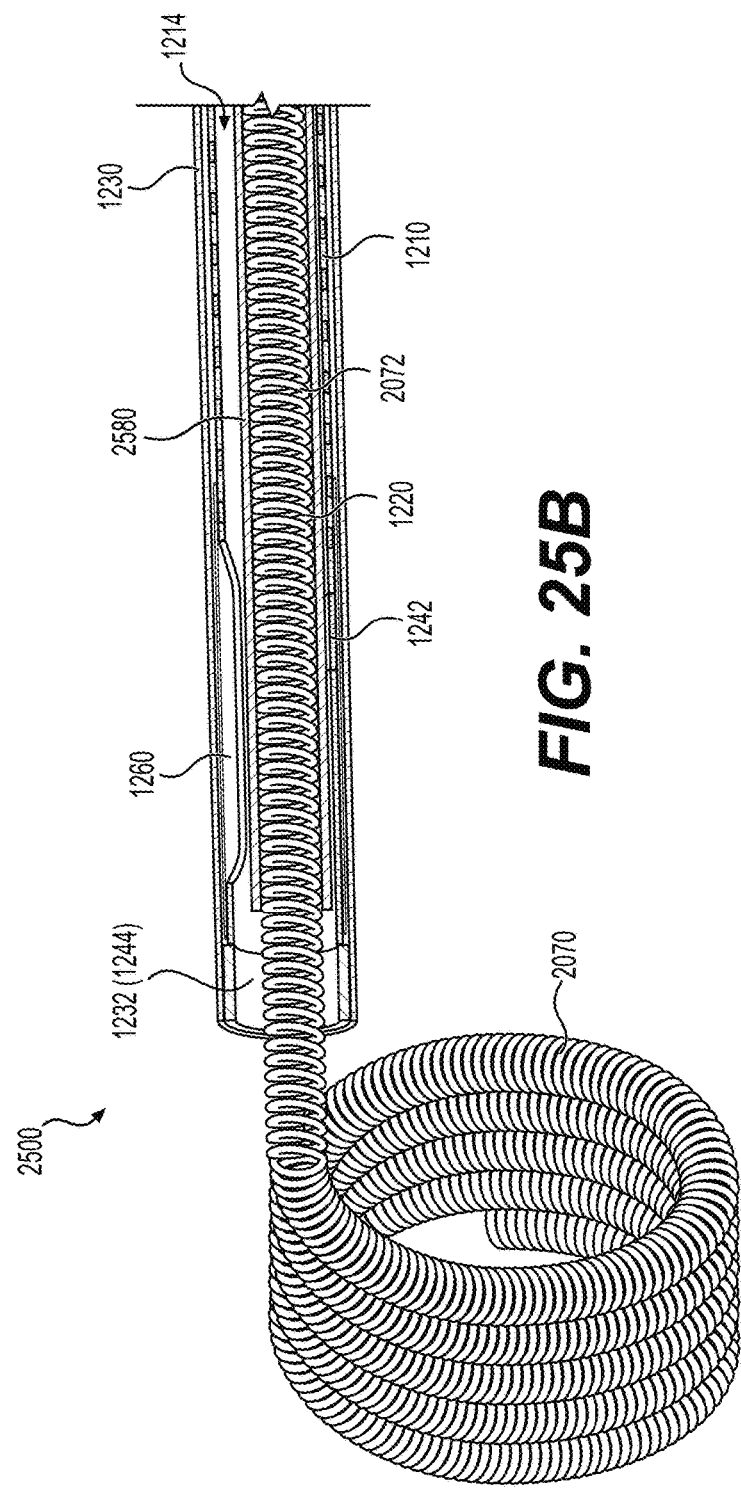

ENDOVASCULAR COIL WITH MULTIPLE SECTIONS

CROSS-REFERENCE TO RELATED APPLICATIONS

This application is a continuation of International Application No. PCT/US2021/060223, filed Nov. 19, 2021, now pending, which claims the benefit of priority of U.S. Provisional Patent Application No. 63/116,105, filed Nov. 19, 2020; U.S. Provisional Patent Application No. 63/221,254, filed Jul. 13, 2021; and U.S. Provisional Patent Application No. 63/260,522, filed Aug. 24, 2021, each of which is hereby incorporated by reference in its entirety.

TECHNICAL FIELD

The present disclosure relates to intravascular medical devices and systems for treatment of vascular aneurysms, and methods of use thereof. In particular, the present disclosure relates to intravascular devices and systems for sizing and delivery of embolic coil implants to vascular aneurysms.

BACKGROUND

An aneurysm is a ballooning or bulging of an artery at a weak spot in the wall of an artery. Aneurysms frequently occur in the brain, aorta, intestines, spleen, and back of the knee. Endovascular treatment of aneurysms, such as intracranial aneurysms, typically involves placing a number of coils inside the aneurysm to stop the flow of blood to the aneurysm, thus removing the aneurysm from circulation and preventing the aneurysm sac from expanding or bleeding. The coils used for aneurysm treatment are available in different sizes, with predetermined coil lengths. Aneurysm treatment includes repeatedly advancing a coil through a catheter to the delivery site and detaching the coil from the catheter to fill the aneurysm; this method continues until the aneurysm is completely filled.

Proper filling of the aneurysm is crucial for treatment success, and significant packing of the coils is very important as remnant blood flow may cause recurrence and aneurysm expansion, which may lead to additional surgery or even patient death. On the other hand, if too many coils are placed in the aneurysm, the coils may protrude from the aneurysm sac into the blood vessel and induce thrombus formation. This may occlude the vessel and cause a stroke, often leading to patient disability or death.

Existing techniques for aneurysm treatment therefore present a dilemma for physicians: if they either over-fill or under-fill the aneurysm, the procedure success and the patient's health outcomes may be at risk. In addition, each coil detachment presents an inherent risk of detachment mechanism failure or coil/microcatheter migration when detachment occurs, as well as wasted time and cost associated with each coil that is not properly used. Thus, there remains a need for improved methods for delivering a desired length of coil to an aneurysm treatment site, so as to ensure that the aneurysm is filled with the proper amount of coil material. There also remains a need for aneurysm coil delivery techniques that provide a reduced number of coil detachment steps, so as to mitigate the risks associated with coil detachment failure.

SUMMARY

Embodiments of the present disclosure may include a system for delivery and cutting of an endovascular coil. The system may include a flexible, elongated microcatheter having a proximal end, a distal end, and at least one inner lumen. The microcatheter may be configured for advancement to a treatment area. The system may also include a helical coil configured to be advanced distally through the inner lumen of the microcatheter and to extend through the distal end of the microcatheter. The system may also include a detachment mechanism situated at the distal end of the microcatheter. The detachment mechanism may be configured to apply electrical current to the coil in order to cut a section of the coil arranged at the distal end of the microcatheter. The system may also include a controller including a power source connected to the detachment mechanism. When a desired length of the coil extends through the distal end of the microcatheter, the detachment mechanism may be configured to receive electrical current from the power source and apply the current to the coil. The application of current may cut the section of the coil arranged at the distal end of the microcatheter and may release the desired length of the coil from the microcatheter.

According to another embodiment of the present disclosure, an apparatus for cutting an endovascular coil may be provided. The apparatus may include a cylindrical base having a proximal end, a distal end, and at least one inner lumen. The cylindrical base may be configured to receive an endovascular coil within the at least one inner lumen. The apparatus may additionally include an elongated spring beam extending from the distal end of the cylindrical base. The apparatus may additionally include a coil-cutting electrode on an inner surface of the spring beam. The coil-cutting electrode may be configured to apply electrical current to the endovascular coil in order to sever a section of the endovascular coil in contact with the coil-cutting electrode. The spring beam may be configured to move between an active position in which the spring beam is configured to press the coil-cutting electrode against a portion of the endovascular coil extending distally from the cylindrical base, and a rest position in which the spring beam reduces the contact force between the coil-cutting electrode and the endovascular coil, relative to the active position.

According to another embodiment of the present disclosure, an endovascular treatment system may be provided. The endovascular treatment system may include a microcatheter configured to deliver an endovascular coil to an endovascular site and having at least one inner lumen. The microcatheter may include an apparatus for cutting an endovascular coil arranged within a distal end of the inner lumen of the microcatheter. The apparatus may include a cylindrical base having a proximal end, a distal end, and at least one inner lumen. The cylindrical base may be configured to receive an endovascular coil within the at least one inner lumen. The apparatus may additionally include an elongated spring beam extending from the distal end of the cylindrical base. The apparatus may additionally include a coil-cutting electrode on an inner surface of the spring beam. The coil-cutting electrode may be configured to apply electrical current to the endovascular coil in order to sever a section of the endovascular coil in contact with the coil-cutting electrode. The spring beam may be configured to move between an active position in which the spring beam is configured to press the coil-cutting electrode against a portion of the endovascular coil extending distally from the cylindrical base, and a rest position in which the spring beam reduces the contact force between the coil-cutting electrode and the endovascular coil, relative to the active position. The endovascular treatment system may additionally include a power source configured to apply electric current to the cylindrical base of the apparatus. When the power source applies the electric current to the cylindrical base, the spring beam of the apparatus may be configured to move into the active position to sever a section of the endovascular coil in contact with the coil-cutting electrode of the apparatus.

According to another embodiment of the present disclosure, a method of manufacturing an apparatus for cutting an endovascular coil may be provided. The method of manufacturing may include providing a cylindrical base having a proximal end, a distal end, and at least one inner lumen. The method of manufacturing may additionally include forming, at the distal end of the cylindrical base, an elongated spring beam extending from the distal end of the cylindrical base. The method of manufacturing may additionally include forming a circumferential slit in a distal portion of the cylindrical base to produce at least first and second torque poles connecting the spring beam to the cylindrical base. The method of manufacturing may additionally include shape-setting the first and second torque poles in a twisted configuration.

Consistent with disclosed embodiments, systems, devices, methods, and computer readable media for filling a hollow body structure are disclosed. For example, an endovascular instrument for filling a hollow body structure is disclosed. The embodiments may include an elongated member configured to exhibit differing coiling properties along a length thereof. The elongated member may include a first region configured to bend in a first manner within the hollow body structure to form a stabilizing frame. The elongated member may further include a second region proximal to the first region. The second region may be configured to bend, after formation of the frame, in a second manner substantially within the frame, thereby forming a curved mass substantially within the frame. The first region and the second region may be interconnected. The embodiments may further include at least one structural property that differs between the first region and the second region.

Consistent with disclosed embodiments, systems, devices, methods, and computer readable media for delivery of an endovascular instrument to a treatment site within a body are disclosed. The embodiments may include a flexible, elongated sheath having a proximal end and a distal end. A distal section of the sheath may terminate at the distal end. The embodiments may further include an inner wall of the sheath delimiting an inner lumen which may extend between the proximal end and the distal end of the sheath. The inner lumen may be sized to enable axial advancement of the endovascular instrument therethrough. The embodiments may also include at least one electrode within the distal section of the sheath. The at least one electrode may be configured to selectively deliver an electric current through a segment of the endovascular instrument within the inner lumen. The at least one electrode may be configured to selectively deliver the electric current through the segment of the endovascular instrument while the distal section of the sheath may be positioned in the body.

Consistent with disclosed embodiments, systems, devices, methods, and computer readable media for causing a flow of electric current within a flexible elongated sheath in a body of a patient are disclosed. Embodiments may include obtaining an input for sending the electric current from an electrode positioned within the flexible elongated sheath through a segment of an endovascular instrument received within an inner lumen of the sheath. Embodiments may further include controlling the flow of the electric current from the electrode through the segment of the endovascular instrument based on the input. The flow of the electric current may be in an amount sufficient to cause the endovascular instrument to be severed.

Consistent with disclosed embodiments, systems, devices, methods, and computer readable media containing instructions for endovascular treatment are disclosed. The embodiments may include an elongated flexible sheath defining a lumen with an inner opening sized for enabling selective advancement of an endovascular instrument therethrough. The sheath may have at least a first region and a second region. The embodiments may further include an electrode within the first region of the sheath. The embodiments may further include a constrictor associated with the first region of the sheath, the constrictor being configured, while at least the first region and the second region of the sheath are positioned within a body and in response to an input received from outside the body, to reversibly narrow the lumen of the sheath in an area adjacent the electrode to thereby bring the electrode into contact with an adjacent portion of the endovascular instrument.

Consistent with additional disclosed embodiments, systems, devices, methods, and computer readable media containing instructions for endovascular treatment are disclosed. The embodiments may include delivering an endovascular instrument to human vasculature via a sheath having an electrode therein. The embodiments may further include while a portion of the sheath having the electrode is within a body, reversibly constricting the portion of the sheath having the electrode to narrow a lumen within the sheath and thereby cause the electrode and the endovascular instrument to make physical contact. The embodiments may further include while the portion of the sheath having the electrode is constricted, supplying electrical energy to the electrode, to thereby deliver electrical energy to the endovascular instrument via the electrode.

Consistent with further disclosed embodiments, systems, devices, methods, and computer readable media containing instructions for endovascular treatment are disclosed. The embodiments may include obtaining an input corresponding to delivery of an endovascular instrument to human vasculature via a sheath having an electrode therein. The embodiments may further include based on the input, and while a portion of the sheath having the electrode is within a body, causing reversible constriction of the portion of the sheath having the electrode to narrow a lumen within the sheath and thereby cause the electrode and the endovascular instrument to make physical contact. The embodiments may further include while the portion of the sheath having the electrode is constricted, controlling supply of electrical energy to the electrode, to thereby deliver electrical energy to the endovascular instrument via the electrode.

Consistent with disclosed embodiments, systems, devices, methods, and computer readable media containing instructions for controlling a balloon affixed to a catheter in a body of a patient are disclosed. The embodiments may include an elongated catheter having an inner lumen extending therethrough. The embodiments may further include a balloon affixed to the catheter for expansion into the inner lumen of the catheter when the balloon is inflated. The embodiments may further include a tube secured relative to the balloon. The tube may be configured to enable selective inflation and deflation of the balloon. An outer diameter of a portion of the catheter adjacent the balloon may be substantially the same when the balloon is inflated and when the balloon is deflated.

Consistent with additional disclosed embodiments, systems, devices, methods, and computer readable media containing instructions for controlling a balloon affixed to a catheter in a body of a patient are disclosed. The embodiments may include obtaining a first input for inflating the balloon. The embodiments may further include, in response to the first input, initiating fluid flow through a conduit connected to the balloon to cause inflation of the balloon. The inflation may cause the balloon to expand into an inner lumen of the catheter. The embodiments may further include, after causing the inflation of the balloon, obtaining a second input for deflating the balloon. The embodiments may further include, in response to the second input, causing deflation of the balloon with the conduit. An outer diameter of a portion of the catheter adjacent the balloon may be substantially the same when the balloon is inflated and when the balloon is deflated.

Consistent with disclosed embodiments, systems, devices, methods, and computer readable media containing instructions for monitoring partitioning of a medical instrument during an endovascular procedure are disclosed. The embodiments may include obtaining an input to activate a partitioning mechanism associated with a medical instrument within a lumen of a catheter, the catheter being positioned within a body. The embodiments may further include in response to the input, activating the partitioning mechanism. The embodiments, following the activation, may also be configured to obtain partitioning outcome data. Embodiments may also determine, based on the partitioning outcome data, whether the medical instrument may be in a served state or a connected state. Some embodiments may, if the severed state of the medical instrument is detected, output a success notification. Further, if the connected state of the medical instrument is detected, embodiments may output at least one of (i) a control signal to vary activation of the partitioning mechanism or (ii) an instruction to reposition the medical instrument relative to the partitioning mechanism.

Consistent with additional disclosed embodiments, systems, devices, methods, and computer readable media containing instructions for monitoring partitioning of a medical instrument during an endovascular procedure are disclosed. The embodiments may include at least one processor configured to obtain an input to activate a partitioning mechanism associated with a medical instrument within a lumen of a catheter, the catheter being positioned within a body. The embodiments may further include in response to the input, activating the partitioning mechanism. The embodiments, following the activation, may also be configured to obtain partitioning outcome data. Embodiments may also determine, based on the partitioning outcome data, whether the medical instrument may be in a severed state or a connected state. In some embodiments, if the severed state of the medical instrument is detected, a success notification may be output. Further, if the connected state of the medical instrument is detected, embodiments may output at least one of (i) a control signal to vary activation of the partitioning mechanism or (ii) an instruction to reposition the medical instrument relative to the partitioning mechanism.

Consistent with further disclosed embodiments, systems, devices, methods, and computer readable media containing instructions for monitoring partitioning of a medical instrument during an endovascular procedure are disclosed. The embodiments may include obtaining an input to activate a partitioning mechanism associated with a medical instrument within a lumen of a catheter, the catheter being positioned within a body. The embodiments may further include in response to the input, activating the partitioning mechanism. The embodiments, following the activation, may also be configured to obtain partitioning outcome data. Embodiments may also determine, based on the partitioning outcome data, whether the medical instrument may be in a served state or a connected state. Some embodiments may, if the severed state of the medical instrument is detected, output a success notification. Further, if the connected state of the medical instrument is detected, embodiments may output at least one of (i) a control signal to vary activation of the partitioning mechanism or (ii) an instruction to reposition the medical instrument relative to the partitioning mechanism.

Consistent with disclosed embodiments, systems, devices, methods, and non-transitory computer readable media containing instructions for facilitating endovascular coil delivery are disclosed. The embodiments may include obtaining a first input from a coil movement sensor associated with an endovascular coil within a lumen of a catheter positioned within a body. The catheter may include a coil partitioning mechanism configured to sever the endovascular coil. The embodiments may further include obtaining, after the first input, a second input to activate the coil partitioning mechanism. The embodiments may further include activating, in response to the second input, the coil partitioning mechanism to sever the endovascular coil into a first coil section for delivery from the catheter and a residual second coil section. The embodiments may further include determining, based on at least the first input and the second input, a length of the second coil section. The embodiments may further include outputting a signal based on the determined length of the second coil section.

Consistent with additional disclosed embodiments, systems, devices, methods, and non-transitory computer readable media containing instructions for monitoring endovascular coil delivery are disclosed. The embodiments may include at least one processor configured to obtain a first input from a coil movement sensor associated with an endovascular coil within a lumen of a catheter positioned within a body. The catheter may include a coil partitioning mechanism configured to sever the endovascular coil. The at least one processor may be further configured to obtain, after the first input, a second input to activate the coil partitioning mechanism. The at least one processor may be further configured to activate, in response to the second input, the coil partitioning mechanism to sever the endovascular coil into a first coil section for delivery from the catheter and a residual second coil section. The at least one processor may be further configured to determine, based on at least the first input and the second input, a length of the second coil section. The at least one processor may be further configured to output a signal based on the determined length of the second coil section.

BRIEF DESCRIPTION OF THE DRAWINGS

The accompanying drawings, which are incorporated in and constitute a part of this disclosure, illustrate various disclosed embodiments. In the drawings:

FIG. 4 illustrates a system for severing an endovascular coil, consistent with disclosed embodiments.

FIG. 10A illustrates another example of an apparatus for severing an endovascular coil, consistent with disclosed embodiments.

FIG. 12A is a side view and FIG. 12B is an interior view of an example of an endovascular device configured for delivery of an endovascular instrument, consistent with disclosed embodiments.

FIG. 13 is a perspective side view of an example of an outer tube of the endovascular device of FIGS. 12A and 12B, consistent with disclosed embodiments.

FIG. 14 is a perspective side view of an example of an elongated sheath of the endovascular device of FIGS. 12A and 12B, consistent with disclosed embodiments.

FIG. 15A is a perspective view of the elongated sheath of FIG. 14 with a balloon in a first configuration, consistent with disclosed embodiments.

FIG. 15B is a perspective view of the elongated sheath of FIG. 14 with the balloon in a second configuration, consistent with disclosed embodiments.

FIG. 16A is an interior view of a distal section of the endovascular device of FIGS. 12A and 12B in an unconstricted state, consistent with disclosed embodiments.

FIGS. 16B and 16C depict cross-sectional views of the endovascular device of FIG. 16A in the unconstricted state, consistent with disclosed embodiments.

FIG. 17A is an interior view of the distal section of the endovascular device of FIGS. 12A and 12B in a constricted state, consistent with disclosed embodiments.

FIGS. 17B and 17C depict cross-sectional views of the endovascular device of FIG. 17A in the constricted state, consistent with disclosed embodiments.

FIGS. 18A and 18B depict an example of an endovascular instrument being severed by the endovascular device of FIGS. 12A and 12B, consistent with disclosed embodiments.

FIG. 25A is an interior view of an example of an endovascular device and an endovascular instrument including a support mechanism, consistent with disclosed embodiments.

FIG. 25B is another interior view of the endovascular device of FIG. 25A, with the endovascular instrument pushed distally by the support mechanism, consistent with disclosed embodiments.

DETAILED DESCRIPTION

Figure 1:
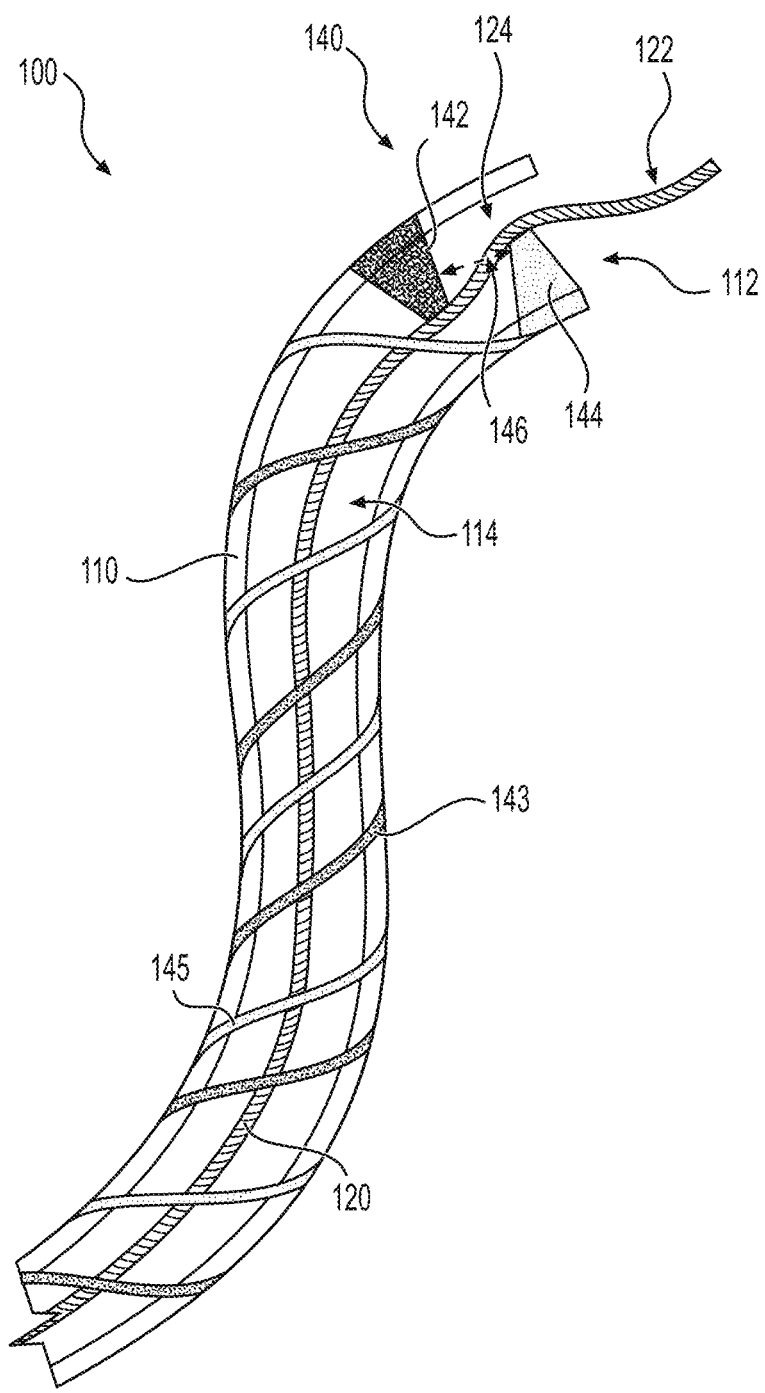
FIG. 1 illustrates a system for severing an endovascular coil, consistent with disclosed embodiments.

Exemplary embodiments are described with reference to the accompanying drawings. In the figures, which are not necessarily drawn to scale, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It should also be noted that as used in the present disclosure and in the appended claims, the singular forms "a," "an," and "the" include plural references unless the context clearly dictates otherwise.

Unless specifically stated otherwise, as apparent from the following description, throughout the specification discussions utilizing terms such as "processing," "calculating," "computing," "determining," "generating," "setting," "configuring," "selecting," "defining," "applying," "obtaining," "monitoring," "providing," "identifying," "segmenting," "classifying," "analyzing," "associating," "extracting," "storing," "receiving," "transmitting," or the like, include actions and/or processes of a computer that manipulate and/or transform data into other data, the data represented as physical quantities, for example such as electronic quantities, and/or the data representing physical objects. The terms "computer," "processor," "controller," "processing unit," "control unit," "computing unit," and "processing module" should be expansively construed to cover any kind of electronic device, component or unit with data processing capabilities, including, by way of non-limiting example, a personal computer, a wearable computer, smart glasses, a tablet, a smartphone, a server, a computing system, a cloud computing platform, a communication device, a processor (for example, digital signal processor (DSP), an image signal processor (ISR), a microcontroller, a field programmable gate array (FPGA), an application specific integrated circuit (ASIC), a central processing unit (CPA), a graphics processing unit (GPU), a visual processing unit (VPU), and so on), possibly with embedded memory, a single core processor, a multi core processor, a core within a processor, any other electronic computing device, or any combination of the above. The operations in accordance with the teachings herein may be performed by a computer specially constructed or programmed to perform the described functions.

As used herein, the phrase "for example," "such as," "for instance" and variants thereof describe non-limiting embodiments of the presently disclosed subject matter. Reference in the specification to features of "embodiments," "one case," "some cases," "other cases" or variants thereof means that a particular feature, structure or characteristic described may be included in at least one embodiment of the presently disclosed subject matter. Thus the appearance of such terms does not necessarily refer to the same embodiment(s). As used herein, the term "and/or" includes any and all combinations of one or more of the associated listed items.

Features of the presently disclosed subject matter, are, for brevity, described in the context of particular embodiments. However, it is to be understood that features described in connection with one embodiment are also applicable to other embodiments. Likewise, features described in the context of a specific combination may be considered separate embodiments, either alone or in a context other than the specific combination.

In embodiments of the presently disclosed subject matter, one or more stages or steps illustrated in the figures may be executed in a different order and/or one or more groups of stages may be executed simultaneously and vice versa. The figures illustrate a general schematic of the system architecture in accordance embodiments of the presently disclosed subject matter. Each module in the figures can be made up of any combination of software, hardware and/or firmware that performs the functions as defined and explained herein. The modules in the figures may be centralized in one location or dispersed over more than one location.

Examples of the presently disclosed subject matter are not limited in application to the details of construction and the arrangement of the components set forth in the following description or illustrated in the drawings. The subject matter may be practiced or carried out in various ways. Also, it is to be understood that the phraseology and terminology employed herein is for the purpose of description and should not be regarded as limiting.

In this document, an element of a drawing that is not described within the scope of the drawing and is labeled with a numeral that has been described in a previous drawing may have the same use and description as in the previous drawings. The drawings in this document may not be to any scale. Different figures may use different scales and different scales can be used even within the same drawing, for example different scales for different views of the same object or different scales for the two adjacent objects.

Consistent with disclosed embodiments, "at least one processor" may constitute any physical device or group of devices having electric circuitry that performs a logic operation on an input or inputs. For example, the at least one processor may include one or more integrated circuits (IC), including application-specific integrated circuit (ASIC), microchips, microcontrollers, microprocessors, all or part of a central processing unit (CPU), graphics processing unit (GPU), digital signal processor (DSP), field-programmable gate array (FPGA), server, virtual server, or other circuits suitable for executing instructions or performing logic operations. The instructions executed by at least one processor may, for example, be pre-loaded into a memory integrated with or embedded into the controller or may be stored in a separate memory. The memory may include a Random Access Memory (RAM), a Read-Only Memory (ROM), a hard disk, an optical disk, a magnetic medium, a flash memory, other permanent, fixed, or volatile memory, or any other mechanism capable of storing instructions. In some embodiments, the at least one processor may include more than one processor. Each processor may have a similar construction or the processors may be of differing constructions that are electrically connected or disconnected from each other. For example, the processors may be separate circuits or integrated in a single circuit. When more than one processor is used, the processors may be configured to operate independently or collaboratively. The processors may be coupled electrically, magnetically, optically, acoustically, mechanically or by other means that permit them to interact.

Disclosed embodiments may include and/or access a data structure. A data structure consistent with the present disclosure may include any collection of data values and relationships among them. The data may be stored linearly, horizontally, hierarchically, relationally, non-relationally, uni-dimensionally, multidimensionally, operationally, in an ordered manner, in an unordered manner, in an object-oriented manner, in a centralized manner, in a decentralized manner, in a distributed manner, in a custom manner, or in any manner enabling data access. By way of non-limiting examples, data structures may include an array, an associative array, a linked list, a binary tree, a balanced tree, a heap, a stack, a queue, a set, a hash table, a record, a tagged union, ER model, and a graph. For example, a data structure may include an XML database, an RDBMS database, an SQL database or NoSQL alternatives for data storage/search such as, for example, MongoDB, Redis, Couchbase, Datastax Enterprise Graph, Elastic Search, Splunk, Solr, Cassandra, Amazon DynamoDB, Scylla, HBase, and Neo4J. A data structure may be a component of the disclosed system or a remote computing component (e.g., a cloud-based data structure). Data in the data structure may be stored in contiguous or non-contiguous memory. Moreover, a data structure, as used herein, does not require information to be co-located. It may be distributed across multiple servers, for example, that may be owned or operated by the same or different entities. Thus, the term "data structure" as used herein in the singular is inclusive of plural data structures.

Embodiments of the present disclosure relate generally to devices, systems, and methods for the continuous filling of a coil from a microcatheter into an aneurysm until the aneurysm is completely filled. The exemplary devices and systems may be configured to cut the coil at the distal end of the microcatheter, thus detaching the coil from the microcatheter. Advantageously, devices, systems, and methods described herein may provide optimal filling of the aneurysm sac with the coil, thus allowing a superior degree of aneurysm occlusion. In addition, the delivery and cutting of a single coil eliminates the need for multiple coil detachment steps; this may reduce the risk for detachment mechanism failure, mitigate microcatheter displacement, and provide shorter procedure time. Further, exemplary devices, systems, and methods described herein may eliminate stiff, rigid detachment junctions present in prior aneurysm treatment devices.

FIG. 1 illustrates an exemplary system 100 for endovascular coil cutting with a coil-cutting apparatus 140. System 100 may include a microcatheter 110, a helical coil 120, and a controller (not shown) including a power source such as an electrical generator. Microcatheter 110 may be navigated to a treatment area within the patient's body using a guidewire, after which the guidewire may be removed. In some embodiments, coil 120 may be constructed of Nitinol, platinum, nickel, iridium, tungsten, an alloy (e.g., a platinum/tungsten alloy) and/or any other suitable material. Coil 120 may be introduced through an inner lumen 114 of microcatheter 110 and into the treatment area. Once a desired length of coil 120 extends from the distal end 112 of the microcatheter (e.g., with the desired coil length situated within the treatment area (not shown)), the coil-cutting apparatus 140 at the distal end 112 of the microcatheter may be connected to the power source and electrical current delivered to the coil 120 via the coil-cutting apparatus 140 to locally melt and cut the coil. The remaining length of coil 120 may then be removed from microcatheter 110.

In some embodiments, the coil-cutting apparatus 140 may include two electrodes 142, 144 situated at the distal end 112 of the microcatheter. Electrodes 142, 144 may be connected via wires 143, 145 (e.g., copper wires) to the proximal end of microcatheter 110 and to the controller and power source. At the distal end 112 of the microcatheter, the electrodes 142, 144 may maintain active or passive contact with coil 120. For example, when a coil detachment action is initiated via the controller, the power source may generate a high current pulse which is delivered to electrodes 142, 144 by wires 143, 145. In some embodiments, the controller may send a signal, wireless or otherwise, to the power source to generate the high current pulse. Electrodes 142, 144 may apply the high current pulse to the coil section 124 arranged between the electrodes; the high resistance of the coil section 124, relative to the coil-cutting apparatus 140, causes the coil section to locally melt and severs the coil 120 at coil section 124. As a result, the distal segment 122 of the coil may be detached from microcatheter 110 and from the remainder of the coil, so that distal segment 122 may remain in an aneurysm or other treatment area.

FIG. 1 illustrates an example of a passive coil-cutting apparatus 140. At the distal end 112 of the microcatheter, electrodes 142, 144 may be embedded within the wall of the microcatheter and may extend into the inner lumen 114 of the microcatheter to create contact between electrodes 142, 144 and coil 120. In the example shown in FIG. 1, electrodes 142, 144 may bulge into the microcatheter lumen from opposite sides, with a short axial distance 146 provided between them (e.g., a distance of between 1-2 mm). This arrangement may force coil section 124 to pass in an "S" path between electrodes 142, 144, which increases electrical contact between coil 120 and electrodes 142, 144.

Figure 2A:
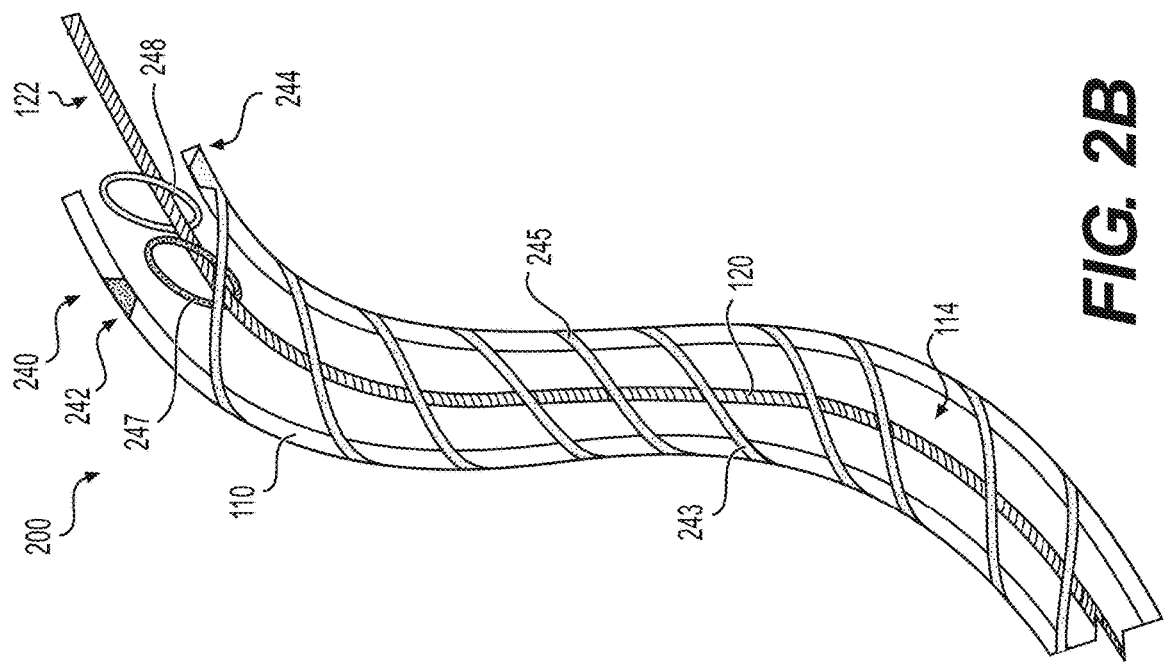
FIGS. 2A and 2B illustrate a system for severing an endovascular coil, consistent with disclosed embodiments.
Figure 2B:
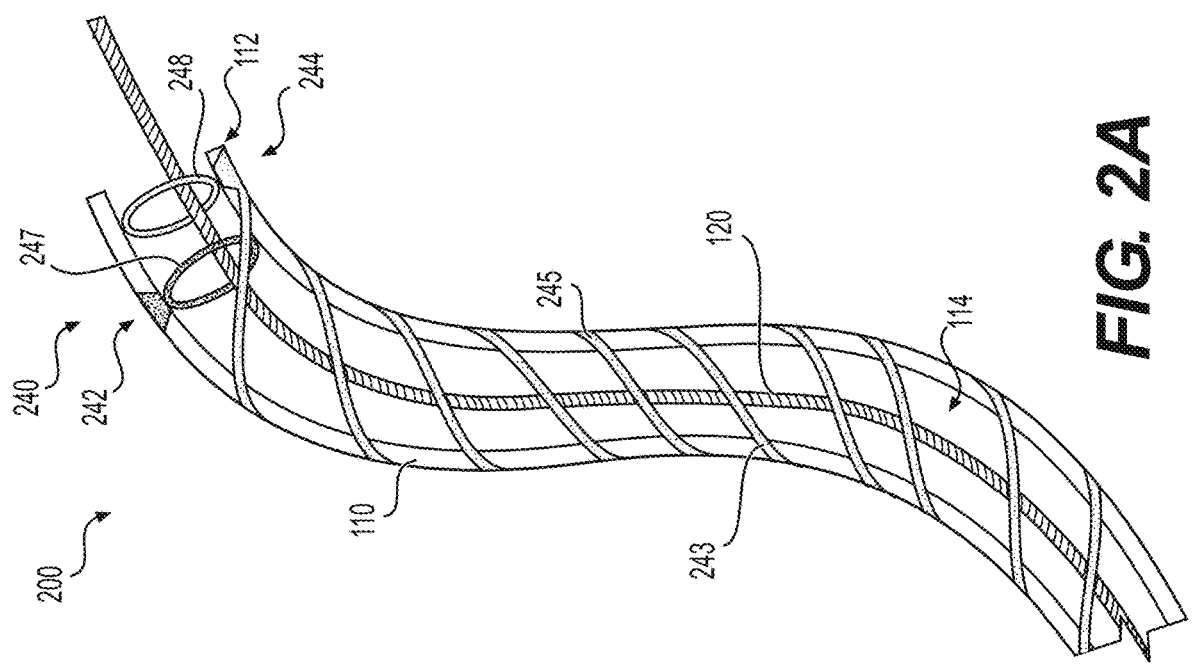

FIGS. 2A and 2B illustrate another exemplary system 200 for endovascular coil cutting. System 200 may include an active coil-cutting apparatus 240 (that is, a coil-cutting apparatus that may be activated by a user). In the example shown in FIGS. 2A and 2B, electrodes 242, 244 may include a conductive ring 247, 248, respectively. Rings 247, 248 may be constructed of the same material as wires 243, 245 (e.g., copper) or, alternatively, rings 247, 248 may be constructed of any suitable conductive material such as copper or beryllium copper, which may be gold-coated. In an inactivated state depicted in FIG. 2A, rings 247, 248 may be held out of contact with coil 120. The coil-cutting apparatus 240 may be activated via the controller and current may be delivered to electrodes 242, 244 via wires 243, 245, respectively. Rings 247, 248 may be actuated (e.g., mechanically, electrically, hydraulically or other means of actuation) to move into contact with coil 120; this is shown in the activated state of FIG. 2B. When the rings 247, 248 are in electrical contact with coil 120 in the activated state, the rings may deliver electrical current to the coil and locally cut the coil, thus detaching the distal coil segment 122.

Figure 3:
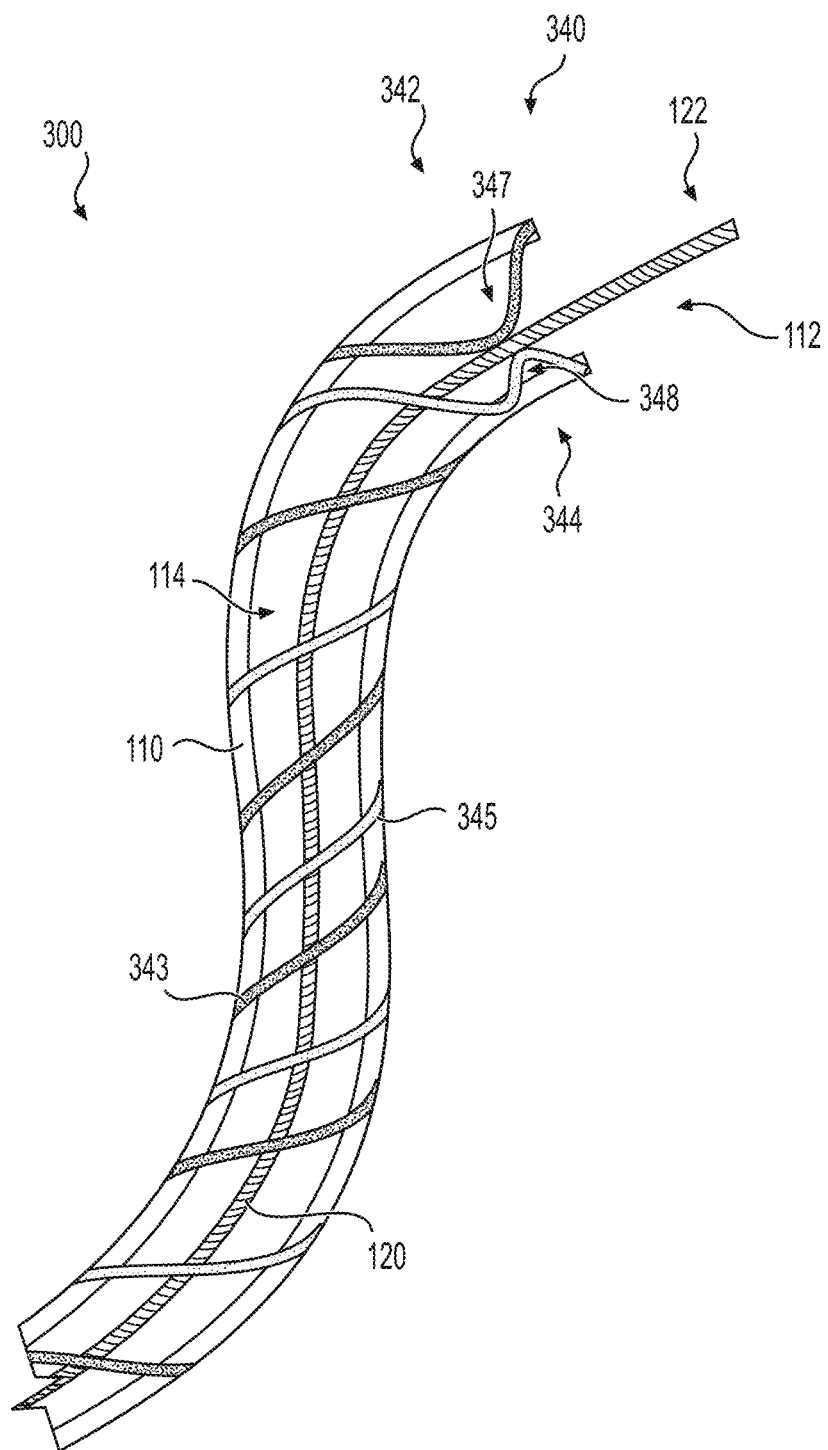
FIG. 3 illustrates a system for severing an endovascular coil, consistent with disclosed embodiments.

FIG. 3 illustrates another exemplary system 300 for endovascular coil cutting having a passive coil-cutting apparatus 340. At the microcatheter distal end 112, coil-cutting apparatus 340 may include electrodes 342, 344 that may bulge into the microcatheter lumen 114 from opposite sides to form passive elements 347, 348 configured, for example, as leaf springs. Passive elements 347, 348 may be biased toward the center of microcatheter 110, such that electrodes 342, 344 may remain in contact with coil 120 even while the coil is moved distally or proximally. When an electrical current pulse is received from the power source and delivered to electrodes 342, 344 via wires 343, 345, respectively, passive elements 347, 348 may pass the current through coil section 124 to sever the coil. As a result, the distal segment 122 of the coil may be detached from microcatheter 110 and from the remainder of the coil 120.

FIG. 4 illustrates another exemplary system 400 for endovascular coil cutting having a passive coil-cutting apparatus 440. Coil-cutting apparatus 440 may include electrodes 442, 444, which may be spaced apart axially along microcatheter 110. Electric current may be delivered to electrodes 442, 444 via wires 443, 445, respectively. In some embodiments, electrodes 442, 444 may include passive elements 447, 448 configured, for example, as leaf springs or elastic fingers. Passive elements 447, 448 may be biased into the microcatheter lumen 114 so that electrodes 442, 444 maintain electrical contact with coil 120. In the example of FIG. 4, electrode 442 may include a plurality of passive elements 447 spaced apart circumferentially, each of which may be biased inwards to contact coil 120. Similarly, electrode 444 may include a plurality of passive elements 448 spaced apart circumferentially, each of which may be biased inwards to contact coil 120. Advantageously, the presence of multiple passive elements on each electrode maximizes the likelihood that electrical contact is maintained between electrodes 442, 444 and coil 120, even when the coil is moved relative to microcatheter 110.

Figure 5A:
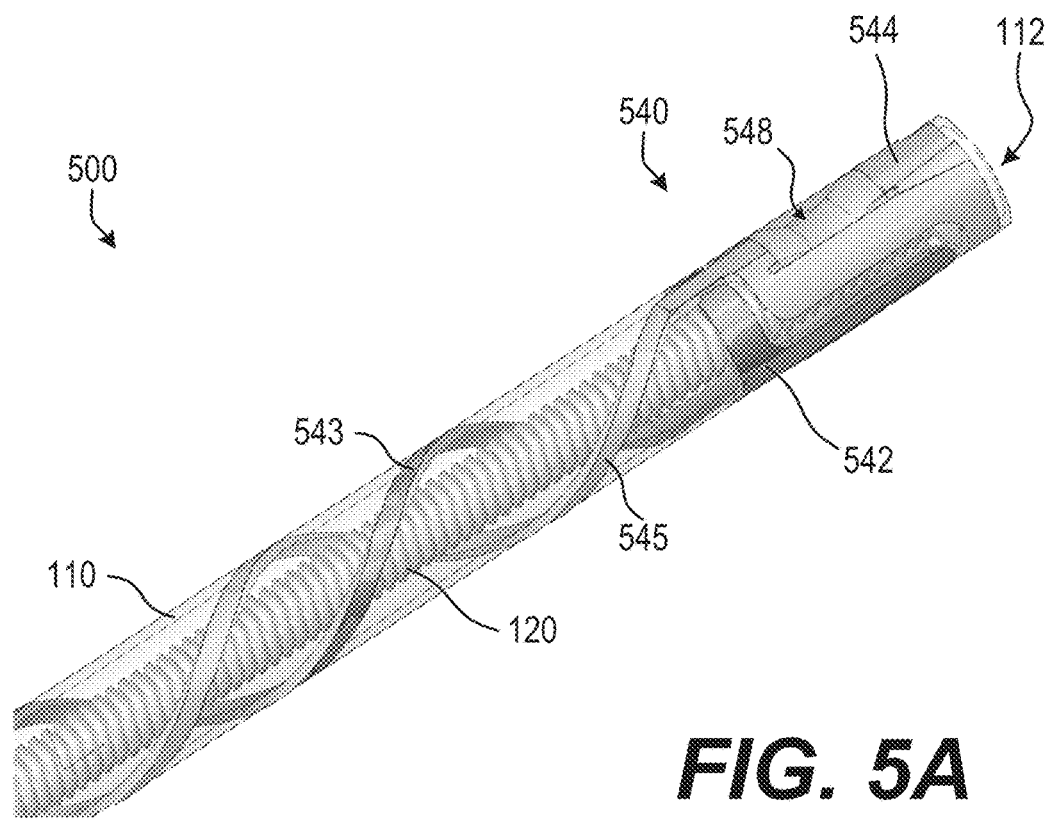
FIG. 5A illustrates a system for severing an endovascular coil, consistent with disclosed embodiments.
Figure 5B:
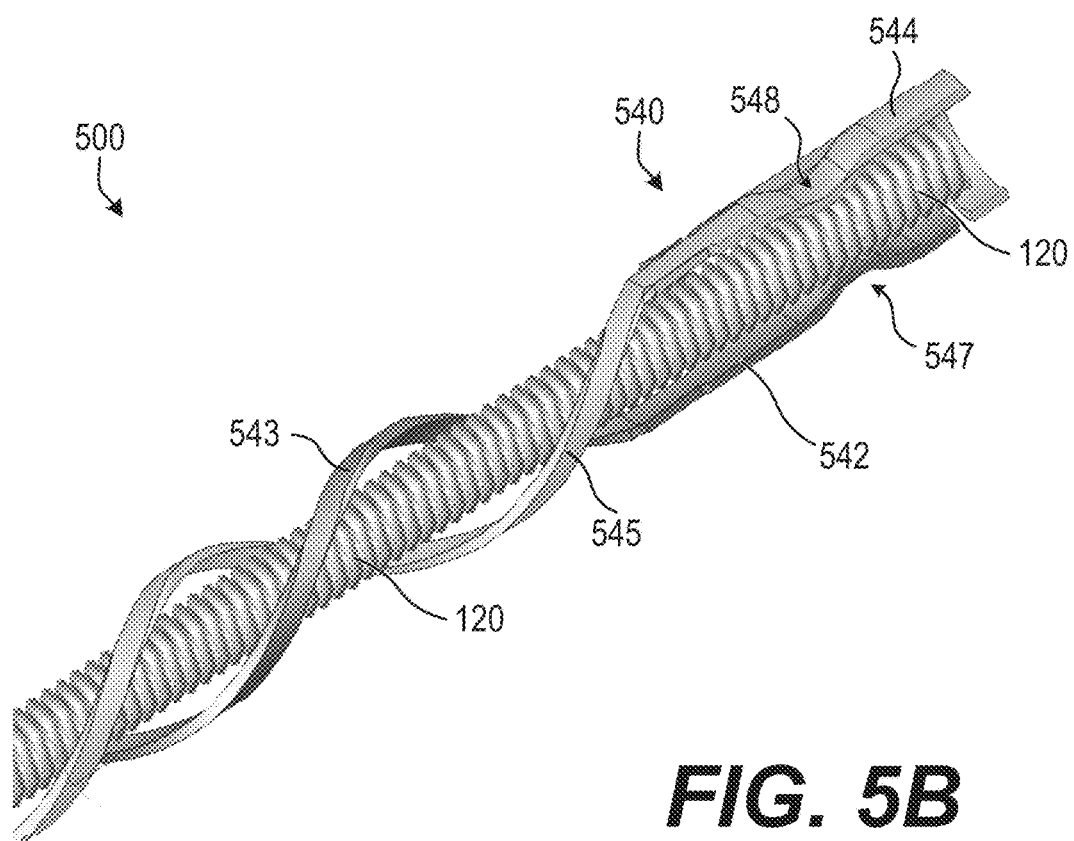
FIG. 5B illustrates the system of FIG. 5A without the microcatheter, consistent with disclosed embodiments.

FIG. 5A illustrates another exemplary system 500 for endovascular coil cutting having a passive coil-cutting apparatus 540. For purposes of illustration, FIG. 5B depicts system 500 and coil-cutting apparatus 540 without microcatheter 110, with a cross-sectional view of electrodes 542, 544 and a perspective view of wires 543, 545. Coil-cutting apparatus 540 may include electrodes 542, 544 having passive elements 547, 548, respectively, which may be biased inwards from opposite sides of the microcatheter. Due to the spring-like configuration of passive elements 547, 548, electrical contact may be maintained between the electrodes and coil 120.

Figure 6:
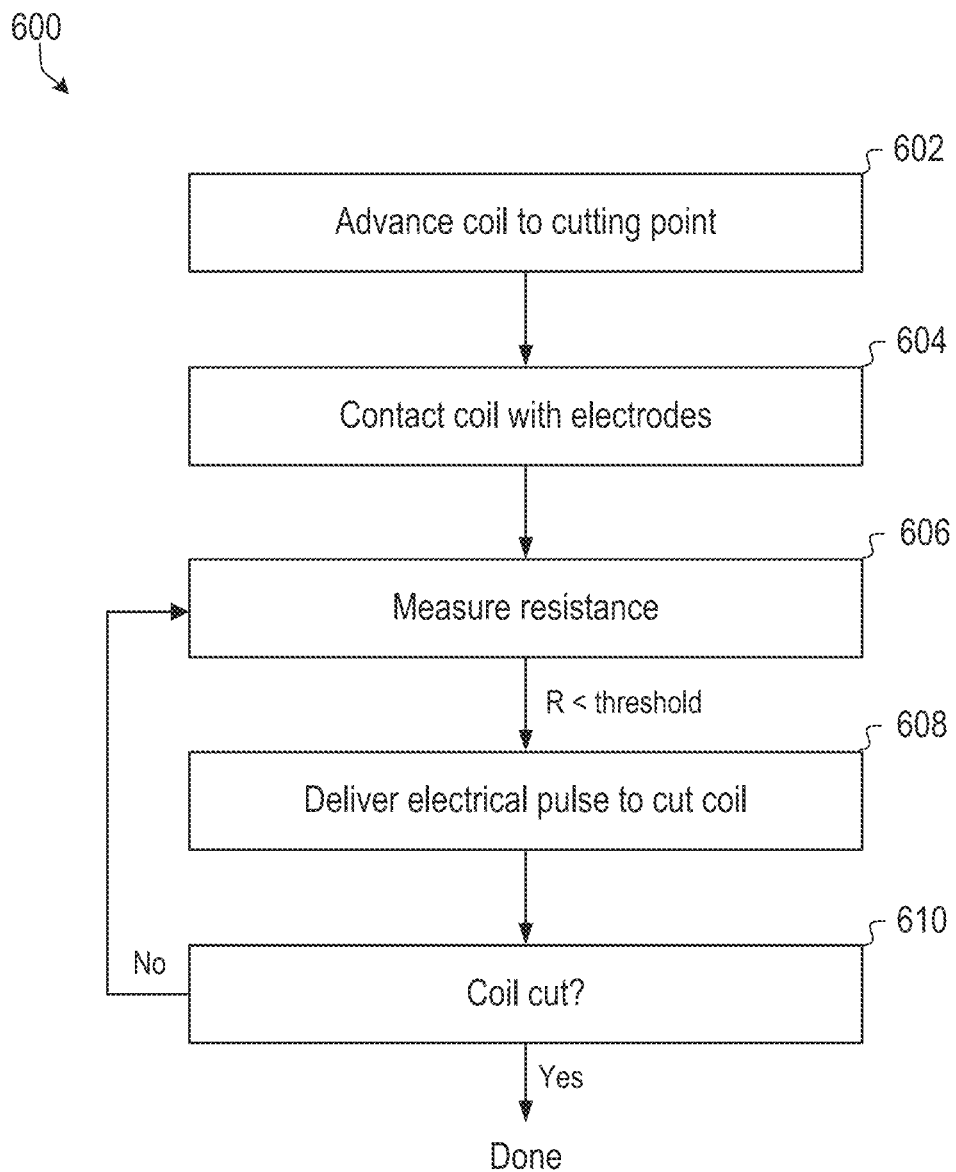
FIG. 6 depicts a flowchart illustrating a method of delivering and severing an endovascular coil, consistent with disclosed embodiments.

FIG. 6 illustrates an exemplary method 600 of delivering and cutting an endovascular coil. The exemplary steps of method 600 are described herein with reference to system 100; however, one of ordinary skill will understand that method 600 may additionally or alternatively be performed using any other system or device disclosed herein (including, and not limited to, systems 200, 300, 400, and 500).

In step 602, coil 120 may be advanced distally relative to microcatheter 110 until a desired length of distal coil segment 122 extends from the distal end 112 of the microcatheter. When distal coil segment 122 has the desired length, coil segment 124 (referred to hereafter as the cutting point) may be situated at the coil-cutting apparatus; in the example of FIG. 1, coil segment 124 is situated between the bulges of electrodes 142, 144.

In step 604, the electrodes of the coil-cutting apparatus may be brought into contact with coil 120. Step 604 may not be necessary for embodiments having a passive coil-cutting apparatus (in which the electrodes maintain contact with the coil even in the absence of user activation). However, for embodiments having an active coil-cutting apparatus, the user may take the requisite activation step (e.g., pressing a button on the controller) to bring the electrodes into electrical contact with coil 120.

In step 606, the controller may measure the electrical resistance at the coil-cutting apparatus to confirm proper contact between the electrodes and coil. Contact may be confirmed when the electrical resistance is determined to be below a threshold (e.g., below 10Ω). In some implementations, the medium between the electrodes may have a relatively high electrical resistance. Thus, when proper contact is established between the electrodes and the coil, the resistance will decrease significantly due to the much lower electrical resistance of the coil material. The decreased resistance results in a sufficiently high electrical current for cutting the coil.

When contact is confirmed, the controller may cause the power source to generate an electrical pulse at step 608 to cut the coil. In some implementations, the electrical pulse may have current between 1.0 and 4.0 A at a voltage of 36 v. The electrical pulse may have a short current pulse duration (e.g., between one and two seconds) to mitigate the heating risk to the patient and to avoid damaging the microcatheter.

In step 610, the controller may re-measure the electrical resistance at the coil-cutting apparatus to determine whether the coil was completely severed. For example, the controller may determine if the resistance has increased, indicating that the coil has been completely severed. If the cut is confirmed ("yes" at step 610), the cutting process is completed. If the cut is not confirmed ("no" at step 610), method 600 may return to step 606 and repeat the steps until the cutting of the coil is confirmed at step 610.

Example 1

A calculation of the electrical parameters for an exemplary system disclosed herein is provided below. This calculation demonstrates concept feasibility.

$$R = \rho \frac{l}{A} \quad \text{(Equation 1)}$$

In which "R" corresponds to electrical resistance [Ω], "ρ" corresponds to electrical resistivity [Ω*m], "l" corresponds to length [m], and "A" corresponds to cross-sectional area [mm²].

$$I = \frac{V}{R} \quad \text{(Equation 2)}$$

In which "I" corresponds to current [A], "R" corresponds to electrical resistance [Ω], and "V" corresponds to voltage [V].

In one implementation, the coil-cutting apparatus may require:
maximum overall allowed resistance: R≤10[Ω];
maximum allowed voltage: V≤36[V]; and
minimum cutting current: 1[A]≤I≤4[A].

Here, overall resistance may include the resistance of the electrode wires and the resistance of the coil contact points.

An example of parameters for an exemplary system for cutting an implantable coil, such as an aneurysm coil, may include:
Microcatheter length: l=1.5 [m];
Electrode wire resistivity: copper resistivity ρ=1.71*10⁻⁸ [Ω*m] (20° C.);
Electrode wire diameter: d=70 μm; and
Electrode wire cross-sectional area: A=π*(35* 10⁻⁶)²=3.848*10⁻⁹[m²].

These parameters of the exemplary system may be used in Equations 1 and 2 as follows:

$$R = \rho \frac{l}{A} = 1.71 * 10^{-8} * \frac{3}{3.848 * 10^{-9}} = 13.2[\Omega]$$

$$I = \frac{V}{R} = \frac{36}{13.2} = 2.72[A] \geq \text{minimum requirement}$$

The determined current value of 2.72 A is greater than the minimum current 1.0 A required to sever an endovascular coil having the dimensions discussed above. Thus, the disclosed system is an effective means for controlled cutting of the coil.

Figure 7A:
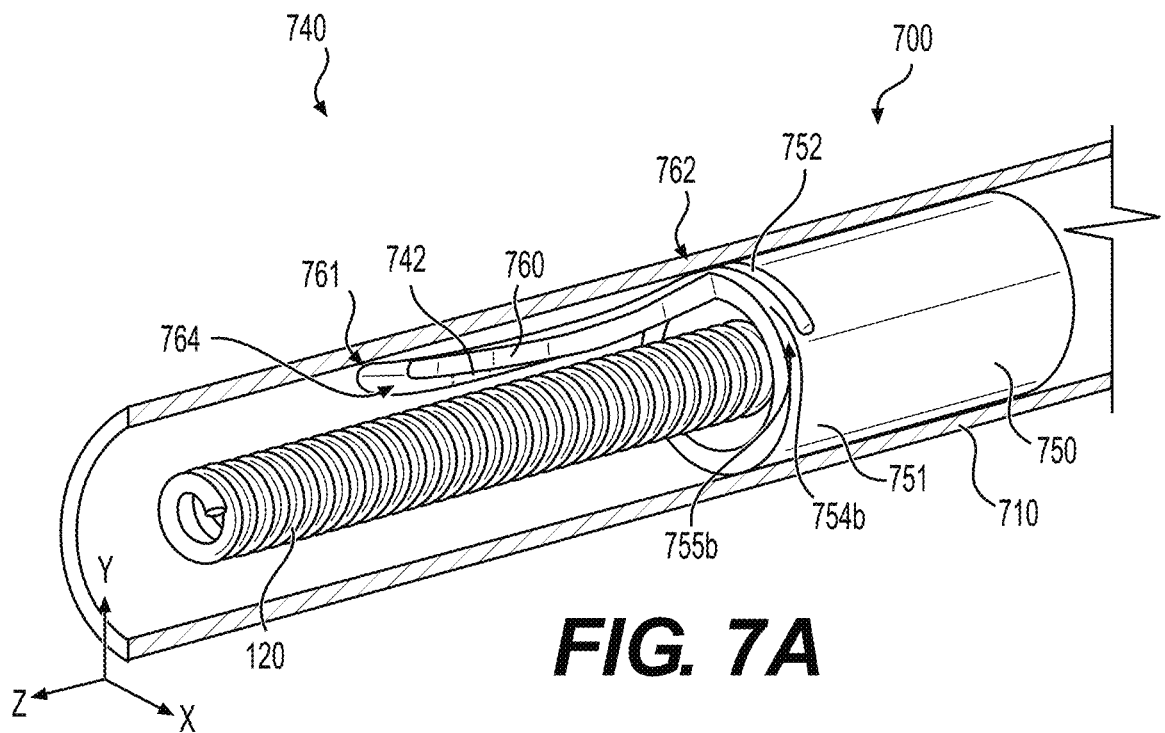
FIG. 7A illustrates an apparatus for severing an endovascular coil having a spring beam in a rest position, consistent with disclosed embodiments.
Figure 7B:
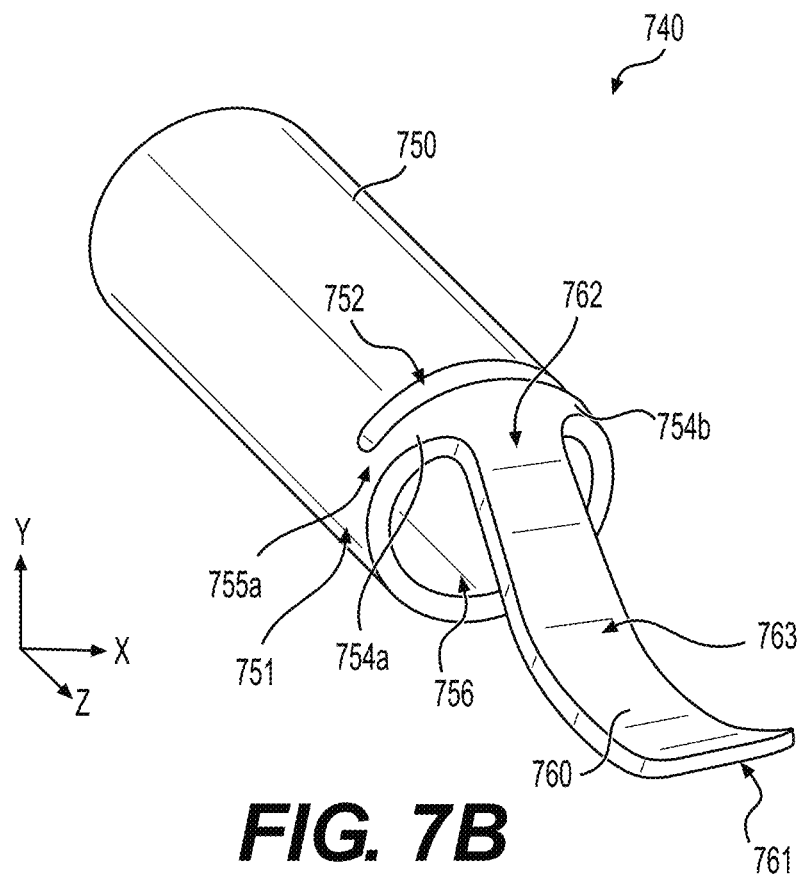
FIG. 7B depicts a front, top perspective view of the apparatus of FIG. 7A, consistent with disclosed embodiments.
Figure 8A:
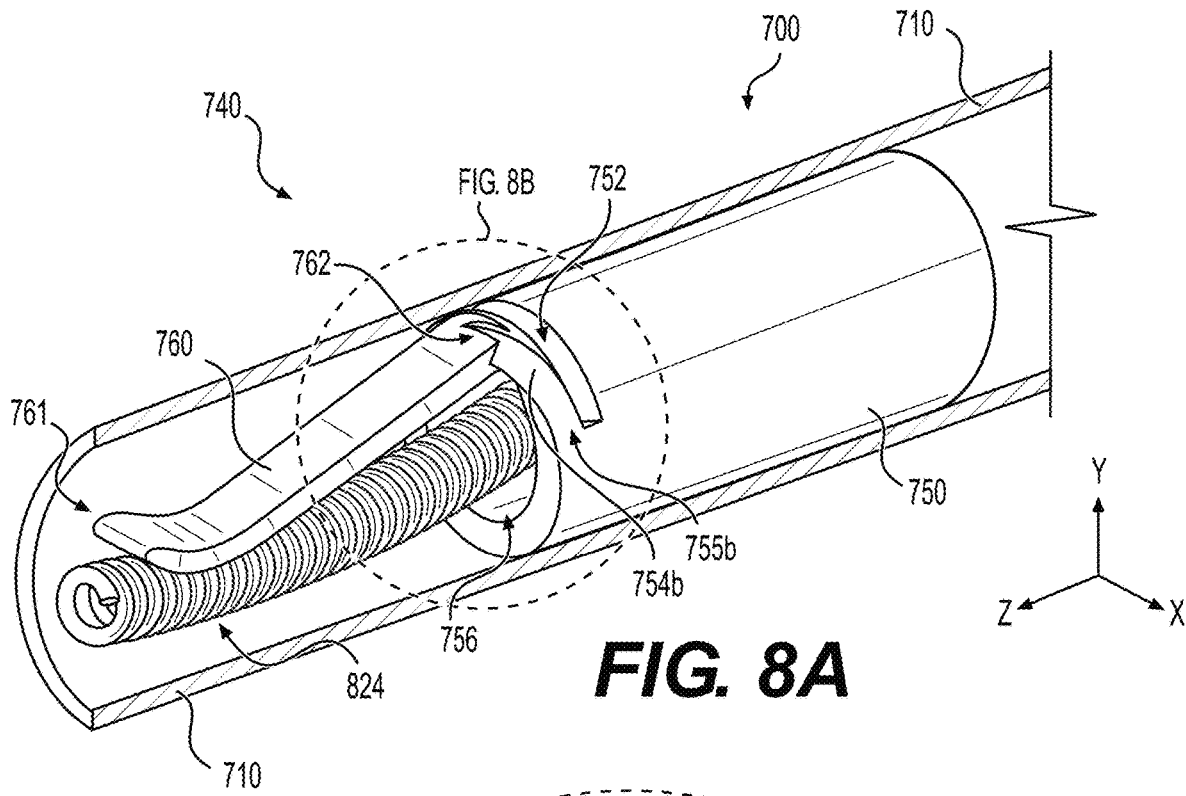
FIG. 8A illustrates the apparatus of FIG. 7A with the spring beam in an active position, consistent with disclosed embodiments.
Figure 8B:
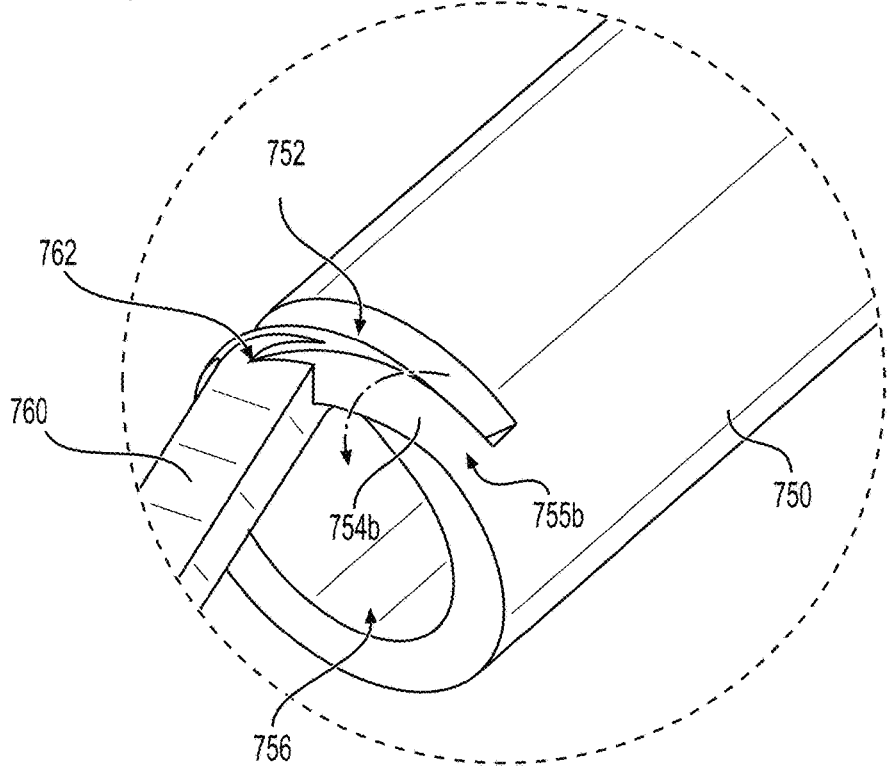
FIG. 8B illustrates an enlarged view of the apparatus of FIG. 8A, consistent with disclosed embodiments.

FIGS. 7A-8B illustrate an exemplary system 700 for delivering and cutting an endovascular coil 120, such as a coil for treatment of an aneurysm. System 700 may include a microcatheter 710 and a coil-cutting apparatus 740 situated partially or entirely within the distal portion of microcatheter 710. (Solely for illustrative purposes, microcatheter 710 is depicted in a cross-sectional view in FIGS. 7A and 8A.) FIGS. 7A and 7B depict coil-cutting apparatus 740 having a spring beam 760 in an exemplary rest position and FIGS. 8A and 8B depict coil-cutting apparatus 740 having a spring beam 760 in an exemplary active position, as discussed in detail below.

Microcatheter 710 may have a similar configuration as microcatheter 110 described above and may be configured for delivery of a therapeutic device, such as coil 120, to a treatment site. Coil-cutting apparatus 740 may be situated within and connected to the inner lumen of microcatheter 710, at or near the distal end of microcatheter 710. In some embodiments, coil-cutting apparatus 740 may be arranged relative to microcatheter 110 such that the distal-most portion of coil-cutting apparatus 740 (i.e., spring beam distal end 761, as discussed below) is even or substantially even with the distal-most end of microcatheter 710. In some alternative embodiments, spring beam distal end 761 may be located in a proximal direction from the distal-most end of microcatheter 710, so as to provide clearance between coil-cutting apparatus 740 and the distal end of the microcatheter.

Coil-cutting apparatus 740 may include a cylindrical base 750 having at least one inner lumen 756. Cylindrical base 750 may have an annular or elliptical cross-sectional shape and may be configured to receive coil 120 within the inner lumen 756. In some embodiments, cylindrical base 750 may have an inner diameter (i.e., the diameter of inner lumen 756) of between approximately 0.38 mm and 0.40 mm. For example, cylindrical base 750 may have an inner diameter of 0.38 mm, 0.39 mm, or 0.40 mm. Additionally, or alternatively, cylindrical base 750 may have an outer diameter of between approximately 0.45 mm and 0.50 mm. For example, cylindrical base 750 may have an outer diameter of 0.45 mm, 0.46 mm, 0.47 mm., 0.48 mm, 0.49 mm, or 0.50 mm. In some embodiments, the outer surface of cylindrical base 750 may be directly connected to the inner wall of microcatheter 710 by adhesive, welding, soldering, or other suitable techniques.

In some embodiments, a slit 752 may be formed near the distal end of cylindrical base 750. Slit 752 may extend through the side wall of cylindrical base 750, passing between inner and outer surfaces of cylindrical base 750. For example, slit 752 may be formed in cylindrical base 750, such as by laser cutting or photochemical etching. In some embodiments, slit 752 may have a length within the range of 0.05 mm to 0.2 mm in the Z-direction of FIG. 7A. For example, slit 752 may have a relatively short length in the Z-direction so that torque poles 754a, 754b may be formed (as discussed in detail below) without comprising the structural integrity of cylindrical base 750. Additionally, or alternatively, slit 752 may be situated a distance within the range of 0.05 mm to 0.3 mm from the distal end of cylindrical base 750, relative to the Z-direction. Slit 752 may extend along a portion of the circumference of cylindrical base 750, such that the slit 752 does not extend into section 751 of the cylindrical base 750. For example, slit 752 may have an arc length within the range of 110° to 130° about the circumference of cylindrical base 750.

As shown in FIG. 7B, cylindrical base 750 may include torque poles 754a, 754b extending longitudinally between slit 752 and the distal end of the cylindrical base. Torque poles 754a and 754b may form a continuous, arc-shaped structure adjacent to slit 752 that is connected to the remainder of the cylindrical base 750 at connection points 755a and 755b. That is, torque poles 754a, 754b may extend in a circumferential direction along the distal end of cylindrical base 750, adjacent to slit 752.

Coil-cutting apparatus 740 may also include an elongated spring beam 760 extending in a distal direction from the distal end of cylindrical base 750. Thus, the distal end 761 of spring beam 760 may be situated distally from the distal end of cylindrical base 750. Proximal end 762 of spring beam 760 may be connected to torque poles 754a, 754b, which may form the connection between spring beam 760 and cylindrical base 750. In some embodiments, outer surface 763 of the spring beam may be even with the outer surface of cylindrical base 750 (i.e., the outer surface of torque poles 754a, 754b). Additionally, or alternatively, outer surface 763 may be rounded with a curvature that is equal to (or substantially similar to) the curvature of the outer surface of cylindrical body 750. Advantageously, this configuration may prevent the formation of sharp edges on the intersection between cylindrical base 750 and spring beam 760 that may be harmful to the patient. In some embodiments, spring beam 760 may have a length within the range of 1.0 mm to 2.0 mm in the Z-direction and a width within the range of 0.1 mm to 0.3 mm in the X-direction. For example, the width of spring beam 760 in the X-direction may be smaller than the inner diameter of cylindrical base 750.

As shown in FIG. 7A, the inner, coil-facing surface 764 of the spring beam 760 may include at least one coil-cutting electrode 742. When coil-facing surface 764 is pressed against coil 120, electrode 742 may apply electrical current to the coil in order to sever the section of the coil in contact with the electrode. As a result, the coil segment distal to electrode 742 may be detached from the remainder of the coil 120. In some embodiments, coil-cutting electrode 742 may simply be the portion of coil-facing surface 764 that contacts coil 120; the portion of coil-facing surface 764 at the location of electrode 742 may be configured as an electrode due to the high conductivity of spring beam 760 and cylindrical base 750. Additionally, or alternatively, one or more electrodes constructed of any suitable conductive material may be attached to spring beam 760 at the location 742. Advantageously, the placement of electrode 742 within microcatheter 710 prevents contact between the electrode and the patient's body.

Cylindrical base 750 (including torque poles 754a and 754b) and spring beam 760 may be constructed from a shape-memory alloy such as Nitinol. In some embodiments, spring beam 760 may be curved or arc-shaped so as to form a convex shape relative to inner lumen 756 of the cylindrical base (i.e., the proximal and distal ends of the spring beam may point away from inner lumen 756). For example, spring beam 760 may be shape-set in the curved or arc-shaped configuration. Electrode 742 may be situated in the middle of spring beam 760, at the apex of the curve or arc. Advantageously, the spring beam distal end 761 may be situated above (relative to the vertical Y-direction) the apex of the curved spring beam 760 in the configuration shown in FIGS. 7A and 7B, minimizing the likelihood of the spring beam 760 interfering with movement of coil 120 through apparatus 740. In some alternative embodiments, the spring beam 760 may have any other suitable shape.

Spring beam 760 may be configured to move, relative to cylindrical base 750 and microcatheter 710, between an active position and a rest position. In the active position, an example of which is depicted in FIG. 8A, spring beam 760 may press its distal end 761 inwards toward inner lumen 756. In some embodiments, arrangement of the spring beam in the active position may be achieved due to the shape-setting of torque poles 754a, 754b to be twisted in a direction towards the inner lumen of the cylindrical base (i.e., in a "twisted configuration"). For example, as shown in FIG. 8B, torque poles 754a, 754b are twisted towards inner lumen 756 (i.e., in a counterclockwise direction), while torque pole connection points 755a, 755b and the remainder of cylindrical base 750 remain stationary. Because torque poles 754a, 754b are shape-set in a twisted configuration, the torque poles apply a torque to spring beam 760 and, as a result, press spring beam distal end 761 inward towards the inner lumen 756. As a result, when a coil 120 extends from the distal end of cylindrical base 750 (such as in FIG. 8A), spring beam 760 may press electrode 742 firmly against portion 824 of the coil. When electrical current is applied to cylindrical base 750, electrode 742 may apply the electrical current to coil 120 and sever coil portion 824 that is in contact with electrode 742. As a result, the segment of the coil that is distal to portion 824 may be separated from the remainder of the coil.

In the rest position, an example of which is depicted in FIG. 7A, the application of torque on spring beam 760 by torque poles 754a, 754b may be reduced. In some embodiments, and as discussed in detail below, the reduction in torque may occur due to a phase change of cylindrical base 750 that increases the pliability and elasticity of torque poles 754a, 754b. As a result, the force pressing electrode 742 against coil 120 may be minimized. In some embodiments, spring beam 760 may maintain light contact with spring beam 760 in the rest position, such that electrode 742 is not firmly pressed against coil 120. Alternatively, spring beam 760 may be moved away from coil 120 such that electrode 742 is held out of contact with coil 120. As a result, apparatus 740 and the rest of microcatheter 710 may freely move in an axial or longitudinal direction relative to coil 120 (and vice versa) while spring beam 760 is in the rest position, since the forceful contact between spring beam 760 and coil 120 (which may impede axial advancement of apparatus 740) is minimized or completely removed. Similarly, microcatheter 710 and apparatus 740 may be advanced over a guidewire to a treatment site while spring beam 760 is in the rest position, since spring beam 760 in the rest position does not interfere with the guidewire or the axial advancement of microcatheter 710.

As discussed above, coil-cutting apparatus 740 may be constructed from Nitinol and/or another shape-memory alloy, which exhibits two distinct phases: the martensite phase at lower temperatures, in which the alloy may be easily twisted or deformed, and the austenite phase at higher temperatures, in which the alloy returns to a pre-formed or "remembered" shape and becomes stiffer and more resistant to deformation. In some embodiments, coil-cutting apparatus 740 may be shape-set with torque poles 754a, 754b in a twisted configuration (e.g., the configuration depicted in FIG. 8B) and spring beam 760 in the active position. As a result, apparatus 740 may be in a "soft" or relaxed state at low temperatures, allowing spring beam 760 to be moved to the rest position so that a guidewire or coil 120 may be freely moved through microcatheter 710 and cylindrical base 750. When a predetermined transformation temperature (e.g., austenite finish temperature) is reached, torque poles 754a, 754b may move to the shape-set twisted configuration, moving spring beam 760 into the active position and pressing electrode 742 against coil 120. Electrode 742 may then apply current to coil 120 in order to sever the coil at coil portion 824. Further, since electrode 742 is retained within microcatheter 710, the patient's body is protected from inadvertent current application.

In some embodiments, the transformation temperature of coil-cutting apparatus 740 (e.g., the austenite finish temperature) may be set to a temperature above body temperature. For example, the transformation temperature may be within the range of 42° C. to 52° C. Apparatus 740 may be more elastic and pliable in the "soft" or relaxed state below the transformation temperature. For example, apparatus 740 may have a Young's modulus of approximately 25 GPa in some embodiments of the relaxed state. In the relaxed state, torque poles 754a, 754b may be untwisted (i.e., twisted away from inner lumen 756) such that the spring beam 760 may be held in the rest position. Because the transformation temperature is above body temperature, spring beam 760 may remain in the rest position while microcatheter 710 is delivered into the body and advanced to the desired treatment site.

When a user desires to move spring beam 760 to the active position (e.g., to cut a treatment coil 120), a power source may be activated to apply electric current to cylindrical base 750 (e.g., via one or more wires connected to cylindrical base 750 and/or spring beam 760). The supplied current heats the Nitinol of apparatus 740 to a temperature above the transformation temperature, causing apparatus 740 to move to the pre-set shape in which spring beam 760 is held in the active position. When a coil 120 extends from the distal end of cylindrical base 750, electrode 742 is firmly pressed against coil 120 and applies current to the coil, severing the coil at the coil section 824 which is in contact with electrode 742. Apparatus 740, including spring beam 760 and torque poles 754a, 754b, may become increasingly stiff in the active state above the transformation temperature (e.g., apparatus 740 may have a Young's modulus of approximately 65 GPa in some embodiments of the active state). In a manner similar to a leaf spring, spring beam 760 may press electrode 742 against a coil 120 extending from cylindrical base 750. As a result, stable contact may be maintained between electrode 742 and coil 120 due to the stiffness of apparatus 740 in the active state, providing a good electrical connection for cutting the coil 120 with apparatus 740.

Advantageously, coil-cutting apparatus 740 is configured to accommodate and cut endovascular coils of different sizes. The outer diameter of endovascular coils typically used for aneurysm coiling come in a variety of sizes and range in diameter from 0.25 mm to 0.37 mm. Coils of different sizes are frequently used during a single operation. Since the inner diameter of cylindrical base 750 is larger than the outer diameter of the largest sized coil used in the field (i.e., 0.37 mm), endovascular coils of any size may be delivered through system 700 to a treatment site. Further, since the forceful contact between spring beam 760 and the coil is removed when in the rest position, the coil may pass through coil-cutting apparatus 740 without interference from the spring beam distal end 761 or any other part of the spring beam 760. When electric current is applied to apparatus 740 to cut the coil, spring beam 760 is shape-set to move inward until electrode 742 contacts the coil and applies current to the coil. Thus, apparatus 740 is configured to cut endovascular coils of any size, since spring beam 760 is shape-set to contact even coils having the smallest diameter (i.e., 0.25 mm coils). As a result, system 700 may be used for the delivery of coils having any diameter, or alternatively, for the delivery of coils of multiple sizes during a single operation.

FIGS. 9A-9D depict an exemplary method of delivering and cutting an endovascular coil 120 with an exemplary coil-cutting apparatus described herein. Although FIGS. 9A-9D depict the use of system 700 to deliver and cut coil 120, any exemplary coil-cutting system and apparatus disclosed herein may be used for the delivery and cutting of an endovascular coil according to the method depicted in FIGS. 9A-9D.

Figure 9A:
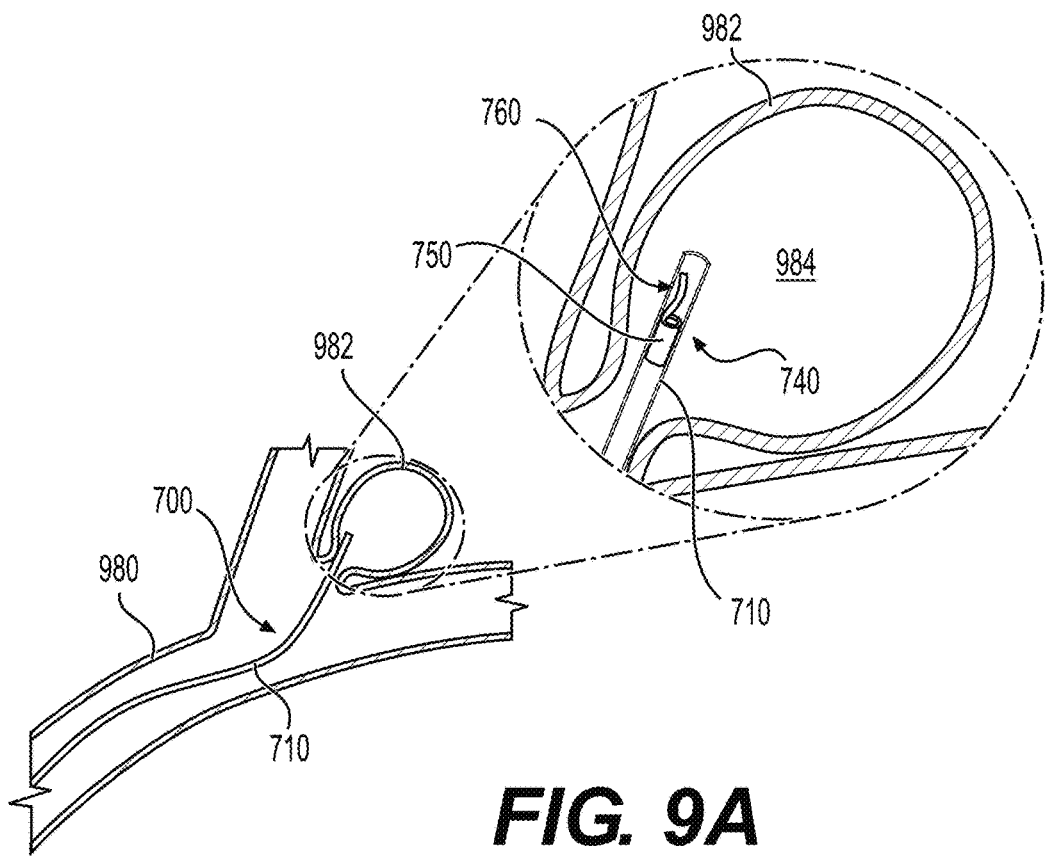
FIGS. 9A-9D illustrate a method of delivering and severing an endovascular coil, consistent with disclosed embodiments.
Figure 9B:
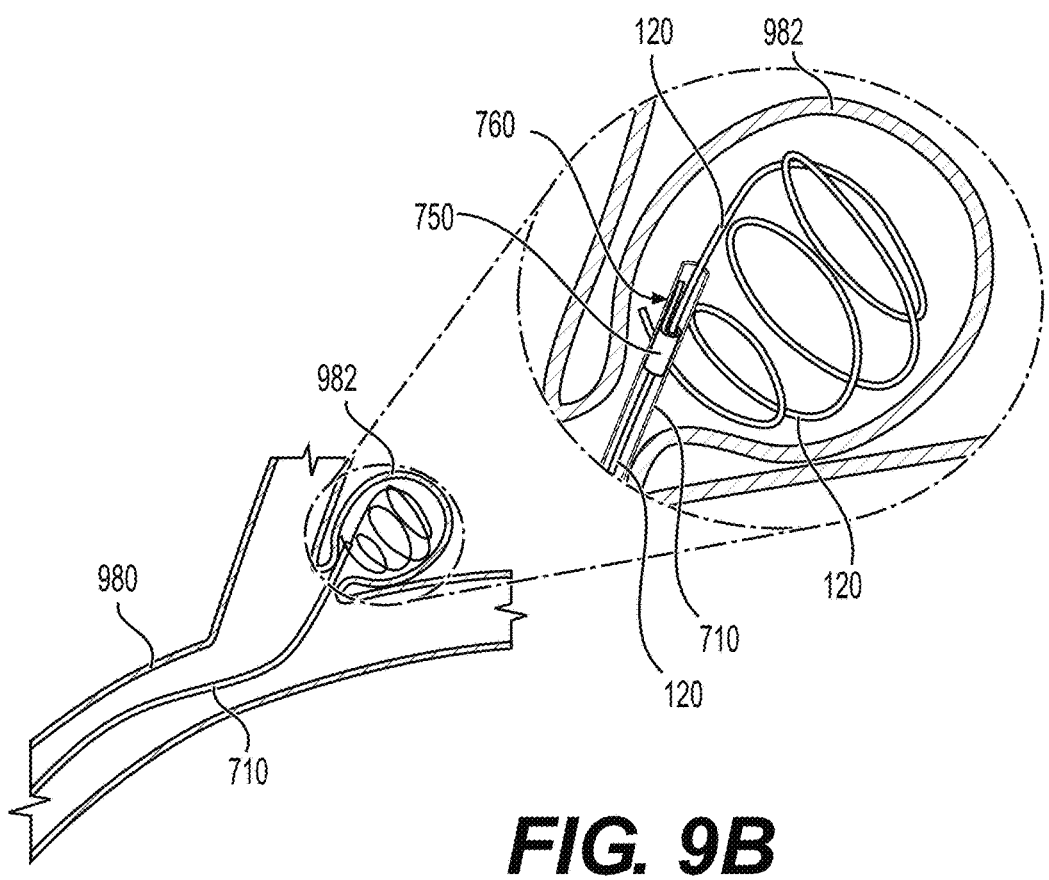
Figure 9C:
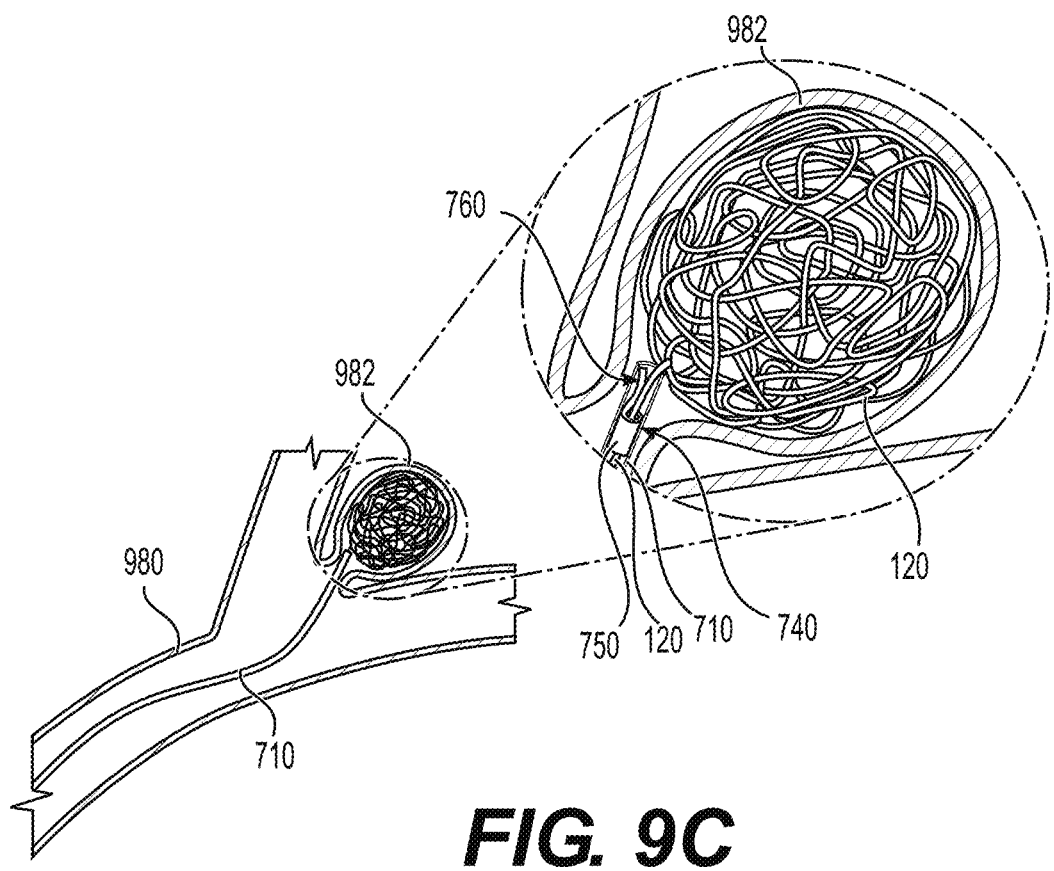

In FIG. 9A, microcatheter 710 with coil-cutting apparatus 740 at its distal end is advanced (e.g., over a guidewire) through a blood vessel 980 to a treatment site, such as aneurysm 982. During delivery of the microcatheter, spring beam 760 of the coil-cutting apparatus may be held in the rest position to avoid interference with the guidewire. In FIG. 9B, once apparatus 740 is positioned in the aneurysm interior 984, an endovascular coil 120 of a desired size is advanced from system 700 into the aneurysm to fill it. Spring beam 760 of the coil-cutting apparatus may continue to be held in the rest position so that the spring beam 760 does not interfere with the axial movement of the coil 120.

Figure 9D:
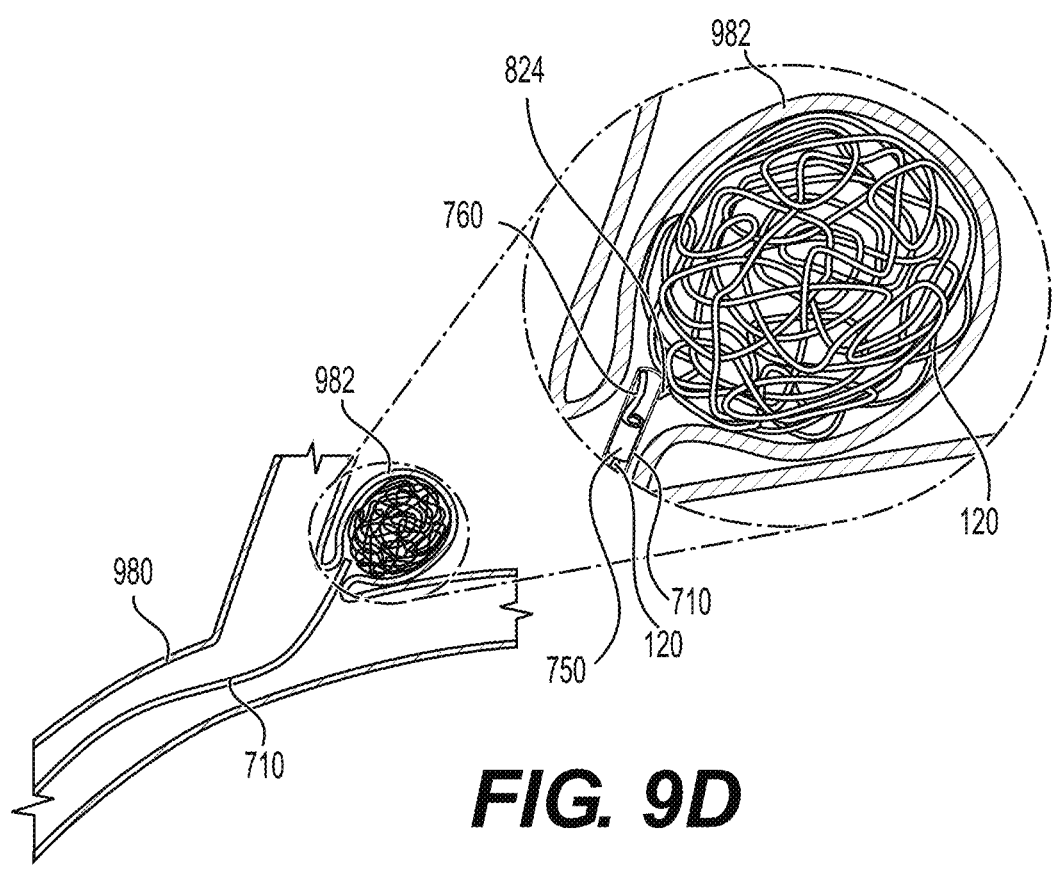

When a desired length of coil 120 has been delivered into aneurysm 982 (FIG. 9C), the power source of system 700 may be activated to move spring beam 760 to the active position, thus cutting the coil portion 824 in contact with electrode 742 (FIG. 9D). As a result, the section of coil 120 that is distal to portion 824 may remain within aneurysm 982 while the rest of the coil is removed. The coil advancement and cutting steps of FIGS. 9B-9D may be repeated as needed with coils of the same or different size until the aneurysm interior 984 is filled. Microcatheter 710 and coil-cutting apparatus 740 may then be removed from aneurysm 982 and vessel 980.

Figure 10B:
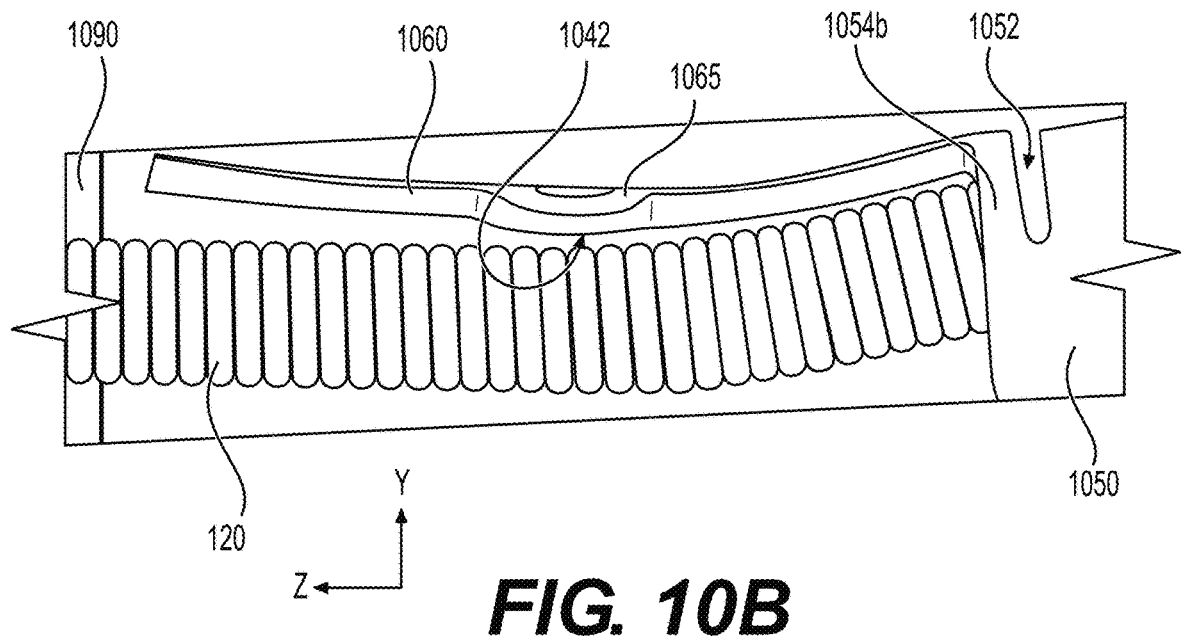
FIG. 10B illustrates the apparatus of FIG. 10A with the spring beam in a rest position, consistent with disclosed embodiments.
Figure 10C:
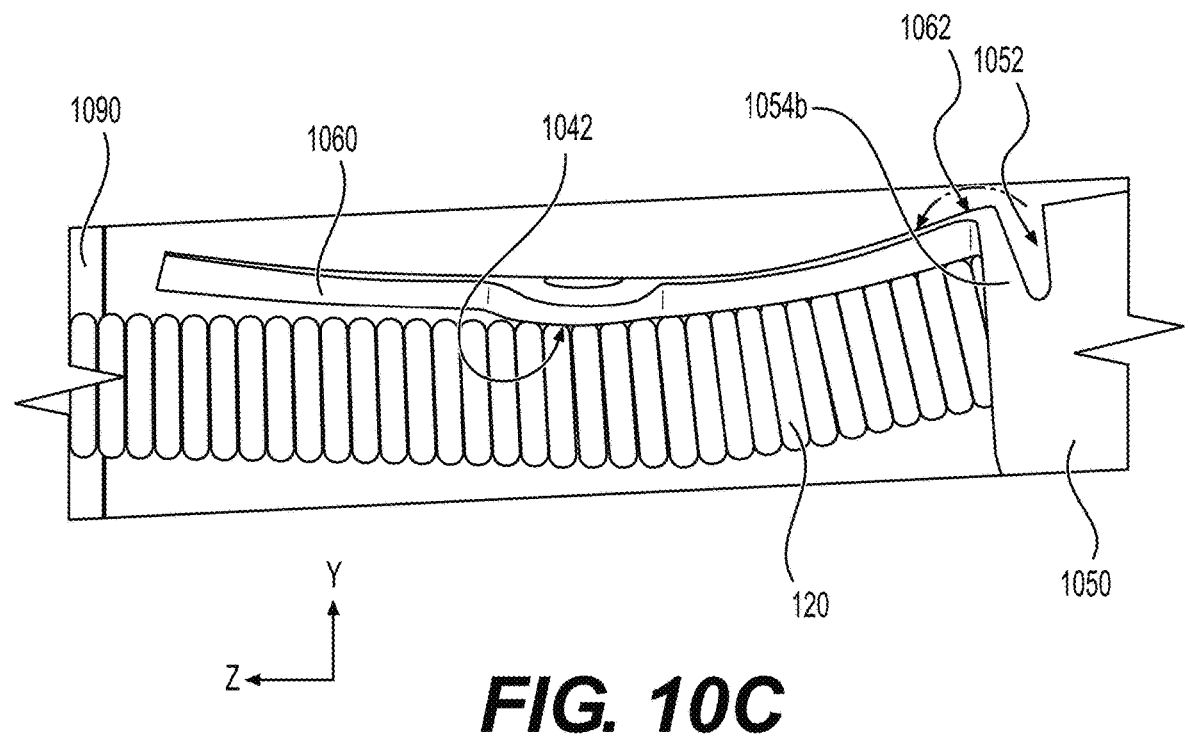
FIG. 10C illustrates the apparatus of FIG. 10A with the spring beam in an active position, consistent with disclosed embodiments.

FIGS. 10A-10C illustrate another exemplary system 1000 for delivering and cutting an endovascular coil, having a coil-cutting apparatus 1040 connected to the distal end of microcatheter 710. Coil-cutting apparatus 1040 may include a spring beam 1060 having a widened portion 1065 at the section of the spring beam 1060 containing electrode 1042. Widened portion 1065 may be situated in the middle of spring beam 1060 (along the longitudinal Z-direction); the spring beam 1060 may have a larger width at widened portion 1065 than at proximal end 1062 or distal end 1061.

FIG. 10B depicts coil-cutting apparatus 1040 with spring beam 1060 in a rest position, in which spring beam 1060 (including electrode 1042) is held away from coil 120. FIG. 10C depicts coil-cutting apparatus 1040 with spring beam 1060 in an active position. In some embodiments, spring beam 1060 may move into the active position when electrical current is applied to cylindrical base 750 (or any other suitable portion of coil-cutting apparatus 1040), heating cylindrical base 750 and causing torque poles 754a, 754b to move into their respective shape-set, twisted configuration (represented by the dot-dash rotational arrow in FIG. 10C). The torque pole twisting may cause spring beam proximal end 1062 to pivot away from the rest of cylindrical base 750 (thus widening slit 752), thus angling spring beam 1060 towards coil 120 until electrode 1042 contacts coil 120. Electrode 1042 may apply electrical current to coil 120 in order to sever the distal portion of coil 120 from the remainder of the coil 120.

Figure 11:
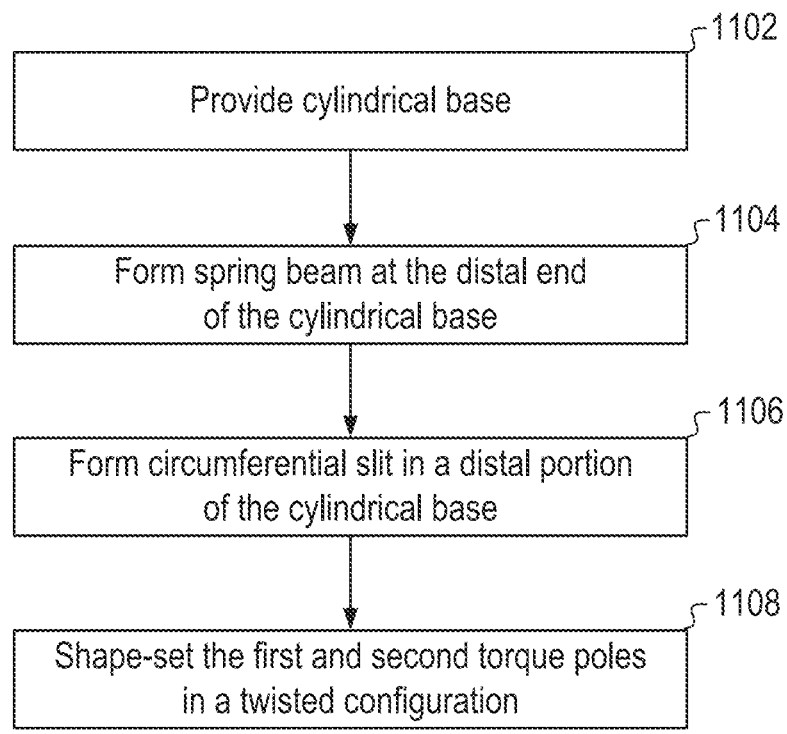
FIG. 11 depicts a flowchart illustrating a method of manufacturing an apparatus for severing an endovascular coil, consistent with disclosed embodiments.

FIG. 11 depicts an exemplary method of manufacturing an apparatus for cutting an endovascular coil. One of ordinary skill will understand that the method of manufacturing disclosed herein may be used to manufacture any suitable apparatus for cutting an endovascular coil, including and not limited to apparatus 740 and apparatus 1040.

In step 1102, the method of manufacturing may include providing a cylindrical base having a proximal end, a distal end, and at least one inner lumen. The cylindrical base may have an annular or elliptical cross-sectional shape and may be constructed at least partially of a shape-memory alloy such as Nitinol. In some embodiments, the cylindrical base may be shaped and configured for placement within, and connection to, the distal end of a microcatheter. Examples of a cylindrical base provided in step 1102 include cylindrical base 750 and cylindrical base 1050.

In step 1104, the method of manufacturing may include forming, at the distal end of the cylindrical base, an elongated spring beam extending from the distal end of the cylindrical base. The spring beam may be formed, such as by laser cutting from a tube constructed of a shape-memory alloy such as Nitinol. In some embodiments, the spring beam may be formed from the same tube as the cylindrical base, such that the spring beam and cylindrical base may be constructed as a single, unitary structure. In alternative embodiments, the spring beam and the cylindrical base may be constructed from separate tubes and connected via adhesive, welding, soldering, or other suitable techniques. Examples of an elongated spring beam formed in accordance with step 1104 include spring beam 760 and spring beam 1060.

In step 1106, the method of manufacturing may include forming a circumferential slit in a distal portion of the cylindrical base. The slit may be formed by laser cutting or other known techniques and may extend through the side wall of the cylindrical base, passing between inner and outer surfaces of the cylindrical base. In some embodiments, the slit may be situated a distance within the range of 0.1 mm to 0.3 mm from the distal end of the cylindrical base. Additionally, or alternatively, the slit may extend along a portion of the circumference of the cylindrical base, such that the slit does not extend into another portion of the cylindrical base. Examples of a circumferential slit formed in accordance with step 1106 include slit 752 and slit 1052.

In step 1106, formation of the circumferential slit may produce at least first and second torque poles connecting the spring beam to the cylindrical base. In some embodiments, the first and second torque poles may form a continuous, arc-shaped structure adjacent to the slit, with a proximal end of the elongated spring beam connected to the middle of the continuous, arc-shaped structure. The torque poles may be constructed from the same material as the cylindrical base (i.e., Nitinol or another shape-memory alloy). In some embodiments, the torque poles may be configured (due, at least in part, to their shape memory properties) to undergo a phase transformation at a predetermined transformation temperature, above which the torque poles may move into a pre-formed or "remembered" shape and become increasingly resistant to deformation. Examples of first and second torque poles formed in accordance with step 1106 include torque poles 754a and 754b, respectively, and torque poles 1054a and 1054b, respectively.

In step 1108, the method of manufacturing may include shape-setting the first and second torque poles in a twisted configuration. For example, according to embodiments in which the torque poles are constructed from Nitinol or another shape memory alloy, step 1108 may include shape-setting the torque poles in the twisted configuration such that the twisted configuration is the "remembered" shape of the torque poles. In some embodiments, the transformation temperature of the torque poles (above which the torque poles move into the "remembered" twisted configuration) may be set to a temperature above body temperature. For example, the transformation temperature of the torque poles may be within the range of 42° C. to 52° C. However, at temperatures below the transformation temperature, the first and second torque poles become more pliable and easily deformed. Thus, in some embodiments, the torque poles may be configured to assume a relaxed configuration at temperatures below the transformation temperature; in the relaxed configuration, the torque poles may be straightened relative to the twisted configuration (i.e., a degree of twisting of the torque poles may be reduced). Examples of the twisted configuration of step 1108 may include the torque pole configurations depicted in FIGS. 8A-8B and in FIG. 10C, while examples of the relaxed configuration may include the torque pole configurations depicted in FIGS. 7A-7B and in FIG. 10B.

In some embodiments, the torque poles may be shape-set to be twisted in a direction towards the inner lumen of the cylindrical base. For example, in the exemplary twisted configuration depicted in FIG. 8B, the middle portion of torque poles 754a, 754b (including the portion where the spring beam proximal end 762 is connected) may be twisted in rotational direction towards inner lumen 756, as represented by the dot-dash arrow in FIG. 8B; meanwhile, connection points 755a and 755b may remain fixed to cylindrical base 750. As a result, when the cylindrical base is heated to a temperature equal to or greater than the transformation temperature, e.g., due to the application of electric current, the torque poles may move into the "remembered" twisted configuration.

In some embodiments, the first and second torque poles may be configured to hold the spring beam in a first position when the first and second torque poles are in the twisted configuration. Examples of the first position may include the active positions depicted in FIGS. 8A-8B and 10B, in which the twisting of the torque poles moves the distal end of the spring beam inward towards the inner lumen of the cylindrical base. Additionally, or alternatively, the first and second torque poles may be configured to hold the spring beam in a second position, different from the first position, when the first and second torque poles are in the relaxed configuration. Examples of the second position may include the rest position depicted in FIGS. 7A-7B, in which the spring beam is held away from the center of the inner lumen of the cylindrical base. As a result, a coil extending from the cylindrical base is not contacted by the electrode on the spring beam when the torque poles hold the spring beam in the second position.

In some embodiments, step 1108 may additionally include shape-setting the elongated spring beam to have a desired shape. For example, the spring beam may be shape-set to be curved or arc-shaped, such that the spring beam has a convex shape relative to the inner lumen of the cylindrical base (i.e., the proximal and distal ends of the spring beam may point away from the inner lumen of the cylindrical base). At least one electrode may be situated at the apex of the curved or arched spring beam, such that the electrode may be pushed against an endovascular coil, and apply electrical current to the endovascular coil, when the cylindrical body is heated, and the torque poles moved into the twisted configuration. In some embodiments, shape-setting the first and second torque poles may be performed simultaneously with shape-setting the spring beam; alternatively, shape-setting the first and second torque poles may be performed before or after the shape-setting of the spring beam. Examples of shape-set spring beams include the curved shapes of spring beams 760 and 1060.

In some embodiments, a coil-cutting apparatus manufactured in accordance with the method of FIG. 11 may be situated at least partially within the distal end of a microcatheter (e.g., microcatheter 710 or 1010) and connected thereto. For example, an outer surface of the cylindrical base may be connected directly to the inner wall of the microcatheter by adhesive, welding, soldering, or other suitable techniques. In some embodiments, the coil-cutting apparatus may be arranged relative to the microcatheter such that the distal end of the spring beam is even or substantially even with the distal-most end of the microcatheter. Alternatively, the distal end of the spring beam may be located in a proximal direction from the distal-most end of the microcatheter. Advantageously, this configuration allows the coil-cutting apparatus and microcatheter to be advanced together through the patient's body and to a treatment site. Additionally, placement of the coil-cutting apparatus entirely within the microcatheter prevents contact between the patient's body and the at least one electrode on the spring beam.

FIG. 12A is a side view and FIG. 12B is an interior view of an endovascular device 1200 configured for delivery of an endovascular instrument 1220, consistent with disclosed embodiments. The endovascular device 1200 may include an elongated sheath 1210 (e.g., a microcatheter). The endovascular device 1200 may include at least one electrode 1242 and 1244. FIG. 14 is a perspective side view of an elongated sheath 1210 of the endovascular device 1200 of FIGS. 12A and 12B, consistent with disclosed embodiments. In FIG. 14, one electrode 1242 may be connected via an embedded wire 1243 to the distal end of the sheath 1210. Additionally, or alternatively, as shown in FIG. 13, a second electrode 1244 may be connected to the distal end of an outer sheath 1230 of endovascular device 1200. As shown in FIGS. 22A-22F, the endovascular instrument 1220 (e.g., an endovascular coil) may be delivered into a hollow body structure 2282 (e.g., an aneurysm). For example, endovascular instrument 1220 may be delivered through an inner lumen 1214 of the endovascular device 1200 into the hollow body structure 2282 in order to permanently implant the endovascular instrument 1220 within the hollow body structure, such that instrument 1220 fills an interior space 2284 of the hollow body structure in order to block blood flow into the hollow body structure and induce blood clotting in the hollow body structure, so that the structure does not rupture.

FIGS. 12A and 12B illustrate an example of the endovascular device 1200 with a pair of electrodes 1242, 1244 configured to selectively deliver an electric current through a segment of the endovascular instrument 1220 within the inner lumen 1214 of the elongated sheath 1210. FIG. 12B also depicts a constrictor 1260 (e.g., a balloon) configured to narrow the inner lumen 1214 of the sheath. FIG. 17A depicts an embodiment in which constrictor 1260 selectively moves at least one of the electrodes 1242 and 1244 relative to a segment of the endovascular instrument 1220 so that a section 1724 of the endovascular instrument 1220 comes into contact with the at least one electrode.

FIGS. 18A and 18B depict an endovascular instrument 1220 being severed by the electrode pair 1244, 1242 of the endovascular device 1200 of FIGS. 12A and 12B, consistent with disclosed embodiments. FIGS. 18A and 18B depict a severed section 1826 of the instrument released from the remainder of the instrument and from device 1200, while a residual section 1828 of the instrument remains within the endovascular device 1200 after the electrodes 1242 and 1244 selectively deliver the electric current through the segment 1724 of the endovascular instrument 1220.

Figure 22A:
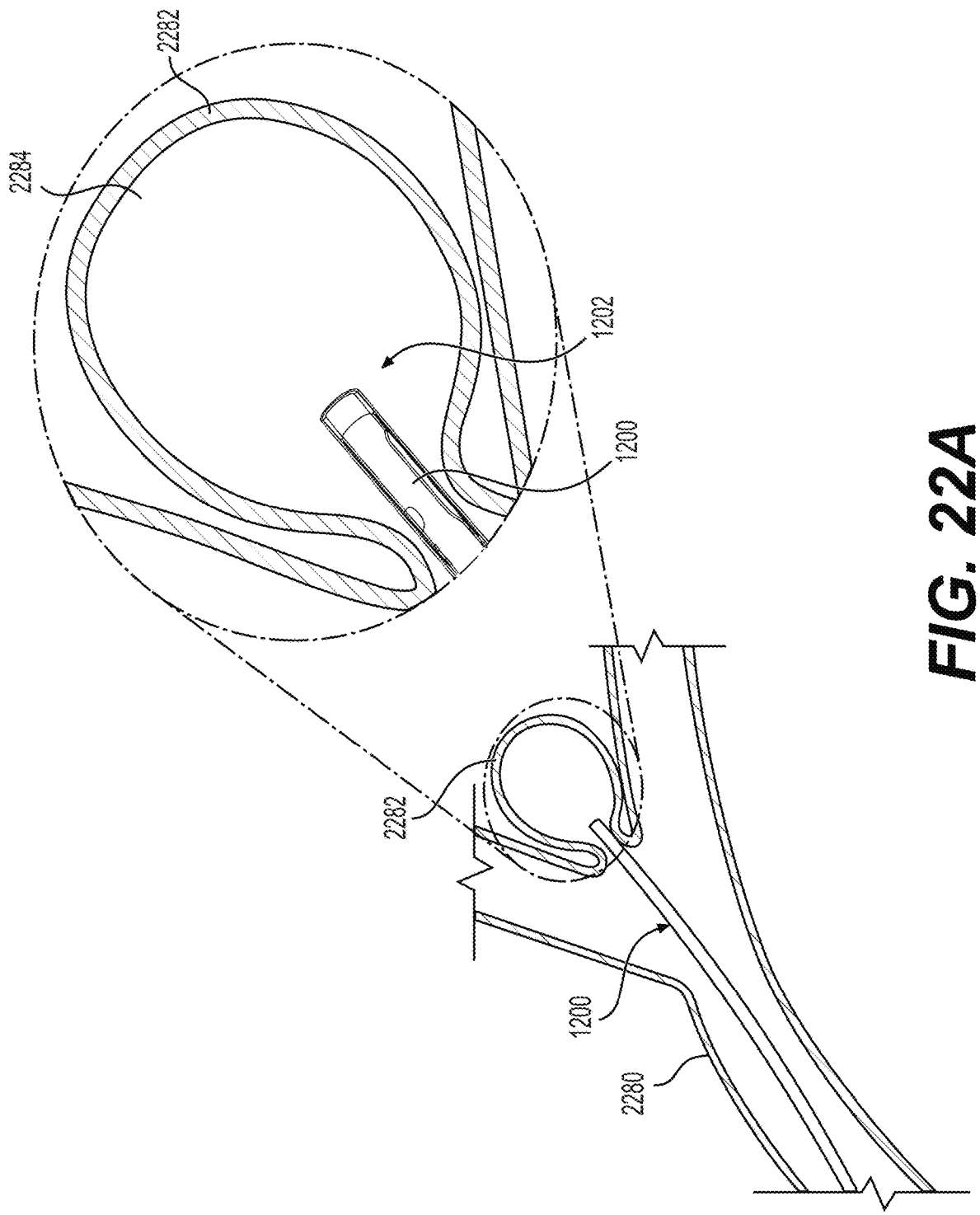
FIGS. 22A-22F depict an example of a method for delivering an endovascular instrument into a hollow body structure with the endovascular device of FIGS. 12A and 12B, consistent with disclosed embodiments.
Figure 22B:
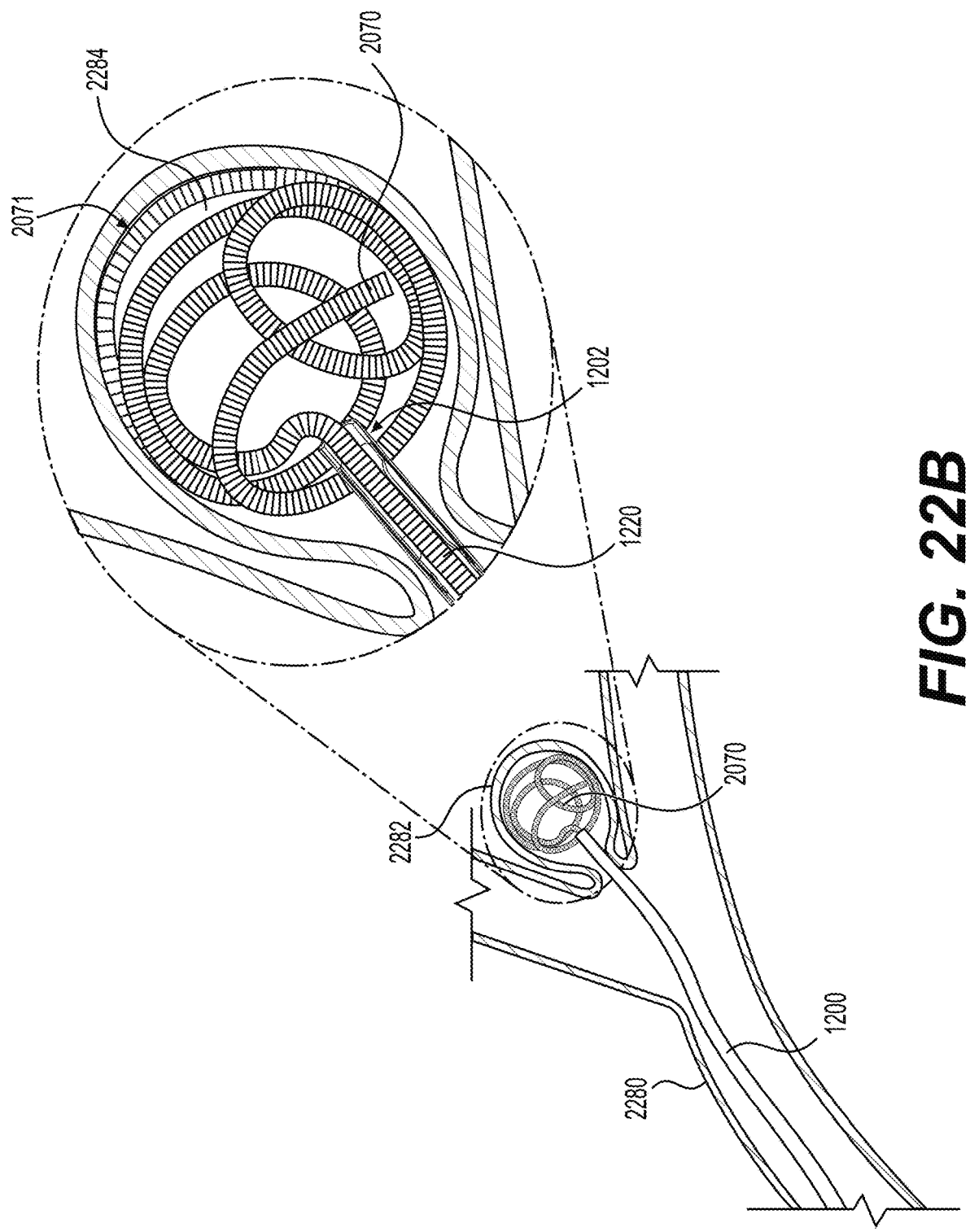
Figure 22C:
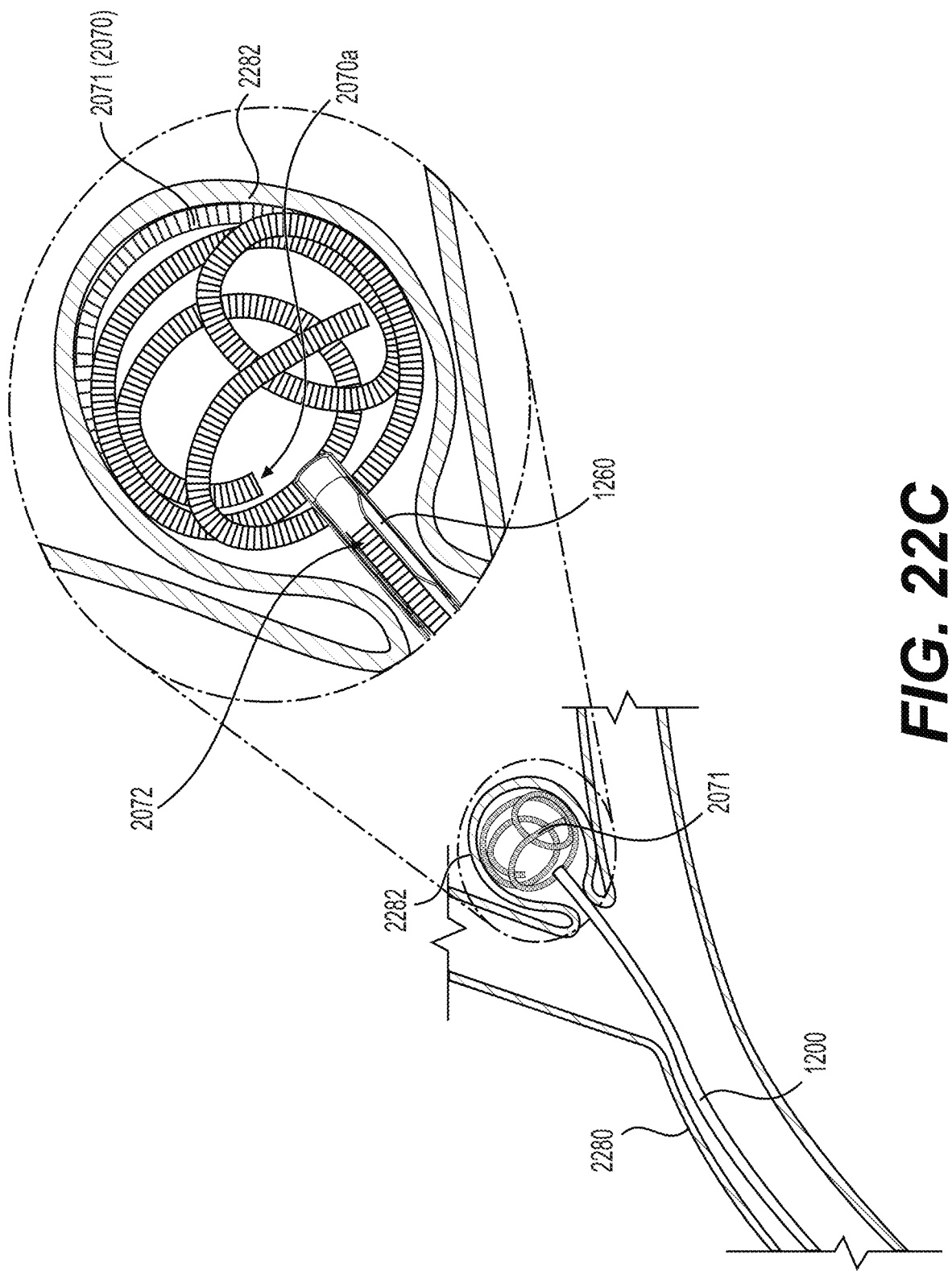
Figure 22D:
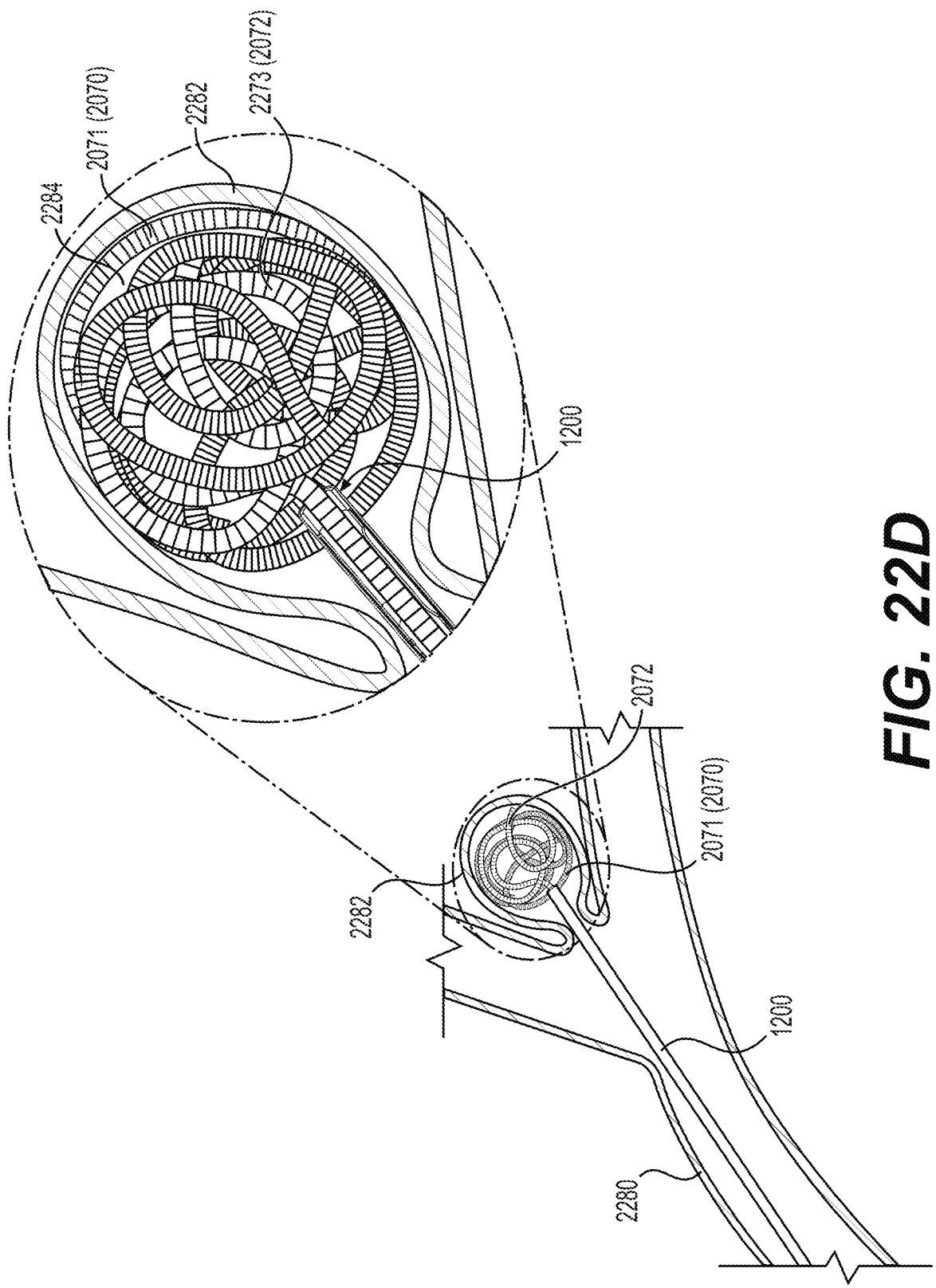
Figure 22E:
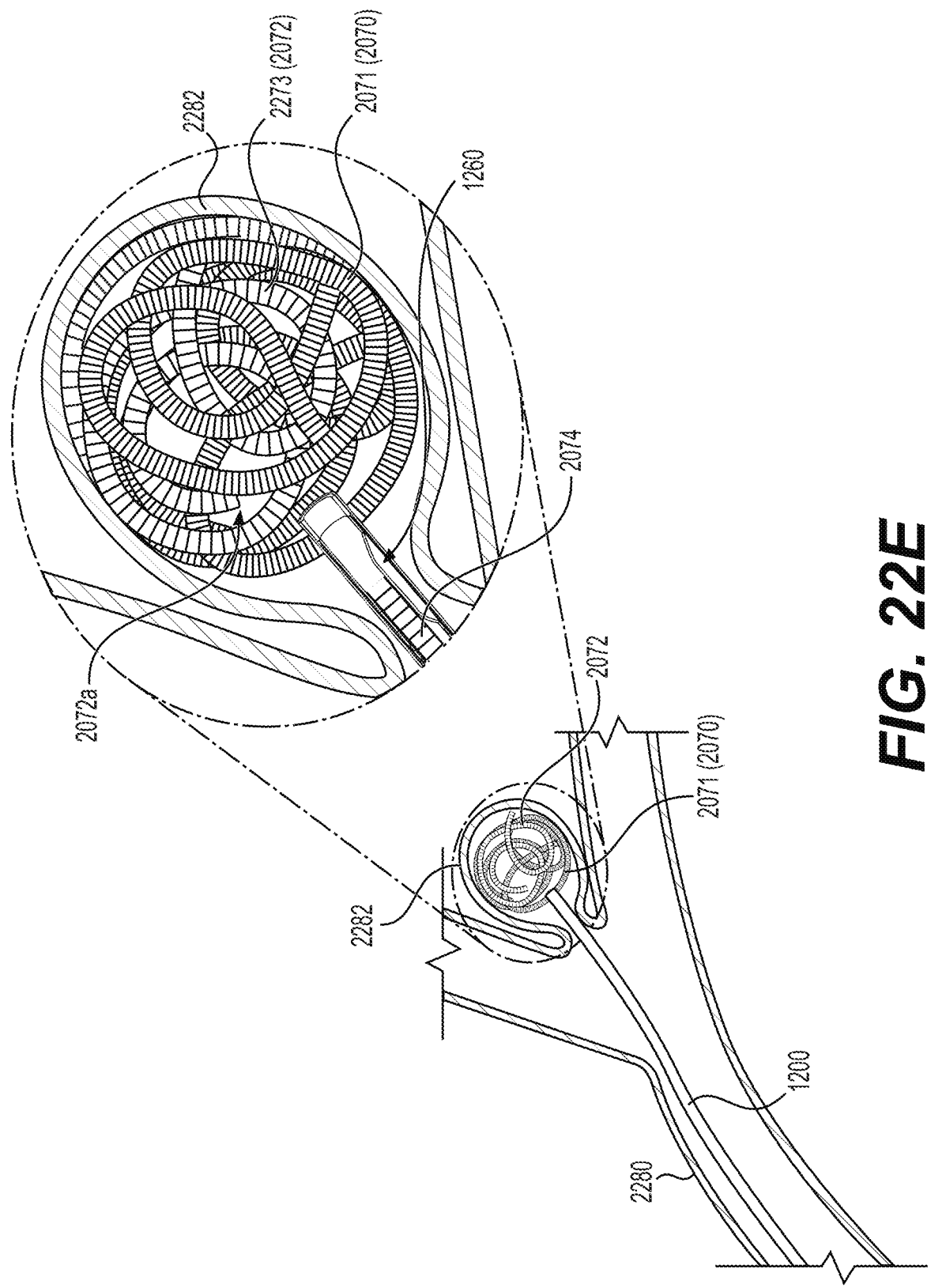
Figure 22F:
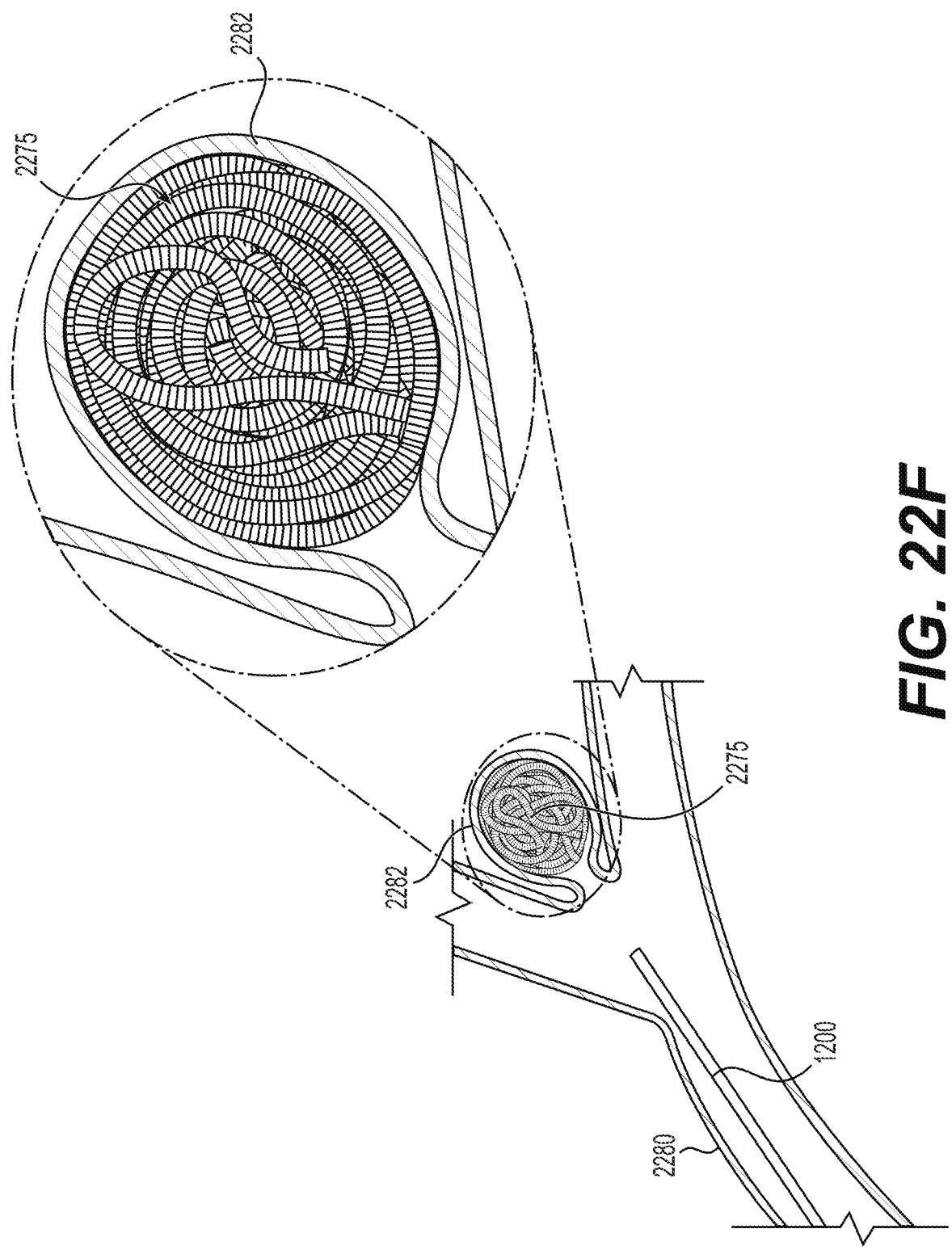

As shown in FIG. 22F, in some embodiments the endovascular device 1200 may be removed from the body, leaving endovascular instrument 1220 configured as an embolic mass 2275 implanted within the hollow body structure 2282.

FIG. 16A is an interior view of a distal section 1213a of the endovascular device 1200 of FIGS. 12A and 12B in an unconstricted state, consistent with disclosed embodiments. FIGS. 16B and 16C depict cross-sectional views of the endovascular device 1200 of FIG. 16A in the unconstricted state, consistent with disclosed embodiments. FIG. 17A is an interior view of the distal section 1213a of the endovascular device 1200 of FIGS. 12A and 12B in a constricted state, consistent with disclosed embodiments. FIGS. 17B and 17C depict cross-sectional views of the endovascular device 1200 of FIG. 17A in the constricted state, consistent with disclosed embodiments. As shown in FIG. 17A, constrictor 1260 may be configured to reduce the size of inner lumen 1214, thus moving instrument 1220 into contact with the electrode pair 1242 and 1244.

"Coil embolization" is a technique for treating aneurysms by filling the aneurysm with a series of metallic coils in order to block blood flow and prevent rupture of the aneurysm or to induce blood clotting in the aneurysm to thereby block blood flow. First, a framing coil may be inserted; the framing coil is the most rigid and often the largest coil and is configured to fill the aneurysm and create a stabilizing frame to be filled with subsequent coils. Then, the remaining space inside the aneurysm is filled using softer, usually smaller coils, such as filling coils and/or finishing coils. Each coil must be delivered one-by-one to the treatment site, extending the duration of the entire operation. Moreover, the length of the coils must be selected beforehand to ensure that the aneurysm is completely filled but not over-packed. Selecting a coil that is too long may require retraction of the entire coil from the body (for replacement with a shorter coil), while selecting a coil that is too short may require usage of additional coils.

Endovascular devices disclosed herein may allow a desired length of coil or any other endovascular instrument to be advanced into an aneurysm and then severed with a partitioning mechanism (e.g., an electrode pair), so that the advanced coil length is detached from the rest of the coil. Endovascular instruments (e.g., coils) also disclosed herein may be configured to be delivered into a hollow body structure with the aforementioned endovascular devices. For example, endovascular coils may have multiple regions that are each configured as a different "type" of coil (e.g., a framing coil region and a filling coil region), yet which are part of a single, continuous structure. Each region of the coil may be delivered into the aneurysm and then cut away, after which the tip of the delivery tool can be moved to another area to immediately begin delivery of the next region of coil. Advantageously, the aneurysm may be filled much more quickly since time is not spent passing individual coils from outside the body to the treatment site. Further, since the exact length of coil that is desired by the operator may be delivered, the risks associated with under-packing or over-packing an aneurysm may be avoided.

Aspects of this disclosure may relate to an endovascular instrument for filling a hollow body structure. In some embodiments, the endovascular instrument described below may be configured to be delivered to a treatment site within a body by an example of an endovascular device disclosed herein. However, the endovascular instrument described below may additionally or alternatively be configured to be delivered by any suitable delivery means known in the art (e.g., delivery catheters and sheaths).

Consistent with disclosed embodiments, an endovascular instrument may refer to any device or instrument configured to be placed within or to operate within a blood vessel, such as during endovascular surgeries and procedures. Some non-limiting examples of endovascular instruments may include catheters, balloon catheters, stent grafts, stents, guidewires, coils, endovascular revascularization devices, embolization devices, or any other device or instrument configured to be placed within a blood vessel in a body.

As described above, the endovascular instrument may be configured for filling a hollow body structure. As used herein, a hollow body structure may refer to any structure within a body that encloses, either partially or entirely, an interior volume. A hollow body structure may refer to an anatomical feature, such as an aortic aneurysm, cerebral aneurysm, popliteal artery, ventricular aneurysm, blood vessel, esophagus, stomach, small intestine, gallbladder, fallopian tubes, or urinary bladder. As used herein, filling a hollow body structure may include placing at least one device or material (e.g., the endovascular instrument) within the interior volume of the hollow body structure. Filling the hollow body structure may include either filling the entirety of the interior volume or a fraction of the interior volume. For example, the endovascular instrument described herein may be configured for filling the entire interior volume within the hollow body structure, such that no free or un-filled areas remain within the hollow body structure. In some embodiments, the at least one device or material used for filling the hollow body structure may be delivered from outside the body to the interior of the hollow body structure.

Figure 20A:
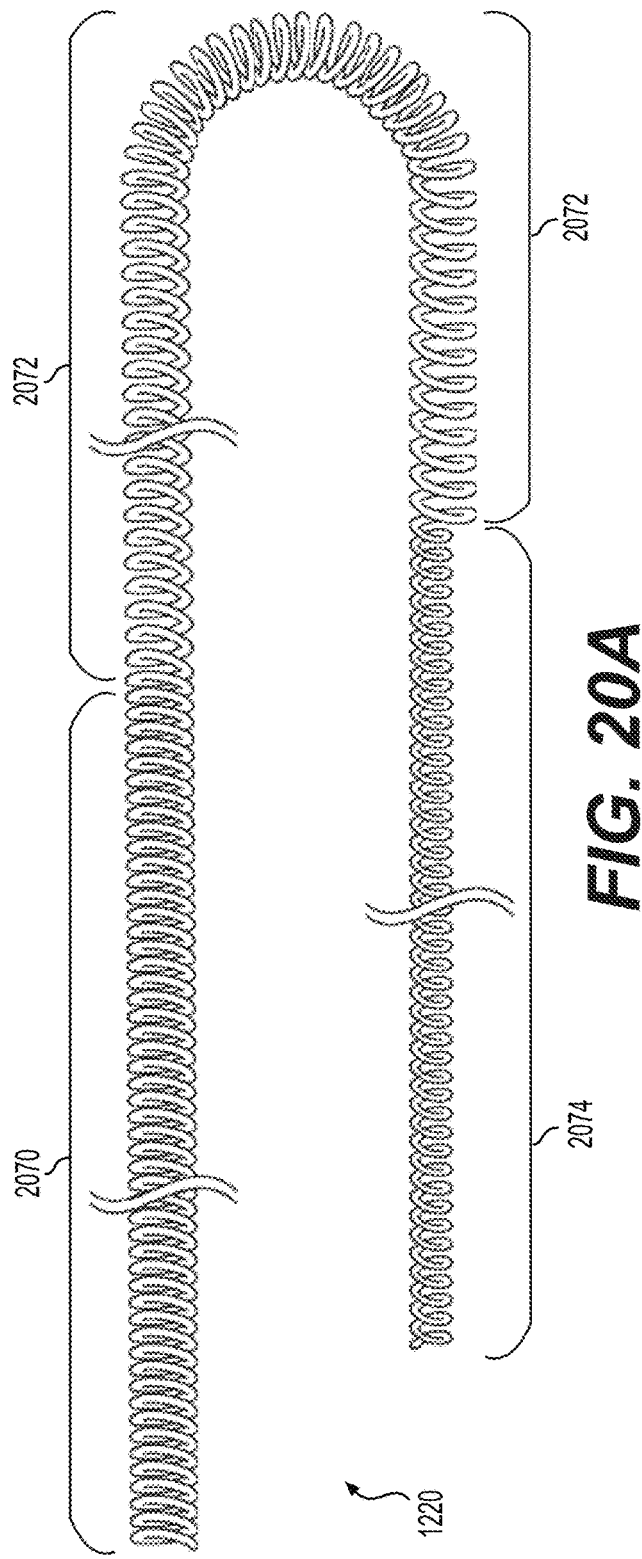
FIG. 20A depicts an example of an endovascular instrument including multiple regions with different structural properties, consistent with disclosed embodiments.
Figure 21A:
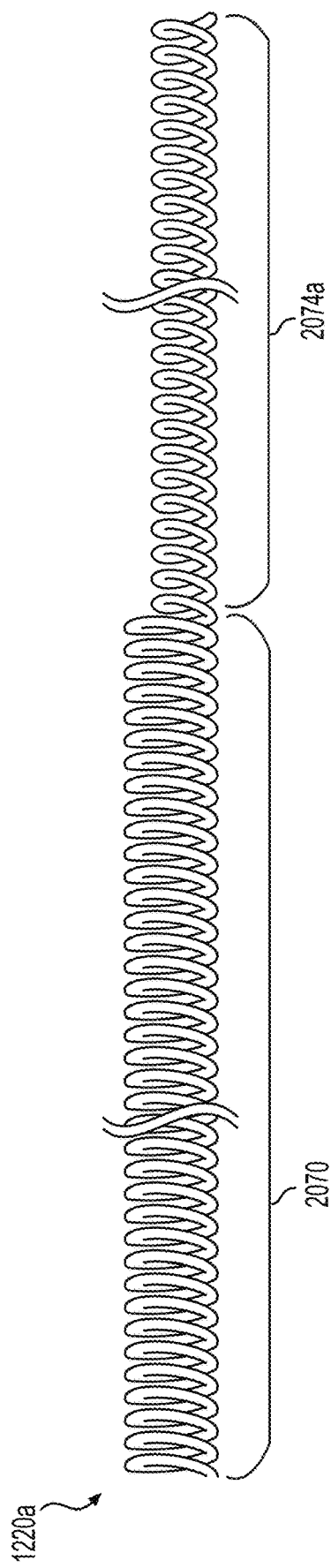
FIG. 21A depicts another example of an endovascular instrument including multiple regions with different structural properties, consistent with disclosed embodiments.

FIG. 20A depicts a first example of an endovascular instrument 1220 configured for filling a hollow body structure, and FIG. 21A depicts a second example of an endovascular instrument 1220a configured for filling a hollow body structure. In some embodiments, instruments 1220 and 1220a may include endovascular coils configured for filling the interior volume of aneurysms and other hollow body structures. However, persons of ordinary skill will understand that endovascular instruments described herein are not limited to endovascular coils. FIGS. 22A-22F depict a process for delivering an example of an endovascular instrument 1220 through a blood vessel 2280 and into a hollow body structure 2282 (e.g., an aneurysm) using an endovascular device 1200 (note that instrument 1220a may similarly be configured for delivery into an aneurysm using endovascular device 1200). Although the example of FIGS. 22A-22F depict the delivery of endovascular instrument 1220 into a hollow body structure 2282 (e.g., an aneurysm), instrument 1220 may additionally or alternatively be delivered into other hollow body structures.

As shown, instrument 1220 may be delivered through an inner lumen of device 1200 from an area outside the patient's body to the interior volume of the aneurysm. As shown in FIGS. 22B-22F, the length of endovascular instrument 1220 may be passed into hollow body structure 2282 using device 1200 until the entire inner volume of the aneurysm is filled with the instrument (i.e., until no additional length of instrument can be delivered into the aneurysm without over-packing it). As also shown in FIGS. 22B-22F, endovascular instrument 1220 may be severed with endovascular device 1200 when the aneurysm is filled and device 1200 may then be removed from the body, leaving instrument 1220 within the aneurysm.

Consistent with disclosed embodiments, the endovascular instrument may include an elongated member. As used herein, an elongated member may refer to any long, thin structure configured to be arranged in a desired shape or three-dimensional arrangement. For example, the elongated member may be configured to be arranged in a helically-coiled shape (i.e., continuous, regularly-spaced rings of consistent diameter or variable diameter). Some non-limiting examples of elongated members may include wires, fibers, tubing, sheaths, catheters, guidewires, or any other suitable device or instrument. Consistent with disclosed embodiments, the elongated member may be configured to be wound into a helical coil and may exhibit differing coiling properties along a length of the elongated member. As used herein, coiling properties may refer to the physical parameters of the coil formed from the elongated member. Some non-limiting examples of coiling properties may include coil pitch (i.e., the space between adjacent windings or rings), wire diameter, outer diameter of the coil, coil angle, and free length (i.e., the axial length of each distinct section of the coil). Thus, the elongated member of the endovascular instrument may be configured to be wound into a coil, and one or more coiling properties may have different values in different sections along the length of the coil.

Consistent with disclosed embodiments, the elongated member may include a first region and a second region proximal to the first region. As used herein, a first region and second region of the elongated member may refer to two separate segments along the length of the elongated member. As used herein, the term "proximal" may refer to a location closer to the user or operator of the elongated member (e.g., a physician), while the term "distal" may refer to a location closer to the treatment location within the patient. Thus, the second region of the elongated member may be closer to the user of the elongated member, while the first region may be further from the user. In some embodiments, the first region of the elongated member may be the distal-most portion of the elongated member (i.e., the first region may include the distal tip of the elongated member). Alternatively, the first region may include some other portion of the elongated member. In some embodiments, the elongated member may include only the first region and second region (that is, the first and second regions may encompass the entire elongated member). In alternative embodiments, the elongated member may include one or more additional regions, such as a third region, fourth region, etc.

In some embodiments, the first region may be integrally connected to the second region. As used herein, integrally connected may mean that the second region may be immediately adjacent to the first region. Alternatively, the second region may be spaced apart from the first region. For example, the elongated member may include one or more regions located in between the first region and second region. Consistent with disclosed embodiments, the elongated member may include a third region positioned between the first region and the second region. At least one structural property of the elongated member, as discussed above, may differ between the first region, the second region, and the third region. That is, the elongated member of the endovascular instrument may be configured to be wound into a coil, and one or more coiling properties (e.g., coil pitch, wire diameter, outer diameter of the coil, coil angle, and free length) may have different values in the first region, the second region, and the third region of the elongated member. In some embodiments, one or more additional regions (e.g., a fourth region) may also be positioned between the first region and second region.

In the example shown in FIG. 20A, endovascular instrument 1220 may include three separate regions: a distal segment 2070 (which may be an example of a first region of the elongated member), a middle segment 2072 (which may be an example of a third region of the elongated member), and a proximal segment 2074 (which may be an example of a second region of the elongated member), each of which may be configured to have different coiling properties. However, endovascular instruments disclosed herein may alternatively include one segment, two segments, four segments, five segments, or any other suitable number of segments, each having different coiling properties. In the example depicted in FIG. 20A, the coil pitch may vary along the length of the elongated member of instrument 1220, with distal segment 2070 having the smallest pitch and proximal segment 2074 having the largest pitch. Additionally, or alternatively, proximal segment 2074 may have a smaller outer diameter than the distal segment 2070 and middle segment 2072.

In the example shown in FIG. 21A, endovascular instrument 1220a may include two separate regions: a distal segment 2070 (which may be an example of a first region of the elongated member) and a proximal segment 2074a (which may be an example of a second region of the elongated member), both of which may be configured to have different coiling properties. In the example depicted in FIG. 21A, distal segment 2070 may have a smaller coil pitch and a larger outer diameter than proximal segment 2074a.

Consistent with disclosed embodiments, the first region and the second region of the elongated member may be interconnected. As used herein, interconnected may mean that the first region and second region are part of a single, continuous structure. Optionally, the first region and second region may be interconnected with additional regions of the elongated member (e.g., a third region, a fourth region, etc.). In some embodiments, the elongated member may be manufactured as a single, unitary piece such that the elongated member portion within the first region is part of the same structure as the elongated member portion within the second region. For example, in embodiments in which the elongated member is formed from one or more wires wound into a coil, the same one or more wires may pass through the first region and the second region of the elongated member, with the wires configured to exhibit different coiling properties in the first region and second region, as discussed above. In alternative embodiments, the portions of the elongated member corresponding to the first region and second region may be manufactured separately and joined together using known means, such as welding, adhesive, mechanical connectors, or other suitable means.

In the example of FIG. 20A, distal segment 2070, middle segment 2072, and proximal segment 2074 of endovascular instrument 1220 may be interconnected as parts of a single, continuous structure. In order to separate these segments of instrument 1220, endovascular device 1200 (which may be configured to deliver instrument 1220 to a treatment site) may include a partitioning mechanism configured to sever endovascular instrument 1220 while device 1200 is positioned within the body of the patient; the segments of endovascular instrument 1220 may be separated using the partitioning mechanism, e.g., during a medical operation or procedure. Additionally, or alternatively, endovascular instrument 1220 may include at least one coil detachment mechanism (discussed in detail below) located at the junction between distal segment 2070 and middle segment 2072 and/or at the junction between middle segment 2072 and proximal segment 2074. The at least one coil detachment mechanism may be actuated to separate the regions of endovascular instrument 1220. In the example of FIG. 21A, distal segment 2070 and proximal segment 2074*a* of endovascular instrument 1220*a* may similarly be interconnected as parts of a single, continuous structure and may similarly be configured to be separated via, e.g., a partitioning mechanism and/or a coil detachment mechanism.

Consistent with disclosed embodiments, the first region and the second region of the elongated member may be configured to bend in a first manner and a second manner, respectively. As used herein, bending of the elongated member may refer to a transition from a first three-dimensional arrangement of the elongated member to a second, different three-dimensional arrangement; the elongated member may be configured to bend due to structural or material properties of the elongated member, a change in the environment surrounding the elongated member, the application of an external force, and/or the removal of an external force. Some non-limiting examples of bending of the elongated member include a transition of the elongated member from a straightened or linear state to a curved or non-linear state; a transition of the elongated member from a curved or non-linear state to a straightened or linear state; and a transition of the elongated member from a first curved or non-linear state to a second, different curved or non-linear state. In some embodiments, bending of the elongated member may occur when a restraining force is removed from the elongated member (e.g., when the elongated member is released from a delivery device) and the elongated member moves into a specific three-dimensional arrangement or shape based on structural and/or material properties of the elongated member. In some embodiments, bending of the elongated member, including bending of the first region and second region in the first manner and second manner, respectively, may occur when the elongated member is exposed to a liquid or is exposed to a particular liquid (such as blood). In some examples, bending of the elongated member may occur in reaction to the elongated member being exposed to a liquid or is exposed to a particular liquid (such as blood).

Consistent with disclosed embodiments, the first region of the elongated member may be configured to bend in the first manner within the hollow body structure to form a stabilizing frame. For example, the first region may be configured to be delivered into the hollow body structure in a straightened or linear delivery state (e.g., within a delivery device) and may bend to form the stabilizing frame when the first region is within the hollow body structure (e.g., when the first region is released from the delivery device). The first region may be configured to bend in the first manner while the first region is interconnected with other regions of the endovascular instrument. Additionally, or alternatively, the first region may be configured to bend in the first manner after the first region has been separated from the rest of the endovascular instrument (e.g., by a partitioning mechanism and/or by a coil detachment mechanism, as described herein). In some embodiments, the first region of the elongated member may be configured to bend in the first manner within the hollow body structure to form a stabilizing frame in reaction to an exposure to blood in the hollow body structure and/or in reaction to a restraining force being removed from the first region of the elongated member (e.g., when the first region of the elongated member is released from a delivery device into the hollow body structure).

As used herein, a stabilizing frame may refer to a structure configured to contact and support the inner wall of the hollow body structure. In some embodiments, the stabilizing frame may be a hollow three-dimensional structure into which additional filling devices or material may be placed; examples of the three-dimensional structure may include a sphere, a basket, a cage, or another complex three-dimensional shape. In a non-limiting example, the first region of the elongated member may be configured as a framing coil. As used herein, a framing coil may be a first coil segment delivered into a hollow body structure, such as an aneurysm, and may bend to form a stabilizing frame configured to support the hollow body structure and within which additional coils may be placed in order to fill the hollow body structure. Thus, when the first region of the elongated member is placed within a hollow body structure, the first region may be configured to bend to form a stabilizing frame configured to support the hollow body structure and within which additional coils may be placed in order to fill the hollow body structure.

Figure 20B:
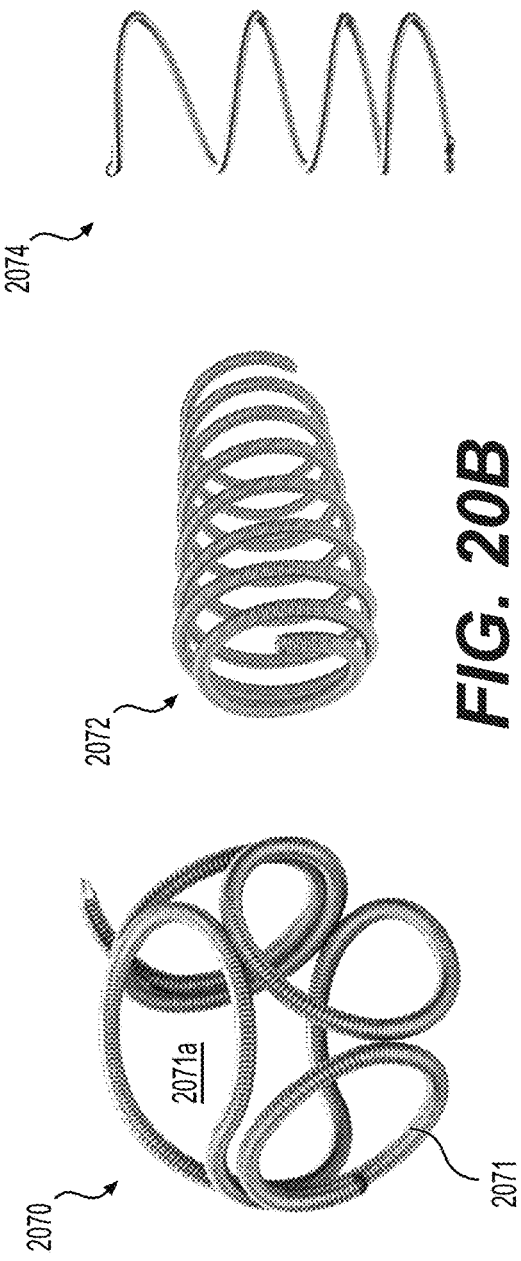
FIG. 20B depicts the regions of the endovascular instrument of FIG. 20A in respective bent states, consistent with disclosed embodiments.

FIGS. 20A and 20B depict an example of an endovascular instrument 1220 including a distal segment 2070, which may be an example of the first region of the elongated member, discussed above. FIG. 20A shows distal segment 2070 of the elongated member in a linear state; in some embodiments, distal segment 2070 may be arranged in the linear state of FIG. 20A when a restraining force is applied thereto (e.g., when distal segment 2070 is restrained within a delivery device). FIG. 20B shows distal segment 2070 of the elongated member bent in the first manner to form stabilizing frame 2071, which may include a three-dimensional structure having interior space 2071*a* configured to receive additional features therein, such as middle segment 2072 and proximal segment 2074 of the elongated member. In some embodiments, distal segment 2070 may be biased to bend into the shape of stabilizing frame 2071 when a restraining force is removed from the distal segment (e.g., when distal segment 2070 is released from a delivery device). As discussed above, distal segment 2070 may be configured to bend into the frame of FIG. 20B while distal segment 2070 is interconnected with the other regions of endovascular instrument 1220 and, additionally or alternatively, when distal segment 2070 has been separated from the rest of endovascular instrument 1220.

In some embodiments, distal segment 2070 may be configured as a framing coil and may bend to form stabilizing frame 2071 when the distal segment is delivered into an aneurysm. As shown in FIGS. 22B-22C, when distal segment 2070 is released from endovascular device 1200 into hollow body structure 2282 (e.g., an aneurysm), the distal segment may bend to form stabilizing frame 2071, which may contact and support the inner wall of hollow body structure 2282. In some embodiments, distal segment 2070 may be severed from the rest of endovascular instrument 1220 (e.g., by a partitioning mechanism) and may remain within hollow body structure 2282 as a stabilizing frame. As shown in FIGS. 22C-22E, stabilizing frame 2071 may have a hollow three-dimensional shape such that additional coil material, including the remaining regions of endovascular instrument 1220, may be delivered into the interior spaces 2071*a* of the stabilizing frame so that the entire inner volume 2284 of the aneurysm may be filled.

Consistent with disclosed embodiments, the second region of the elongated member may be configured to bend, after formation of the frame, in a second manner substantially within the frame. As used herein, bending substantially within the frame may refer either to a state in which the second region is situated entirely within the frame when the second region is bent in the second manner, or to a state in which the majority of the second region is situated within the frame when the second region is bent in the second manner, with the remainder of the second region being positioned outside the frame but within the hollow body structure. For example, the second region of the elongated member may be configured to be delivered into the hollow body structure in a straightened or linear delivery state (e.g., within a delivery device) and may bend in the second manner when the second region is released from the delivery device and placed substantially within the interior volume of the frame. In some embodiments, the second region may be configured to bend in the second manner while the second region is interconnected with other regions of the endovascular instrument. Additionally, or alternatively, the second region may be configured to bend in the second manner after the second region has been separated from the rest of the endovascular instrument (e.g., by a partitioning mechanism and/or by a coil detachment mechanism, as described herein). Additionally, or alternatively, the second region may be partitioned into multiple portions, each of which may be configured to bend in the second manner. In some embodiments, the second region of the elongated member may be configured to bend in the second manner substantially within the frame in reaction to an exposure to blood in the hollow body structure and/or in reaction to a restraining force being removed from the second region of the elongated member (e.g., when the second region of the elongated member is released from a delivery device).

In the embodiment of FIGS. 20A and 20B, proximal segment 2074 may be an example of the second region of the elongated member. FIG. 20A shows proximal segment 2074 in a linear state; in some embodiments, proximal segment 2074 may be arranged in the linear state of FIG. 20A when a restraining force is applied thereto (e.g., when proximal segment 2074 is restrained within a delivery device). FIG. 20B shows proximal segment 2074 bent in the second manner into a three-dimensional structure, such as a helix, a sphere, a convex three-dimensional shape, or a concave three-dimensional shape. In some embodiments, proximal segment 2074 may be biased to bend in the second manner when a restraining force is removed from the proximal segment (e.g., when proximal segment 2074 is released from a delivery device). As discussed above, segment 2074 may be configured to bend in the second manner while interconnected with the other regions of endovascular instrument 1220 and, additionally or alternatively, when separated from the rest of endovascular instrument 1220. Proximal segment 2074 may also be configured to be partitioned into multiple sections, each of which may be configured to bend in the second manner. Additionally, in the embodiment of FIGS. 21A and 21B, proximal segment 2074*a* may be another example of the second region of the elongated member. Proximal segment 2074*a* may similarly be configured to bend in the second manner into a three-dimensional structure, such as a helix, as shown in FIG. 21B, or a sphere.

Consistent with disclosed embodiments, the second region of the elongated member may be configured to bend in the second manner to form a curved mass substantially within the frame. As used herein, a curved mass may include a structure formed from one or more pieces of the elongated member which are bent, twisted, or otherwise arranged to fill the interior volume of the stabilizing frame and, in some cases, portions of the hollow body structure outside of the stabilizing frame. As discussed above, the second region may be configured to assume a particular three-dimensional shape when removed from the delivery device, such as a helix, a sphere, a convex three-dimensional shape, a concave three-dimensional shape, or another three-dimensional shape. In some embodiments, the curved mass may be formed from a single, continuous piece of the second region bending in the second manner when it is delivered into the stabilizing frame; this piece of the second region may include the entire second region or a portion of the second region. In alternative embodiments, the second region may be severed in multiple pieces (as discussed in detail below), which may be delivered into the stabilizing frame to form the curved mass. As used herein, the curved mass being substantially within the frame may refer either to a state in which the curved mass is situated entirely within the frame, or to a state in which the majority of the curved mass is situated within the frame with the remainder of the curved mass being positioned outside the frame but within the hollow body structure.

In some embodiments, the second region of the elongated member may be configured as a filling coil. As used herein, a filling coil may be an endovascular coil configured for delivery into the aneurysm after the framing coil to promote thrombus formation; as a filling coil, the second region may be caged within the stabilizing frame. For example, in the above-discussed embodiments in which the elongated member includes a third region positioned between the first region and the second region, the second region may constitute a finishing coil and the third region may constitute a filling coil.

Figure 21B:
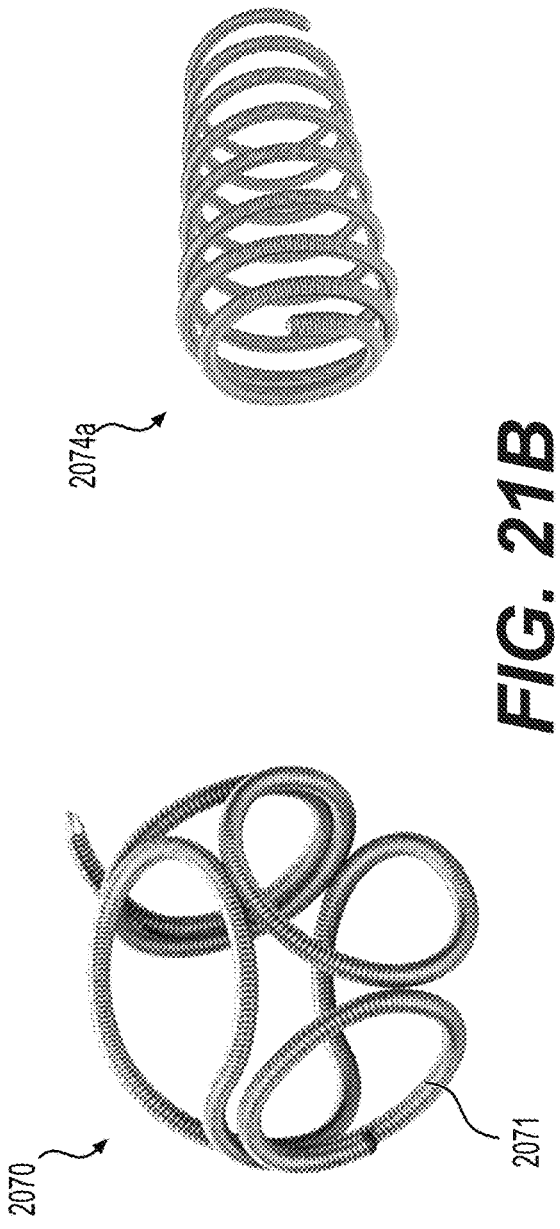
FIG. 21B depicts the regions of the endovascular instrument of FIG. 21A in respective bent states, consistent with disclosed embodiments.

FIGS. 21A and 21B illustrate an example in which first region 2070 may be configured as a framing coil and second region 2074*a* may be configured as a filling coil. As discussed above, first region 2070 and second region 2074*a* may be integrally formed as a single structure and may be configured to be detached from each other, such as with a partitioning mechanism (discussed in further detail below). As also discussed above, at least one coiling property may differ between the first region 2070 and second region 2074*a*; for example, first region 2070 may have a smaller pitch and a larger outer diameter than second region 2074*a*.

As shown in FIGS. 22B-22C, first region 2070 may be delivered first into the hollow body structure and may bend within the hollow body structure to form the stabilizing frame 2071. First region 2070 may be detached from the remainder of elongated instrument 1220*a* (i.e., from second region 2074*a*) before, during, or after the first region completes the bending into stabilizing frame 2071. As shown in FIGS. 22C-22E, second region 2074*a* (which may be configured as a filling coil) may then be delivered into the interior of stabilizing frame 2071 in one piece or in multiple pieces and may be caged substantially within the stabilizing frame, bending within the interior volume of the stabilizing frame to form a curved mass 2273. Optionally, remaining space within hollow body structure 2282 may be filled with one or more finishing coils. As shown in FIGS. 22E-22F, endovascular device 1200 may be removed from the body, leaving the delivered pieces of coil 1826 within hollow body structure 2282 in an embolic mass 2275 that is configured to block blood flow into the hollow body structure 2282 or to induce blood clotting in the hollow body structure 2282.

In alternative embodiments, the second region of the elongated member may be configured as a finishing coil. As used herein, a finishing coil may be an endovascular coil configured to compact and fill remaining space within the aneurysm to increase occlusion, prevent catheter kickbacks, and prevent coil migration; as a finishing coil, the second region may be inserted into the aneurysm after a framing coil and one or more filling coils and may be softer than filling coils used in the procedure.

FIGS. 20A and 20B illustrate an example in which the first region 2070 may be configured as a framing coil, the third region 17154 (i.e., the middle segment) may be configured as a filling coil, and the second region 17156 (i.e., the proximal segment) may be configured as a filling coil. As discussed above, first region 2070, third region 17154, and second region 2074 may be integrally formed as a single structure and may be configured to be detached from each other, such as with a partitioning mechanism (discussed in further detail below). As also discussed above, at least one coiling property may differ between the first region 2070, third region 17154, and second region 2074. For example, second region 2074 may be configured as a finishing coil, having a larger pitch and a smaller outer diameter than the other segments of endovascular instrument 1220 such that the second region 2074 may be the softest portion of instrument 1220.

First region 2070 (configured as a framing coil) and third region 2072 (configured as a filling coil) may be delivered first into the hollow body structure in the manner discussed above for FIGS. 21A-21B. Second region 2074 (when configured as a finishing coil) may then be delivered to compact the other coils and fill remaining space within hollow body structure 2282 (e.g., an aneurysm), such that the inner volume 2284 of the aneurysm may be filled. In some embodiments, second region 2074 may bend in a three-dimensional shape to fill space within the stabilizing frame, thus forming a curved mass substantially within the frame.

Consistent with disclosed embodiments, the elongated member may be configured to block blood flow into the hollow body structure. For example, and as discussed above, the first region of the elongated member may bend within the hollow body structure to form the stabilizing frame and the second region of the elongated member may then form the curved mass substantially within the frame. The stabilizing frame, with the curved mass therein, may fill at least a portion or the majority of the interior volume of the hollow body structure. Optionally, remaining space within the hollow body structure may be filled with at least one additional portion of the elongated member (e.g., a portion of the elongated member configured as a finishing coil). Additionally, or alternatively, the elongated member within the hollow body structure may induce blood clotting in the hollow body structure, and thereby block blood flow into the hollow body structure. The resulting structure may tightly pack the hollow body structure and block the flow of blood into the hollow body structure. Advantageously, isolating the hollow body structure from circulation minimizes the risk of rupturing the hollow body structure.

For example, FIGS. 22E-22F show an example of an embolic mass 2275 formed from the delivered sections of endovascular instrument 1220, including the stabilizing frame 2071 and curved mass 2273. Embolic mass 2275 may tightly pack the interior volume 2284 of the hollow body structure and block the flow of blood into the hollow body structure. In another example, embolic mass 2275 may induce blood clotting in the interior volume 2284 of the hollow body structure and thereby block the flow of blood into the hollow body structure.

Consistent with disclosed embodiments, a tertiary structural configuration of the first region may differ from a tertiary structural configuration of the second region. As used herein, a tertiary structural configuration may refer to a three-dimensional shape resulting from the bending or curving of the coiled elongated member. For example, the elongated member may have a coiled or helically-wound secondary structural configuration formed from winding a wire, or an equivalent structure, in continuous, regularly-spaced rings of consistent diameter or variable diameter. As an example, FIG. 20A shows the elongated member of instrument 1220 arranged as a coil with one or more variable coiling properties; this coiling shown in FIG. 20A is the secondary structural configuration of instrument 1220. The coiled first region and second region of the elongated member may then bend in the first manner and second manner, respectively, into their respective tertiary structural configurations. In some embodiments, the first region and/or the second region may be biased to bend into their tertiary structural configurations due to, e.g., their shape-memory or other structural and/or material properties. Additionally, or alternatively, the first region and second region may be configured to bend further into quaternary and/or quinary structures. In some embodiments, the elongated member may include one or more additional regions (e.g., a third region) having a tertiary structural configuration that differs from the tertiary structural configurations of one or both of the first region and second region.

The first region of the elongated member may have a tertiary structural configuration that includes a sphere, a basket, a cage, a convex three-dimensional shape, a concave three-dimensional shape, or another three-dimensional shape having an interior space within which the curved mass of the second region may be formed. For example, the first region may have a tertiary structural configuration of a framing coil. In some embodiments, the tertiary structural configuration of the first region may additionally or alternatively include the shape of the stabilizing frame; thus, the first region may assume its tertiary structural configuration when the first region bends in the first manner to form the stabilizing frame. FIG. 20B illustrates an example of a tertiary structural configuration of first region 2070, which includes the three-dimensional shape of stabilizing frame 2071. In some embodiments, the first region may be configured to assume a predetermined, three-dimensional structural configuration in the presence of body fluid to form the frame within the hollow body structure. As used herein, a predetermined, three-dimensional structural configuration of the first region may refer to the final three-dimensional shape of the first region within the hollow body structure; this shape may include the tertiary structural configuration or, alternatively, this shape may include further bending of the first region into a predetermined quaternary or quinary configuration. The first region of the elongated member may be configured to bend into its final three-dimensional shape when the first region is exposed to a liquid or to body fluid such as blood, urine, cerebrospinal fluid, etc. Thus, when the first region is delivered into a hollow body structure having body fluid therein, the first region may be configured to bend into its predetermined, three-dimensional structural configuration to form the stabilizing frame within the hollow body structure.

The second region of the elongated member may have a tertiary structural configuration that includes a helix, a sphere, or another three-dimensional shape. In some embodiments, the second region may have a tertiary structural configuration of a filling coil or of a finishing coil. For example, FIG. 20B shows an example of a second region 2074 having a first helical shape, and FIG. 21B shows another example of a second region 2074a having a second, different helical shape. In some embodiments, the second region may bend, either partially or completely, into its tertiary structural configuration within the stabilizing frame to form the curved mass, as discussed above. Consistent with disclosed embodiments, the second region may be configured to be delivered into the hollow body structure after the first region and to fill space in the three-dimensional structural configuration of the first region. For example, after the first region is delivered into the hollow body structure and bends in the first manner to form the stabilizing frame, the second region may bend in the second manner to form the curved mass substantially within the frame, thus filling at least some of the space within the frame.

Consistent with disclosed embodiments, at least one structural property may differ between the first region and the second region of the elongated member. As used herein, a structural property may include a design feature of the elongated member (e.g., outer diameter, three-dimensional shape, cross-sectional shape, or axial length) and/or a material property of the elongated member (e.g., material composition, elasticity, or stiffness). Consistent with disclosed embodiments, the at least one structural property differing between the first region and second region may include at least one of stiffness, flexibility, material composition, outer diameter of the first and second regions, diameter of the elongated member, three-dimensional shape, cross-sectional shape, axial length, and number of turns per unit of length. It is due to the different structural properties that the first region and second region may be configured as different types of endovascular coils (e.g., the first region may be configured as a framing coil and the second region may be configured as one of a filling coil or a finishing coil).

Consistent with disclosed embodiments, an outer diameter of the first region may be larger than an outer diameter of the second region. For example, the first region and the second region may have respective outer diameters within the range of 1 mm to 45 mm, with the difference between the outer diameters of the first region and second region falling within the range of 0%-50%. In another example, one or more of the outer diameters of the first and second regions may be outside the range of 1 mm to 45 mm, or the difference between the outer diameters may be outside the range of 0%-50%.

Consistent with disclosed embodiments, the first region may be stiffer than the second region. In some non-limiting examples, the greater stiffness of the first region may be due to the first region having a smaller coil angle than the second region, the first region having a smaller coil pitch than the second region, the first region having a larger outer diameter than the second region, the diameter of the elongated member being larger in the first region than in the second region, and/or the first region being constructed from a more rigid material than the second region. In some embodiments, the first region and second region may have respective spring constants within the range of 0.12 to 0.28 N/m, with the spring constant of the first region being at least 10% greater than the spring constant of the second region. In other examples, one or more of the spring constants of the first region and second region may be outside the range of 0.12 to 0.28 N/m. In other examples, the spring constant of the first region may be smaller than, equal to, or less than 10% greater than the spring constant of the second region.

Consistent with disclosed embodiments, an axial length of the first region may be shorter than an axial length of the second region. In some embodiments, the first region may be configured as an entire framing coil and may have, for example, an axial length of between 5 cm and 60 cm. In another example, the axial length of the first region may less than 5 cm or more than 60 cm. Additionally, or alternatively, the second region may include the totality of all filling coils to be used in an endovascular procedure, optionally with a surplus length of coil. In some embodiments, the second region may have an axial length of between 10 cm and 500 cm. In another example, the axial length of the second region may be less than 10 cm or more than 500 cm. In some examples, the axial length of the second region may be at least twice the axial length of the first region, at least three times the axial length of the first region, at least five times the axial length of the first region, or at least ten times the axial length of the first region. In other example, the axial length of the second region may be less than twice the axial length of the first region, less than the axial length of the first region, and so forth.

Consistent with disclosed embodiments, the endovascular instrument may be constructed from one or more materials, such as Nitinol, platinum, tungsten, iridium, platinum-tungsten alloy, platinum-iridium alloy or any other suitable metal or metallic alloy. In some embodiments, the entire endovascular instrument (including the first region, second region, and any other regions therein) may be constructed from the same material. Alternatively, two or more regions of the endovascular instrument may be constructed from different materials. For example, in some embodiments the first region may be constructed of a first alloy (e.g., platinum-tungsten alloy, platinum-iridium alloy, or any other suitable metallic alloy) and the second region may be constructed of a second alloy differing from the first alloy (e.g., platinum-tungsten alloy, platinum-iridium alloy, or any other suitable metallic alloy).

Consistent with disclosed embodiments, the endovascular instrument may include a support mechanism configured to push the first region in a distal direction, the support mechanism being selectively detachable from the elongated member. As used herein, a support mechanism may include a structure configured to stabilize or confine the second region of the elongated member, such that twisting and kinking of the second region is reduced or prevented when a distally-directed force is applied to the second region. For example, since the second region of the elongated member may be proximal to the first region, a distally-directed force may be applied to the second region in order to push the first region distally. As the second region may be softer and more flexible than the first region in various embodiments, this application of force may cause unintended twisting or kinking of the second region. By stabilizing the second region with a support mechanism, the distally-directed force may be applied to the second region with reduced twisting and kinking, while also delivering the applied force (at least in part) to the first region, thus pushing the first region in a distal direction.

In some embodiments, the support mechanism may include at least one delivery wire arranged parallel to the second region. The at least one delivery wire may be arranged to extend through an interior of the elongated member or may be arranged external to the elongated member. The at least one delivery wire may have a first end that may be connected to the elongated member at, for example, the proximal end of the first region, the distal end of the second region, a connector between the first region and the second region, or any other suitable part of the elongated member. The second end of the at least one delivery wire may be connected to a feature that is proximal to the first end of the delivery wire; examples of the feature may include a distal end of a shaft or handle, a proximal end of the second region of the elongated member, a torquer of the endovascular instrument, a connector connecting the proximal end of the second region with another region of the elongated member or with another device, or any other suitable location. In some embodiments, the at least one delivery wire may be configured to exert force on at least a part of the second region of the elongated member and/or exert force on at least one end of the second region of the elongated member and/or exert opposing forces on the proximal and distal ends of the second region of the elongated member, thus preventing the second region from twisting or buckling over itself when a pushing force is applied to the endovascular device. Thus, some or all of the applied force may be transferred to the first region of the endovascular device, pushing the first region in a distal direction. When desired, the at least one delivery wire may be removed from the portions of the endovascular device to which it may be connected.

In alternative embodiments, the support mechanism may include a sleeve configured to engulf at least a portion of the second region of the elongated member. In some embodiments, the sleeve may engulf the entire length of the second region or a portion thereof; the sleeve may engulf the proximal end of the second region, the distal end of the second region, and/or a middle section of the second region. In some embodiments, the proximal end of the sleeve may be connected to a manipulable control element (e.g., a control wire, a torquer, a shaft, or a handle) so that axial movement of the sleeve and, through the sleeve, the second region of the elongated member may be controlled. Alternatively, the sleeve may extend proximally to a location of a user of the endovascular device, such that the user may directly manipulate the sleeve.

At least a portion of the sleeve may be connected to the second region of the elongated member by, for example, friction fit, a mechanical engagement or connector, adhesive, or any other suitable connection means. For example, the distal end of the sleeve may be connected to the second region. Due to the connection, a distally-directed force applied to the sleeve may be transferred to the second region so that the sleeve may be configured to advance in the distal direction together with the second region. The second region may, in turn, exert the distally-forced force on the first region of the elongated member, pushing the first region in the distal direction without twisting or buckling the second region.

In some embodiments, the sleeve may be configured to be selectively detached from the elongated member through movement in a proximal direction relative to the second region of the elongated member. For example, the distal end of the sleeve may engage a portion of the second region and may push the second region in a distal direction. However, the engagement between the sleeve and the second region of the elongated member may be lost when the sleeve is moved in a proximal direction, such that the elongated member may remain stationary when the sleeve is pulled proximally. By this mechanism, the sleeve may be used to push the second region of the elongated member and, through it, the first region of the elongated member in the distal direction. When the elongated member is advanced to a desired location, the sleeve may be disengaged from the second region (either manually or automatically) via proximal movement of the sleeve away from the elongated member.

In some embodiments, such as the example of endovascular device 2500 depicted in FIGS. 25A and 25B, a support mechanism 2580 may include a sleeve configured to engage second region 2072 of an endovascular instrument. In this example, a distal end of the support mechanism may abut a portion of second region 2072, such that the support mechanism 2580 may be actuated to push endovascular instrument in a distal direction (i.e., to the left in FIGS. 25A and 25B). As shown in FIG. 25B, distal movement of the support mechanism 2580 and second region 2072 may, in turn, cause distal movement of the first region 2070 of the elongated member until the first region is moved to a desired position. Support mechanism 2580 may then be selectively detached from the elongated member by being moved in a proximal direction, while the elongated member may remain in place.

Consistent with disclosed embodiments, the first region of the elongated member may be configured to be detached from the second region of the elongated member following delivery of the first region to the hollow body structure. As a result, the first region may remain in place within the hollow body structure while the second region is moved relative to the hollow body structure, such as during delivery of the second region into the hollow body structure or removal of the second region from the patient's body. In embodiments in which the first region is configured as a framing coil, detachment of the first region from the second region may separate the framing coil from the remainder of the elongated member such that the framing coil may bend to form the stabilizing frame within the hollow body structure.

Additionally, or alternatively, at least a first portion of the second region of the elongated member may be configured to be detached from a second portion of the second region within the hollow body structure after detachment of the first region of the elongated member from the second region. In some embodiments, the first portion of the second region may include a distal portion of the second region, and the second portion of the second region may include a proximal portion of the second region. For example, after the first region of the elongated member is detached from the second region, the second region may be the distal-most region of the elongated member. When it is desired to deliver a first portion (e.g., a distal portion) of the second region into the hollow body structure without delivering a second portion (e.g., a proximal portion) of the second region, the first portion may be separated from the second portion so that the first portion may remain in place within the hollow body structure while the second portion is moved relative to the hollow body structure (e.g., subsequently delivered to the hollow body structure) or else removed from the patient's body.

Advantageously, in situations in which only a fraction of the second region is needed for delivery to the hollow body structure, this configuration may allow a desired length of the second region to be delivered to the hollow body structure without requiring the entire second region to be delivered, which might result in over-packing the hollow body structure.

In some embodiments, the first region of the elongated member may be detached from the second region of the elongated member by a coil detachment mechanism (discussed in detail below). Similarly, the first portion (e.g., distal portion) of the second region may be detached from the second portion (e.g., proximal portion) of the second region by a coil detachment mechanism. Additionally, or alternatively, a partitioning mechanism may be provided to detach the first region of the elongated member from the second region of the elongated member and/or to detach the first portion (e.g., distal portion) of the second region from the second portion (e.g., proximal portion) of the second region. For example, the partitioning mechanism may be connected to an endovascular device used to deliver the endovascular instrument to the hollow body structure. Once the first region of the elongated member has been advanced to a desired position (e.g., advanced out of the endovascular device into the hollow body structure), the partitioning mechanism may be activated to sever (i.e., completely detach or separate) the first region of the elongated member from the second region. Advantageously, the partitioning mechanism may allow the first region to be detached from the second region even if a coil detachment mechanism is not provided in between the first and second regions. Additionally, or alternatively, once a desired length of the second region is advanced from the endovascular device into the hollow body structure, the partitioning mechanism may be activated to sever the first portion (e.g., distal portion) of the second region from the rest of the elongated member. Advantageously, the partitioning mechanism may allow a desired length of the second region to be delivered to the hollow body structure without requiring the entire second region to be delivered, which might result in over-packing the hollow body structure.

Consistent with disclosed embodiments, the endovascular instrument may include at least one coil detachment mechanism configured to sever the elongated member while the elongated member is within a patient's body. As used herein, a coil detachment mechanism may include a feature provided on the endovascular instrument that is configured to detachably connect two sections of the elongated member together or to detachably connect the elongated member to another structure such as a delivery wire or support mechanism (e.g., shaft). The coil detachment mechanism may be activated (e.g., by a user) to detach (i.e., remove the connection between) the two features being connected by the coil detachment mechanism. Some non-limiting examples of a coil detachment mechanism may include electrolytic detachment features, mechanical detachment features (e.g., screw connectors, male-female connectors, or removable latch or pin connectors), degradable adhesive (e.g., degradable polymer adhesive), connections detached by heat application, and connections detached by application of electric current. Consistent with disclosed embodiments, the coil detachment mechanism may be configured to sever the elongated member in at least one of a first detachment location between the first region and the second region, a second detachment location between the second region and a delivery wire, or a third detachment location along a length of the second region. In some embodiments, only one of the detachment locations includes a coil detachment mechanism. Alternatively, multiple or all of the detachment locations may include a coil detachment mechanism. One or more coil detachment mechanisms may additionally be provided at other portions of the elongated member or at the location of a connection between the elongated member and another structure (e.g., a delivery wire or sheath, or a support mechanism).

Consistent with disclosed embodiments, the second region of the elongated member may be configured to connect to a delivery wire. As used herein, a delivery wire may include a wire, fiber, sheath, or other structure configured to connect to the second region of the elongated member so as to control movement of the elongated member relative to a delivery device and/or relative to the body of the patient. In some embodiments, the distal end of the delivery wire may have a removable connection to the second region of the elongated member, such as a screw connector, male-female connector, or removable latch or pin connector. The proximal end of the delivery wire may be connected to a manipulable control element (e.g., a control wire, a torquer, a shaft, or a handle) or, alternatively, may be directed manipulated by a user. The delivery wire may be moved distally, proximally, or rotationally to cause a corresponding movement of the elongated member; under control of the delivery wire, the elongated member may be advanced to a desired location within the body of the patient and arranged in a desired configuration at the location. The delivery wire may then be detached from the elongated member and removed, while the elongated member may remain in a delivery location. Additionally, or alternatively, another region of the elongated member may be configured to connect to a delivery wire, such as any region of the elongated member located proximal to the second region.

Consistent with disclosed embodiments, the elongated member may include at least one imaging marker. As used herein, an imaging marker may include a feature or material on or within the elongated member that is configured to be visualized or detached from outside the patient's body so that the location of the marker, and thus the location of the elongated member, may be determined. Some non-limiting examples of imaging markers may include radiopaque markers (e.g., gold, platinum, tantalum, or tungsten), ultrasound-visible markers (e.g., glass or ceramic microballoons or microspheres), magnetic resonance markers (e.g., gadolinium foil and powder, gadolinium salts, nanocrystalline iron oxide, or iron powder), or any other fiducial markers configured to be detected under one or more imaging modalities. The at least one imaging marker may be configured on the elongated member as a band, strip, paddle, dot, or any other shape or configuration.

In some embodiments, at least one imaging marker may be included on the elongated member in a first marker location between the first region of the elongated member and the second region of the elongated member. Additionally, or alternatively, at least one imaging marker may be included on the elongated member in a second marker location between the second region of the elongated member and a delivery wire. Additionally, or alternatively, at least one imaging marker may be included on the elongated member in a third marker location at a distal tip of the first region of the elongated member. Additionally, or alternatively, at least one imaging marker may be included on the elongated member in a fourth marker location at a proximal end of the second region of the elongated member. Advantageously, the at least one imaging marker may allow the elongated member to be visualized as it is moved within the patient's body, e.g., by the support mechanism or a delivery wire.

Aspects of the present disclosure may relate to a novel device for the delivery of endovascular instruments, including but not limited to endovascular coils, to a treatment site within a body, including but not limited to aneurysms and other hollow body organs. The novel device may further include a flexible, elongated sheath, which may be, for example, a hollow delivery catheter or microcatheter. Further, in some embodiments, an electrode may be configured on an inner surface of the flexible, elongated sheath near the distal tip of the flexible, elongated sheath. Consistent with disclosed embodiments, an electrode may be configured to deliver electric current to an endovascular instrument, which may be, for example, an endovascular coil. The endovascular instrument may be axially advanced through the flexible, elongated sheath, resulting in the cutting or severing of the portion of the endovascular instrument that may be in contact with the electrode. Thus, in such embodiments, the severed section of the endovascular instrument may remain within an aneurysm while the rest of the endovascular instrument may be removed from the body with the flexible, endovascular sheath, or may be used for further filling of the aneurysm.

In some embodiments of the present disclosure, a novel device may be configured with an electrode on an inner surface of a microcatheter. Microcatheters, and other types of flexible, elongated sheaths, incorporating electrodes may be used for ablation procedures, whereas electrodes on the outer surface of a microcatheter, and other types of flexible, elongated sheaths, may selectively destroy tissue. The novel device may have electrodes mounted only on the inner surface for delivery of current through the inner lumen. Thus, current may not flow to the surrounding tissue and may not injure the patient. Advantageously, this may allow the coil-cutting mechanism to be used while the microcatheter, or other type of flexible, elongated sheath, may be within the patient's body, without risk of accidental damage to healthy tissue.

Aspects of the present disclosure may relate to medical devices configured for the delivery of an endovascular instrument to a treatment site within a body. As used herein, a medical device may include any apparatus, device or instrument configured to be delivered into, or to otherwise come in contact with, the body of a patient for use in the diagnosis of a disease or condition, in the cure, mitigation, treatment, or prevention of disease, to perform a medical operation or procedure, or any other suitable medical purpose. Some non-limiting examples of the medical device may include catheters, microcatheters, trocars, cannulae, needles, or any other hollow medical tubing or device configured to be inserted or delivered into a patient's body.

Consistent with disclosed embodiments, the exemplary medical device may be configured for delivery of an endovascular instrument to a treatment site within a body. As used herein, delivery of the endovascular instrument to a treatment site may include using the medical device for conveying, carrying, transporting, distributing, or any other similar means of facilitating movement of the endovascular instrument from an origin site (e.g., outside of the patient's body) to an area of a patient's body intended to receive medical treatment, optionally from the medical device. In some embodiments, the treatment site may include a hollow body structure such as an aneurysm, as discussed herein. In some embodiments, the medical device may be advanced through the body (e.g., over a guidewire) until the distal end of the medical device is located at or in close proximity to the treatment site. Then, the medical device may be used to pass the endovascular instrument from outside the patient's body to the treatment site. In some embodiments, the endovascular instrument may be passed through an inner lumen of the medical device to reach the treatment site. Additionally, or alternatively, the endovascular instrument may be delivered over the medical device to reach the treatment site.

FIGS. 12A and 12B depict an exemplary medical device 1200, which may include an elongated sheath 1210 (e.g., a microcatheter). As shown in FIGS. 12A and 12B, the medical device 1200 may be configured to deliver an endovascular instrument 1220, such as an endovascular coil. As shown in FIG. 22A, the endovascular coil 1250 may be delivered to a hollow body structure 2282, such as an aneurysm. For example, endovascular instrument 1220 may be delivered through inner lumen 1214 of medical device 1200 to the hollow body structure 2282, for example to permanently implant at least part of the endovascular instrument 1220 within the hollow body structure 2282. As shown in FIGS. 22E-22F, medical device 1200 may then be removed from the body, and in some examples may leave at least part of endovascular instrument 1220 implanted within the hollow body structure 2282.

Consistent with disclosed embodiments, the medical device may include a flexible, elongated sheath having a proximal end and a distal end. As used herein, the term "proximal" may refer to a location closer to the user or operator of the sheath (e.g., a physician). The term "distal" may refer to a location closer to the treatment location, as discussed herein.

FIGS. 12A and 12B depict an example of a medical device 1200, which may include a flexible, elongated sheath 1210. For example, sheath 1210 may include a catheter, a microcatheter, or any other suitable sheath. The sheath 1210 may have a distal end 1212 and a proximal end (not shown).

Consistent with disclosed embodiments, the medical device may include an inner wall of the flexible, elongated sheath delimiting an inner lumen extending between the proximal end and the distal end of the flexible, elongated sheath. Embodiments may include a distal section of the flexible, elongated sheath that terminates at the distal end of the flexible, elongated sheath. Some embodiments of the medical device may be configured such that a distal section of the flexible, elongated sheath has an axial length of one inch or less, ten inches or less, one centimeter or less, two millimeters or less, or any other similar measurement. As used herein, axial length may refer to the length of the distal section of the flexible, elongated sheath measured in relation to or around a real or imaginary line (such as a straight line, a curved line, etc.) going through the center of the endovascular instrument. As used herein, the inner lumen may include an interior passage or inside space of a tubular or hollow structure. As discussed herein, delimiting may refer to determining, establishing, setting, fixing, defining, delineating or any other means of determining the limits or boundaries of the inner lumen. Advantageously, an inner wall of the flexible, elongated sheath may form the inner lumen within the flexible, elongated sheath that may extend between the proximal end and the distal end of the flexible, elongated sheath. Additionally, or alternatively, the inner lumen formed by the inner wall of the flexible, elongated sheath may provide space for an endovascular instrument to pass through to the treatment site. In alternative embodiments, one, two, three or multiple inner walls of the flexible, elongated sheath may form one, two, three or many inner lumens within the flexible, elongated sheath that may extend between the proximal end and the distal end of the flexible, elongated sheath.

FIGS. 12A and 12B depict an exemplary medical device 1200 which may include an outer tube 1230 with an inner wall 1211 of the flexible, elongated sheath 1210. The inner wall 1211 may form an inner lumen 1214 extending between a proximal end and a distal end of the flexible, elongated sheath. As depicted in FIGS. 12A and 12B, the flexible, elongated sheath 1210 may be a microcatheter. In some embodiments, an endovascular instrument 1220 may be advanced through the inner lumen 1214 to the treatment site. FIGS. 12A and 12B also illustrate a distal section of the flexible, elongated sheath 1210, not necessarily drawn to scale, configured to any axial length including but not limited to one inch or less, ten inches or less, one centimeter or less, two millimeters or less or any other similar measurement.

Consistent with disclosed embodiments, the medical device's inner lumen may be sized to enable axial advancement of the endovascular instrument therethrough. As used herein, axial advancement may be the forward, onward or backward movement relating to or around a real or imaginary line (such as a straight line, a curved line, etc.) going through the center of the endovascular instrument. A non-limiting example of an inner wall size of a flexible, elongated sheath may include an inner lumen with a larger diameter than an outer diameter of the flexible, elongated sheath. Another non-limiting example of the inner wall size of the flexible, elongated sheath may include a stretchable sheath that enables an endovascular instrument to axially advance through, where a perimeter of a cross section of the inner lumen of the flexible, elongated sheath stretches during axial advancement of the endovascular instrument. For example, the medical device may have a diameter smaller than the diameter of the inner lumen of the flexible, elongated sheath so that the endovascular instrument (for example, an endovascular coil) may axially advance to the treatment site. Additionally, or alternatively, the flexible, elongated sheath may not have the inner lumen with a larger diameter than the outer diameter of the endovascular instrument. Thus, when the endovascular instrument axially advances through the inner lumen or multiple inner lumens, the flexible, elongated sheath may stretch to allow the endovascular instrument to reach the treatment site.

FIG. 16A depicts an example of a medical device 1200 axially advancing towards the treatment site. FIGS. 16B-16C illustrate a cross sectional view of the example of the medical device 1200 depicted in FIG. 16A. FIG. 16B provides a depiction of an inner lumen 1214 having a smaller diameter 1668 than an outer diameter 1666 of a flexible, elongated sheath 1210 for axial advancement of an endovascular instrument 1220 (e.g., an endovascular coil) to reach the treatment site.

Consistent with disclosed embodiments, the medical device may include at least one electrode within the distal section of the flexible, elongated sheath. As used herein, at least one electrode refers to an electrical conductor used to selectively make contact with an object and to enable an electrical current to flow from the at least one electrode to the object or from the object to the at least one electrode. The at least one electrode may be made of, for example, copper, zinc, gold, platinum, titanium, brass, graphite or any other suitable material, including combinations of the same. Other non-limiting examples of such objects may include an endovascular instrument, an endovascular coil, and so forth. In some embodiments, the at least one electrode may permanently or selectively make contact with an object by connecting the at least one electrode to a wire made of electrical conductor material, and the current may flow from the wire to the object through the at least one electrode or from the object to the wire through the at least one electrode. In some examples, selectively making contact with the object may include making contact with the object when particular conditions are fulfilled and not making contact with the object when the particular conditions are not fulfilled. For example, the at least one electrode may be configured to selectively make contact with a segment of the endovascular instrument within an inner lumen. In some examples, the particular conditions may include any combination of: (i) the segment of the endovascular instrument being within a particular region of the inner lumen, (ii) the segment of the endovascular instrument having a diameter of at least a selected threshold, and (iii) the at least one electrode being in a position (of a plurality of alternative possible positions of the electrode) that fulfills a condition. In some examples, one or more of the above conditions may be controlled by a user, by an automated process, and so forth.

FIGS. 12A and 12B depict an example of a medical device 1200 with at least one electrode 1242 within the distal section 1213a of the sheath. In FIG. 14, the at least one electrode 1242 may be connected via an embedded wire 1243 (e.g., copper wires) to the distal end 1213a of a flexible, elongated sheath and to the controller and power source. FIG. 16A depicts the at least one electrode 1242 selectively not in contact with an object (e.g., an endovascular instrument 1220). FIG. 17A depicts a section of the endovascular instrument 1220 selectively in contact with the at least one electrode 1242, 1244.

Consistent with disclosed embodiments, at least one electrode may be configured to selectively deliver an electric current through a segment of the endovascular instrument within the inner lumen. As used herein, an electric current may be any movement or stream of electric charge carriers including electrons, protons, ions or any other electrically charged particle through an electrical conduct or space. As discussed herein, the electric current may be delivered selectively, restrictively, individually, personally, particularly, specifically or in any other way that involves the selection of a parameter. In some examples, the at least one electrode may be configured to selectively deliver the electric current through the segment of an endovascular instrument within an inner lumen, for example to deliver the electrical current when particular conditions are fulfilled. In some examples, the particular conditions may include any combination of: (i) the at least one electrode may be making contact with a segment of an endovascular instrument within the inner lumen (which may be controlled as described above), or with another particular part of the endovascular instrument; and (ii) there may be an electric potential difference between the at least one electrode and a segment of the endovascular instrument, or between the at least one electrode and a second electrode making contact with a segment or other particular part of the endovascular instrument. The electric potential difference may be controlled, for example by connecting or disconnecting the at least one electrode to an electric power source, for example using the wire described above, for example by a user, by an automated process, and so forth.

FIGS. 12A and 12B illustrate an exemplary medical device with at least one electrode 1242 configured to selectively deliver an electric current through a segment of an endovascular instrument 1220 (e.g., an endovascular coil) within an inner lumen 1214 of a flexible, elongated sheath 1210 (e.g., a microcatheter). FIG. 18A depicts a severed coil section 1826 with a severed coil end 1826a and a remaining coil section 1828 after the at least one electrode 1242 selectively delivers the electric current through the segment of the endovascular instrument 1220 (e.g., the endovascular coil).

Consistent with disclosed embodiments, an electric current may be delivered selectively through the segment of the endovascular instrument while the distal section of the sheath may be positioned within the body. The distal section of an elongated, flexible sheath may be positioned, deposed, deposited, disposed, emplaced, fixed, laid, placed, put, set, set up, situated or arranged in any other way within the body. For example, the distal section the elongated, flexible sheath may be advantageously axially advanced to a treatment site within a patient's body to a hollow body structure, such as an aneurysm. Upon arrival of the distal section, the electric current may be delivered selectively through an endovascular instrument.

FIGS. 12A and 12B illustrate an exemplary medical device 1200 for delivery to a treatment site, such as an aneurysm 2282 within a body. The medical device 1200 may include a flexible, elongated sheath 1210 having a proximal end and a distal end. The flexible, elongated sheath 1210 (e.g., a microcatheter) may have a distal end 1212 to be axially advanced to a hollow body structure 2282 (e.g., an aneurysm). Once the distal end of the flexible, elongated sheath 1212 has reached the aneurysm, an electric current may be delivered selectively through the segment of an endovascular instrument 1220 (e.g., an endovascular coil).

Consistent with disclosed embodiments, the at least one electrode may be configured to sever a portion of the endovascular instrument in contact with the at least one electrode, such that a region of the endovascular instrument distal to the severed portion may be detached from a second region of the endovascular instrument. An endovascular instrument may be in contact with the at least one electrode when a union or junction of surfaces or any other method of meeting occurs. As discussed herein, sever may refer to disconnecting, separating, splitting, cutting, slicing, or any other means to partition the endovascular instrument into two or more individual pieces, which are distinct from and can be moved relative to the other parts of the endovascular instrument. For example, the endovascular instrument can make contact with the at least one electrode in a plethora of ways including, but not limited to, (i) on an inner wall of an inner lumen across from a constrictor (for example, across from a balloon), (ii) on the inner wall of the inner lumen next to a constrictor (for example, next to a balloon), (iii) on a constrictor (for example, on a balloon), or (iv) on no inner wall of the inner lumen but within the inner lumen.

FIG. 18A illustrates an exemplary medical device 1200 with at least one electrode 1242. FIG. 17A depicts a coil section 1724 in contact with the at least one electrode 1242, 1244. Some embodiments, including but not limited to FIG. 18A, may depict a severed coil section 1826, a severed coil end 1826*a*, and a remaining coil section 1828. As shown in FIG. 18B, the severed coil section 1826 may be detached from the remaining coil section 1828. Advantageously, FIG. 16A depicts the at least one electrode 1242 on an inner wall of an inner lumen 1214 across from a balloon 1260.

Consistent with disclosed embodiments, the at least one electrode may include at least one conductive filament connected to the inner wall of the distal section of the sheath. As used herein, the at least one conductive filament may be positioned in an internal part of a distal portion of a flexible, elongated sheath. As used herein, the at least one conductive filament may be one where electricity can flow through a filament. As used herein, connected may include filaments mounted directly to, attached directly to, attached indirectly to an inner wall of a distal section of a flexible, elongated sheath via a third object or any other similar means. Some non-limiting examples of at least one conductive filament may include copper, silicon, rubber, elastic or any other property so that the at least one conductive filament, two conductive filaments, or multiple conductive filaments may be pushed away towards the inner wall of an elongated, flexible sheath by an endovascular instrument passing through an inner lumen which may create contact with the endovascular instrument without blocking it. Advantageously, the at least one conductive filament may be configured to wrap helically around the inner wall of the distal section of the flexible, elongated sheath. In other embodiments, the at least one conductive filament may also be configured to line the inner wall of the distal section of the flexible, elongated sheath. Alternatively, or additionally, one conductive filament may wrap helically around the inner wall of the distal section of the flexible, elongated sheath and another or multiple other conductive filaments may wrap helically by crossing the one conductive filament.

FIG. 3 illustrates an exemplary system 300 for endovascular coil cutting. At the flexible, elongated sheath distal end 112, coil-cutting apparatus 340 may include electrodes 342, 344 that may bulge into the flexible, elongated sheath's lumen 114 from opposite sides to form passive elements 347, 348 configured, for example, as leaf springs. Passive elements 347, 348 may be biased toward the center of the flexible, elongated sheath 110, such that electrodes 342, 344 may remain in contact with coil 120 even while the coil is moved distally or proximally. When an electrical current pulse is received from the power source and delivered to electrodes 342, 344 via wires 343, 345, respectively, passive elements 347, 348 may pass the current through coil section 124 to sever the coil. As a result, the distal segment 122 of the coil may be detached from the flexible, elongated sheath 110 and from the remainder of the coil 120.

Consistent with disclosed embodiments, the at least one electrode may be a first electrode in a pair of spaced-apart electrodes. In some embodiments, the at least one electrode may be a second or any other electrode in the pair or pairs of spaced-apart electrodes. As used herein, a pair of spaced-apart electrodes may be arranged with space or spaces between two or more electrodes. Non-limiting examples of the pair of spaced-apart electrodes may include two or more electrodes proximally or distally situated to the balloon, on a surface of the balloon at the extremum point, proximal to the extremum point, distal to the extremum point, left of the extremum point, right of the extremum point or any other similarly situated relation of space. Other non-limiting examples of the pair of spaced-apart electrodes may include two or more electrodes proximally or distally situated to a constrictor, on a surface of the constrictor at the extremum point, proximal to the extremum point, distal to the extremum point, left of the extremum point, right of the extremum point or any other similarly situated relation of space. More examples of the pair of spaced-apart electrodes may further include situating two or more electrodes on a flexible, elongated sheath to either side of the constrictor or the balloon, on the opposite side of the flexible, elongated sheath from the constrictor or the balloon or on any other side of a wall of an inner lumen.

FIGS. 12A and 12B illustrate an example of a medical device 1200 with at least one electrode 1242. FIGS. 12A and 12B depict a sealing distal tip 1232 at a distal end of the endovascular device 1202. In some embodiments, sealing distal tip 1232 may be made of a conductive material, and thus, sealing distal tip 1232 may be or include the at least one electrode 1242. In such embodiments, sealing distal tip 1232 may be a second electrode. In FIG. 12B, a balloon 1260 may be depicted across from the at least one electrode 1242. FIG. 13 illustrates an embedded wire 1345 within an outer tube 1230 of a flexible, elongated sheath 1210 (e.g., a microcatheter) which runs to a distal end of the outer sheath to the sealing distal tip 1232. Advantageously, in embodiments in which sealing distal tip 1232 is made of conductive material, FIGS. 12A and 12B depict the at least one electrode 1242 in relation to the second electrode within the sealing distal tip 1232 which forms one non-limiting example of a pair of spaced-apart electrodes.

Consistent with disclosed embodiments, the first electrode and the second electrode may be situated at different longitudinal positions along the medical device. As used herein, different longitudinal position may relate to a space or spaces relative to the instrument's length rather than width. Some non-limiting examples may include the first and second electrode or more electrodes spaced one inch or less, ten inches or less, one centimeter or less, two millimeters or less or any other similar measurement measured in relation to the length of the medical device.

FIGS. 12A and 12B illustrate an example of a medical device 1200 with the at least one electrode 1242 in a pair of spaced-apart electrodes. In some embodiments, as discussed above, FIGS. 12A and 12B also depict a second electrode within at the distal end of an endovascular device 1202 at a sealing distal tip 1232. Further, FIGS. 12A and 12B depict the at least one electrode 1242 and the second electrode within the distal end of the endovascular device 1202 at the sealing distal tip 1232 at different longitudinal positions.

Further consistent with disclosed embodiments, the pair of electrodes may be configured to cause electric current to flow along a path from the first electrode to a second electrode of the pair of electrodes and be configured to sever the endovascular instrument along the path. As used herein, flow may refer to the stream or movement of electric current. As used herein, path may refer to a line, pathway, route or any other direction between two points. A non-limiting example of electric current flowing along a path may include taking a wire and connecting the positive and negative terminals on a battery together. The electric current may flow along any path between two or more electrodes including but not limited to: (i) through an inner lumen, (ii) through a flexible, elongated sheath, (iii) around a flexible, elongated sheath and then through the sheath or any other path formed between two or more electrodes. Further consistent with disclosed embodiments, the path from the first electrode to the second electrode passes through the inner lumen of the flexible, elongated sheath. As used herein, passing through may refer to moving, transferring, traveling or going through some place, thing, or space on the way to some other place, thing, or space. A non-limiting example may include electrical current passing through a metal, aqueous solution, graphite or any other substance in which an electrical charge can flow.

FIGS. 12A and 12B illustrate an example of a medical device 1200 with an embedded wire 1243 within a flexible, elongated sheath 1210. FIG. 16C depicts, solely for illustrative purposes, a cross sectional view of the example of a medical device 1200 and the embedded wire 1243 within the inner lumen 1214 of the flexible, elongated sheath 1210. FIG. 18A illustrates the aftermath of an electric current flowing along a path from the at least one electrode 1242 to the second electrode located within the sealing distal tip 1232. FIG. 17A illustrates the coil section 1724 in contact with the at least one electrode 1242, 1244, resulting in a severed coil section 1826 and a remaining coil section 1828.

Consistent with disclosed embodiments, the medical device may include an outer tube covering and fixedly connected to at least the distal section of the flexible, elongated sheath. As used herein, an outer tube covering may enclose the medical device. A non-limiting example of the outer tube covering may be a hydrophilic or any other covering with an affinity for water. The outer tube covering may further include the second electrode. As used herein, include may refer to the outer tube covering configured to comprise, contain, embed or any other similar mean to make the second electrode part of the whole outer tube covering. As used herein, fixedly connected may relate to holding the outer tube firmly in position, stationary, established, not subject to change or variation, unchanging or any other means of fastened connection to the at least distal section of the sheath. Further, embodiments may be fixedly connected by mounting the outer tube directly to, attached directly to, attached indirectly to medical device via a third object or any other similar means.

FIGS. 12A and 12B illustrate an exemplary medical device 1200 with an outer tube covering 1230 (e.g., an outer sheath). Further, FIGS. 12A and 12B may depict the outer tube 1230 to be configured with a sealing distal tip 1232 embedded therein. In some embodiments, as discussed above, sealing distal tip 1232 may include a second electrode.

Consistent with disclosed embodiments, the second electrode may be situated on an inner surface of the outer tube at a position distal to the first electrode. As used herein, the outer tube covering may have an inner surface and an outer surface. As used herein, situated may refer to the location, site, position, or any other certain place. Embodiments may be configured where the second electrode may be situated on the inner surface of the outer tube covering distally positioned to the first electrode. For example, the second electrode may be situated within the distal end of the endovascular device next to the at least one electrode. Another non-limiting example might be configured where the second electrode may be situated nearer the distal end of the endovascular device further away from the at least one electrode.

Consistent with disclosed embodiments, the at least one electrode may be positioned on the inner wall of the sheath and may be configured to contact the segment of the endovascular instrument to cause the electric current to flow through the endovascular instrument. Some non-limiting examples of the at least one electrode may be positioned on the inner wall of the sheath opposite a balloon, on the inner wall of the sheath next to a balloon, on the inner wall of the distal portion, on the inner wall of the proximal portion or any other space along the inner wall of the sheath. Further, the at least one electrode on the inner wall of the sheath at any space may be configured to contact a segment of an endovascular instrument.

FIGS. 12A and 12B illustrate an exemplary medical device 1200 with the at least one electrode 1242 positioned on the inner wall 1211 of the flexible, elongated sheath 1210. FIGS. 12A and 12B also illustrate an endovascular instrument 1220 (e.g., an endovascular coil). FIG. 17A depicts a coil section 1724 in contact with the at least one electrode 1242, 1244.

Consistent with disclosed embodiments, the medical device may include an electrode position element configured for selectively moving the at least one electrode relative to the segment of the endovascular instrument. As used herein, electrode position element may refer to the part of the medical device where the at least one electrode sits. Consistent with disclosed embodiments, the electrode position element may include a portion adjacent to a side wall of the flexible, elongated sheath and may have a flexibility greater than a flexibility of the side wall of the flexible, elongated sheath. As used herein, portion may refer to a part, piece, bit, section, segment, fragment or any other similar part of a whole. As used herein, adjacent may refer to adjoining, abutting, close to, near to, by, by the side of, beside, alongside or any other relation relating to next to. As used herein, side wall may refer to a wall of the sheath forming a side of the sheath. As used herein, flexibility may refer to elasticity, stretch or any other descriptor relating to the quality of bending easily without breaking. In some embodiments, the at least one electrode may sit within the distal end of the endovascular instrument. Additionally, or alternatively the at least one electrode may sit within the proximal end of the endovascular instrument. Some non-limiting examples may be configured where the at least one electrode sits on the same or opposite side of the inner lumen from a balloon or balloons, sits in proximal relation to a balloon or balloons, sits in distal relation to a balloon or balloons, sits on the apex of a balloon or balloons, sits on the side of a balloon or balloons, sits on the end of a balloon or balloons or another similar configuration relative to the segment of the endovascular instrument. Further, the electrode position element may also be configured to include a constrictor and/or balloon, as discussed herein.

FIGS. 12A and 12B illustrate an example of a medical device with an electrode position element 1242 and a balloon 1260. FIGS. 12A and 12B depict at least one electrode 1242 in the distal end of an endovascular instrument 1220 (e.g., an endovascular coil). FIGS. 16A-17C may depict the balloon 1260 selectively moving the at least one electrode 1242 relative to a segment of the endovascular instrument 1220. As depicted in FIG. 16A, in some embodiments the endovascular instrument 1220 may be within the inner lumen 1214 with some space between the balloon 1260 and the at least one electrode 1242. As depicted in FIG. 17A, in some embodiments part of the balloon remains fixed to an outer surface of a flexible, elongated sheath 1210 (e.g., a microcatheter). A portion of the balloon may protrude into the flexible, elongated sheath 1210, so that a section 1724 of the endovascular instrument 1220 comes into contact with the at least one electrode 1242, 1244. In some embodiments, the balloon 1260 may have a flexibility greater than the flexibility the flexibility of the side wall of the flexible, elongated sheath 1210 as indicated by the portion 1562 of the balloon protruding into the flexible, elongated sheath.

Consistent with disclosed embodiments, the electrode position element may be configured to reduce a distance between the at least one electrode and the endovascular instrument through flexing of the electrode position element. As used herein, reduce may refer to lessening, lowering, bringing down, decreasing, diminishing, shrinking, narrowing, contracting, shortening or any other term denoting to make smaller or less in amount, degree, or size. As used herein, between may refer to the space in the middle of the at least one electrode and the endovascular instrument. As used herein, flex may refer to contracting, extending, tensing or any other reference of binding or becoming bent. For example, one or more balloons may be configured to reduce a distance between the at least one electrode and an endovascular instrument through flexing of the electrode position element. This may be accomplished by the electrode position element configured on the apex of one or more balloons so that when biological material flows through an inflation passage and into one or more balloons they fill or flex to reduce the distance between the at least one electrode and the endovascular instrument.

FIG. 17A illustrates an example of a medical device 1200 with a portion 1562 of a balloon 1260 protruding into a flexible, elongated sheath 1210 (e.g., a microcatheter). FIG. 17B depicts a reduced distance between at least one electrode 1242 and an endovascular instrument 1220 (e.g., an endovascular coil). The balloon 1260 may flex due to blood or other biological material passing through the inflation passage 1662 into and filling the balloon 1260. This may push the balloon 1260 into the flexible, elongated sheath 1210.

Consistent with disclosed embodiments, the electrode position element may include a shape-memory component associated with the distal section of the flexible, elongated sheath. The shape-memory component, in some embodiments, may be configured to be selectively deformable for pressing the at least one electrode against the endovascular instrument. As used herein, deformable may refer to contorting, twisting, warping, disfiguring, misshaping or any other term relating to changing the form of a shape-memory component. As used herein, pressing may refer to bearing down on, leaning on, forcing on, squeezing on or any other term relating to moving or causing movement into a position of contact with something by exerting continuous physical force. As used herein, a shape-memory component may be configured to be an alloy that can be deformed with applying various temperature or temperatures but can also return to its pre-deformed or remembered shape when applying various temperature or temperatures. For example, the alloy can be Nitinol. In some embodiments, a shape-memory component may be curved or arc-shaped so as to form a convex shape relative to the inner lumen. Any alloy which makes a shape-memory component exhibits two distinct phases: the martensite phase at lower temperatures, in which the alloy may be easily twisted or deformed, and the austenite phase at higher temperatures, in which the alloy returns to a pre-formed or "remembered" shape and becomes stiffer and more resistant to deformation.

FIG. 7A illustrates a cylindrical base 750 and spring beam 760, either or both of which may be constructed from a shape-memory alloy such as Nitinol. In a similar manner, some embodiments of the example of a medical device 1200 depicted in FIGS. 12A and 12B may be configured to use a shape-memory alloy. The balloon 1260 may be configured to be made of a shape-memory component within the distal section 1212 of a flexible, elongated sheath 1210 (e.g., the microcatheter). The shape-memory component of the balloon 1260 may be configured to be selectively deformable so as to press the at least one electrode 1214 against the endovascular instrument 1220 (e.g., the endovascular coil).

Consistent with disclosed embodiments, the medical device may include at least one controller. The at least one controller is described in greater detail within the introduction. The controller, in some embodiments, may be configured to obtain an input and control the flow of the electric current from the at least one electrode through the segment of the endovascular instrument based on the input. Some examples of such input are discussed below. As used herein, input may refer to what may be put in, taken in, or operated on by any process or system for example. As used herein, control may refer to running, managing, directing, administering, guiding, or determining the behavior of or supervising the running of the flow of electric current from the at least one electrode through the segment of the endovascular instrument based on the input. For example, a use may use a keyboard, joystick, or mouse as the at least one controller. Advantageously, the medical device may be configured to obtain an input such as the press of a button, click of a joystick, or click of a mouse to control the flow of the electric current from the at least one electrode through the segment of the endovascular instrument based on the input.

Figure 19:
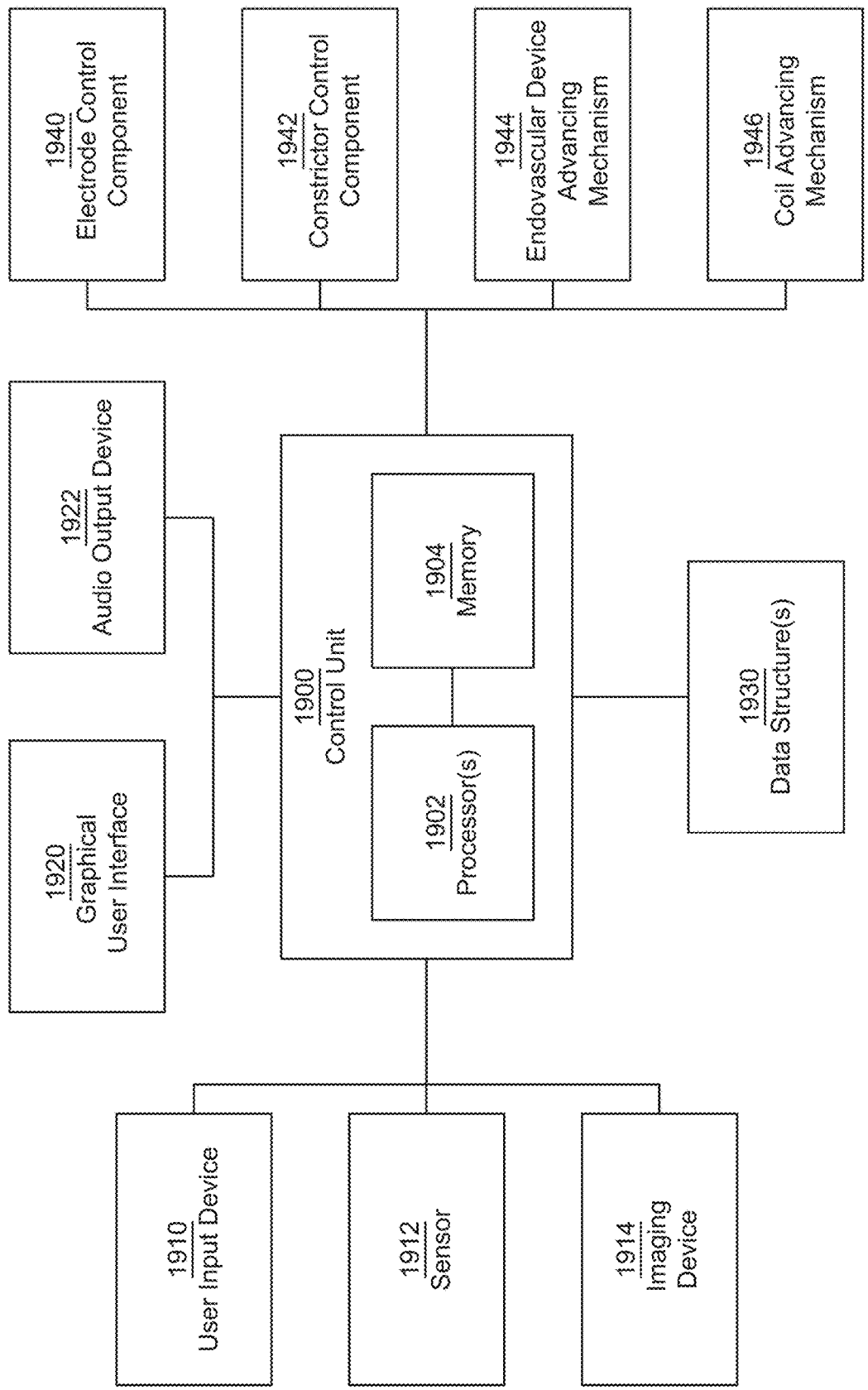
FIG. 19 is a block diagram of an example of a system for monitoring and controlling endovascular devices and procedures, consistent with disclosed embodiments.
Figure 37:
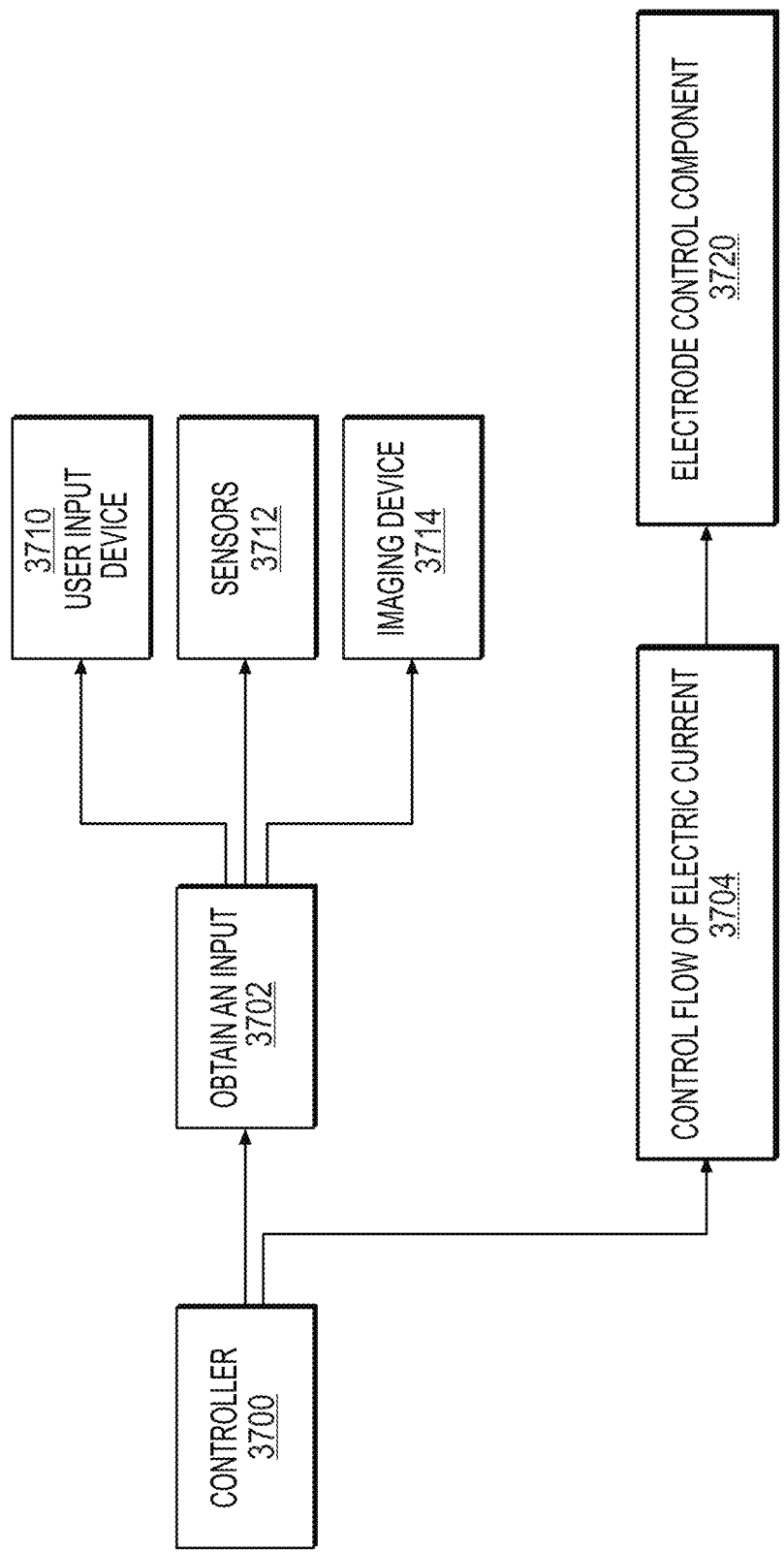
FIG. 37 depicts at least one controller with an input configured to control flow of electric current, consistent with disclosed embodiments.

FIG. 19 illustrates an exemplary medical non-transitory computer readable medium for the medical device with instructions configured to cause a flow of electric current. FIG. 37 illustrates at least one controller 3700. In some embodiments, the at least one controller 3700 may be configured to obtain an input 3702 and control the flow of electric current 3704 within the electrode control component output 1940 to the endovascular device advancing mechanism component 1944.

Consistent with disclosed embodiments, the input may be configured to include at least one but not limited to one of:

(i) an input from a user of the medical device, (ii) first data derived from at least one sensor output, or (iii) second data derived from at least one medical image. The flow of electric current from the at least one electrode through the segment of an endovascular instrument may be controlled based on an input. In one example, the input from a user may be indicative of a desire of the user to initiate, stop or adjust the flow of the electric current. In some examples, the input may include an input from a user of the medical device, such as a press of a button, a turn of a dial, an input through a user interface, a voice command recognized in a captured audio data through voice recognition algorithms, a gesture recognized in a captured image data through gesture recognition algorithms, and so forth. In some examples, the input may include data derived from at least one sensor output. For example, the sensor may measure electrical impedance, for example using the electrode. In some examples, the input may include data derived from at least one medical image, such as an x-ray image or a CT image of the medical device inside the body of the patient. In one example, the data derived from at least one sensor output or the data derived from at least one medical image may be analyzed using a classification model to determine a desired effect on the flow of the electric current.

FIG. 19 illustrates an exemplary non-transitory computer readable medium. In some embodiments, FIG. 19 depicts different inputs (a user input device 1910, sensors 1912, and an imaging device 1914). FIG. 37 depicts the input may be configured to include at least one but not limited to a user input device 1910, sensor or sensors 1912, or an imaging device 1914. In some embodiments, one or more of the inputs may be configured to be included in controlling the flow of electric current 3704 from the at least one electrode 1242 through the segment of the endovascular instrument 1220. For example, the user input device 1910 and the data derived from the imaging device 1914 may be included in the input. In other non-limiting examples, the first data derived from the at least one sensor output 1912 and the data derived from the imaging device 1914 may be included in the input. Advantageously, the user input device 1910, the first data derived from the at least one sensor output 1912, and/or the data derived from the imaging device 1914 may be included in the input.

Consistent with disclosed embodiments, the endovascular instrument may include an endovascular coil. Embodiments may further include the at least one electrode configured to sever a portion of the endovascular coil in contact with the at least one electrode. Consistent with disclosed embodiments, the medical device may be configured to enable selective cutting of the endovascular coil at a plurality of locations along the endovascular coil via the at least one electrode.

In some examples, methods and non-transitory computer readable media for facilitating operation of endovascular catheters are provided. An endovascular catheter may be configured to enable passage of an endovascular device through it.

According to another embodiment of the present disclosure, medical non-transitory computer readable medium instructions configured to cause a flow of electric current within a flexible elongated sheath in a body of a patient may be provided. Embodiments may further include instructions including the steps, in no particular order of: (i) obtaining an input for sending the electric current from an electrode positioned within the flexible elongated sheath through a segment of an endovascular instrument received within an inner lumen of the sheath and (ii) controlling the flow of the electric current from the electrode through the segment of the endovascular instrument based on the input. In one example, input from the user may be indicative of a desire of the user to initiate, stop or adjust the flow of the electric current. In some examples, the input may include an input from a user of the medical device, such as a press of a button, a turn of a dial, an input through a user interface, a voice command recognized in a captured audio data through voice recognition algorithms, a gesture recognized in a captured image data through gesture recognition algorithms, and so forth. In some examples, the input may include data derived from at least one sensor output. For example, the sensor may measure electrical impedance, for example using the electrode. In some examples, the input may include data derived from at least one medical image, such as an x-ray image or a CT image of the medical device inside the body of the patient.

FIG. 19 illustrates an example of a medical non-transitory computer readable medium instruction configured to cause a flow of electric current. In some embodiments, and as depicted in FIG. 37, the instructions may obtain an input 3702 from a variety of sources (not limited to a user input device 1910, a sensor or sensors 1912, and an imaging device 1914) for sending the electric current from the at least one electrode 1242 positioned within the flexible, elongated sheath 1210 through a segment of the endovascular instrument 1220 (e.g., the endovascular coil) received within an inner lumen of the flexible, elongated sheath 1214. Further, consistent with disclosed embodiments, the instruction depicted in FIG. 37 may control the flow of the electric current 3704 from the at least one electrode 1242 through the segment of the endovascular instrument based on the input through various outputs (not limited to the electrode control component 1940, the balloon control component 1942, the endovascular device advancing mechanism 1944 or the coil advancing mechanism 1946).

Consistent with disclosed embodiments, the flow of the electric current may be controlled to cause the endovascular instrument to be severed.

FIGS. 12A and 12B illustrate an example of a medical device 1200. As discussed above, embodiments may also include at least one electrode 1242. The at least one electrode 1242 may further be configured to sever a portion 1724 of the endovascular instrument 1220 in contact with the at least one electrode 1242 through the output or outputs of electrode control component 1940 or balloon control component 1942. This may result in a severed coil section 1826 with a severed coil end 1826a and a remaining coil section 1828.

Consistent with disclosed embodiments, the instructions may be configured to further include the steps, in no particular order of: (i) obtaining a medical image of the body captured while the sheath may be positioned at least partially within the body and (ii) controlling the flow of the electric current from the electrode through the segment of the endovascular instrument based on data derived from the medical image. In some examples, the input may include data derived from at least one medical image, such as an x-ray image or a CT image of the medical device inside the body of the patient. In one example, the data derived from at least one sensor output or the data derived from at least one medical image may be analyzed using a classification model to determine a desired effect on the flow of the electric current.

FIG. 19 illustrates an example set of medical instructions. In some embodiments, input 3702 from an imaging device 1914 may be used to control the flow of the electric current 3704 from the at least one electrode 1242 through the segment of the endovascular instrument 1220 based on data derived from the imaging device 1914.

Consistent with disclosed embodiments, the medium may be configured to control the flow of the electric current based on the data derived from the medical image. Embodiments may further include data derived by calculating a convolution of at least part of the medical image to derive at least one output value of the calculated convolution. As used herein, a one-dimensional convolution is a function that transforms an original sequence of numbers to a transformed sequence of numbers. The one-dimensional convolution may be defined by a sequence of scalars. Each particular value in the transformed sequence of numbers may be determined by calculating a linear combination of values in a subsequence of the original sequence of numbers corresponding to the particular value. A value of a calculated convolution may include any value in the transformed sequence of numbers. Likewise, an n-dimensional convolution may be a function that transforms an original n-dimensional array to a transformed array. The n-dimensional convolution may be defined by an n-dimensional array of scalars (known as the kernel of the n-dimensional convolution). Each particular value in the transformed array may be determined by calculating a linear combination of values in an n-dimensional region of the original array corresponding to the particular value. An output value of a calculated convolution may include any value in the transformed array.

Embodiments may also include, in response to a first output value of the calculated convolution, causing a first electric current to flow from the electrode through the segment of the endovascular instrument.

Further, embodiments may also include, in response to a second output value of the calculated convolution, causing at least one of, but not limited to: (i) stopping the flow of electric current from the electrode through the segment of the endovascular instrument, and (ii) causing a second electric current to flow from the electrode through the segment of the endovascular instrument, the second electric current differing from the first electric current.

According to another embodiment of the present disclosure, a method for causing a flow of electric current within a flexible, elongated sheath in a body of a patient may be provided. Embodiments of the method may be configured for obtaining an input for sending the electric current from an electrode positioned within the flexible, elongated sheath through a segment of an endovascular instrument received within an inner lumen of the flexible, elongated sheath. Embodiments may also be configured for controlling the flow of the electric current from the electrode through the segment of the endovascular instrument based on the input in an amount sufficient to cause the endovascular instrument to be severed.

Aspects of this disclosure may relate to an endovascular device having a hollow sheath and a constrictor configured to reversibly narrow a portion of the inner lumen while the sheath is positioned, at least partially, within the body of a patient. In some embodiments, the endovascular device described below may be configured for delivery of an endovascular instrument. However, the endovascular device may additionally or alternatively be configured for use with other instrumentation and/or for other suitable purposes.

Various embodiments of the current disclosure may relate to an endovascular device. As used herein, an endovascular device may include any device or instrument configured to be placed within or to operate inside a blood vessel for a medical purpose, for example to diagnose and/or treat a patient. In some embodiments, an endovascular device may include any device or instrument configured to be used during, or to otherwise facilitate, endovascular surgeries and procedures, as described in greater detail herein. In some embodiments, an endovascular device may be configured to deliver a device, drug, or material from a first location (e.g., a location outside the body) to a treatment site in a blood vessel. Some non-limiting examples of endovascular devices may include catheters, microcatheters, balloon catheters, medical sheaths, guidewires, coils, endovascular revascularization devices, embolization devices, or any other device configured to be placed within a blood vessel.

For example, the present application depicts different views of an exemplary endovascular device 1200. As illustrated in FIGS. 12A, 12B, and 22A-22F, exemplary endovascular device 1200 may be configured to deliver an endovascular instrument (e.g., endovascular coil 1220) to a treatment site within the body, such as aneurysm 2282. Endovascular device 1200 may include an elongated flexible sheath 1210, a constrictor (e.g., balloon 1260, or any other constrictor, for example as described below), and, optionally, at least one electrode 1242. Additionally or alternatively to at least one electrode 1242, endovascular device 1200 may include other elements, as described below.

Consistent with disclosed embodiments, the endovascular device may include an elongated flexible sheath defining a lumen with an inner opening. As used herein, an elongated flexible sheath may refer to a cylindrical, hollow, or enveloping structure constructed of any suitable compliant polymeric material such as PTFE, PEBA, nylon, polyethylene, etc. Non-limiting examples of an elongated flexible sheath may include a microcatheter, a catheter, or a tube, and may include a thin, flexible tube which may be inserted through a narrow opening into a body cavity, e.g. to treat diseases or perform a surgical procedure, as described in greater detail herein. As used herein, a lumen with an inner opening may include a central cavity or channel of a tubular or other hollow structure. In some embodiments, the lumen may extend along the entire length of the sheath, such that the lumen has a first opening at the proximal end of the sheath and a second opening at the distal end of the sheath. Alternatively, the lumen may extend along a portion of the sheath. The exemplary endovascular device may include a single lumen or, alternatively, multiple lumens (e.g., two lumens, three lumens, four lumens, or any other suitable number of lumens).

Consistent with disclosed embodiments, the inner opening of the lumen may be sized for enabling selective advancement of an endovascular instrument therethrough. Thus, a lumen with an inner opening sized for enabling selective advancement of an endovascular instrument therethrough may refer to the lumen of the sheath having a large enough cross-sectional area to allow for an endovascular instrument such as an endovascular coil to pass through the lumen, such as during use of the endovascular device for delivery of the instrument to a treatment site. As used herein, selective advancement of the instrument may refer to the movement of the endovascular instrument through the inner opening being controllable (e.g., by a user of the endovascular device), such that the direction, speed, and length of the endovascular instrument passed through the inner opening may be controlled. For example, selective advancement of the endovascular instrument may enable proximal, distal, and rotational movement of the instrument relative to the endovascular device. Additionally, or alternatively, selective advancement may enable control over the length of the endovascular instrument that is delivered from the distal end of the endovascular device (and, thus, the length of the instrument remaining within the lumen of the endovascular device).

For example, as depicted in FIGS. 12A and 12B, endovascular device 1200 may include microcatheter 1210, which may be an example of an elongated flexible sheath. Microcatheter 1210, or the elongated flexible sheath, may define an inner lumen 1214 with an inner opening sized for selective advancement of an endovascular instrument 1220 (such as endovascular coil) therethrough. In addition, as shown in FIGS. 22A-22F, endovascular coil 1220 may be configured to remain in a straightened delivery configuration while constrained within endovascular device 1200 and may bend into a three-dimensional structure, such as a helix or cage, when discharged from endovascular device 1200 into the interior volume 2284 of the aneurysm.

Consistent with disclosed embodiments, the sheath may have at least a first region and a second region. Optionally, the sheath may have additional regions (e.g., a third region, a fourth region, etc.). In some embodiments, the first region of the sheath may refer to an area of the elongated flexible sheath beginning at a distal tip of the sheath and extending a predetermined distance in the proximal direction. As discussed in detail below, the first region may optionally include at least one electrode. The second region of the sheath may be located in a proximal direction from the first region and may encompass either the entirety or a fraction of the portion of the sheath which is not a part of the first region. In some embodiments, the second region may be immediately adjacent to the first region, such that a proximal end of the first region abuts a distal end of the second region. Alternatively, one or more additional regions may be positioned in between the first and second regions. As an example, the microcatheter 1210 depicted in FIGS. 12A and 12B may include a first region 1213a and a second region 1213b. First region 1213a may be located in a distal direction from second region 1213b and may include the distal end 1202 of the microcatheter.

Consistent with disclosed embodiments, the endovascular device may include an electrode within the first region of the sheath. As used herein, an electrode may include an electrical conductor used to selectively make contact with an object and to enable an electrical current to flow from the electrode to the object and/or from the object to the electrode, as described in further detail herein. In some embodiments, multiple electrodes may be included within the first region of the sheath. For example, the first region may include at least a first electrode configured as a cathode and a second electrode configured as an anode.

For example, as depicted in FIGS. 12A and 12B, endovascular device 1200 may include a first electrode 1242 within first region 1213a (i.e., the distal region) of microcatheter 1210 or of the elongated flexible sheath. Electrode 1242 may be mounted on, or otherwise connected to, the inner wall of microcatheter 1210 (or of the elongated flexible sheath) and may be located across the inner lumen from balloon 1260 and/or from the constrictor, such that endovascular coil 1220 may pass between them. In another example, electrode 1242 may be positioned on balloon 1260 and/or on the constrictor. Endovascular device 1200 may also include a sealing distal tip 1232 at its distal end; distal tip 1232 may be configured as a second electrode. For example, when a circuit is closed by endovascular coil 1220 contacting first electrode 1242 and distal tip (i.e., second electrode) 1232, electric current may flow between electrode 1242 and distal tip 1232. In alternative embodiments, one or both of the first and second electrodes may be situated in other locations within the endovascular device. Additionally or alternatively to first electrode 1242, endovascular device 1200 may include other elements mounted on, or otherwise connected to, the inner wall of microcatheter 1210 (or of the elongated flexible sheath). The other elements may be located across the lumen 1214 from balloon 1260 and/or from the constrictor, such that endovascular coil 1220 may pass between the other elements and balloon 1260 and/or the constrictor. In another example, the other elements may be located on balloon 1260 and/or on the constrictor.

Some embodiments may exclude the electrode. For example, in place of an electrode, a mechanically actuated cutter or other manner of severing the endovascular instrument may be used. Energy may be selectively delivered to the electrode, for example, through an electrical wire extending from outside the body to the electrode or wirelessly.

Consistent with disclosed embodiments, the endovascular device may include a constrictor associated with the first region of the sheath. As used herein, a constrictor may include any device configured to narrow, or reduce the cross-sectional area of, a lumen, channel, or passageway, such as the inner lumen of the exemplary endovascular device. As used herein, the term "associated with" includes embodiments in which the constrictor is situated within the first region of the sheath (e.g., placed within the inner lumen of the sheath, or connected to the sidewall of the sheath) and embodiments in which the constrictor is external to the sheath, but is configured to act on the sheath to narrow the inner lumen. In some embodiments, the constrictor may be configured to narrow the inner lumen of the sheath without narrowing, or otherwise altering, the outer diameter of the sheath. Additionally, or alternatively, the constrictor may be configured to narrow the inner lumen and the outer diameter of the sheath. In some embodiments, the constrictor may be configured to reduce a diameter of a cross-section of the lumen, while preserving the shape of the cross-section of the lumen (for instance, when the cross-section of the lumen is circular both when narrowed and when not narrowed, but with different diameters). In another example, the constrictor may be configured to change a cross-sectional shape of the lumen when the lumen is constricted (for instance, when the cross-section of the lumen is circular when unconstricted and non-circular when constricted).

In some embodiments, the constrictor may be configured to control the degree of constriction (i.e., narrowing) of the inner lumen of the sheath. For example, the constrictor may cause the lumen to be in an unconstricted state, in which there is no narrowing of the lumen, or in a fully-constricted state, in which the lumen is narrowed to the full extent allowed by the constrictor. In some embodiments, the constrictor may be configured to close or obstruct the entire inner lumen while in the fully-constricted state. The constrictor may additionally or alternatively be configured to cause the lumen to be in a semi-constricted state, such that the lumen is partially narrowed by the constrictor.

For example, as depicted in FIGS. 16A and 17A, endovascular device 1200 may include a balloon 1260, which may be configured as a constrictor. Balloon 1260 may be associated with (i.e., located within) first region 1213a of microcatheter 1210 (or with a first region of the elongated flexible sheath). FIG. 16A and FIG. 16B show balloon 1260 in an uninflated state, in which the balloon may not protrude into or otherwise narrow inner lumen 1214; the uninflated state of balloon 1260 may therefore correspond to an unconstricted state of lumen 1214. FIG. 17A and FIG. 17B show balloon 1260 in an inflated state, in which the balloon protrudes into inner lumen 1214 and thus narrows the inner lumen; the inflated state of balloon 1260 may therefore correspond to a constricted state of lumen 1214. Additionally or alternatively to balloon 1260, endovascular device 1200 may include a constrictor associated with (i.e., located within) first region 1213a of microcatheter 1210 (or with a first region of the elongated flexible sheath), which may be in a plurality of states, such as an unconstricted state, a constricted state, and so forth.

Consistent with disclosed embodiments, the constrictor may be configured to reversibly narrow the lumen of the sheath in an area adjacent the electrode. As used herein, "reversibly narrow" may mean that the constrictor is configured to narrow (i.e., reduce the cross-sectional area of) the lumen and subsequently widen the lumen; the constrictor may widen the lumen back to its original size or to some other size. Thus, the constrictor may effectively reverse or undo prior narrowing operations of the lumen. Additionally, or alternatively, the constrictor may be configured to reversibly widen the lumen. That is, the constrictor may be configured to widen the lumen from a starting condition (e.g., from a fully-constricted state to an unconstricted state) and subsequently narrow the lumen, either back to its starting size or to some other size.

In some embodiments, the constrictor may be configured to reversibly narrow only a portion of the inner lumen, without narrowing the other portions of the lumen. For example, and consistent with disclosed embodiments, the constrictor may be configured to reversibly narrow a portion of the inner lumen that is adjacent to the electrode; that is, the section of the sheath that encompasses the reversibly narrowed portion of the lumen also includes the electrode. In some embodiments, the electrode may be positioned on the balloon or a portion thereof (or on the constrictor or a portion thereof). Additionally, or alternatively, the electrode may be mounted on the inner wall of the sheath at a location directly across the lumen from the balloon (or from the constrictor). Additionally, or alternatively, the electrode may be mounted on any portion of the inner wall of the sheath between a distal end of the balloon (or of the constrictor) and a proximal end of the balloon (or of the constrictor). In another example, the electrode may be positioned on any portion of the inner wall of the sheath. Additionally or alternatively to the electrode, other one or more elements may be positioned on any portion of the inner wall of the sheath. For example, the other one or more elements may be positioned on the balloon (or on the constrictor) or a portion thereof, may be positioned on the inner wall of the sheath at a location directly across the lumen from the balloon (or from the constrictor), may be positioned on any portion of the inner wall of the sheath between a distal end of the balloon (or of the constrictor) and a proximal end of the balloon (or of the constrictor), and so forth.

Consistent with disclosed embodiments, the reversible narrowing, by the constrictor, of the lumen of the sheath in the area adjacent the electrode may bring the electrode into contact with an adjacent portion of the endovascular instrument. As discussed above, the inner lumen of the sheath is configured to receive the endovascular instrument therein. Thus, when the portion of the lumen adjacent to the electrode is narrowed by the constrictor, the electrode may be brought into physical contact with the portion of the endovascular instrument that is adjacent to it.

For example, as depicted in FIGS. 12B, 16A, and 17A, electrode 1242 and balloon 1260 may be located on opposing sides of inner lumen 1214, with electrode 1242 positioned in between the proximal and distal ends of balloon 1260. When balloon 1260 is inflated to cause constriction of inner lumen 1214, the apex of the balloon may contact and push against endovascular coil 1220, pushing the coil towards the opposite side of the lumen until the coil comes into physical contact with electrode 1242; the contact between balloon 1260, coil 1220, and electrode 1242 is shown in FIG. 17A. Additionally or alternatively to electrode 1242, other one or more elements may be located on an opposing side to balloon 1260 on lumen 1214, for example, between the proximal and distal ends of balloon 1260. When balloon 1260 is inflated to cause constriction of lumen 1214, the apex of the balloon may contact and push against endovascular coil 1220, pushing the coil towards the opposite side of lumen 1214 until endovascular coil 1220 comes into physical contact with the other one or more elements. In some embodiments, balloon 1260 may additionally bring endovascular coil 1220 into contact with sealing distal tip 1232 (i.e., the second electrode). For example, sealing distal tip 1232 may be cylindrical, with an inner wall that is even with the inner wall of microcatheter 1210 (or of the elongated flexible sheath). Thus, when endovascular coil 1220 is pressed against electrode 1242, it is also pressed against the portion of sealing distal tip 1232 that is directly distal to the electrode. When it is desired to reverse the narrowing of inner lumen 1214, balloon 1260 may be uninflated by removing the inflation fluid via inflation passage 1662. Once all of the inflation fluid is removed, balloon 1260 may return to the uninflated state of FIG. 16A and inner lumen 1214 may return to an unconstricted state.

In another example, electrode 1242 and the constrictor may be located on opposing sides of lumen 1214, with electrode 1242 positioned in between the proximal and distal ends of the constrictor. When the constrictor is in constricted state to cause constriction of lumen 1214, the apex of the constrictor may contact and push against endovascular coil 1220, pushing endovascular coil 1220 towards the opposite side of lumen 1214 until coil 1220 comes into physical contact with electrode 1242. Additionally or alternatively to electrode 1242, other one or more elements may be located on an opposing side to the constrictor of lumen 1214, for example, between the proximal and distal ends of the constrictor. When the constrictor is in constricted state to cause constriction of lumen 1214, the apex of the constrictor may contact and push against endovascular coil 1220, pushing endovascular coil 1220 towards the opposite side of lumen 1214 until endovascular coil 1220 comes into physical contact with the other one or more elements. In some embodiments, the constrictor may additionally bring endovascular coil 1220 into contact with sealing distal tip 1232 (i.e., a second electrode). For example, sealing distal tip 1232 may be cylindrical, with an inner wall that is even with the inner wall of microcatheter 1210 (or of the elongated flexible sheath). Thus, when endovascular coil 1220 is pressed against electrode 1242, it is also pressed against the portion of sealing distal tip 1232 that is directly distal to the electrode. When it is desired to reverse the narrowing of lumen 1214, the constrictor may be turned into an unconstricted state. Once the constrictor is in an unconstricted state, lumen 1214 may return to an unconstricted state.

Consistent with disclosed embodiments, the constrictor may be configured to reversibly narrow the lumen and bring the electrode into contact with the endovascular instrument (as discussed above) while at least the first region and the second region of the sheath are positioned within a body and in response to an input received from outside the body. Regarding the first and second regions being positioned within the body, the constrictor is configured to reversibly narrow and widen the lumen while the endovascular device is being used in a medical operation or is otherwise disposed within a patient, for example, within a blood vessel. The constrictor may therefore be operated without affecting the surrounding tissue; this may be due, in part, to the fact that the outer diameter of the endovascular device may remain constant during narrowing and widening of the inner lumen, consistent with various embodiments.

As used herein, input received from outside the body may include manual control actions performed by a user of the endovascular device. Non-limiting examples of manual control actions may include user actuation of the constrictor, repositioning the endovascular device and/or endovascular instrument, and user actuation of the electrode. In some examples, the manual control actions may be based on and/or include voice commands given by the user (which may be recognized using speech recognition algorithms), may be based on and/or include gesture commands given by the user (which may be recognized using image analysis with gesture recognition algorithms), may be based on and/or include keystrokes by the user, may include touch input from the user, may be based on and/or include input from a user through a user interface, may be based on and/or include textual input from the user, may be based on and/or include tactile input from the user, may be based on and/or include mechanical force applied by the user, and so forth. Additionally, or alternatively, input received from outside the body may include control signals transmitted from a control device positioned outside the body to a control component of the constrictor (e.g., to a pump controlling inflation and deflation of a constricting balloon) and/or to another component of the endovascular device. In some embodiments, the control device may be configured to receive a command from a user input device, such as by a press of a button or key, a turn of a dial, an input through a computer-generated user interface, a voice command recognized in captured audio data through a voice recognition algorithm, a gesture recognized in captured image data through a gesture recognition algorithm, or any other action which may be performed by a user. The control unit may then transmit a corresponding control signal to the control component of the constrictor to cause the constrictor to perform the requested action (e.g., to constrict the inner lumen of the sheath). The signals from the control device may be transmitted to the control component of the constrictor wirelessly and/or via a wired connection. Additionally, or alternatively, the control device may receive data, such as from a sensor associated with the endovascular device and/or an imaging device; may generate the control signal based on the received data; and transmit the control signal to the control component of the constrictor. The constrictor may be configured to selectively narrow the lumen in response to the control signal received from the control device positioned outside the body. That is, the constrictor is configured to widen or narrow the lumen of the sheath by a desired degree, based on the control signal received from the control device.

In the example depicted in FIGS. 12A and 12B, the endovascular device may include a balloon 1260 configured as a constrictor. Balloon 1260 may be configured, while at least first region 1213a and second region 1213b are positioned within a body and in response to an input received from outside the body (by, for example, one of user device 1910, sensors 1912, or imaging device 1914 of FIG. 19), to reversibly narrow lumen 1214 of microcatheter 1210 (or reversibly narrow the lumen of the elongated flexible sheath) in an area 1213a adjacent electrode 1242 (as shown in FIGS. 17A, 17B, 17C, 18A, 18B, 23, and 24) to thereby bring electrode 1242 into contact with an adjacent portion 1724 of endovascular coil 1220, as shown in FIG. 17A. Additionally or alternatively to electrode 1242, balloon 1260 may be configured, while at least first region 1213a and second region 1213b are positioned within a body and in response to an input received from outside the body, to reversibly narrow lumen 1214 of microcatheter 1210 (or to reversibly narrow the lumen of the elongated flexible sheath), for example in an area adjacent other element. In one example, the narrowing of the lumen may bring the other element into contact with an adjacent portion 1724 of endovascular coil 1220. Balloon 1260 may be configured to selectively narrow lumen 1214 in response to a control signal received from a control device 1900 positioned outside the body, as shown in FIG. 19. After narrowing lumen 1214 of microcatheter 1210 (or after narrowing the lumen of the elongated flexible sheath) in response to the input received from outside the body, balloon 1260 may be configured to widen lumen 1214 in response to a second input received from outside the body, as shown in FIGS. 17B and 17C.

In the example depicted in FIGS. 12A and 12B, the endovascular device may include a constrictor. The constrictor may be configured, while at least first region 1213a and second region 1213b are positioned within a body and in response to an input received from outside the body (by, for example, one of user device 1910, sensors 1912, or imaging device 1914 of FIG. 19), to reversibly narrow lumen 1214 of microcatheter 1210 (or to reversibly narrow the lumen of the elongated flexible sheath) in the region 1213a adjacent electrode 1242 (as shown in FIGS. 17A, 17B, 17C, 18A, 18B, 23, and 24) to thereby bring electrode 1242 into contact with an adjacent portion 1724 of endovascular coil 1220, as shown in FIG. 17A. Additionally or alternatively to electrode 1242, the constrictor may be configured, while at least first region 1213a and second region 1213b are positioned within a body and in response to an input received from outside the body, to reversibly narrow lumen 1214 of microcatheter 1210 (or to reversibly narrow the lumen of elongated flexible sheath), for example in an area adjacent other element. In one example, the narrowing of lumen 1214 may bring the other element into contact with an adjacent portion 1724 of endovascular coil 1220. The constrictor may be configured to selectively narrow lumen 1214 in response to a control signal received from a control device 1900 positioned outside the body, as shown in FIG. 19. After narrowing lumen 1214 of microcatheter 1210 (or after narrowing the lumen of the elongated flexible sheath) in response to the input received from outside the body, the constrictor may be configured to widen lumen 1214 in response to a second input received from outside the body, as shown in FIGS. 17B and 17C.

In some embodiments, the constrictor may be configured to constrict the first region of the sheath, and automatically unconstrict the first region of the sheath after a specified period of time. For instance, a control device may cause the constrictor to automatically unconstrict the first region of the sheath after 0.1 s, 1 s, 2 s, 5 s, 10 s, or any other appropriate interval of time elapses after constriction which will not harm the endovascular device, the endovascular instrument, or the patient. In some embodiments, after narrowing the lumen of the sheath in response to the input received from outside the body, the constrictor may be configured to widen the lumen in response to a second input received from outside the body. In some cases, the widening in response to a second input may bring the endovascular instrument out of contact with the electrode. Widening the lumen may include unconstricting the first region of the sheath.

Consistent with disclosed embodiments, the endovascular device may be constructed such that during constriction of the first region of the sheath, the second region of the sheath is configured to remain unconstricted. Thus, the constrictor may be configured to cause constriction of a portion of the lumen, without causing constriction of other portions of the lumen (such as the section of the lumen within the second region of the sheath). In some embodiments, the second region of the sheath may fall outside the area that is acted upon by the constrictor. In alternative embodiments, the constrictor may be configured to selectively and independently constrict the first region of the sheath and the second region of the sheath. In such embodiments, the constrictor may cause narrowing of the lumen within the first region and may cause the lumen within the second region to remain unchanged. FIGS. 16C and 17C depict an example of a second region of the sheath 1210 when inner lumen 1214 is unconstricted and constricted, respectively. In this example, the second region may not include any part of balloon 1260 (and/or of the constrictor); thus, when the balloon is inflated (or when the constrictor is in constricted state), it may not protrude into the second region or otherwise change the cross-sectional shape of inner lumen 1214 within the second region. Instead, the diameter and shape of inner lumen 1214 is the same in FIG. 16C and in FIG. 17C.

Consistent with disclosed embodiments, a first section of the lumen within the first region of the sheath may have a circular cross-section during non-constriction. In some embodiments, the first section of the lumen may be adjacent to, or bounded by, a portion of the constrictor. Additionally, or alternatively, the first section of the lumen may be adjacent to, or bounded by, the electrode. Consistent with disclosed embodiments, the constrictor may be configured to cause the cross-section of the first section of the lumen in an area of the constrictor to become non-circular. In some embodiments, the constrictor may be configured to protrude into the first section of the lumen, causing the lumen to have a non-circular cross-sectional shape (i.e., due to the inward protrusion of the constrictor). Consistent with disclosed embodiments, a second section of the lumen within the second region of the sheath may have a circular cross-section during constriction and during non-constriction. For example, and as discussed above, the cross-sectional shape of the lumen within the second region may remain constant between constriction and non-constriction. For example, FIGS. 16B and 17B depict an exemplary first region of sheath 1210 in an unconstricted state and in a constricted state, respectively, while FIGS. 16C and 17C depict an exemplary second region of sheath 1210 in the unconstricted state and constricted state, respectively. As shown in FIGS. 16B and 16C, inner lumen 1214 has a circular cross-section in both the first region and second region. However, in the first region depicted in FIG. 17B, inner lumen 1214 has a non-circular cross-section (specifically, a moon-shaped cross-section) because balloon 1260 (and/or the constrictor) protrudes into the inner lumen at the first region. In contrast, in the second region depicted in FIG. 17C, inner lumen 1214 has the same circular cross-section as in the unconstricted state since the second region of sheath 1210 may not include any part of balloon 1260 (or of the constrictor).

Figure 23:
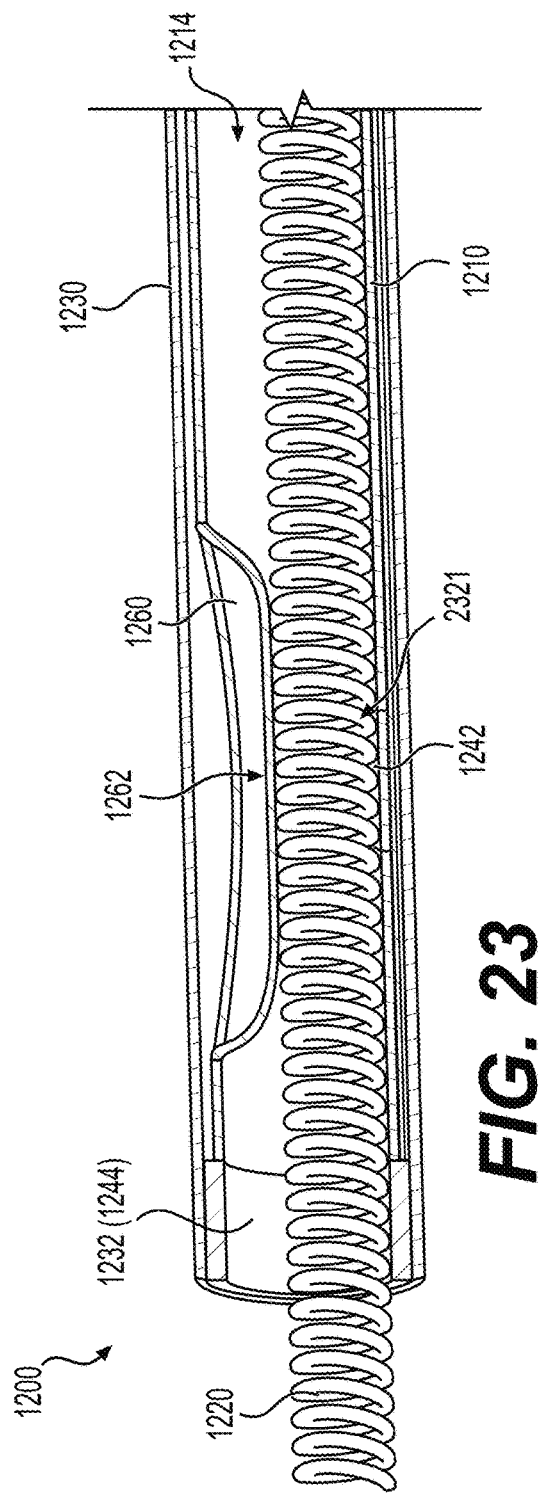
FIG. 23 is an interior view of the endovascular device of FIGS. 12A and 12B in a configuration for obstructing axial advancement of an endovascular instrument, consistent with disclosed embodiments.

Consistent with disclosed embodiments, during constriction, the constrictor may be configured to obstruct axial advancement of the endovascular instrument within the first region of the sheath. In some embodiments, the constrictor may be configured to either completely block the lumen or narrow the lumen to such an extent that there is insufficient space for the endovascular instrument to pass the constrictor. An example is shown in FIG. 23: endovascular device 1200 may include a constrictor (such as balloon 1260, or any other type of constrictor as described herein) configured to be constricted (for example, inflated) until apex 1562 contacts the opposite side of the sheath 1210. Since balloon 1260 (or the constrictor) fills the inner lumen 1214, endovascular coil 1220 is blocked from advancing proximally past the balloon (or the constrictor). In some alternative embodiments, balloon 1260 (or the constrictor) may only partially fill the inner lumen, but may still obstruct axial advancement of coil 1220 by leaving insufficient open space in the lumen for the coil to fit through.

Figure 24:
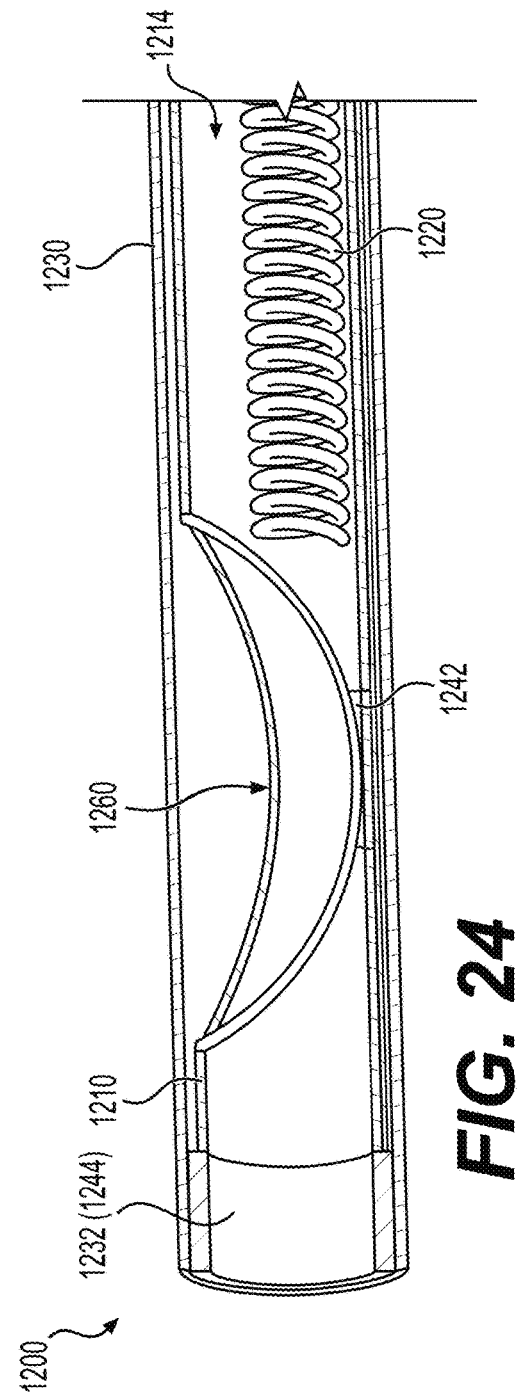
FIG. 24 is an interior view of the endovascular device of FIGS. 12A and 12B exerting a frictional force on an endovascular instrument, consistent with disclosed embodiments.

In some embodiments, when the endovascular instrument is located adjacent to the constrictor, the constrictor may be configured to expand around the instrument and exert a grasping-type force upon it. For example, the constrictor may be configured to cause exertion of a stronger friction force on the endovascular instrument when constricted than when unconstricted. As a result, the constrictor may hold the endovascular instrument in place and preventing it from moving. An example is shown in FIG. 24: endovascular device 1200 may include a constrictor (such as balloon 1260, or any other type of constrictor as described herein) configured to expand around coil section 2321 and exert a grasping-type force upon it. As a result, balloon 1260 (or the constrictor) may secure endovascular coil 1220 against axial and rotational movement until coil section 2321 is released from the balloon and/or from the constrictor (e.g., by deflating the balloon, by unconstricting the constrictor, etc.).

In some embodiments, at least a first portion of the constrictor may be located within the lumen of the sheath during constriction, and at least a second portion of the constrictor may be located outside the lumen of the sheath, adjacent an external surface of the sheath.

Consistent with disclosed embodiments, the constrictor may include at least one obstructer. As used herein, an obstructer may refer to a structure configured to narrow a lumen by protruding inward from the lumen wall into the interior of the lumen. In some embodiments, the endovascular device may include a single obstructer. Alternatively, the endovascular device may include two obstructers, three obstructers, four obstructers, or any other suitable number of obstructers. In some embodiments, the at least one obstructer may include at least two obstructers spaced about a circumference of the lumen of the sheath. For example, the at least two obstructers may be spaced at a regular interval around the circumference (e.g., three obstructers may be spaced 120-degrees apart); alternatively, the at least two obstructers may be spaced at some other, non-regular interval around the circumference. In some embodiments, the at least one obstructer may include a plurality of obstructers located substantially at a same distance from a distal tip of the endovascular device. As used herein, "substantially at a same distance" from the distal tip may include obstructers located at the same distance from the distal tip and obstructers having respective distances from the distal tip where the differences in the distances from the distal tip are less than a particular length. For example, the particular length may be shorter than 1 mm, shorter than 5 mm, shorter than 1 cm, shorter than 2 cm, shorter than 1 inch, shorter than 2 inches, and so forth. Additionally, or alternatively, the at least one obstructer may include a plurality of obstructers, each located at differing distances from the distal tip of the endovascular device.

In some embodiments, the at least one obstructer may be mounted on, or otherwise connected to, the inner surface of the sheath and may be enlarged (e.g., mechanically expanded, inflated with fluid, etc.) in order to constrict the inner lumen. In alternative embodiments, the at least one obstructer may be connected to the sheath at a location outside the lumen and may be configured to protrude into the inner lumen to cause constriction. For example, the at least one obstructer may be configured to lie substantially flush with an outer surface of the first region of the sheath when the first region is non-constricted, and to protrude into the lumen of the sheath when the first region is constricted. For example, FIGS. 17A, 15A, and 15B depict an example in which balloon 1260 may correspond to the at least one obstructer. Outer portion 1564 of the balloon may be secured to the outer surface of sheath 1210 (e.g., by adhesive or a mechanical connection), while inner portion 1562 of the balloon may be configured to pass through the sheath opening 1216 and into the inner lumen 1214 when the balloon is inflated. In the inflated state, balloon 1260 is configured as an obstructer that protrudes into, and thus narrows, the inner lumen 1214. In another example, an outer portion of the constrictor may be secured to the outer surface of sheath 1210 (e.g., by adhesive or a mechanical connection), while inner portion 1562 of the constrictor may be configured to invade lumen 1214 when the constrictor is constricted. In the constricted state, the constrictor may be configured as an obstructer that protrudes into, and thus narrows, the lumen 1214.

Consistent with disclosed embodiments, the at least one obstructer may include a selectively inflatable balloon configured for expansion into the lumen of the sheath when inflated. As used herein, a balloon may refer to a device that may be inflated with fluid that is delivered to the balloon via an inflation fluid conduit or passageway. In one example, a balloon may be constructed of an airtight flexible bag. In the absence of external obstructions, in one example, a balloon may be configured to inflate and/or deflate symmetrically (for example, in an axis of symmetry, in a plane of symmetry, or in any other symmetrical manner), while in another example, a balloon may be configured to inflate and/or deflate asymmetrically. As used herein, selective inflation may refer to controlled inflation or deflation of the balloon to a desired degree. For example, the balloon may be selectively inflated to a desired semi-inflated state (rather than proceeding to a fully-inflated state). In another example, the inflated balloon may be selectively deflated until a desired state of inflation is achieved.

In some embodiments, the system controller may be configured to perform an automated process for determining when to inflate and/or deflate the balloon (and/or when to constrict and when to unconstrict the constrictor). For example, based on an analysis of data captured using a sensor (such as medical images, electrical impedance data, mechanical tension data, or any other data which may relay information from inside the body), a desired of a particular state of the balloon may be determined and, if the balloon is not in a desired particular state, the controller may output a signal to a balloon control component (e.g., an inflation pump) to inflate or deflate the balloon until the desired particular state is achieved. Additionally, or alternatively, a user may input control signal to the system controller to selectively inflate or deflate the balloon. In another example, based on an analysis of data captured using a sensor (such as medical images, electrical impedance data, mechanical tension data, or any other data which may relay information inside the body), a desire of a particular state of the constrictor may be determined and, if the constrictor is not in a desired particular state, the controller may output a signal to change the state of the constrictor until the desired particular state is achieved.

Consistent with disclosed embodiments, the endovascular instrument may be an endovascular coil configured for bending within a hollow body structure upon discharge from the sheath. As used herein, an endovascular coil may refer to a helically-coiled structure, often formed from a metallic wire, configured to be delivered into an aneurysm or another hollow body structure in order to pack the interior volume of the aneurysm and reduce blood circulation thereto. As discussed herein, the endovascular coil may be configured for bending within a hollow body structure (e.g., in the first manner or second manner discussed above) upon the removal of a restraining force from the coil, such as when the coil is discharged from the distal end of the sheath and delivered into the aneurysm. In some embodiments, the electrode may be located in a distal region of the sheath. In some embodiments, the electrode may be configured to sever the endovascular coil following discharge of at least a portion of the coil from the sheath. As used herein, to sever the coil may mean to partition or separate the coil into multiple distinct pieces. As discussed in further detail herein, the endovascular coil may be advanced through the endovascular device until a desired length of coil has been advanced beyond the distal end of the device and to a delivery location (e.g., into an aneurysm). The electrode may then be actuated to pass electric current to the coil in a sufficient amount to sever the coil at the portion thereof that is adjacent to the electrode.

In some embodiments, the electrode may be configured to make physical contact with the endovascular instrument during constriction to enable the electrode to deliver energy to the endovascular instrument. As used herein, physical contact may include the electrode and the endovascular instrument directly touching each other or being close enough that sufficient levels of electric current may be delivered from the electrode to the endovascular instrument to sever the instrument. In some embodiments, the constrictor may be configured to move the electrode closer to the endovascular instrument, or vice versa, until the electrode and instrument are brought into physical contact. That is, consistent with disclosed embodiments, the constrictor may be configured to press the electrode and the endovascular instrument together in a manner reducing electrical impedance during energy delivery. As a result of the reduces impedance, the electrode may be configured to deliver sufficient electric current to the endovascular instrument to sever the instrument. Additionally, or alternatively, the constrictor may be configured such that constriction of the first region of the sheath closes an electrical circuit including the electrode and the endovascular instrument, such as by bringing the instrument into physical contact with the electrode and with a second electrode to complete the circuit.

For example, electrode 1242 depicted in FIGS. 12A, 12B, 17A, and 18A may be configured to make physical contact with endovascular coil 1220 during constriction to enable electrode 1242 to deliver energy to endovascular coil 1220, balloon 1260 (or the constrictor) may be configured to press electrode 1242 and endovascular coil 1220 together in a manner reducing electrical impedance during energy delivery, and balloon 1260 (or the constrictor) may be configured such that constriction of first region 1213*a* of microcatheter 1210 (or of the first region of the elongated flexible sheath) closes an electrical circuit including electrode 1242 and endovascular coil 1220, as shown in FIGS. 17A and 18A. A first section of lumen 1214 within first region 1213*a* may have a circular cross-section during non-constriction, and balloon 1260 (or the constrictor) may be configured to cause the cross-section of the first section of lumen 1214 in an area of balloon 1260 (or of the constrictor) to become non-circular, as shown in FIG. 17B. Additionally or alternatively, endovascular device 1200 may be constructed such that during constriction of first region 1213*a* of microcatheter 1210, second region 1213*b* of microcatheter 1210 may be configured to remain unconstricted, as shown in FIG. 18A. Additionally or alternatively, endovascular device 1200 may be constructed such that during constriction of first region 1213*a* of the sheath 1210, second region 1213*b* of the sheath 1210 may be configured to remain unconstricted.

Consistent with disclosed embodiments, the electrode may be configured to deliver energy in an amount sufficient to sever the endovascular instrument while at least the first region and the second region of the sheath are positioned within the body. Thus, the endovascular instrument may be successfully severed without risk of injury to the patient. In some examples, the amount sufficient to sever the endovascular instrument may be a function of the characteristics of the endovascular instrument, such as a material composition of the endovascular instrument, a structure of the endovascular instrument, a diameter of the endovascular instrument, an electrical resistance of the endovascular instrument, and so forth. Moreover, in some examples, the amount sufficient to sever the endovascular instrument may be a function of the manner in which the energy is delivered, such as the distribution of energy delivered over time, the concentration of energy delivered at a specific portion of the endovascular instrument, and so forth. For some common endovascular coils, delivering energy of between 10 to 300 watt per second for a duration of 0.1 to 10 seconds is typically an amount sufficient to sever the endovascular instrument, but other amounts may be required as described above.

Disclosed embodiments may further include electrical circuitry, wherein the electrode may be configured for connection to the circuitry for selectively delivering the energy to the electrode. Electrical circuitry may include an interconnection of electrical components configured to deliver current via the electrode in such a way as to separate an endovascular instrument in two. The electrical circuitry may have at least a first state and a second state, wherein at the first state the electrical circuitry may be configured to cause a first electrical voltage between two particular points, and at the second state the electrical circuitry may be configured to cause a second electrical voltage between the two particular points, the second electrical voltage differing from the first electrical voltage. The electrical circuitry may be disposed such that no current is transferred to a patient being treated in a way which could cause bodily harm.

For example, as depicted in FIGS. 12A, 12B, 18A, and 18B, endovascular device 1200 may include an electrode 1242 within the first region 1213*a* of the sheath (for example, of microcatheter 1210). Electrode 1242 may be located in a distal region 1213*a*, or first region 1213*a*, of microcatheter 1210 (or in a distal region or the first region of the elongated flexible sheath) and may be configured to sever endovascular coil 1220 following discharge of at least a portion of the coil from the sheath, as depicted in FIGS. 18A and 18B. Electrode 1242 may be configured to deliver energy in an amount sufficient to sever endovascular coil 1220 while at least first region 1213*a* and second region 1213*b* of microcatheter 1210 (or at least the first region and the second region of the elongated flexible sheath) are positioned within the body, as depicted in FIGS. 22A-22C.

As another example, as depicted in FIGS. 12A and 12B, endovascular device 1200 may include electrical circuitry 1243, including wires connecting electrode 1242 to a power source. Additionally or alternatively to electrode 1242, endovascular device 1200 may include other one or more elements within the first region 1213*a* of the sheath (for example, the microcatheter 1210). The other element may be located in a distal region 1213*a*, or first region 1213*a*, of microcatheter 1210 (or may be located in the distal region or the first region of the elongated flexible sheath).

Consistent with disclosed embodiments, the constrictor may be configured to selectively narrow the lumen in response to at least one of: a change in temperature of at least a portion of the constrictor, delivery of electric current to the constrictor, an application of electromagnetic force on the constrictor, or an application of mechanical force on the constrictor. A non-limiting example of a constrictor may include a constrictor configured to constrict and/or to unconstrict in response to a change in temperature of at least a portion of the constrictor. For example, the constrictor may include a shape-memory element that narrows the lumen when the transformation temperature is reached and/or unconstrict the lumen when the temperature falls below a threshold. Further, the temperature of the shape-memory element may be controllable, for example, by an interventional radiologist. For example, the shape-memory element may be configured to heat in response to flow of electric current passing through it or through an element adjunct to it.

Another non-limiting example of a constrictor may include a constrictor configured to constrict and/or to unconstrict in response to delivery of electric current to the constrictor, for example, as described above. In one example, the electric current may flow through an electrical wire extending from outside the body and connected to the constrictor.

Yet another non-limiting example of a constrictor may include a constrictor configured to constrict and/or to unconstrict in response to significant change in a magnetic field. An additional non-limiting example of a constrictor may include a constrictor configured to constrict and/or to unconstrict in response to an application of a mechanical force (such as pressure, stress, or any other applicable mechanical force) on the constrictor. For example, the constrictor may include a moveable element configured to be in a first position that narrows the lumen when a first mechanical force is exerted on the moveable element, and/or configured to be in a second position that may not narrow the lumen when a second mechanical force is exerted on the moveable element. In one example, an interventional radiologist may cause an exertion of a mechanical force on the moveable portion, for example by pulling and/or pushing a wire extended from outside the body and connected to the moveable element, by increasing and/or decreasing gas or liquid pressure in a tube extending from outside the body and connected to the moveable element, by pushing a volume of gas or liquid into a tube extending from outside the body and connected to the moveable element.

Figure 28:
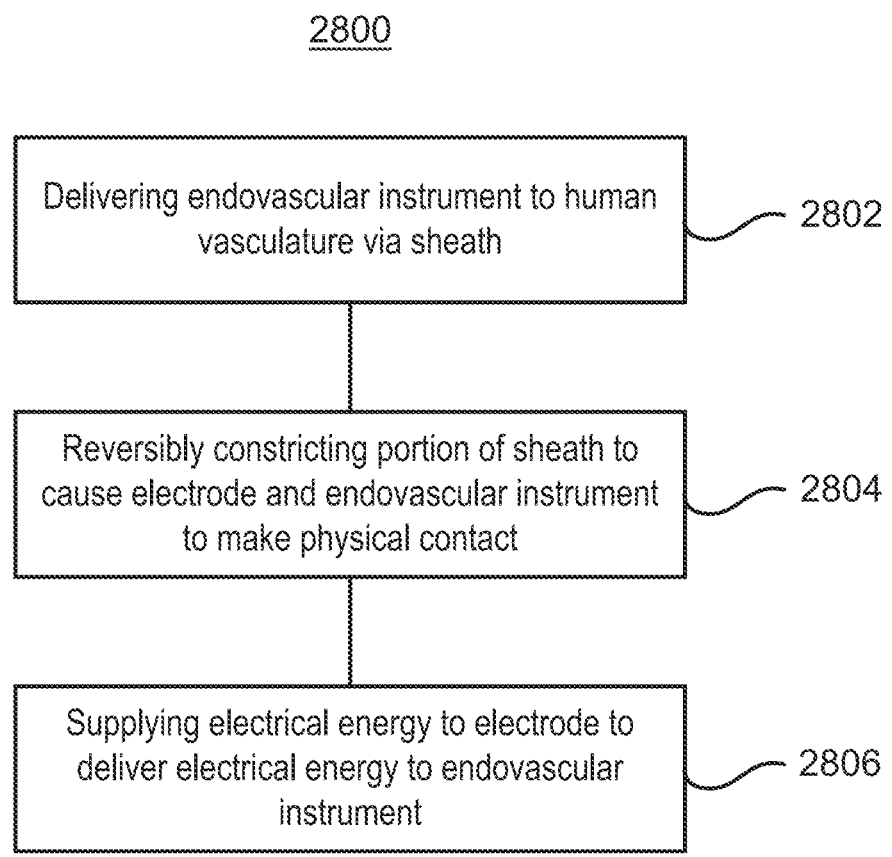
FIG. 28 is a flowchart of an example of an endovascular treatment method, consistent with disclosed embodiments.

Various embodiments of the current disclosure include an endovascular treatment method. An endovascular treatment method may refer to an action or set of actions occurring inside a blood vessel for healing a patient or a condition medically or surgically. For example, an endovascular treatment method may include a set of actions for treating an aneurysm. The endovascular treatment method may correspond to endovascular treatment method 2800 of FIG. 28.

The endovascular treatment method of the current disclosure may include delivering an endovascular instrument to human vasculature via a sheath having an electrode therein, which may include inserting a sheath having an electrode disposed near an inserted end of the sheath into a vessel of a patient (e.g., a blood vessel), and delivering an endovascular instrument through the sheath. Delivering an endovascular instrument to human vasculature via a sheath having an electrode therein may correspond to step 2802 of FIG. 28.

The endovascular treatment method of the current disclosure may further include, while a portion of the sheath having the electrode is within a body, reversibly constricting the portion of the sheath having the electrode to narrow a lumen within the sheath and thereby cause the electrode and the endovascular instrument to make physical contact. A portion of the sheath having the electrode being within a body may refer to the sheath not having to be fully disposed within the body to perform the step of constricting the portion of the sheath having the electrode. Constricting the portion of the sheath having the electrode may be performed by a constrictor, as described in greater detail herein. Causing the electrode and the endovascular instrument to make physical contact may be advantageous to reduce electrical impedance in an electrical circuit associated with the endovascular instrument and the electrode, as described in greater detail herein. In some embodiments, constricting the sheath may occur via expansion of a balloon within the lumen of the sheath, as described in greater detail herein. Reversibly constricting the portion of the sheath having the electrode to narrow a lumen within the sheath and thereby cause the electrode and the endovascular instrument to make physical contact, while a portion of the sheath having the electrode is within a body, may correspond to step 2804 of FIG. 28.

The endovascular treatment method of the current disclosure may further include, while the portion of the sheath having the electrode is constricted, supplying electrical energy to the electrode, to thereby deliver electrical energy to the endovascular instrument via the electrode, as described in greater detail herein. In some embodiments, supplying the electrical energy to the electrode may include delivering electrical energy in a quantity sufficient to sever the endovascular instrument, as described in greater detail herein. Supplying electrical energy to the electrode, to thereby deliver electrical energy to the endovascular instrument via the electrode, while the portion of the sheath having the electrode is constricted, may correspond to step 2806 of FIG. 28.

Various embodiments of the current disclosure include non-transitory computer readable media containing instructions for endovascular treatment. Consistent with other disclosed embodiments, computer-readable media may store program instructions, which are executable by at least one processing device and perform any of the steps and/or methods described herein. The instructions for endovascular treatment may be performed in conjunction with endovascular treatment method 2800 of FIG. 28 by, for example, processor 1902 of control unit 1900 of FIG. 19.

The instructions for endovascular treatment of the current disclosure may include obtaining an input corresponding to delivery of an endovascular instrument to human vasculature via a sheath having an electrode therein, which may refer to instructions for receiving, retrieving, or otherwise acquiring an input which confirms delivery of an endovascular instrument (e.g., an endovascular coil) to human vasculature via a sheath having an electrode therein, as described in greater detail herein.

By way of example, processor 1902 of FIG. 19 may receive a confirmation from at least one of endovascular device advancing mechanism 1944 and/or coil advancing mechanism 1946 that delivery of endovascular coil 1220 of FIGS. 22E-22F to aneurysm 2282 is complete. The instructions of obtaining an input corresponding to delivery of an endovascular instrument to human vasculature via a sheath having an electrode therein may be performed in conjunction with step 2802 of FIG. 28.

The instructions for endovascular treatment of the current disclosure may further include, based on the input, and while a portion of the sheath having the electrode is within a body, causing reversible constriction of the portion of the sheath having the electrode to narrow a lumen within the sheath and thereby cause the electrode and the endovascular instrument to make physical contact, which may refer to causing reversible constriction of the portion of the sheath having the electrode based on a confirmation that delivery of the endovascular instrument was successful, as described in greater detail herein. In some embodiments, constricting the sheath may occur via expansion of a balloon (or via constriction of the constrictor) within the lumen of the sheath, as described in greater detail herein.

By way of example, processor 1902 of FIG. 19 may send a signal via constrictor control component 1942 to cause reversible constriction of portion 1213a of microcatheter 1210 (or of a portion of the elongated flexible sheath) having electrode 1242 (and/or another element) to narrow lumen 1214 within microcatheter 1210 and thereby cause electrode 1242 (and/or the other element) and endovascular coil 1220 to make physical contact, as shown in FIG. 17A. In some embodiments, constricting microcatheter 1210 (or constricting the elongated flexible sheath) may occur via constriction of the constrictor (for example, via expansion of balloon 1260) within lumen 1214 of microcatheter 1210 (or within the lumen of the elongated flexible sheath). The instructions of, based on the input, and while a portion of the sheath having the electrode is within a body, causing reversible constriction of the portion of the sheath having the electrode to narrow a lumen within the sheath and thereby cause the electrode and the endovascular instrument to make physical contact may be performed in conjunction with step 2804 of FIG. 28.

The instructions for endovascular treatment of the current disclosure may further include, while the portion of the sheath having the electrode is constricted, controlling supply of electrical energy to the electrode, to thereby deliver electrical energy to the endovascular instrument via the electrode, which may refer to delivering electrical energy to the endovascular instrument via the electrode based on the portion of the sheath having the electrode being constricted, as described in greater detail herein. In some embodiments, supplying the electrical energy to the electrode may include delivering electrical energy in a quantity sufficient to sever the endovascular instrument, as described in greater detail herein.

By way of example, processor 1902 of FIG. 19 may, while portion 1213a of microcatheter 1210 (or while a portion of the elongated flexible sheath) is constricted (which may be determined by one or more of electrode control component 1940, constrictor control component 1942, coil advancing mechanism 1946, sensors 1912, and/or imaging device 1914 sending a signal to processor 1902) controlling supply of electrical energy to electrode 1242, to thereby deliver electrical energy to endovascular coil 1220 via electrode 1242, as shown in FIGS. 18A and 18B. In some embodiments, supplying the electrical energy to electrode 1242 may include delivering electrical energy in a quantity sufficient to sever endovascular coil 1220, as shown in FIGS. 18A and 18B. The instructions of, while the portion of the sheath having the electrode is constricted, controlling supply of electrical energy to the electrode, to thereby deliver electrical energy to the endovascular instrument via the electrode may be performed in conjunction with step 2806 of FIG. 28.

Aspects of this disclosure may relate to an endovascular apparatus having an elongated catheter, a balloon, and a tube configured to cause expansion of the balloon into an inner lumen of the catheter when the balloon is inflated. In some embodiments, the endovascular apparatus may be configured to secure or obstruct axial advancement of a medical instrument within the inner lumen of the catheter. However, the endovascular apparatus may additionally or alternatively be configured for use with other instrumentation and/or for other suitable purposes.

Various embodiments of the current disclosure may relate to an endovascular apparatus. As used herein, and endovascular apparatus may include any device or instrument configured to be placed within or to operate inside a blood vessel for a medical purpose, for example, to diagnose and/or treat a patient. In some embodiments, an endovascular apparatus may include any device or instrument configured to be used during, or to otherwise facilitate, endovascular surgeries and procedures, as described in greater detail herein. In some embodiments, an endovascular apparatus may be configured to deliver a device, drug, or material from a first location (e.g., a location outside the body) to a treatment site in a blood vessel, and may be configured to secure or obstruct axial advancement of said device, drug, or material. Some non-limiting examples of endovascular devices may include catheters, microcatheters, balloon catheters, medical sheaths, guidewires, coils, endovascular revascularization devices, embolization devices, or any other device configured to be placed within a blood vessel.

For example, the present application depicts different views of an endovascular apparatus 1200. As illustrated in FIGS. 12A, 12B, and 22A-22F, endovascular apparatus 1200 may be configured to deliver a medical instrument 1220 (e.g., an endovascular coil) to a treatment site within the body, such as aneurysm 2282. Endovascular device 1200 may include a catheter 1210, a balloon 1260, and, optionally, at least one electrode 1242.

Consistent with disclosed embodiments, the endovascular apparatus may include an elongated catheter having an inner lumen extending therethrough. As used herein, an elongated catheter may refer to a cylindrical, hollow, or enveloping structure constructed of any suitable compliant polymeric material such as PTFE, PEBA, nylon, polyethylene, etc. Non-limiting example of an elongated catheter may include a microcatheter, a catheter, or a tube, and may include a thin, flexible tube which may be inserted through a narrow opening into a body cavity, e.g., to treat diseases or perform a surgical procedure, as described in greater detail herein. As used herein, an inner lumen extending therethrough may include a central cavity or channel of a tubular or other hollow structure. In some embodiments, the inner lumen may extend along the entire length of the elongated catheter, such that the inner lumen has a first opening at a proximal end of the elongated catheter and a second opening at a distal end of the elongated catheter. Alternatively, the inner lumen may extend along a portion of the elongated catheter. The exemplary endovascular apparatus may include a single inner lumen or, alternatively, multiple inner lumens (e.g., two inner lumens, three inner lumens, four inner lumens, or any other suitable number of inner lumens).

For example, as depicted in FIGS. 12A and 12B, endovascular apparatus 1200 may include catheter 1210, which may be an example of an elongated catheter. Catheter 1210, or the elongated catheter, may define an inner lumen 1214.

Consistent with disclosed embodiments, the endovascular apparatus may include a balloon affixed to the catheter for expansion into the inner lumen of the catheter when the balloon is inflated. As used herein, a balloon may refer to a device that may be inflated with fluid that is delivered to the balloon via an inflation fluid conduit or passageway. In one example, a balloon may be constructed of an airtight flexible bag. In at least one example, the balloon may be made of at least one of polyester and/or nylon. A non-limiting example of such polyester may include polyethylene terephthalate. In another example, the balloon may be made of a plastic polymer, such as polyvinyl chloride, polyethylene, or other appropriate plastic polymers which may allow the balloon to inflate and deflate into the inner lumen of the catheter without causing damage to itself or the catheter. In another example, the balloon may be made of reinforced polyurethane. In yet another example, the balloon may be made of polyether block amide. In the absence of external obstructions, in one example, a balloon may be configured to inflate and/or deflate symmetrically (for example, in an axis of symmetry, in a plane of symmetry, or in any other symmetrical manner), while in another example, a balloon may be configured to inflate and/or deflate asymmetrically. The balloon may be affixed to the catheter such that it surrounds and/or covers at least a portion of the catheter or an entire section of the catheter. In some examples, the balloon may be affixed to the catheter with adhesive, with staples, with stitches, by fusing them together (for example, welding them together), by fabricating the balloon and the catheter together, by planting at least part of the balloon in the catheter, and so forth. In one example, the balloon may be directly affixed to the catheter. For example, an extremity of the balloon may be affixed an extremity of the catheter. For example, this extremity of the catheter may be part of the inner wall of the catheter, may be part of an external wall of the catheter, may be part of a distal tip of the catheter, and so forth. In another example, the balloon may be indirectly affixed to the catheter, for example through a third object. For example, the balloon may be affixed to the third object, and the third object may be affixed to the catheter. In one example, a particular part of the balloon may be immovable with respect to a particular part of the catheter. In another example, a particular part of the balloon may be free to move within a selected range of distances from a particular part of the catheter. The balloon may expand into the inner lumen via an opening in the catheter when fluid is delivered to the balloon via an inflation fluid conduit or passageway, causing the balloon to inflate. In some examples, the endovascular apparatus may include a balloon not affixed to the catheter for expansion into the inner lumen of the catheter when the balloon is inflated. For example, the balloon may be situated in the inner lumen of the catheter. In another example, the balloon may be free to move within the inner lumen of the catheter and/or outside the inner lumen of the catheter. In some embodiments, the balloon may be situated outside of the inner lumen of the catheter when the balloon is deflated. In other examples, at least part of the balloon may be situated inside the inner lumen of the catheter when the balloon is deflated.

For example, as depicted in FIGS. 12A, 12B, 15A-15B, and 23-24, endovascular apparatus 1200 may include balloon 1260 affixed to catheter 1210 for expansion into inner lumen 1214 when balloon 1260 is inflated. Balloon 1214 may be affixed to catheter 1210 such that it surrounds and/or covers at least a portion of catheter 1210, as shown in FIGS. 15A-15B. As another example, balloon 1260 may be situated outside of inner lumen 1214 when balloon 1260 is deflated, as shown in FIG. 15A, and may expand into inner lumen 1214 when 1260 is inflated, as shown in FIG. 15B.

Consistent with disclosed embodiments, the endovascular apparatus may include a tube secured relative to the balloon, wherein the tube may be configured to enable selective inflation and deflation of the balloon. The tube may refer to a cylindrical, hollow, or enveloping structure constructed of any suitable compliant polymeric material such as PTFE, PEBA, nylon, polyethylene, etc., which may envelop the catheter to create an airtight inflation fluid conduit or passageway between the tube and the catheter. The tube may include a thin, flexible tube or outer sheath which may be inserted through a narrow opening into a body cavity, e.g., to treat diseases or perform a surgical procedure, as described in greater detail herein. The tube may be secured relative to the balloon due to a distal tip securing the tube and the microcatheter together. The tube may be configured to enable selective inflation and deflation of the balloon by delivering a fluid through the airtight inflation fluid conduit or passageway created by the space between the tube and the catheter.

As used herein, selective inflation may refer to controlled inflation or deflation of the balloon to a desired degree, as described in greater detail herein. For example, the balloon may be selectively inflated to a desired semi-inflated state (rather than proceeding to a fully-inflated state). In another example, the inflated balloon may be selectively deflated until a desired state of inflation is achieved. In some embodiments, the balloon may be selectively inflated and/or deflated to any state within a predetermined viable inflation range. In another example, the balloon may be selectively inflated and/or deflated to one of a finite number of states (for example, two states, three states, more than three states, and so forth). For instance, the balloon may be selectively inflated and/or deflated to two states, an inflated state and a deflated state. In another example, the balloon may be selectively inflated and/or deflated to one deflated state and multiple inflated states of different inflating levels.

For example, as shown in FIGS. 12A-18B, endovascular apparatus 1210 may include a tube 1230 secured relative to balloon 1260, wherein tube 1230 may be configured to enable selective inflation and deflation of balloon 1260 by delivering an inflation fluid through an inflation passage 1662, created by the space between tube 1230 and catheter 1210.

Consistent with disclosed embodiments, an outer diameter of a portion of the catheter adjacent the balloon may be substantially the same when the balloon is inflated and when the balloon is deflated. The portion of the catheter adjacent the balloon may be a section of the catheter near to or surrounded by the balloon. During inflation and deflation, the change to the outer diameter of the portion of the catheter adjacent the balloon may be less than 20% of the original outer diameter, less than 10%, less than 1%, less than 0.5%, less than 0.1%, or less than 0.01%. Alternatively, the outer diameters may be identical or substantially identical during inflation and deflation of the balloon. For example, when balloon 1260 is inflated, as in FIG. 17B, the outer diameter of the portion of catheter 1210 adjacent balloon 1260 is substantially the same as when balloon 1260 is deflated, as in FIG. 16B. In other examples, the outer diameter of a portion of catheter 1210 adjacent balloon 1260 may be substantially different when the balloon is inflated and when the balloon is deflated. For example, during inflation and deflation, the change to the outer diameter of the portion of the catheter adjacent the balloon may be more than 20% of the original outer diameter.

In some embodiments, the balloon may be situated in an opening formed in a side wall of the catheter. The opening may be a hole or an aperture in the wall of the catheter which may allow the balloon to expand into the inner lumen of the catheter. In some embodiments, the catheter may include two or more openings formed in the side wall of the catheter. In some embodiments, the balloon may be configured to expand through the opening and into the inner lumen of the catheter when the balloon is inflated. The balloon may be inflated and deflated by transferring a material to and from the balloon from outside the catheter, as described in greater detail herein. When the catheter includes two or more openings formed in the side wall of the catheter, the balloon may be configured to expand through the two or more openings. For example, as shown in FIGS. 12A-18B, balloon 1260 may be situated in an opening 1216 formed in a side wall of catheter 1210. In some embodiments, balloon 1260 may be configured to expand through opening 1216 and into inner lumen 1214 of catheter 1210 when balloon 1260 is inflated, as shown in FIG. 17A. In some embodiments, catheter 1210 may include two or more openings formed in the side wall of the catheter.

In some embodiments, an internal volume of the portion of the catheter adjacent the balloon may be smaller when the balloon is inflated than when the balloon is deflated. The internal volume of the portion of the catheter adjacent the balloon may refer to a space within the catheter defined by the cross-section multiplied by the length of the portion of the catheter adjacent the balloon, the portion of the catheter adjacent the balloon being described in greater detail herein. For instance, inflation of the balloon may cause the internal volume to be more than 5% smaller than when the balloon is deflated, more than 10% smaller, more than 20% smaller, more than 40% smaller, or more than 50% smaller. For example, the internal volume of the portion of catheter 1210 adjacent balloon 1260 is smaller when balloon 1260 is inflated, as shown in FIG. 17B, than when balloon 1260 is deflated, as shown in FIG. 16B.

In some embodiments, an internal shape of the catheter adjacent the balloon may be substantially circular when the balloon is deflated and non-circular when the balloon is inflated. The internal shape of the catheter may refer to the form, contour or outline of a cross-section of the catheter, defined by the walls of the catheter and optionally the balloon. When the balloon is inflated, the balloon may create a protuberance into the inner lumen. In at least one example, these protuberances may cause the internal shape of the catheter to be an intersection of a first circular shape (the original circular shape of the inner lumen) and the area not including in a second circular shape (created by the balloon), where the diameter of the second circular shape may be much larger than the diameter of the first circular shape. When the balloon is deflated, the balloon may be situated outside of the inner lumen, as described in greater detail above, and so may not have an effect on the internal shape of the catheter. For example, the internal shape of catheter 1210 adjacent balloon 1260 is substantially circular when balloon 1260 is deflated, as shown in FIG. 16B, and non-circular when balloon 1260 is inflated, as shown in FIG. 17B.

In some embodiments, the tube may be arranged over the catheter, with an inflation passage formed between an outer surface of the catheter and an inner surface of the tube for delivery of inflation fluid to the balloon. The tube may be arranged such that it completely or at least partially covers or encloses the catheter, defining a space between the tube and the catheter, the inflation passage, configured to deliver an inflation fluid to the balloon. For instance, a tip of the tube may be positioned outside and/or distal to the catheter. The inflation passage may be configured to enable a transfer of material from outside the catheter to and from the balloon. For example, the transferred material may be a fluid. For example, the transferred material may be at least one of a gas and/or a liquid. In at least one example, the balloon may be configured to inflate in response to a transfer of material to the balloon via the passage, and to deflate in response to a transfer of material from the balloon via the passage. For example, tube 1230 may be arranged over catheter 1210, as shown in FIGS. 12A-18B, with an inflation passage 1662 formed between the outer surface of catheter 1210 and the inner surface of tube 1230 for delivery of inflation fluid to balloon 1260. For instance, balloon 1260 may inflate in response to a transfer of the inflation fluid to balloon 1260 via inflation passage 1662, and to deflate in response to a transfer of the inflation fluid from balloon 1260 via inflation passage 1662.

In some embodiments, the tube may include an airtight seal on an opposite side of the balloon from the inflation passage, wherein the airtight seal may be configured to secure the catheter and the tube against relative movement. The airtight seal of the tube and/or the catheter may be a connector joining the tube and the catheter in a connection that may be impermeable to air or nearly so. In some examples, the connector may be made of glue. In other examples, the connector may be made of a metal alloy, such as Nitinol. The airtight seal may be provided on an opposite side of the balloon from the inflation passage, that is, on a distal end of the catheter, as described in greater detail herein. In at least one example, the connector may connect the tube to a tip of the catheter. In at least one example, the connector may connect the tube to an inner wall of the catheter, for example, at a distal portion of the catheter (such as the last one inch of the catheter, the last 10 inches of the catheter, or any appropriate distal portion of the catheter). In at least one example, the tube may encircle the tip of the catheter and the connector may connect the tube to an external wall of the catheter. The airtight seal may be affixed such that the tube and the catheter do not move relative to each other in at least an axial direction. For example, tube 1230 may include an airtight seal 1232 on an opposite side of balloon 1260 from inflation passage 1662, as shown in FIGS. 16A-18B, wherein airtight seal 1232 may be configured to secure catheter 1210 and tube 1230 against relative movement.

In some embodiments, the airtight seal may include an inner surface delimiting an interior volume contiguous with the inner lumen of the catheter, and wherein the inner lumen of the catheter and the interior volume of the airtight seal may form a delivery channel for advancement of a medical instrument therethrough. For example, the airtight seal may have a cross-section similar to the catheter, and may define an interior volume corresponding to the cross-section multiplied by the length of the airtight seal. The interior volume may be contiguous with the inner lumen of the catheter, forming a channel between the interior volume of the airtight seal and the inner lumen. In some embodiments, the channel may be a delivery channel for advancement of a medical instrument therethrough. Thus, the inner lumen and the interior volume of the airtight seal may form a delivery channel for enabling selective advancement of a medical instrument therethrough, such as an endovascular coil, for example, during use of the endovascular apparatus for delivery of the medical instrument to a treatment site. As used herein, selective advancement of the medical instrument may refer to the movement of the medical instrument through the delivery channel being controllable (e.g., by a user of the endovascular apparatus), such that the direction, speed, and length of the medical instrument passed through the delivery channel may be controlled. For example, selective advancement of the medical instrument may enable proximal, distal, and rotational movement of the instrument relative to the endovascular apparatus. Additionally or alternatively, selective advancement may enable control over the length of the medical instrument that is delivered from the distal end of the endovascular apparatus (and, thus, the length of the instrument remaining within the delivery channel of the endovascular apparatus). For example, airtight seal 1232 may include an inner surface delimiting an interior volume, as shown in FIGS. 12A-18B, contiguous with inner lumen 1214 of catheter 1210. Inner lumen 1214 and the interior volume of airtight seal 1232 may form a delivery channel for advancement of a medical instrument 1220 therethrough.

In some embodiments, the balloon may be configured to be selectively inflated and deflated based on control signals from a control device positioned outside a body of a patient. In some embodiments, a control device may be an apparatus which may be configured to selectively inflate and/or deflate the balloon by sending control signals to a device capable of delivering the inflation fluid to the balloon. In some embodiments, the control device may be configured to receive a command from a user input device, such as by a press of a button or key, a turn of a dial, an input through a computer-generated user interface, a voice command recognized in captured audio data through a voice recognition algorithm, a gesture recognized in captured image data through a gesture recognition algorithm, or any other action which may be performed by a user. The control unit may then transmit a corresponding control signal to a control component of the balloon to cause the balloon to perform the requested action (e.g., to expand into the inner lumen of the catheter). The signals from the control device may be transmitted to the control component of the constrictor wirelessly and/or via a wired connection. Additionally, or alternatively, the control device may receive data, such as from a sensor associated with the endovascular apparatus and/or an imaging device; may generate the control signal based on the received data; and transmit the control signal to the control component of the balloon For example, the balloon may be configured to inflate in response to a first action of a user of the endovascular apparatus, for example, an interventional radiologist, and may be configured to deflate in response to a second action of the user. For example, when the balloon is in a blood vessel, the user may perform a first action such as activating an inflation pump and a second action such as deactivating the inflation pump or operating the pump to remove the inflation fluid from the balloon. The pump and the control device may be configured to be positioned outside the body of the patient. For example, balloon 1260 may be configured to be selectively inflated and deflated based on control signals from a control device 1900 of FIG. 19 positioned outside a body of a patient. For instance, control device 1900 may be configured to receive a command from a user input device 1910 or may be configured to receive an input from sensors 1912 or imaging device 1914 allowing control device 1900 to take an action. Control unit 1900 may then transmit a control signal to balloon control component 1942 to cause balloon 1260 to perform the requested action (e.g., to inflate or deflate).

In some embodiments, the endovascular apparatus may include at least one additional balloon affixed to the catheter for expansion into the inner lumen of the catheter when the at least one additional balloon is inflated. The at least one additional balloon may be appended to the catheter at a position different than the position of the balloon and may be configured to expand into the inner lumen through a different opening in the catheter when the at least one additional balloon is inflated. In some embodiments, the balloon and the at least one additional balloon may be configured to be inflated simultaneously. For example, the balloon and the at least one additional balloon may share the same inflation passageway and may be configured to receive the inflation material simultaneously. Alternatively, the balloon and the at least one additional balloon may have different inflation passageways and may be configured to receive the inflation material simultaneously or at different times. In one example, the at least one additional balloon may be configured to inflate inside the catheter after the inflation of the balloon or before the inflation of the balloon. In one example, the at least one additional balloon may not be connected to the tube but instead connected to a different tube. In another example, the at least one additional balloon may not be connected to any tube. For example, endovascular apparatus 1200 may include at least one additional balloon, which may be located at the same axial location as balloon 1260 or which may be located proximal to or distal to balloon 1260. Where the apparatus includes multiple openings in the catheter 1210, a balloon may be arranged to cover each of the openings.

In some embodiments, the balloon may be configured to exert a stronger friction force on a medical instrument within the inner lumen of the catheter when the balloon is inflated, compared to when the balloon is deflated. A friction force may refer to a force resisting the relative motion of solid surfaces sliding against each other, for example, a relative motion of the medical instrument and the catheter or a relative motion of the medical instrument and the balloon. As an example, when the balloon is inflated, the balloon may expand within the inner lumen of the catheter, causing the balloon to come into contact with the medical instrument, in turn exerting a friction force on the medical instrument which is larger than the friction force exerted when the balloon is deflated. In another example, inflation of the balloon may cause the catheter to constrict, causing the inner walls of the catheter to exert a greater friction force on the medical instrument than when the balloon is deflated. In some embodiments, upon inflation, the balloon may be configured to secure the medical instrument within the inner lumen of the catheter against axial movement. For example, the stronger friction force exerted on the medical instrument due to the inflation of the balloon may inhibit, limit, or resist axial advancement and/or retraction, i.e., inhibit the medical instrument from moving along the length of the inner lumen catheter. In some embodiments, the balloon may be configured to obstruct axial advancement of the medical instrument through the inner lumen of the catheter when the balloon is inflated. For example, the inflation of the balloon may completely or at least partially block the inner lumen of the catheter, inhibiting axial advancement of the medical instrument. For example, balloon 1260 may be configured to exert a stronger force on medical instrument 1220 within inner lumen 1214 when balloon 1260 is inflated, as in FIG. 17A, compared to when balloon 1260 is deflated, as in FIG. 16A. In some embodiments, upon inflation, balloon 1260 may be configured to secure medical instrument 1220 within inner lumen 1214 of catheter A1210 against axial movement by clamping medical instrument 1220 at a clamped region 2321, as shown in FIG. 24. In some embodiments, balloon 1260 may be configured to obstruct axial displacement of medical instrument 1220 through inner lumen 1214 of catheter 1210, inhibiting axial advancement of medical instrument 1220, as shown in FIG. 23, where the inflation of balloon 1260 causes inner lumen 1214 to be completely or at least partially blocked.

In some embodiments, an axial distance between the balloon and a distal tip of the catheter may be equal to one inch or less. The distal tip of the catheter may refer to a tip of catheter closest to the distal end of the catheter, as described in greater detail herein. The axial distance may refer to a distance between the distal tip of the catheter and the balloon, which may be ten inches or less, five inches or less, two inches or less, one inch or less, one centimeter or less, or two millimeters or less. For example, an axial distance may be defined by the distance between balloon 1260 and a distal tip 1212 of catheter 1210.

In some embodiments, the endovascular apparatus may include at least one electrode which may be located at the same axial position along the catheter as the balloon, wherein upon inflation of the balloon, the balloon may be configured to press a medical instrument within the inner lumen of the catheter against the at least one electrode. As used herein, an electrode may include an electrical conductor used to selectively make contact with an object and to enable an electrical current to flow from the electrode to the object and/or from the object to the electrode, as described in further detail herein. The at least one electrode may be positioned along the catheter at a location near the balloon. In some embodiments, the at least one electrode may be within the inner lumen of the catheter opposite the balloon. When the balloon is inflated, the balloon may provide enough force so as to push on the medical instrument being delivered within the inner lumen of the catheter, causing the medical instrument to come into contact with the electrode. For example, endovascular apparatus 1200 may include at least one electrode 1242 which may be located at the same axial position along catheter 1210 as balloon 1260, as shown in FIGS. 12A-18B. Upon inflation of balloon 1260, balloon 1260 may be configured to press medical instrument 1220 within inner lumen 1214 of catheter 1210 against at least one electrode 1242, as shown in FIG. 17A, where a coil section 1724 comes into contact with at least one electrode 1242.

In some embodiments, the at least one electrode may be connected to an electrical circuit configured to deliver energy in a quantity sufficient to sever the medical instrument within the inner lumen of the catheter when the balloon presses the medical instrument against the at least one electrode. As used herein, an electrical circuit may include an interconnection of electrical components configured to deliver current via the electrode in such a way as to separate an endovascular instrument in two, as described in greater detail herein. In some example, the quantity sufficient to sever the medical instrument may be a function of the characteristics of the medical instrument, such as a material composition of the medical instrument, a structure of the medical instrument, a diameter of the medical instrument, an electrical resistance of the medical instrument, or any other appropriate characteristic of the medical instrument. Moreover, in some examples, the quantity sufficient to sever the medical instrument may be a function of the manner in which the energy is delivered, such as the distribution of energy delivered over time, or the concentration of energy delivered at specific portion of the endovascular instrument. For example, provided that the medical instrument is an endovascular coil, for some common endovascular coils, delivering energy of between 10 to 300 watt per second for a duration of 0.1 to 10 seconds is typically a quantity sufficient to sever the medical instrument, but other amounts may be required as described above. For example, at least one electrode 1242 may be connected to an electrical circuit 1243, as shown in FIG. 14, configured to deliver energy in a quantity sufficient to sever medical instrument 1220 within inner lumen 1214 of catheter 1210 when balloon 1260 presses medical instrument 1220 against at least one electrode 1242, as shown in FIG. 18A.

Figure 29:
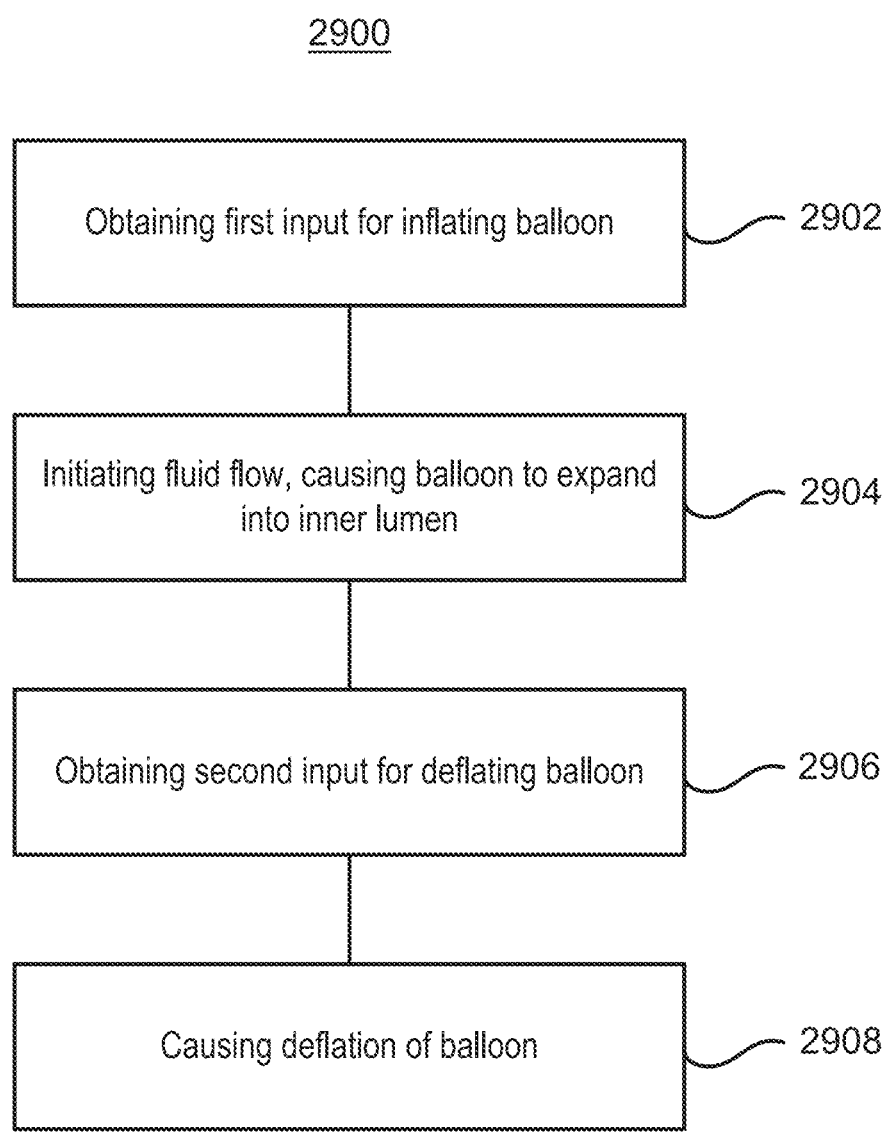
FIG. 29 is a flowchart of an example of a method for controlling a balloon affixed to a catheter in a body of a patient, consistent with disclosed embodiments.

Various embodiments of the current disclosure include non-transitory computer readable media containing instructions for controlling a balloon affixed to a catheter in a body of a patient. Consistent with other disclosed embodiments, computer-readable media may store program instructions, which are executable by at least one processing device and perform any of the steps and/or methods described herein. The instructions for controlling a balloon may correspond to method 2900 of FIG. 29, and may be performed by, for example, processor 1902 of control device 1900 of FIG. 19.

The instructions for controlling a balloon of the current disclosure may include obtaining a first input for inflating the balloon, which may refer to instructions for receiving, retrieving, or otherwise acquiring an input which confirms that the balloon is to be inflated. By way of example, processor 1902 of FIG. 19 may receive a first input from at least one of user input device 1910, sensors 1912, or imaging device 1914 containing instructions for inflating the balloon. The instructions for obtaining a first input for inflating the balloon may correspond to step 2902 of FIG. 29.

The instructions for controlling a balloon of the current disclosure may further include, in response to the first input, initiating fluid flow through a conduit connected to the balloon to cause inflation of the balloon, wherein inflation causes the balloon to expand into an inner lumen of the catheter. By way of example, processor 1902 of FIG. 19 may initiate fluid flow through conduit 1662 (also inflation passage 1662) of FIGS. 16A-18B to cause inflation of balloon 1260 by sending a control signal to balloon control component 1942, which may include a pump for providing balloon 1260 with an inflation fluid. This may cause balloon 1260 to expand into inner lumen 1214 of catheter 1210, as described in greater detail herein. The instructions of initiating fluid flow through a conduit connected to the balloon to cause inflation of the balloon may correspond to step 2904 of FIG. 29.

The instructions for controlling a balloon of the current disclosure may further include, after causing the inflation of the balloon, obtaining a second input for deflating the balloon. By way of example, processor 1902 of FIG. 19 may obtain a second input from at least one of user input device 1910, sensors 1912, or imaging device 1914 containing instructions for deflating the balloon. The instructions for obtaining a second input for deflating the balloon may correspond to step 2906 of FIG. 29.

The instructions for controlling a balloon of the current disclosure may further include, in response to the second input, causing deflation of the balloon with the conduit, wherein an outer diameter of a portion of the catheter adjacent the balloon is substantially the same when the balloon is inflated and when the balloon is deflated. By way of example, processor 1902 of FIG. 19 may cause deflation of balloon 1260 by sending a control signal to balloon control component 1942 to remove the inflation fluid from conduit 1662. The instructions for causing deflation of the balloon with the conduit may correspond to step 2908 of FIG. 29.

The instructions for controlling a balloon of the current disclosure may further include obtaining a medical image of the body of the patient captured while the catheter is positioned at least partially within the body. A medical image of the body of the patient may refer to a depiction of the interior of the body of the patient for clinical analysis and medical intervention, as well as visual representation of the function of some organs or tissues. The medical image may be obtained while the catheter is provided within the body, for example, during a medical procedure. By way of example, processor 1902 of FIG. 19 may obtain a medical image of the body of the patient by sending a signal to imaging device 1914 while catheter 1210 is positioned at least partially within the body.

The instructions for controlling a balloon of the current disclosure may further include controlling at least one of the inflation or the deflation of the balloon based on data derived from the medical image. By way of example, processor 1902 of FIG. 19 may determine whether to send instructions for inflating or deflating balloon 1260 to balloon control component 1942 based on data derived from an analysis of the medical image. Said analysis may be performed by processor 1902 based on instructions stored in memory 1904, or by a user of endovascular apparatus 1200, who may review the medical image and provide an input via user input device 1910.

Figure 30:
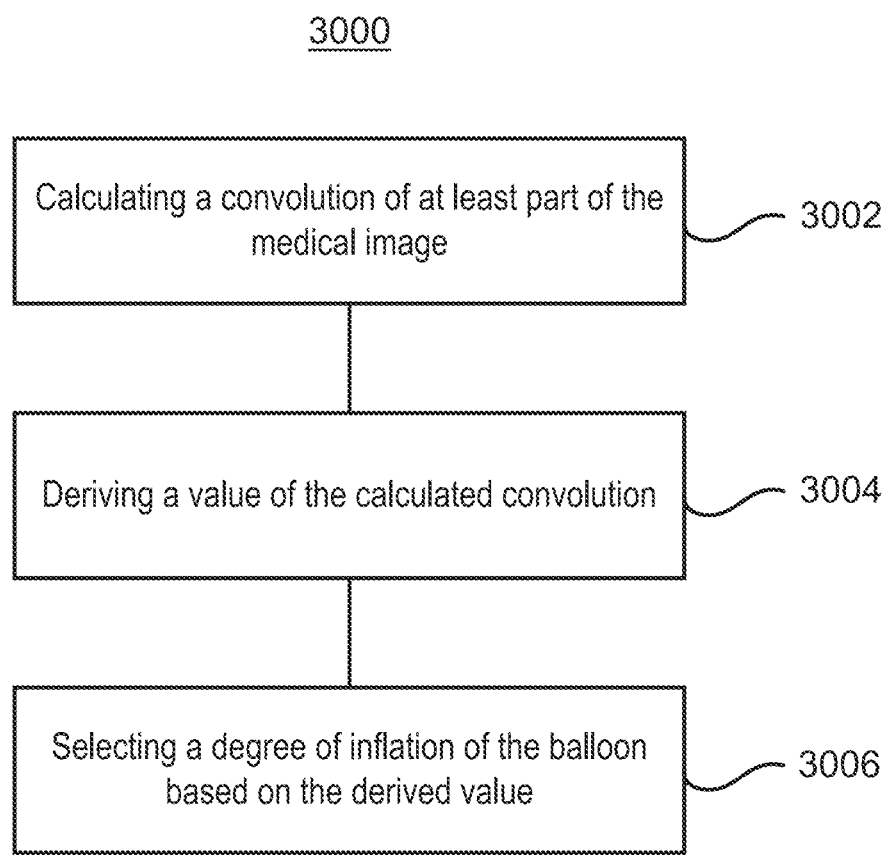
FIG. 30 is a flowchart of an example of a method for controlling at least one of inflation or deflation of a balloon based on data derived from a medical image, consistent with disclosed embodiments.

Consistent with the disclosed embodiments, controlling the at least one of the inflation or the deflation of the balloon based on the data derived from the medical image may include calculating a convolution of at least part of the medical image, deriving a value of the calculated convolution, and selecting a degree of inflation of the balloon based on the derived value. A one-dimensional convolution may refer to a function that transforms an original sequence of numbers to a transformed sequence of numbers, as described in greater detail herein. A value of a calculated one-dimensional convolution may include any value in the transformed sequence of numbers. An n-dimensional convolution may be defined by an n-dimensional array as scalars (known as the kernel of the n-dimensional convolution), as described in greater detail herein. Each particular value in the transformed array may be determined by calculating a linear combination of values in an n-dimensional region of the original array corresponding to the particular value. Deriving a value of the calculated convolution may include using machine learning or deep learning algorithms to determine the value of the calculated convolution. Selecting a degree of inflation of the balloon based on the derived value may refer to determining an appropriate level at which the balloon must be inflated based on the derived value. For example, if the derived value indicates that the endovascular apparatus must inflate the balloon because data derived from the medical image indicates that an aneurysm is completely filled and advancement of an endovascular coil must be stopped to prevent overfilling, the instructions provide for choosing an appropriate degree of inflation to inflate the balloon to secure the endovascular coil, inhibit axial displacement, and optionally severing the endovascular coil. By way of example, processor 1902 of FIG. 19 may perform method 3000 of FIG. 30 for controlling the at least one of the inflation or the deflation of the balloon based on the data derived from the medical image to calculate a convolution of at least part of the medical image, corresponding to step 3002, derive a value of the calculated convolution, corresponding to step 3004, and select a degree of inflation of balloon 1260 of FIGS. 17A-18B based on the derived value, corresponding to step 3006.

Aspects of this disclosure may relate to novel non-transitory computer readable medium instructions for operating a sensor that may monitor when medical instrument, e.g., an endovascular coil, may be about to be or may have been completely severed by the delivery catheter and thus, may be detached from the remainder of the coil. In some embodiments, the coil-cutting electrode may be configured as the sensor. Additionally, or alternatively, the sensor may be configured to detect motion of the coil relative to the catheter, which may indicate that the coil has been detached and released from the catheter. Sensor output may be used to alert the physician or an automated process when coil detachment has failed. Alternatively, or advantageously, sensor output may be used before the coil detachment attempt to indicate that the conditions may be unsuitable for coil detachment and an action may be required before the coil detachment attempt may be made so that the physician or the automated process may reposition the coil within the catheter or may cause a narrowing of the catheter before attempting or repeating the attempt of the coil detachment operation. Further, sensor output may also be used to control functions of the delivery catheter. For example, sensor output may indicate poor contact between the electrode and medical instrument and may cause the catheter to execute a function that may increase electrode-to-coil contact and then repeat the coil detachment operation. However, the instructions may additionally or alternatively be configured for use with other instrumentation and/or for other suitable processes.

Various embodiments of the current disclosure may relate to non-transitory computer readable medium containing instructions for monitoring partitioning of a medical instrument during an endovascular procedure. As used herein, an endovascular procedure may refer to any procedure used on arteries, veins, blood vessels or other similar parts of the body for a medical purpose, for example to diagnose and/or treat a patient. As used herein, monitoring may refer to observing, watching, or any other means of checking the progress, status or quality of partitioning the medical instrument during the procedure. As used herein, partitioning may refer to separating, subdividing, splitting, or any other process of dividing the medical instrument into parts. Some non-limiting examples of endovascular procedures may include aneurysm repair, peripheral bypass surgery, carotid angioplasty and stenting, carotid endarterectomy, dialysis access surgery, endovascular repair, stent graft delivery, thromboendarterectomy, thrombolytic therapy, varicose vein treatment or other minimally invasive catheter technique procedures. For example, the user (e.g., a doctor) may monitor the partitioning of a medical instrument during an aneurysm repair surgery or a similar medical instrument during an endovascular procedure.

Figure 31:
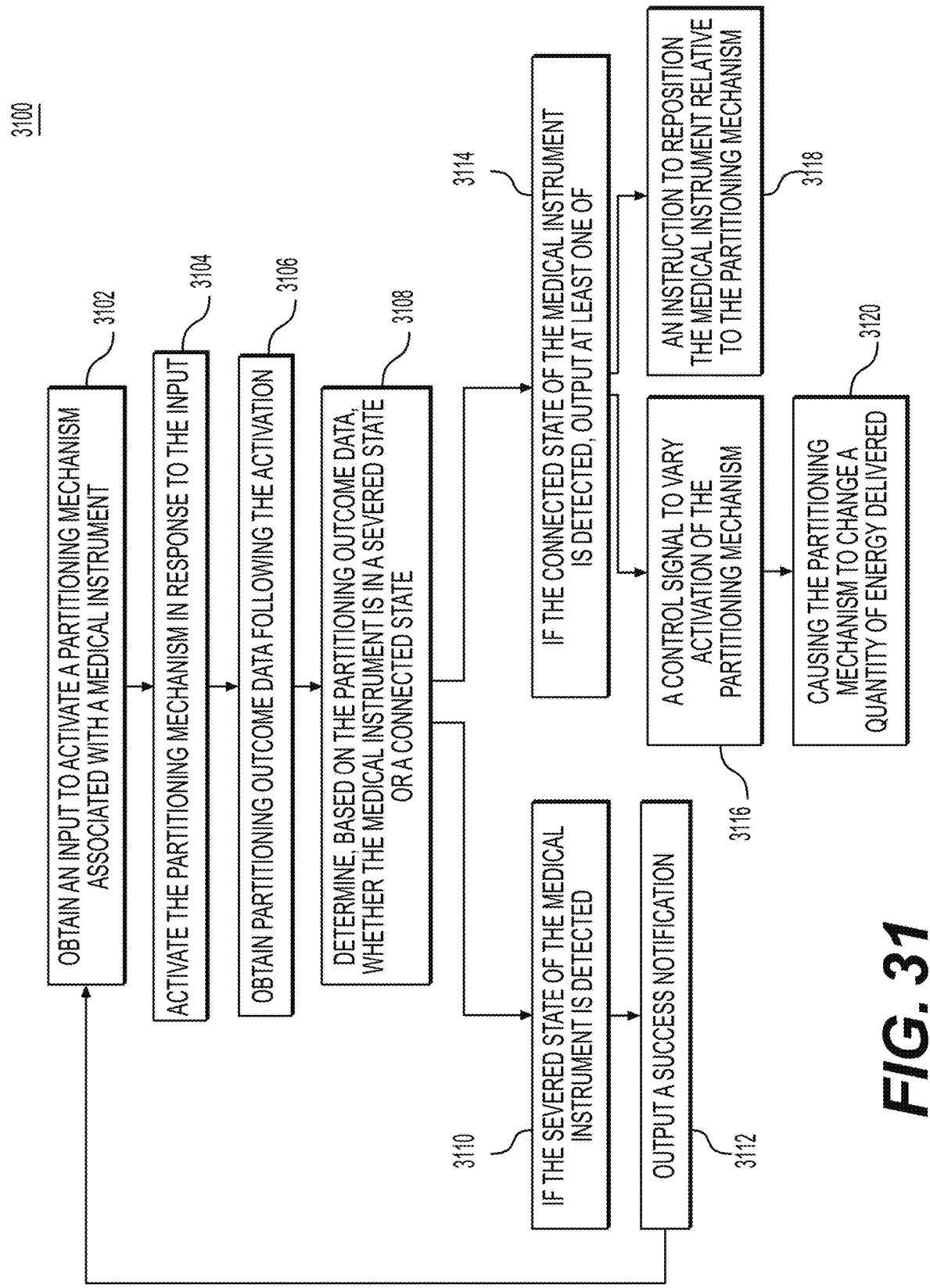
FIG. 31 is a flowchart of an operation for monitoring partitioning of a medical instrument during an endovascular procedure, consistent with disclosed embodiments.

FIG. 31 depicts instructions for monitoring partitioning 3100 of a medical instrument 1220 (e.g., an endovascular coil) during an endovascular procedure as shown in FIGS. 22A-22F.

Consistent with disclosed embodiments, the medical instrument may include an endovascular coil configured for delivery through the lumen of the catheter. As discussed herein, an endovascular coil may be defined herein FIGS. 12A and 12B depict a medical instrument 1220 (e.g., an endovascular coil) configured for delivery through a lumen 1214 (e.g., an inner lumen) of a catheter 1210 (e.g., a microcatheter).

Consistent with disclosed embodiments, the operations may include obtaining an input to activate a partitioning mechanism associated with a medical instrument within a lumen of a catheter, the catheter being positioned within a body. In some examples, an input to activate a partitioning mechanism may be obtained. As used herein, obtain may refer to getting, acquiring, coming by, procuring or any other means of securing something. As used herein, activate may refer to switching on, turning on, starting, triggering or any other means to make something operative. In some examples, the input may be indicative of a desire of an interventional radiologist to activate the partitioning mechanism. For example, the interventional radiologist may perform an action indicative of the desire to activate the partitioning mechanism (such as pressing a button, sliding a slider, turning a dial, entering data in a user interface, touching a touch sensitive sensor, audibly providing a voice command, and so forth), and the input may be a result of the action. In some examples, the input may be indicative of an automated system determining a need to activate the partitioning mechanism. For example, a medical image of the medical instrument within the lumen of the catheter positioned within the body may be received, and the medical image may be analyzed to determine the need to activate the partitioning mechanism. In another example, sensor readings from one or more sensors affixed to the catheter may be received, and the sensor readings may be analyzed to determine the need to activate the partitioning mechanism. In one example, the input may include at least one of a digital signal received from an external device, a signal received from a sensor, and data read from memory. As used herein, a partitioning mechanism may include any device configured to sever a medical instrument (such as one including an endovascular coil). In some examples, the partitioning mechanism may be affixed to a catheter, for example to an internal wall of the catheter, to an external wall of the catheter, to a distal tip of the catheter, to a distal portion of the catheter (such as the last one inch of the catheter, the last ten inches, etc.), and so forth. In some examples, the partitioning mechanism may be configured to sever the medical instrument while in a body of a patient. Some non-limiting examples of a partitioning mechanism may include one or more electrodes configured to cause flow of an electrical current through a portion of the medical instrument, a device including a sharp edge configured to sever the medical instrument by applying force focused on a particular region of the medical instrument, a looped wire configured to tightening around the medical instrument to sever it, a heat source configured to heat a portion of the medical instrument to sever it, and so forth.

FIG. 31 depicts an example of instructions for monitoring partitioning 3100 with the operations including obtaining an input (step 3102) to activate a partitioning mechanism (step 3104) associated with a medical instrument 1220 (e.g., an endovascular coil) within a lumen 1214 (e.g., an inner lumen) of a catheter 1210 (e.g., a microcatheter), the catheter being positioned within a body. FIG. 19 depicts a non-transitory computer readable medium with different inputs including an imaging device 1914. For example, a medical image of the medical instrument 1220 (e.g., endovascular coil) within the inner lumen 1214 of the catheter 1210 positioned within the body may be received, and the medical image may be analyzed to determine the need to activate the partitioning mechanism by step 3104. FIG. 19 also depicts a sensor or sensors input 1912. For example, the sensor readings may be analyzed to determine the need to activate the partitioning mechanism by step 3104. FIGS. 12A and 12B may depict an example of a partitioning mechanism which may include at least one electrode 1242 configured to cause flow of an electrical current through a portion of the medical instrument 1220.

Consistent with disclosed embodiments, the partitioning mechanism may be located at least partially within the lumen of the catheter. As used herein, partially may refer to partly, somewhat, or to a limited extent. For example, the partitioning mechanism can be partially a quarter, half, three quarters, or any other measurement within a lumen of a catheter. In some examples, part of the partitioning mechanism may be affixed to an internal wall of the catheter and the other part of the partitioning mechanism may be affixed to an external wall of the catheter, and so forth.

FIGS. 12A and 12B depict a partitioning mechanism with an at least one electrode 1242 that may be affixed to an internal wall 1211 (e.g., an inner wall of a sheath) within the inner lumen 1214 of a catheter 1210 (e.g., microcatheter).

Consistent with disclosed embodiments, the operations may include in response to the input, activating the partitioning mechanism. As used herein, response may refer to feedback, a reply, a return, an acknowledgment or any other reaction to something or the input. For example, the operations may provide feedback or a reply to the input (such as pressing a button, sliding a slider, turning a dial, entering data in a user interface, touching a touch sensitive sensor, audibly providing a voice command, and so forth) to activate the partitioning mechanism. In an example, the input may include at least one of a digital signal received from an external device, a signal received from a sensor, and data read from memory. Advantageously, some embodiments may be configured wherein activating the partitioning mechanism may include at least one electrode in a catheter to delivery energy to an adjacent portion of a medical instrument. As used herein, deliver energy may refer to bringing, taking, conveying, carrying or any other means of providing energy, power, activity, force or any other property to a site to perform work on the site or heat it. For example, energy may exist in potential, kinetic, thermal, helictical, chemical, nuclear, electric or other forms. In some embodiments, the at least one electrode or more than one electrode may deliver energy in the form of electricity to a catheter next to the at least one electrode, across from the at least one electrode, distal to the at least one electrode, or proximal to the at least one electrode. Alternatively, the at least one electrode or more than one electrode may deliver thermal energy to the catheter next to the at least one electrode, across from the at least one electrode, distal to the at least one electrode, or proximal to the at least one electrode.

FIG. 31 depicts instructions for monitoring partitioning 3100 with the operations including activating the partitioning mechanism (step 3104) in response to the input obtained by step 3102. FIGS. 12A and 12B depict an embodiment wherein activating the partitioning mechanism by step 3104 may include an at least one electrode 1242 in a catheter 1210 (e.g., a microcatheter) to deliver energy to an adjacent portion of a medical instrument 1220 (e.g., an endovascular coil). FIG. 17A depicts an example of the adjacent portion of the medical instrument 1220 as a coil section in contact with the least one electrode 1242 for energy to be delivered.

Consistent with disclosed embodiments, activating the partitioning mechanism in response to the input may include: (i) determining whether the medical instrument is in a partitioning readiness state, (ii) if the partitioning readiness state of the medical instrument may be detected, activating the partitioning mechanism to sever the medical instrument, and/or (iii) if the partitioning readiness state of the medical instrument is not detected, outputting a second instruction to reposition the medical instrument relative to the partitioning mechanism and re-determining whether the medical instrument is in the partitioning readiness state. As used herein, a partitioning readiness state may refer to the medical instrument's shape, situation, position, particular condition, or state of being prepared to be partitioned at a specific time. For example, sensors or a medical image of the medical instrument (e.g., an endovascular coil) may be used to determine whether the medical instrument may be in a specific position relative to the partitioning mechanism to be partitioned. Advantageously, some embodiments may be configured to activate the partitioning mechanism to sever the medical instrument by inducing an electric current from the at least one electrode through the medical instrument if the partitioning readiness state of the medical instrument is detected. Alternatively, embodiments may be configured to output a second instruction to reposition the medical instrument relative to the partitioning mechanism and re-determine whether the medical instrument is in the partitioning readiness state if the partitioning readiness state of the medical instrument is not detected. As used herein, an instruction may refer to an order, command, directive, dictation, demand, or other detailed information telling how something should be done. As used herein, reposition may refer to moving, shifting, relocating or placing in a different position before the next activation of the partitioning mechanism. For example, if the partitioning readiness state of the medical instrument is not detected, the second instruction may be outputted to instruct the user to reposition the medical instrument forward, backward, to one side, or to the other side relative to the partitioning mechanism and then re-determining whether the medical instrument is in the partitioning readiness state.

Figure 32:
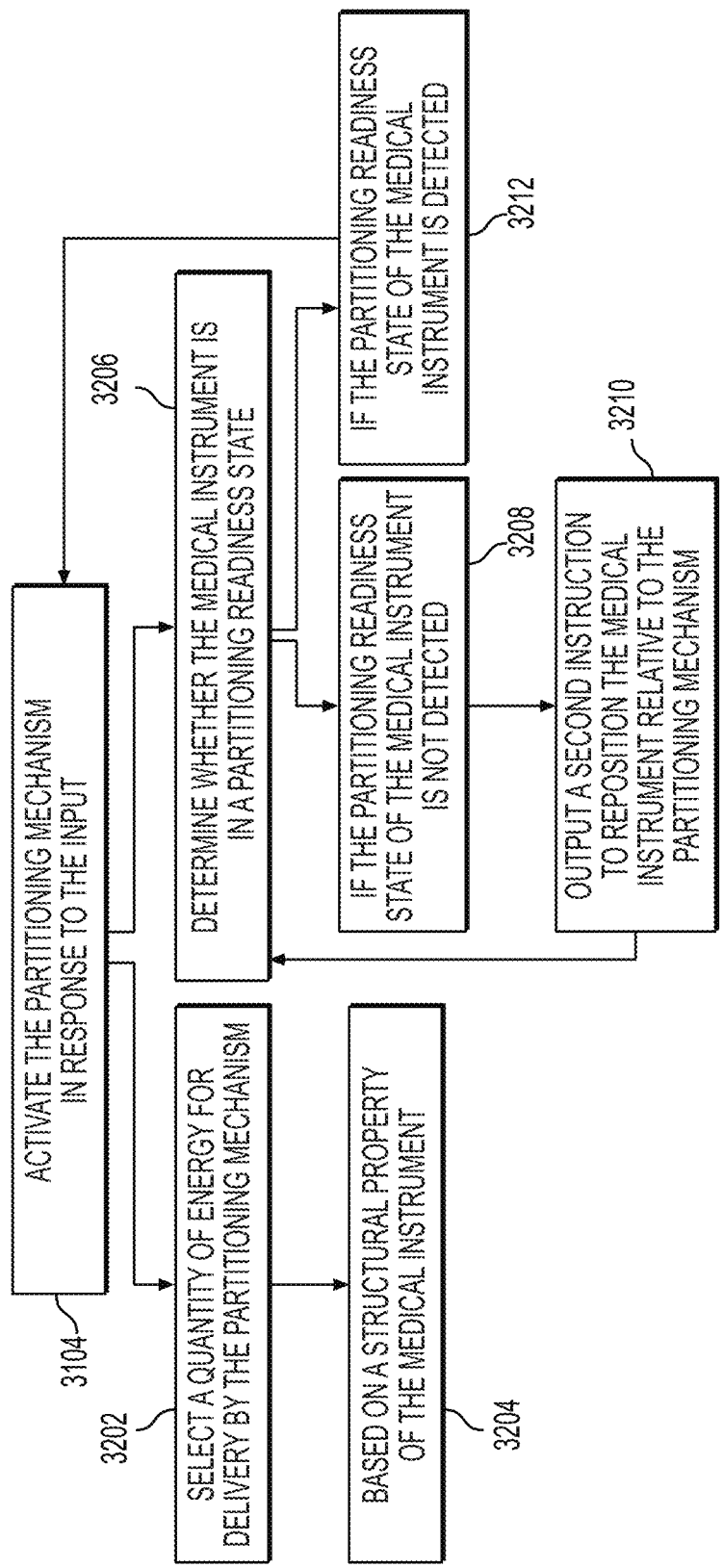
FIG. 32 is a flowchart of an operation for activating the partitioning mechanism in response to an input, consistent with disclosed embodiments.

FIG. 32 depicts instructions for activating the partitioning mechanism by step 3104, for example in response to the input received by step 3102. Embodiments may be configured to include determining whether a medical instrument 1220 (e.g., an endovascular coil) is in a partitioning readiness state (step 3206). Further, if the partitioning readiness state of medical instrument 1220 is detected (case 3102), then the instructions may activate the partitioning mechanism in response to input (for example, as described in relation to step 3104). Alternatively, if the partitioning readiness state is not detected (case 3104), then the instructions may output a second instruction to reposition the medical instrument 1220 relative to the partitioning mechanism (step 3210), and may further re-determine whether medical instrument 1220 is in the partitioning readiness state after the repositioning, for example using step 3206. For example, if the partitioning readiness state is detected (case 3212), the second instruction may be outputted to instruct the user to reposition the endovascular coil (step 3210), for example forward, backward, to one side, and/or to the other side relative to the partitioning mechanism, and may further re-determining whether medical instrument 1220 is in the partitioning readiness state after the repositioning, for example using 3206.

Consistent with disclosed embodiments, the partitioning readiness state of the medical instrument may be determined based on at least one of (i) a position of the medical instrument relative to the partitioning mechanism, (ii) a degree of contact between the partitioning mechanism and the medical instrument, (iii) a flow of electric current from the partitioning mechanism through the medical instrument, or (iv) an electrical impedance of an electrical circuit including the partitioning mechanism and the medical instrument. As used herein, a degree of contact may refer to an amount, extent or point of a union or junction of surfaces between the electrode and the medical instrument (e.g., an endovascular coil). For example, the partitioning readiness state may be determine based on where the medical instrument is located relative to the partitioning mechanism (e.g., parallel with, close to, far from). In an example, a degree of contact may be a measure of at least one of electrical conductivity, electrical resistance, electrical capacity and electrical impedance between the medical instrument and the partitioning mechanism. In another example, a degree of contact may be based on an area of contact region between the medical instrument and the partitioning mechanism. Non-limiting examples may include a degree of contact in the shape of a narrow rectangle between two parallel cylinders or a circular degree of contact between two spheres. For example, the degree of contact may be closer to 90° where the electrode and medical instrument may not be exactly flush with each other. Advantageously, or alternatively the degree of contact may be 180° where the electrode and medical instrument may be flush against each other. In yet another example, a degree of contact may be based on contact pressure between the medical instrument and the partitioning mechanism. Some non-limiting examples may include the degree of contact measured between the medical instrument (e.g., an endovascular coil) and the partitioning mechanism affixed to a catheter, for example to an internal wall of the catheter, to an external wall of the catheter, to a distal tip of the catheter, to a distal portion of the catheter (such as the last one inch of the catheter, the last ten inches, etc.), and so forth. Further, the degree of contact may include the degree of contact measured between one or more electrodes configured to cause flow of an electrical current through a portion of the medical instrument, the degree between a device including a sharp edge configured to sever the medical instrument by applying force focused on a particular region of the medical instrument, the degree between a looped wire configured to tightening around the medical instrument to sever it, the degree between a heat source configured to heat a portion of the medical instrument to sever it, and so forth.

Figure 33:
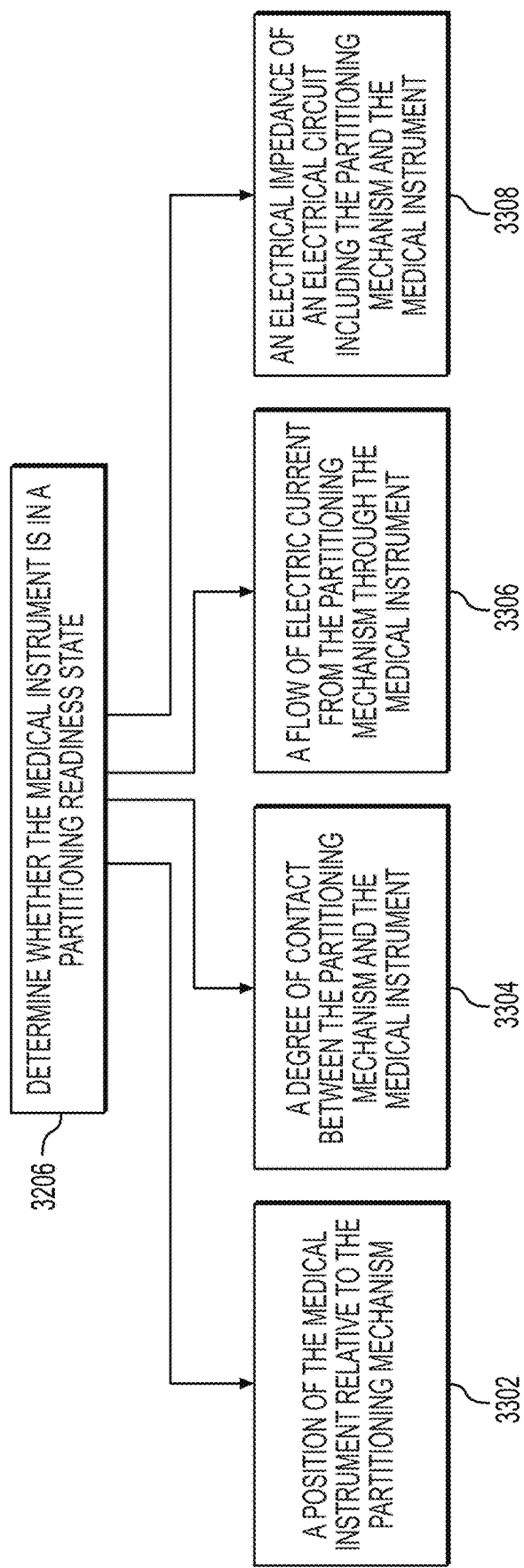
FIG. 33 is a flowchart of an operation for determining whether the medical instrument is in a partitioning readiness state, consistent with disclosed embodiments.

FIG. 33 depicts instructions for determining the partitioning readiness state of a medical instrument 1220 (e.g., an endovascular coil) by step 3206 based on at least one of (i) a position of the medical instrument relative to the partitioning mechanism (step 3302), (ii) a degree of contact between the partitioning mechanism and the medical instrument (step 3304), (iii) a flow of electric current from the partitioning mechanism through the medical instrument (step 3306), or (iv) an electrical impedance of an electrical circuit including the partitioning mechanism and the medical instrument (step 3308). FIG. 17A may depict a degree of contact of 180° between the at least one electrode 1242 and a medical instrument 1220 flush against each other where a coil section 1724 may be in contact with the at least one electrode.

Consistent with disclosed embodiments, the partitioning readiness state of the medical instrument may be determined based on at least a flow of electric current from the partitioning mechanism through the medical instrument. For example, the partitioning readiness state may indicate whether electrical current flowed from the electrode through the medical instrument (e.g., an endovascular coil). Alternatively, or additionally, the partitioning readiness state may indicate whether electrical current did not flow from the electrode through the medical instrument. Further, the partitioning readiness state may indicate how much or how little electrical current flowed from the electrode through the medical instrument.

FIG. 33 depicts instructions for determining the partitioning readiness state of a medical instrument 1220 (e.g., an endovascular coil) by step 3206 based on at least a flow of electric current from the partitioning mechanism through the endovascular coil (step 3306).

Consistent with disclosed embodiments, the partitioning readiness state of the medical instrument may be determined based on at least an electrical impedance of an electrical circuit including the partitioning mechanism and the medical instrument. As used herein, electrical impedance may refer to electrical resistance, ohms, resistance, resistivity, ohmic resistance, ohmage or any other amount of opposition to the electrical current. As used herein, an electrical circuit may refer to a course, route, wiring, bridge or any other closed path in which electrons move to produce electric current. For example, the partitioning readiness state may indicate the electrical impedance or resistance of the electrical circuit including the electrode and the medical device (e.g., an endovascular coil) or multiple electrodes and multiple medical devices. Alternatively, the partitioning readiness state may indicate a lower electrical impedance or resistance of the electrical circuit indicating that the flow of electricity easily flows. Or some embodiments may be configured where the partitioning readiness state indicates a higher electrical impedance or resistance of the electrical circuit indicating that the flow of electricity does not easily flow. Advantageously, the partitioning readiness state may indicate the degree of contact, the flow of electrical current, and the electrical impedance in relation to the electrode and the medical instrument.

FIG. 33 depicts instructions for determining the partitioning readiness state of a medical instrument 1220 (e.g., an endovascular coil) by step 3206 based on at least an electrical impedance of an electrical circuit including the partitioning mechanism and the endovascular coil (step 3308).

Consistent with disclosed embodiments, activating the partitioning mechanism may include selecting a quantity of energy for delivery by the partitioning mechanism. As used herein, selecting may refer to picking, limiting, electing, choosing, preferring or any other method of choosing something. As used herein, a quantity of energy may refer to a sum, mass, weight, volume, load or any other amount or number of energy. For example, a selection of the quantity of energy may be one, less than one, or more than one watt, kilowatt, joule, calorie, erg, kilowatt-hour, BTU, and so forth. Advantageously, the quantity may be selected based on a structural property of the medical instrument. As used herein, structural property may refer to an anatomical, architectural, skeletal, assembled, form, make, manufacture or any other arrangement of parts that gives property its basic form. For example, a smaller quantity of energy, like a milliwatt or picowatt, may be chosen based on the medical instrument being a microcatheter. Alternatively, a larger quantity of energy, like a centiwatt or deciwatt, may be chosen based on the medical instrument being a catheter. Alternatively, or additionally, activating the partitioning mechanism may include controlling the partitioning mechanism for delivery of the selected quantity of energy. As used herein, control may refer to regulating, restraining, restricting, limiting, subjecting, manipulating or otherwise influencing. In some embodiments, activating the partitioning mechanism may include both selecting a quantity of energy and controlling the partitioning mechanism for delivery of the selected quantity of energy. Embodiments may be configured to select a smaller quantity of energy and then may advance the partitioning mechanism a relatively shorter distance than other embodiments that may be configured to select a larger quantity of energy and then may advance the partitioning mechanism a relatively larger distance. Another example may be an embodiment configured to retract or restrict the partitioning mechanism if the selected quantity of energy does not reach a threshold value. Other examples of embodiments may be configured to extend or advance the partitioning mechanism if the selected quantity of energy does reach a threshold value.

FIG. 32 depicts instructions for activating the partitioning mechanism by step 3104, for example in response to the input obtained by step 3102. In some embodiments, activating the partitioning mechanism may include selecting a quantity of energy for delivery by the partitioning mechanism (step 3202). Advantageously, in step 3204, the quantity of energy for delivery selected may be based on a structural property of the medical instrument 1220 (e.g., an endovascular coil).

Consistent with disclosed embodiments, the operations may include following the activation, obtaining partitioning outcome data. In some examples, partitioning outcome data may include data indicative of whether the medical instrument was successfully severed. In other examples, partitioning outcome data may include data indicative of whether the medical instrument was not successfully severed. Consistent with disclosed embodiments, obtaining the partitioning outcome data may include obtaining a medical image of at least a portion of the body while the catheter may be positioned within the body. For example, the medical image may provide an image of the aneurysm, an image of the aneurysm and catheter, an image of the catheter, or a similar image within the body near a treatment site to provide data and/or be analyzed whether the medical instrument was successfully severed and/or whether the medical instrument may be in a position that enables the partitioning mechanism to sever it. Advantageously, in some embodiments, obtaining the partitioning outcome data may include determining the partitioning outcome data based at least partially on the medical image. For example, the medical image may partially be used in conjunction with other variables, sensors, inputs, or outputs to determine the partitioning outcome data. In one example, the medical image of the aneurysm and catheter may provide data or be analyzed in conjunction with a contact, motion, or pressure sensor within a lumen of the catheter to determine the partitioning outcome data. In another example, a convolution of at least part of the medical image may be calculated to derive at least one output value of the calculated convolution. Further, in response to a first output value of the calculated convolution, it may be determined that the medical instrument is in a severed state, while in response to a second output value of the calculated convolution, it may be determined that the medical instrument is in connected state. In yet another example, the medical image may be analyzed to detect (for example, using object detection algorithms) the partitioning mechanism, as well as the medical instrument from both sides of the partitioning mechanism. Further, the medical image may be analyzed to determine whether the portion of the medical instrument from one side of the partitioning mechanism is connected to the portion of the medical instrument from the other side of the partitioning mechanism (for example, using crack detection algorithms) to determine whether the medical instrument is in a connected state (for example, when no crack is detected, when it is determined that the two portions are connected, etc.) or in a severed state (for example, when a crack is detected, when it is determined that the two portions are not connected, etc.).

FIG. 31 depicts instructions for monitoring partitioning 3100 of a medical instrument 1220 (e.g., an endovascular coil) during an endovascular procedure as shown in FIGS. 22A-22F. Some embodiments may include obtaining partitioning outcome data (step 3106) following the activation by step 3104. Further, in FIG. 34, obtaining partitioning outcome data by step 3106 may include obtaining a medical image of at least a portion of the body while a catheter 1210 (e.g., a microcatheter) may be positioned within the body (step 3402).

Consistent with disclosed embodiments, obtaining the partitioning outcome data may include receiving output from at least one sensor. As used herein, output may refer to a product, thing, object, consequence or any other place where information leaves a system. As used herein, sensor may refer to a detector, a sensing element or any device that receives a signal or stimulus and responds to it in a distinctive manner. Non-limiting examples of outputs may be visual, data, print, or sound forms. Non-limiting examples of sensors may include ones based on temperature, proximity, infrared, pressure, light, ultrasonic, and so forth. Advantageously, embodiments may be configured to obtain partitioning outcome data including output from at least one proximity sensor, from at least one proximity sensor and at least one pressure sensor, or from at least one proximity, at least one pressure sensor, and/or one temperature sensor. In some examples, the partitioning outcome data may include or be based on data captured using the at least one sensor affixed to a catheter, for example to an internal wall of the catheter, to an external wall of the catheter, to a distal tip of the catheter, to a distal portion of the catheter (such as the last one inch of the catheter, the last ten inches, etc.), to a portion of the catheter position in the body, and so forth. Embodiments may be configured wherein the at least one sensor may be situated within the lumen of the catheter in a distal region thereof. For example, the at least one sensor may be positioned within the center of the lumen of the catheter in the distal region. Alternatively, and advantageously, the at least one sensor may be positioned along an inner wall of the lumen of the catheter in the distal region. In other embodiments, two or more sensors may be positioned within the lumen next to each other or across from each other in the distal region.

Figure 34:
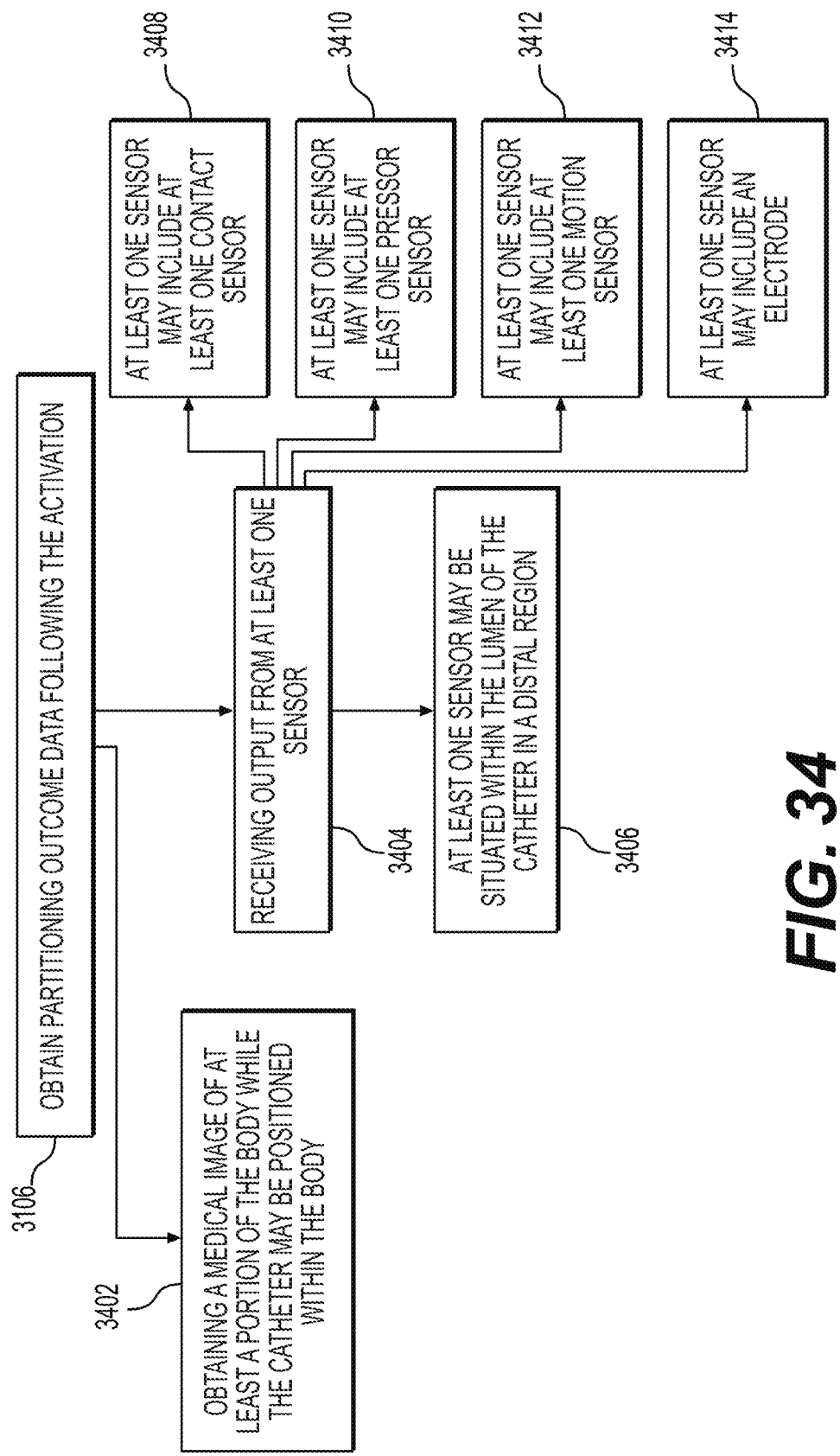
FIG. 34 is a flowchart of an operation for obtaining partitioning outcome data following the activation, consistent with disclosed embodiments.

FIG. 34 depicts instructions for obtaining partitioning outcome data by step 3106 following the activation by step 3104. In some embodiments, obtaining the partitioning outcome data in step 3106 may include receiving output from at least one sensor (step 3404). Further, the at least one sensor may be situated within a lumen 1214 (e.g., an inner lumen) of a catheter 1210 (e.g., a microcatheter) in a distal region thereof (case 3406).

Consistent with disclosed embodiments, the at least one sensor may include at least one of a contact sensor, a pressure sensor, or a motion sensor. As used herein, a contact sensor may refer to a sensor where there may be a union or junction of surfaces between the sensor and another object. For example, the at least one sensor may include at least one contact sensor, and the partitioning outcome data may include data indicative of a contact of a medical instrument with a particular region of a catheter or with an element affixed to the catheter (such as an element of the partitioning mechanism, the at least one sensor affixed to the catheter, etc.). In one example, the contact sensor may be positioned in the internal wall or lumen of the catheter distal to the partitioning mechanism. In one example, in a severed state, after a distal portion of the medical instrument is detached from the remaining portion of the medical instrument, the distal portion may be pulled and/or pushed out of the catheter. As a result, the distal portion of the medical instrument, which may be in contact with the contact sensor when the medical instrument is in a connected state, may be pulled and/or pushed away of the contact sensor when the medical instrument is in a severed state. The contact sensor may determine whether the distal portion of the medical instrument is in contact with the contact sensor. In response to a determination that the distal portion of the medical instrument is in contact with the contact sensor, a connected state may be detected, while in response to a determination that the distal portion of the medical instrument is not in contact with the contact sensor, a severed state may be detected. As used herein, a pressure sensor may refer to a sensor where there may be a coercion, force, pressing, pushing, squeezing or other continuous physical force exerted on or against the sensor by something in contact with it. For example, the at least one sensor may include a pressure sensor in the form of a vibration sensor which may capture data associated with vibrations of the catheter and/or the medical instrument, and the data may be analyzed to identify vibration patterns associated with a contact of the medical instrument with the partitioning mechanism and/or associated with a successful activation of the partitioning mechanism that severs the medical instrument and/or associated with a failure of the partitioning mechanism to sever the medical instrument. In one example, the pressure sensor may be positioned in the internal wall or lumen of the catheter distal to the partitioning mechanism. In one example, in a severed state, after a distal portion of the medical instrument is detached from the remaining portion of the medical instrument, the distal portion may be pulled and/or pushed out of the catheter. As a result, the distal portion of the medical instrument, which may apply pressure on the pressure sensor when the medical instrument is in a connected state, may be pulled and/or pushed away of the pressure sensor when the medical instrument is in a severed state. The pressure sensor may determine whether the distal portion of the medical instrument is applying pressure on the pressure sensor. In response to a determination that the distal portion of the medical instrument is applying pressure on the pressure sensor, a connected state may be detected, while in response to a determination that the distal portion of the medical instrument is not applying pressure on the pressure sensor, a severed state may be detected. As used herein, a motion sensor may refer to a movement, shifting or other change in position of an object relative to the sensor. For example, embodiments with the motion sensor may be configured to detect when the medical instrument extends past the location of the motion sensor in obtaining partitioning outcome data. The motion sensor may provide data of the position, length, and amount of the medical instrument extending through to the treatment site. In one example, the motion sensor may be positioned in the internal wall or lumen of the catheter distal to the partitioning mechanism. In one example, in a severed state, after a distal portion of the medical instrument is detached from the remaining portion of the medical instrument, the distal portion may be pulled and/or pushed out of the catheter. As a result, the distal portion of the medical instrument moves, a movement that may be detected by the movement sensor. In response to a detected axial motion of the distal portion (or axial motion greater than a selected threshold) of the medical instrument, a severed state may be detected, while in response to no axial motion of the distal portion (or axial motion smaller than the selected threshold), a connected state may be detected. Advantageously, or additionally, the at least one sensor may include one, two, multiple, or any other combination of sensors (for example, one contact sensor, one pressure sensor, and/or one motion sensor).

FIG. 34 depicts instructions for obtaining partitioning outcome data by step 3106 following the activation by step 3104. Some embodiments may be configured where the at least one sensor may include at least one of a contact sensor (case 3408), a pressure sensor (case 3410), or a motion sensor (case 3412).

Consistent with disclosed embodiments, the at least one sensor may include an electrode associated with the partitioning mechanism, the electrode being configured to deliver energy for severing the medical instrument. For example, the at least one sensor may include at least one electrode affixed to the catheter, and the partitioning outcome data may include electromagnetic data (for example, indicative of a flow of electrical current through the medical instrument, indicative of at least one of a flow of electrical current, an electrical resistance, an electrical capacitance and an electrical impedance between a first electrode and a second element, and so forth). Advantageously, the at least one sensor with an electrode may be used as part of the partitioning mechanism to deliver energy to sever the medical instrument. Embodiments may be configured to deliver energy from the electrode directly to the medical instrument to sever. Alternatively, embodiments may be configured to deliver energy from one electrode to a second electrode across the medical instrument to sever.

FIG. 34 depicts instructions for obtaining partitioning outcome data by step 3106 following the activation by step 3104. In some embodiments, the at least one sensor may include an at least one electrode 1242 associated with the partitioning mechanism, the at least one electrode 1242 being configured to deliver energy for severing a medical instrument 1220 (e.g., an endovascular coil).

Consistent with disclosed embodiments, the partitioning outcome data may indicate at least one of (i) a degree of contact between the electrode and the medical instrument, (ii) a flow of electrical current from the electrode through the medical instrument, or (iii) an electrical impedance of an electrical circuit including the electrode and the medical instrument. Further, some embodiments may be configured wherein the partitioning outcome data may be indicative of a degree of contact between the medical instrument and the partitioning mechanism. In one example, a degree of contact may be a measure of at least one of electrical conductivity, electrical resistance, electrical capacity and electrical impedance between the medical instrument and the partitioning mechanism. In another example, a degree of contact may be based on an area of contact region between the medical instrument and the partitioning mechanism. Non-limiting examples may include a degree of contact in the shape of a narrow rectangle between two parallel cylinders or a circular degree of contact between two spheres. For example, the degree of contact may be closer to 90° where the electrode and medical instrument may not be exactly flush with each other. Advantageously, or alternatively the degree of contact may be 180° where the electrode and medical instrument may be flush against each other. Embodiments may also be configured where the degree of contact refers to the degree between the medical instrument and the partitioning mechanism. In yet another example, a degree of contact may be based on contact pressure between the medical instrument and the partitioning mechanism. Some non-limiting examples may include the degree of contact measured between the medical instrument (e.g., an endovascular coil) and the partitioning mechanism affixed to a catheter, for example to an internal wall of the catheter, to an external wall of the catheter, to a distal tip of the catheter, to a distal portion of the catheter (such as the last one inch of the catheter, the last ten inches, etc.), and so forth. Further, the degree of contact may include the degree of contact measured between one or more electrodes configured to cause flow of an electrical current through a portion of the medical instrument, the degree between a device including a sharp edge configured to sever the medical instrument by applying force focused on a particular region of the medical instrument, the degree between a looped wire configured to tightening around the medical instrument to sever it, the degree between a heat source configured to heat a portion of the medical instrument to sever it, and so forth.

Figure 35:
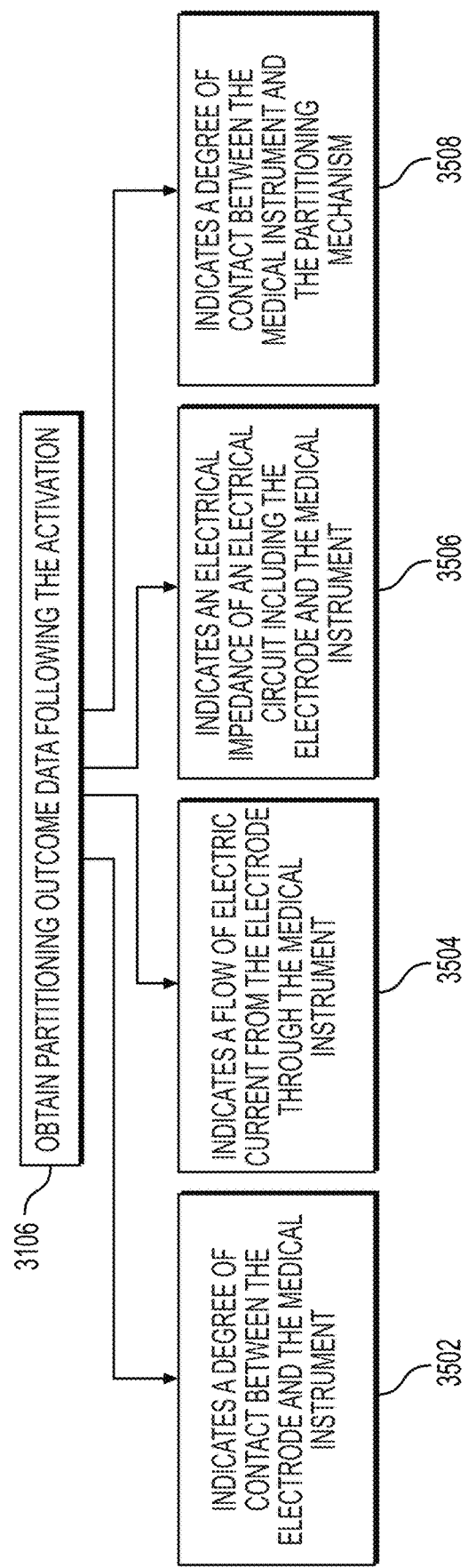
FIG. 35 is another flowchart of an operation for obtaining partitioning outcome data following the activation, consistent with disclosed embodiments.

FIG. 35 depicts instructions for obtaining partitioning outcome data by step 3106 following the activation by step 3104. In some embodiments, the partitioning outcome data may indicate at least one of (i) a degree of contact between the at least one electrode 1242 and the medical instrument 1220 (e.g., an endovascular coil) (case 3502), (ii) a flow of electric current from the at least one electrode 1242 through the endovascular coil (case 3504), or (iii) an electrical impedance of an electrical circuit including the at least one electrode 1242 and the endovascular coil (case 3506).

Consistent with disclosed embodiments, the partitioning outcome data may indicate at least a flow of electrical current from the electrode through the medical instrument. As used herein, flow may be defined above. For example, the partitioning outcome data may indicate whether electrical current flew from the electrode through the medical instrument (e.g., an endovascular coil). Alternatively, or additionally, the partitioning outcome data may indicate whether electrical current did not flow from the electrode through the medical instrument. Further, the partitioning outcome data may indicate how much or how little electrical current flew from the electrode through the medical instrument.

FIG. 35 depicts instructions for obtaining partitioning outcome data by step 3106 following the activation by step 3104. In some embodiments, the partitioning outcome data may indicate at least a flow of electric current from the at least one electrode 1242 through the medical instrument 1220 (e.g., an endovascular coil) (case 3504).

Consistent with disclosed embodiments, the partitioning outcome data may include an electrical impedance of an electrical circuit including the electrode and the medical instrument. As used herein, electrical impedance may refer to electrical resistance, ohms, resistance, resistivity, ohmic resistance, ohmage or any other amount of opposition to the electrical current. As used herein, an electrical circuit may refer to a course, route, wiring, bridge or any other closed path in which electrons move to produce electric current. For example, the partitioning outcome data may include the electrical impedance or resistance of the electrical circuit including the electrode and the medical device or multiple electrodes and multiple medical devices. Alternatively, the partitioning outcome data may include a lower electrical impedance or resistance of the electrical circuit indicating that the flow of electricity easily flows. Or some embodiments may be configured where the partitioning outcome data includes a higher electrical impedance or resistance of the electrical circuit indicating that the flow of electricity does not easily flow. Consistent with disclosed embodiments, the partitioning outcome data may indicate (i) a degree of contact between the electrode and the medical instrument, (ii) a flow of electrical current from the electrode through the medical instrument, and/or (iii) an electrical impedance of an electrical circuit including the electrode and the medical instrument. Advantageously, the partitioning outcome data may include the degree of contact, the flow of electrical current, and the electrical impedance in relation to the electrode and the medical instrument.

FIG. 35 depicts instructions for obtaining partitioning outcome data by step 3106 following the activation by step 3104. Some embodiments may be configured where the partitioning outcome data may include an electrical impedance of an electrical circuit including the at least one electrode 1242 and the medical instrument 1220 (e.g., an endovascular coil) (case 3506).

Consistent with disclosed embodiments, the operations may include determining, based on the partitioning outcome data, whether the medical instrument may be in a severed state or a connected state. As used herein, connected may refer to attached, linked, secured, fixed, or associated or related in some respect. Some non-limiting examples of a severed state may include the medical instrument (e.g., an endovascular coil) in two or more individual pieces. Some non-limiting examples of connected may include the medical instrument not broken in two or more individual pieces. For example, some embodiments may be configured to include partitioning outcome data, which may include a medical image (such as x-ray or CT image) of the medical instrument (e.g., endovascular coil), to indicate whether the medical instrument may be connected after an unsuccessful sever attempt or severed after a successful sever attempt.

FIG. 31 depicts instructions which may include, in step 3108, determining, based on the partitioning outcome data obtained by step 3106, whether the medical instrument 1220 (e.g., an endovascular coil) may be in a severed state (case 3110) or a connected state (case 3114). FIG. 16A depicts the endovascular device 1200 with a medical instrument 1220 in the connected state. FIG. 18A depicts the endovascular device 1200 with a medical instrument 1220 in the severed state with a severed coil end 1826a and a remaining coil section 1828.

Consistent with disclosed embodiments, determining whether the medical instrument is in a severed state or a connected state may include (i) calculating, based on the partitioning outcome data, a quantity of energy delivered to the medical instrument, (ii) comparing the calculated quantity of delivered energy to a threshold, and (iii) based on a result of the comparison, determining whether the medical instrument is fully severed. As used herein, calculating may refer to computing, figuring, quantifying or any other means of determining the amount or number of something mathematically. For example, based on the partitioning outcome data (e.g., a medical image of an endovascular coil and/or outputs from various sensors monitoring an endovascular coil), the quantity of energy (e.g., may be one, less than one, or more than one watt, kilowatt, joule, picowatt) may be calculated to deliver to the endovascular coil. As used herein, threshold may refer to a point, lower-limit, level, the-limit, upper-limit or any other starting point for a new state or experience. Advantageously, the threshold may be based, at least in part, on a structural property of the medical instrument. For example, a smaller quantity of energy, like a milliwatt or picowatt, may be chosen for the threshold based on the medical instrument being a microcatheter. Alternatively, a larger quantity of energy, like a centiwatt or deciwatt, may be chosen for the threshold based on the medical instrument being a catheter. Some non-limiting examples may include a threshold of one or less than one, two or less than two, three or less than three picowatts, and so forth. Advantageously, the threshold value may be compared to the calculated quantity of delivered energy to determine if the calculated quantity of energy delivered is greater or less than the threshold value. Further, the comparison may be used to determine whether the medical instrument may be partially, fully, or not severed. For example, the threshold level may be five picowatts and the calculated quantity of energy may be two picowatts, thus indicating the threshold level was not met and thus the medical instrument is not severed. In another example, the threshold level may be five picowatts and the calculated quantity of energy may be four picowatts, thus indicating the threshold level was not met and thus the medical instrument was partially severed. In another example, the threshold level may be five picowatts and the calculated quantity of energy may be seven picowatts, thus indicating the threshold level was met and thus the medical instrument was fully severed.

Figure 36:
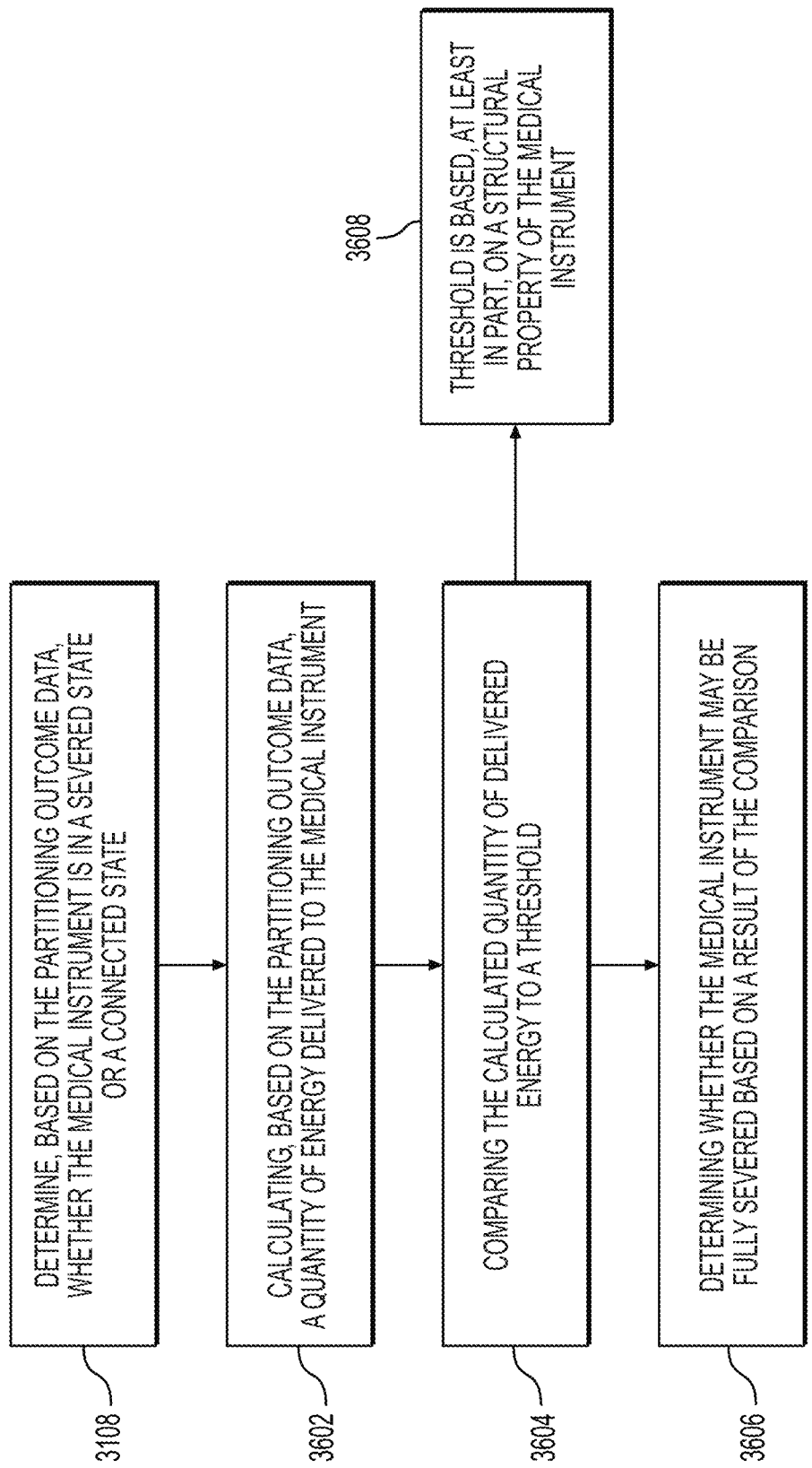
FIG. 36 is a flowchart of an operation for determining, based on the partitioning outcome data, whether the medical device is in a severed state or a connected state, consistent with disclosed embodiments.

FIG. 36 depicts instructions where embodiments may be configured where determining whether a medical instrument 1220 (e.g., an endovascular coil) is in a severed state or a connected state (step 3108) may include (i) calculating, based on the partitioning outcome data, a quantity of energy delivered to the endovascular coil 1220 (step 3602), (ii) comparing the calculated quantity of delivered energy to a threshold (step 3604), and (iii) based on a result of the comparison, determining whether the medical instrument 12160 is fully severed (step 3606). Advantageously, the threshold may be based, at least in part, on a structural property of the medical instrument (case 3608). For example, a smaller quantity of energy, like a milliwatt or picowatt, may be chosen for the threshold based on the medical instrument 1220 being an endovascular coil. Alternatively, a larger quantity of energy, like a centiwatt or deciwatt, may be chosen for the threshold based on the medical instrument 1220 being something other than an endovascular coil.

Consistent with disclosed embodiments, the operations may include, if the severed state of the medical instrument is detected, outputting a success notification. As used herein, detect may refer to finding, identifying, recognizing or any other means of discerning. As used herein, a success notification may refer to proclaiming, warning, alerting, communicating, declaring, informing, messaging or any other action of notifying someone or something that an aim or purpose of severing has been accomplished or achieved. In some examples, success notification may include a digital signal transmitted to an external device, may include storage of a success indicator at a predetermined location in a memory device, may include an audible notification, may include a visual notification, may include a notification provided to a user (for example, audibly, visually, through a user interface, etc.), and so forth. Some non-limiting examples of success notifications may include a blinking light-emitting diode (LED), an LED turning and staying on, an LED turning off, a graphical interface displaying a check, thumbs-up, or smiley face icon, a message stating "SUCCESS," "SUCCESSFUL," or "SUCCESSFUL OPERATION," a sound (e.g., a ping noise), haptic feedback to the user, and so forth. For example, if the severed state of the medical instrument (e.g., an endovascular coil) is detected, an LED may start blinking or turn on to indicate the endovascular coil was severed. Embodiments may be configured to make a sound or use haptic feedback if the severed state of the medical instrument is detected.

FIG. 31 depicts instructions for monitoring partitioning 3100 of a medical instrument 1220 (e.g., an endovascular coil) during an endovascular procedure as shown in FIGS. 22A-22F. Some embodiments may be configured to output a success notification (step 3112), for example if the severed state of the medical instrument 1220 is detected by step 3108 (case 3110).

Consistent with disclosed embodiments, the success notification may indicate that a distal section of the medical instrument may be released from the catheter while a proximal section of the medical instrument, having been severed from the distal section, may remain within the lumen of the catheter. As used herein, indicate may refer to demonstrating, expressing, illustrating, making apparent, signaling or another means of suggesting. As used herein, release may refer to freeing, letting go, liberating, breaking or allowing or enabling something to move or act freely. As used herein, remain may refer to continuing, lingering, persisting or staying in a place that an object has been occupying. For example, the medical instrument (e.g., an endovascular coil) may be severed into two pieces where the distal section of the endovascular coil may be released from the catheter and advance into a treatment site (e.g., an aneurysm) and the proximal section of the endovascular coil may remain within the lumen of the catheter. Thus, the success notification (e.g., a blinking LED) may turn on to indicate that the distal section may be released from the catheter and the proximal section may remain within the lumen of catheter. In another example, in which the endovascular coil is severed into two pieces, the distal section may still be partially or wholly within the lumen of the catheter along with the proximal section. Thus, the success notification, a blinking LED, will not turn on to indicate that the distal section is still within the lumen of the catheter.

FIG. 18A depicts a severed coil section 1826 and a remaining coil section 1828 of a medical instrument 1220. FIG. 18B depicts an embodiment where the success notification outputted by step 3112 may indicate that a severed distal section of the endovascular coil (i.e., section 1826) has been released from a catheter 1210 while a proximal section 1828 of the endovascular coil, having been severed from the distal section 1826, remains within an inner lumen 1214 of the catheter 1210.

Consistent with disclosed embodiments, after the success notification, embodiments may be further configured to obtain a second input to activate the partitioning mechanism while the catheter may be positioned within the body, the second input associated with the proximal section of the medical instrument. As used herein, a second input may refer to the next, subsequent, succeeding or other input coming after the first input. For example, the second input may be associated with the proximal end, or the end closer to the user or operator of the medical instrument. Consistent with disclosed embodiments, the operations may further be configured to activate the partitioning mechanism in response to the second input. Further, the operations may be configured wherein activating the partitioning mechanism in response to the second input may include selecting an additional quantity of energy for delivery by the partitioning mechanism, wherein the additional quantity is selected based on a structural property of the proximal section of the medical instrument and controlling the partitioning mechanism for delivery of the selected additional quantity of energy. Further, the operations may be configured to obtain additional partitioning outcome data following the activation of the partitioning mechanism in response to the second input. Consistent with disclosed embodiments, the operations may determine, based on the additional partitioning outcome data, whether the proximal section of the medical instrument may be in a severed state or a connected state. Further, the operations may output a second success notification if the severed state of the proximal section of the medical instrument may be detected. Consistent with disclosed embodiments, if the connected state of the proximal section of the medical instrument may be detected, the operations may output at least one of (i) a second control signal to vary activation of the partitioning mechanism or (ii) an instruction to reposition the proximal section of the medical instrument relative to the partitioning mechanism.

FIG. 31 depicts instructions for monitoring partitioning 3100 of a medical instrument 1220 (e.g., an endovascular coil) during an endovascular procedure as shown in FIGS. 22A-22F. Some embodiments may further be configured such that after outputting a success notification by step 3112, a second input is obtained to activate the partitioning mechanism while a catheter 1210 (e.g., a microcatheter) is positioned within the body, the second input being associated with the proximal section of the endovascular coil 1220. The operations may further be configured to activate the partitioning mechanism in response to the second input (step 3104). Further, the operations may be configured to obtain additional partitioning outcome data (step 3106) following the activation of the partitioning mechanism in response to the second input by step 3104. Additionally, the operations may determine, based on the additional partitioning outcome data, whether the proximal section of the medical instrument 1220 (e.g., endovascular coil) is in a severed state or a connected state (step 3108). Further, the operations may output a second success notification (step 3112) if the severed state of the proximal section of the medical instrument 1220 is detected (case 3110). Consistent with disclosed embodiments, if the connected state of the proximal section of medical instrument 1220 is detected (case 3114), the operations may output at least one of (i) a second control signal to vary activation of the partitioning mechanism (step 3116) or (ii) an instruction to reposition the proximal section of medical instrument 1220 relative to the partitioning mechanism (step 3118).

Consistent with disclosed embodiments, the operations may include, if the connected state of the medical instrument may be detected, outputting at least one of: (i) a control signal to vary activation of the partitioning mechanism, or (ii) an instruction to reposition the medical instrument relative to the partitioning mechanism. As used herein a control signal may refer to a prompt, indicator, indication, communication, message, alert, movement, action or other action used to convey information or instructions. As used herein, vary activation may refer to differing in amount, degree or nature of switching on, turning on, starting, triggering or any other means to make the partitioning mechanism operative. For example, if the connected state of the medical instrument (e.g., an endovascular coil) is detected, a blinking LED, a sound, a display message, or haptic feedback may be made known to the user of the medical device to either start the partitioning mechanism again, stop the partitioning mechanism and/or repetitively start and stop the partitioning mechanism after advancing the medical device or retreating the medical device in relation to the treatment site (e.g., an aneurysm). Some embodiments may be configured to output the control signal to vary the activation of the partitioning mechanism which may include causing the partitioning mechanism to change a quantity of energy delivered by the at least one electrode to the adjacent portion of the medical instrument. For example, the control signal may output a faster blinking LED or a louder sound which may cause the partitioning mechanism to change the quantity of energy delivered to be larger than the quantity of energy delivered before the output by the at least one electrode to the adjacent portion of the medical instrument. In another example, the control signal may output a slower blinking LED or a softer sound which may cause the partitioning mechanism to change the quantity of energy delivered to be smaller than the quantity of energy delivered before the output by the at least one electrode to the adjacent portion of the medical instrument.

FIG. 31 depicts instructions for monitoring partitioning 3100 of a medical instrument 1220 (e.g., an endovascular coil) during an endovascular procedure as shown in FIGS. 22A-22F. Some embodiments may be configured to include, if the connected state of medical instrument is detected (case 3114), outputting at least one of: (i) a control signal to vary activation of the partitioning mechanism (by step 3116), or (ii) an instruction to reposition the medical instrument 1220 relative to the partitioning mechanism (by step 3118). Further, some embodiments may be configured to output the control signal to vary the activation of the partitioning mechanism (step 3116) which may include causing the partitioning mechanism to change a quantity of energy delivered (step 3120) by the at least one electrode 1242 to the adjacent portion of the medical instrument 1220.

Consistent with disclosed embodiments, if the connected state of the medical instrument may be detected, the operations may output an instruction to reposition the medical instrument relative to the partitioning mechanism. As used herein, an instruction may refer to an order, command, directive, dictation, demand or other detailed information telling how something should be done. As used herein, reposition may refer to moving, shifting, relocating or placing in a different position before the next activation of the partitioning mechanism. For example, the operations may instruct the user to move the medical instrument (e.g., an endovascular coil) forward, backward, to one side, or to the other side relative to the partitioning mechanism.

FIG. 31 depicts instructions for monitoring partitioning 3100 of a medical instrument 1220 (e.g., an endovascular coil) during an endovascular procedure as shown in FIGS. 22A-22F. Some embodiments, if the connected state of the medical instrument 1220 is detected (case 3114), the operations may output an instruction to reposition the medical instrument 1220 relative to the partitioning mechanism (step 3118).

According to another embodiment of the present disclosure, a system for monitoring partitioning of a medical instrument during an endovascular procedure may be provided. Consistent with disclosed embodiments, the system may be configured to comprise at least one processor. The at least one processor may be configured to obtain an input to activate a partitioning mechanism associated with a medical instrument within a lumen of a catheter, the catheter being positioned within a body. The at least one processor may be configured to activate the partitioning mechanism in response to the input. The at least one processor may obtain partitioning outcome data following the activation. The at least one processor may determine, based on the partitioning outcome data, whether the medical instrument may be in a severed state or a connected state. The at least one processor, if the severed state of the medical instrument may be detected, output a success notification. The at least one process, if the connected state of the medical instrument may be detected, output at least one of (i) a control signal to vary activation of the partitioning mechanism or (ii) an instruction to reposition the medical instrument to the partitioning mechanism.

According to another embodiment of the present disclosure, a method for partitioning of a medical instrument during an endovascular procedure may be provided. The method may be configured to obtain an input to activate a partitioning mechanism associated with a medical instrument within a lumen of a catheter, the catheter being positioned within a body. The method may be configured to activate the partitioning mechanism in response to the input. The method may obtain partitioning outcome data following the activation. The method may determine, based on the partitioning outcome data, whether the medical instrument may be in a severed state or a connected state. The method, if the severed state of the medical instrument may be detected, output a success notification. The method, if the connected state of the medical instrument may be detected, output at least one of (i) a control signal to vary activation of the partitioning mechanism or (ii) an instruction to reposition the medical instrument to the partitioning mechanism.

In some embodiments, an endovascular device may be provided that is configured to deliver an endovascular coil to a treatment location, such as an aneurysm or another hollow body structure. The endovascular device may include a coil partitioning mechanism, such as an electrode pair or a mechanical cutter, that may be configured to sever the coil at any location along its length. Advantageously, the coil partitioning mechanism may allow treatment of a hollow body structure using a single, continuous coil structure rather than multiple pieces of coil having a predetermined, standardized length which must be delivered one-by-one to the treatment location. For example, a desired length of the single, continuous coil structure may be advanced from the endovascular device and severed using the coil partitioning mechanism, thus separating the desired length of coil from the remainder of the single, continuous coil structure and providing for delivery of the desired length of coil to the hollow body structure.

Embodiments disclosed herein may provide a mechanism for tracking the amount of coil that has been advanced from the endovascular device and the length of coil remaining in the endovascular device for future use. This coil tracking data may be used, for example, to determine when a desired length of coil has been advanced from the endovascular device and can be severed using the coil partitioning mechanism. Additionally, or alternatively, the coil tracking data may be provided to determine whether a remaining length of coil in the endovascular device is sufficient to treat the patient (e.g., to fill a hollow body structure), or whether the coil must be replaced with another, different coil. Replacement of the coil is time consuming, therefore prolonging the procedure and increasing the risk of complications. Thus, minimizing the number of coil replacements is desired. Advantageously, these embodiments may ensure that the hollow body structure is neither over- nor under-packed, but that it has instead been packed with the correct amount of coil to achieve a desired therapeutic outcome, such as blocking blood flow into the hollow body structure.

Aspects of this disclosure may relate to systems, devices, methods, and non-transitory computer readable media containing instructions to perform operations for monitoring and facilitating endovascular coil delivery. For ease of discussion, a method for monitoring and facilitating endovascular coil delivery is described below, with the understanding that aspects of the method apply equally to systems, devices, and instructions contained by non-transitory computer readable media. For example, some aspects of such a method may occur electronically over a network that is either wired, wireless, or both. Other aspects of such a method may occur using non-electronic means. In a broadest sense, the method is not limited to particular physical and/or electronic instrumentalities, but rather may be accomplished using many differing instrumentalities.

As used herein, operations for monitoring and facilitating endovascular coil delivery may include methods, steps, and processes for obtaining information related to at least one of movement of an endovascular coil relative to a delivery device (e.g., a coil delivery catheter) and/or relative to the patient's body, release of the endovascular coil from the delivery device, placement of the endovascular coil within the treatment location, and partitioning or severing of the endovascular coil by a coil partitioning mechanism. Additionally, or alternatively, operations for monitoring and facilitating endovascular coil delivery may include methods, steps, and processes for obtaining information related to delivery of an endovascular coil and, based on the obtained information, outputting feedback for the endovascular coil delivery operation. Non-limiting examples of outputting feedback may include providing at least one indication to a user related to the endovascular coil delivery operation, outputting a control signal for an automated coil delivery process, and recording the obtained information related to the endovascular coil delivery.

Consistent with disclosed embodiments, methods for monitoring and facilitating endovascular coil delivery may include obtaining a first input from a coil movement sensor associated with an endovascular coil within a lumen of a catheter positioned within a body. As used herein, a coil movement sensor may include any device or mechanism configured to measure at least one variable related to movement of an endovascular coil through an inner lumen of a catheter (e.g., a coil delivery catheter) or another type of flexible medical tubing. The coil movement sensor may be configured to measure the at least one variable related to the movement of the endovascular coil while the catheter and the coil are positioned within the body of a patient, such as during an endovascular procedure.

In some embodiments, a coil movement sensor may be configured to measure displacement of the endovascular coil relative to the catheter. For example, the coil movement sensor may be configured to measure an axial length of the endovascular coil that passes in a distal direction past a designated location of the catheter. Some non-limiting examples of the designated location of the catheter may include a distal tip of the catheter, a proximal tip of the catheter, any location within or upon the catheter, a location of a second device affixed to the catheter (such as the location of a coil partitioning mechanism or a location of the coil movement sensor), or any other suitable location of the catheter relative to which movement of the endovascular coil may be measured. Additionally, or alternatively, a coil movement sensor may be configured to measure the speed, linear direction, and/or rotational direction of movement of the endovascular coil relative to the catheter. As used herein, "associated with" may mean that the coil movement sensor is configured to measure at least one variable related to movement of the endovascular coil relative to the catheter, as discussed above.

In some embodiments, the coil movement sensor may include an electromagnetic sensor. For example, the endovascular coil may be constructed at least partially from a metal or may otherwise be configured to have magnetic properties. In one example, movement of the endovascular coil relative to the designated location of the catheter may cause electric current to flow through conductive material included in the electromagnetic sensor. In this example, the coil movement sensor may be configured to measure the electric current flowing through the conductive material and/or characteristics thereof and may determine at least one variable related to the movement of the endovascular coil based on the measured electrical current and/or the characteristics of the electrical current. Some non-limiting examples of such characteristics of electrical current may include net rate of flow, amplitude, frequency, and so forth. In another example, movement of the endovascular coil relative to the designated location of the catheter may cause changes in an electrical resistance of an element. In this example, the coil movement sensor may be configured to measure the electrical resistance of the element and may determine at least one variable related to the movement of the endovascular coil based on the measured electrical resistance. In yet another example, movement of the endovascular coil relative to the designated location of the catheter may cause changes in an electrical capacitance of an element. In this example, the coil movement sensor may be configured to measure the electrical capacitance of the element and may determine at least one variable related to the movement of the endovascular coil based on the measured electrical capacitance. In an additional example, movement of the endovascular coil relative to the designated location of the catheter may cause changes in an electromagnetic field. In this example, the coil movement sensor may be configured to measure the electromagnetic field in at least one place and may determine at least one variable related to the movement of the endovascular coil based on the measured electromagnetic field in the at least one place. In yet another example, movement of the endovascular coil relative to the designated location of the catheter may cause changes in a difference of electrical potential between two places. In this example, the coil movement sensor may be configured to measure the difference of electrical potential between the two places and may determine at least one variable related to the movement of the endovascular coil based on the measured difference of electrical potential between the two places. The at least one variable related to movement of the endovascular coil may include a position of the endovascular coil, a speed and/or a direction of movement of the endovascular coil relative to the catheter, and a length of endovascular coil that passes through the designated location of the catheter. A non-limiting example of an electromagnetic sensor may include a linear variable displacement transducer.

In some embodiments, the coil movement sensor may include a mechanical sensor. In some embodiments, the mechanical sensor may include a structure configured to be moved by the endovascular coil, either directly or indirectly, as the endovascular coil moves through the designated location of the catheter. Some non-limiting examples of the structure of the mechanical sensor may include a roller configured to be rotated by movement of the endovascular coil, or a structure configured to be moved in a lateral direction away from the center of the lumen of the catheter during movement of the endovascular coil. The coil movement sensor may be configured to measure the motion of the structure of the mechanical sensor and may determine at least one variable related to the movement of the endovascular coil based on the measured motion of the structure. The at least one variable related to movement of the endovascular coil may include a position of the endovascular coil, a speed and/or a direction of movement of the endovascular coil relative to the catheter, and a length of endovascular coil that passes through the designated location of the catheter.

In some embodiments, the coil movement sensor may include an imaging device configured to obtain at least one image of the endovascular coil or of a feature connected to the endovascular coil (e.g., an imaging marker) while the endovascular coil is advanced through the catheter within the body of a patient. Based on the at least one image, the coil movement sensor may be configured to determine the position of the endovascular coil relative to the catheter, including the length of the coil positioned distal to (i.e., advanced beyond) the designated location of the catheter. For example, the imaging device may be located outside the body of the patient and may be configured as a computed tomography (CT) device, a magnetic resonance imaging (MM) device, an X-ray imaging device, an ultrasonic imaging device, or a device configured to employ any other imaging modality to capture an image of the endovascular coil or of a feature connected to the endovascular coil. Additionally, or alternatively, an imaging device may be provided on the catheter and may obtain images of the endovascular coil as the coil is advanced through the catheter. In one example, the coil movement sensor may analyze the images to determine the location of the endovascular coil, for example using object detection algorithms. In one example, the coil movement sensor may analyze the images using object tracking algorithms to determine the motion of the catheter or to determine the length of the coil passing through a particular region (such as a particular region of the catheter, the tip of the catheter, the coil partitioning mechanism, and so forth).

Some other non-limiting examples of a coil movement sensor may include a linear inductive position sensor, a draw-wire sensor, a linear potentiometer, a Hall effect sensor, an eddy current sensor, a laser triangulation sensor, and a magnetostrictive linear position sensor.

Consistent with disclosed embodiments, obtaining the first input from the coil movement sensor may include obtaining data related to movement of the endovascular coil relative to the catheter within a certain length of time. Some non-limiting examples of data of the first input may include linear displacement data and/or rotational displacement data of the endovascular coil relative to the catheter, an axial length of the endovascular coil that passes in a specified direction (e.g., in a distal direction) beyond a designated location of the catheter, the speed of the movement of the endovascular coil, the direction of the movement of the endovascular coil, a length of time over which the movement of the endovascular coil is measured by the coil movement sensor, the position of the coil movement sensor relative to the catheter, and the position of the designated location of the catheter (i.e., a reference point on the catheter for evaluating movement of the endovascular coil relative to the catheter).

Figure 26A:
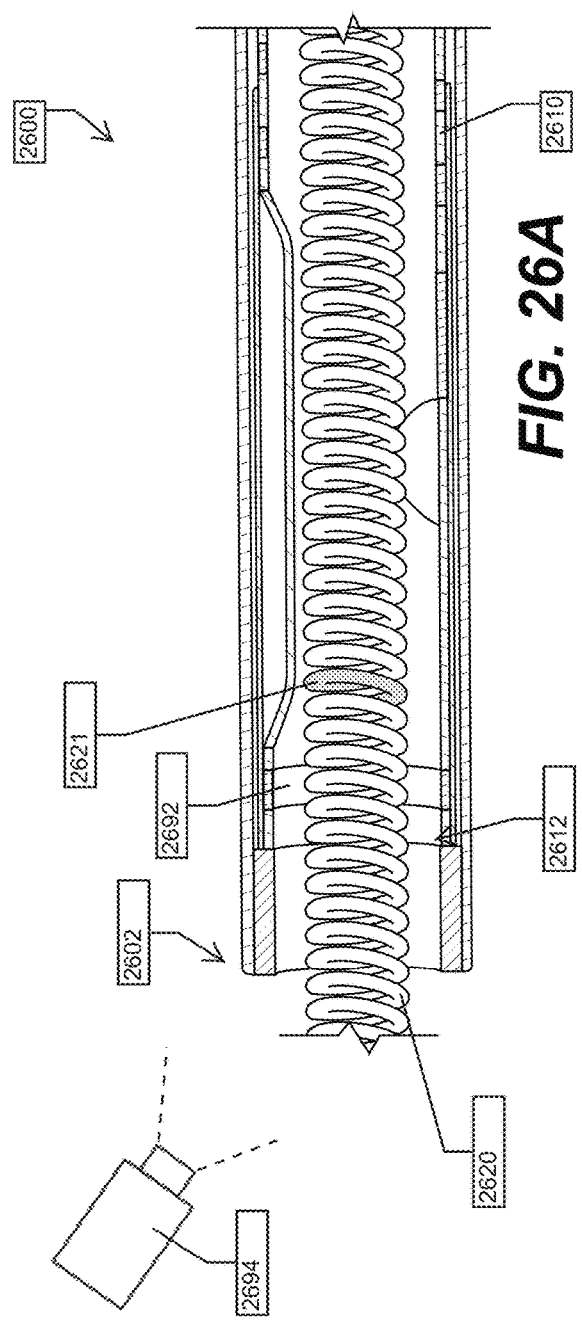
FIGS. 26A and 26B depict interior views of an example of an endovascular device including a coil movement sensor, consistent with disclosed embodiments.
Figure 26B:
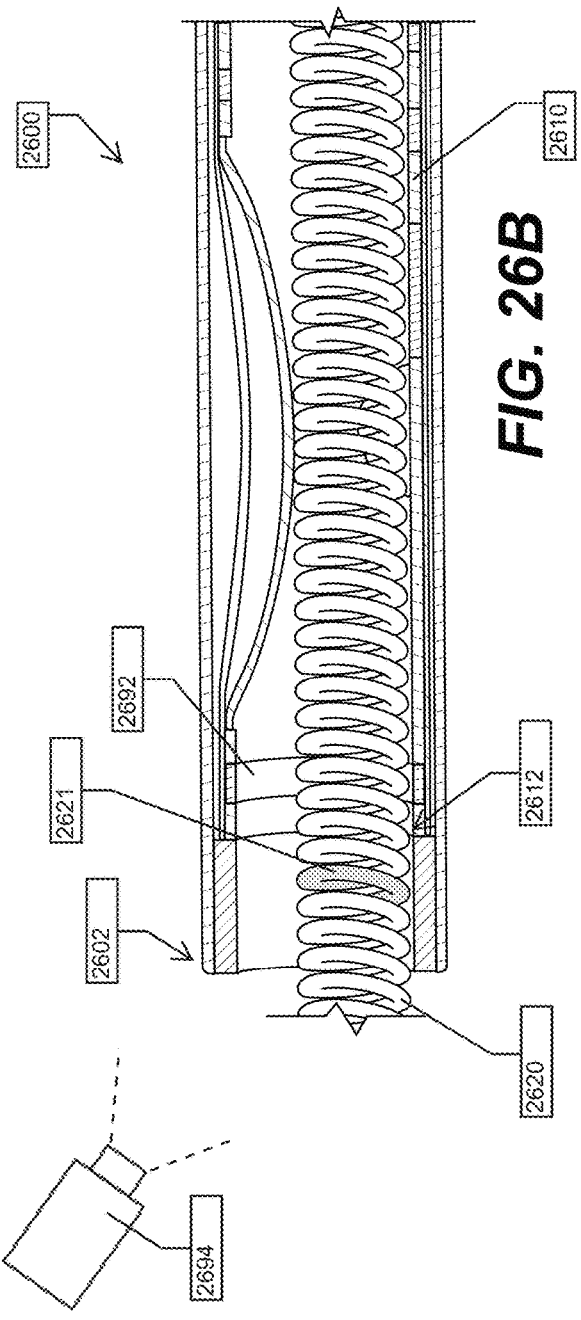

FIGS. 26A and 26B depict an endovascular device 2600 with a first non-limiting example of a coil movement sensor 2692. Endovascular device 2600 may include a flexible, elongated sheath 2610, which may be configured as a catheter in various embodiments. The first coil movement sensor 2692 may be connected to sheath 2610 and may be configured to measure movement of endovascular instrument 2620 (e.g., an endovascular coil) relative to endovascular device 2600 and sheath 2610. In the example depicted in FIGS. 26A and 26B, first coil movement sensor 2692 may be embedded in or otherwise affixed to the inner wall of the sheath within a distal region of the sheath (e.g., within one inch of distal tip 2612 of the sheath and/or within one inch of the distal end 2602 of the endovascular device). However, first coil movement sensor 2692 may alternatively be situated at any location along the length of the sheath 2610. In the example depicted in FIGS. 26A and 26B, first coil movement sensor 2692 may include an electromagnetic sensor having conductive material through which electric current flows when endovascular instrument 2620 is moved relative to endovascular device 2600. In one example, first coil movement sensor 2692 may be configured to measure the electric current flowing through the conductive material and/or characteristics thereof and may determine at least one variable related to the movement of endovascular instrument 1220 based on the measured electrical current and/or the measured characteristics of the electrical current, as discussed above. Some non-limiting examples of such characteristics of electrical current may include net rate of flow, amplitude, frequency, and so forth. In alternative examples, endovascular device 2600 may include a mechanical coil movement sensor connected to sheath 2610, as also discussed above. Other possible implementations of first coil movement sensor 2692 are discussed herein.

FIGS. 26A and 26B additionally depict a second non-limiting example of a coil movement sensor 2694 including an imaging device positioned outside of the patient's body. Second coil movement sensor 2694 may be configured to obtain images of endovascular instrument 2620 or of a feature connected to the instrument (e.g., an imaging marker) while the instrument is moved through the inner lumen of the endovascular device 2600 within the body of a patient. Based on the images of endovascular instrument 2620 or the feature connected to the instrument, the second coil movement sensor 2694 may be configured to measure the movement of instrument 2620 relative to endovascular device 2600, as discussed above.

FIGS. 10A-10C depict a system 1000 for delivering and cutting an endovascular coil 120, including another non-limiting example of a coil movement sensor 1090. Coil movement sensor 1090 may be connected to the inner wall of microcatheter 1010 in a distal region of the microcatheter (e.g., coil movement sensor 1090 may be spaced a distance of one inch or less from the distal end of microcatheter 1010). Alternatively, coil movement sensor may be placed at any other location along the length of microcatheter 1010. Coil movement sensor 1090 may include an electromagnetic sensor configured to measure movement of endovascular coil 120 through the inner lumen of microcatheter 1010 and may be configured to determine a length of endovascular coil 120 located in a distal direction from a designated location of microcatheter 1010, such as the distal end of microcatheter 1010, the location of sensor 1090, the location of electrode 1042, or the distal end of cylindrical base 1050. Microcatheter 1010 may additionally, or alternatively, include a different configuration of coil movement sensor, as discussed above (e.g., a mechanical sensor and/or an imaging device).

Consistent with disclosed embodiments, the catheter may include a coil partitioning mechanism configured to sever the endovascular coil. In some embodiments, the coil partitioning mechanism may include at least one electrode associated with the catheter and configured to deliver energy to the endovascular coil in a quantity sufficient to sever the endovascular coil. As used herein, "associated with" may mean that the at least one electrode is affixed or connected to the catheter or that the at least one electrode is connected to a structure outside of the catheter and may be brought into physical contact with an endovascular coil within the lumen of the catheter. As discussed herein, the at least one electrode may be configured to deliver energy to the endovascular coil in a quantity sufficient to sever the endovascular coil into multiple segments, so that a first segment of the coil (e.g., a distal segment) may be delivered out of the endovascular device to a treatment location while a second segment of the coil (e.g., a proximal segment) may remain within the endovascular device.

In some embodiments, the at least one electrode of the coil partitioning mechanism may be situated within an inner lumen of the catheter in a distal portion of the catheter In some embodiments, the coil partitioning mechanism may include an electrode pair, with both electrodes affixed or connected to the inner wall of the catheter lumen and configured to be brought into physical contact with the endovascular coil to deliver electrical current to the coil.

Consistent with disclosed embodiments, methods for monitoring and facilitating endovascular coil delivery may include obtaining, after the first input, a second input to activate the coil partitioning mechanism. In some embodiments, the second input may be obtained when it is determined (e.g., by a user or a processor) that a desired length of the endovascular coil is arranged distal to the coil partitioning mechanism. Thus, when the coil partitioning mechanism is activated, the segment of coil that is severed from the rest of the endovascular coil has the desired length and is therefore suitable for delivery to the treatment location.

In some embodiments, a user such as a doctor may input a command to activate the coil partitioning mechanism with a user input device, which may in turn convey a second input corresponding to the user command to at least one system processor. A non-limiting example of a user input device may include user input device 1910 of FIG. 19, which may convey a user command to activate the coil partitioning mechanism to control unit 1900. Additionally, or alternatively, the second input may include a signal received from a system processor as part of an automated process for endovascular coil delivery. For example, a system processor executing an automated endovascular coil delivery process may determine when to activate the coil partitioning mechanism (e.g., based on sensor data indicative of the location of the endovascular coil) and may output the second input when it is determined that the coil partitioning mechanism should be activated. For example, control unit 1900 of FIG. 19 may be configured to execute an automated process for delivering and severing an endovascular coil with a delivery catheter. Control unit 1900 may obtain data indicative of the location of the endovascular coil (e.g., from the coil movement sensor) and may output the second input to activate the coil partitioning mechanism when it is determined that the endovascular coil is correctly placed to be severed by the coil partitioning mechanism. In some embodiments, control unit 1900 may output the second input to a processor of electrode control component 1940, which may be configured to control activation of the coil partitioning mechanism.

Consistent with disclosed embodiments, methods for monitoring and facilitating endovascular coil delivery may include activating, in response to the second input, the coil partitioning mechanism to sever the endovascular coil into a first coil section for delivery from the catheter and a residual second coil section. In some embodiments, activating the coil partitioning mechanism may include controlling at least one electrode to deliver electrical current to the endovascular coil in order to sever the coil. Optionally, activating the coil partitioning mechanism may also include controlling the constrictor to narrow the inner lumen of the catheter in order to bring the endovascular coil in physical contact with the electrode pair, thus closing the electrical circuit. As a result, the electrode pair may be configured to deliver a sufficient amount of energy to the endovascular coil to sever the coil.

In some embodiments, the first coil section may include the distal-most portion of the endovascular coil prior to activation of the coil partitioning mechanism. That is, the first coil section may be a portion of the endovascular coil that is severed from the remainder of the coil and may be released from the catheter for delivery to a treatment location. In some embodiments, the residual second coil section may be a portion of the endovascular coil that is proximal to the first coil section. That is, the second coil section may remain within the catheter and/or a coil storage mechanism after activation of the coil partitioning mechanism, such that the second coil section is not released from the catheter along with the first coil section. The second coil section may become the distal-most portion of the endovascular coil after the first coil section is severed.

In a non-limiting example, FIGS. 18A and 18B depict activation of a coil partitioning mechanism to sever endovascular coil 1220 into a first coil section 1826 and a residual second coil section 1828. In the embodiment shown in FIGS. 18A and 18B, activation of the coil partitioning mechanism may include causing constrictor 1260 to push endovascular coil 1220 into contact with first electrode 1242 and sealing distal tip 1232 (i.e., the second electrode), and activating electrode 1242 to deliver current to the adjacent coil section 1724 in order to sever the coil. As a result, the first coil section 1826 may be severed from the rest of the endovascular coil (i.e., from second coil section 1828) and, as shown in FIG. 18B, may be released from the distal end of catheter 1210 for delivery to a treatment location in the body of the patient. Second coil section 1828 may remain within catheter 1210, becoming the distal-most remaining portion of the endovascular coil.

Consistent with disclosed embodiments, methods for monitoring and facilitating endovascular coil delivery may include determining, based on at least the first input and the second input, a length of the second coil section. In some embodiments, the length of the second coil section may indicate how much of the endovascular coil remains within the catheter for future use. For example, and as discussed above, the first input may include data indicating displacement of the endovascular coil relative to the catheter. In some embodiments, coil displacement data of the first input may be used to determine the length of coil that is arranged distal to the coil partitioning mechanism. Then, when the second input is obtained, it may indicate that the coil partitioning mechanism has been activated and severed the coil. The length of the second coil section may then be determined as the difference between the length of the endovascular coil prior to activation of the coil partitioning mechanism and the length of coil removed by the activation of the coil partitioning mechanism (e.g., the length of coil arranged distal to the coil partitioning mechanism when activation occurred).

In some embodiments, the coil movement sensor may be positioned at a different location on the catheter than the coil partitioning mechanism. Thus, the coil displacement measured by the coil movement sensor may be different from the true value of the length of coil arranged distal to the coil partitioning mechanism. The difference between these values may be equal to the linear distance between the sensor and the partitioning mechanism. Thus, this linear distance may be obtained in order to correct this difference and obtain an accurate measurement of the length of coil distal to the partitioning mechanism.

In some embodiments, disclosed methods may include obtaining a third input corresponding to a passage of a distal tip of the endovascular coil through the coil partitioning mechanism and determining the length of the second coil section based on at least the first input, the second input, and the third input. For example, the third input may designate the beginning of the coil delivery operation, when the first piece of coil is being delivered through the catheter. In such cases, the third input may signal the beginning of measuring movement of the endovascular coil (that is, the time 0 for obtaining data from the coil movement sensor). In alternative embodiments, the third input may correspond to passage of the distal tip of the endovascular coil through another location on the catheter, such as the distal end of the catheter, the proximal end of the catheter, the location of the coil movement sensor, or any other location on the catheter.

In some embodiments, disclosed methods may include determining, based on at least the first input and the second input, a total length of a plurality of sections of the endovascular coil severed by the coil partitioning mechanism for delivery from the catheter. For example, the endovascular coil may be severed into three or more pieces by multiple activations of the coil partitioning mechanism. In such cases, the displacement data for each severed coil section may be obtained and added to determine the total length of the severed coil sections. The length of the second coil section (i.e., the amount of coil remaining in the catheter) may be determined as the difference between the original length of the endovascular coil and the total length of the severed coil sections.

Consistent with disclosed embodiments, methods for monitoring and facilitating endovascular coil delivery may include outputting a signal based on the determined length of the second coil section. For example, outputting the signal may include providing at least one indication of the determined length of the second coil section to a user. For example, the at least one indication of the determined length may be provided visually, textually, numerically, audibly, through a graphical user interface, and so forth. In another example, outputting the signal may include providing at least one indication of the determined length of the second coil section to at least one of an automated process, an external device or a memory unit. For example, the at least one indication of the determined length of the second coil section may be transmitted to an external device using a digital communication device, may be stored in a memory unit, may be provided digitally, and so forth. In yet another example, outputting the signal may include adding at least one indication of the determined length of the second coil section to a log, for example to an electronic log stored in a digital memory unit. In some embodiments, disclosed methods may also include outputting a second signal based on the determined total length of the plurality of severed sections of the endovascular coil (as discussed above). Advantageously, the second signal may indicate (e.g., to a user or processor) the total length of endovascular coil that has already been delivered to the treatment location.

For example, outputting the signal based on the determined length of the second coil section may include displaying, on a graphical user interface, at least one visual indication of the determined length of the second coil section. In some embodiments, outputting the signal may include displaying, on the graphical user interface, at least one additional visual indication, such as an indication of the original length of the endovascular coil, an indication of the length of the first coil section, an indication of the total amount of coil delivered to the treatment location, an identifier of the endovascular coil, imaging data obtained from an imaging device, an indication or image of the delivery location, a patient identifier, or a timer.

As used herein, a graphical user interface (GUI) may include an interface through which a user may interact with electronic devices such as computers, laptops, surgical control devices and panels, display screens, televisions, handheld devices, smartphones, tablets, touchscreen devices, and other appliances. The graphical user interface may be configured to output data (e.g., display at least one visual indication) and also to receive input data directly (e.g., via manipulation of a touch screen with a finger) or indirectly (e.g., via a user input device such as a mouse, trackball, or stylus). The graphical user interface may use icons, menus and/or other visual indicator (graphics) representations to display information and related user controls.

In some embodiments, the graphical user interface may be associated with the at least one processor or other device performing the disclosed operations for monitoring and facilitating endovascular coil delivery. In a non-limiting example, control unit 1900 depicted in FIG. 19 may include at least one processor 1902 configured to determine the length of the second coil section, as discussed herein, and to output a signal to graphical user interface 1920 to display at least one visual indication of the determined length of the second coil section. Additionally, or alternatively, the graphical user interface may be associated with an external computing device, such as a surgical control device or panel, a mobile phone, a tablet, a laptop, a desktop computer, a computer terminal, a wearable device (including smart watches, smart glasses, smart jewelry, head-mounted displays, etc.), or any other electronic device capable of receiving a user input and displaying information.

In some embodiments, the at least one visual indication of the determined length of the second coil section may be displayed by the graphical user interface such that the at least one visual indication is clearly visible on a screen of the graphical user interface as an alphanumeric representation, a pictorial representation, and/or a user instruction based at least in part on the determined length of the second coil section. Some non-limiting examples of a user instruction may include an instruction to withdraw or remove the second coil section from the catheter, or a user instruction to replace the second coil section with another endovascular coil.

Consistent with disclosed embodiments, outputting the signal based on the determined length of the second coil section may additionally or alternatively include providing at least one audible indication of the determined length of the second coil section. In some embodiments, providing the at least one audible indication may include causing a speaker or another audio output device to emit a sound, such as a verbal (i.e., spoken) indication of the determined length of the second coil section, a ping, beep, ringtone, or any other audible alert. In some embodiments, providing the at least one audible indication may additionally include causing a speaker or another audio output device to emit at least one additional audible indication, such as an indication of the original length of the endovascular coil, an indication of the length of the first coil section, an indication of the total amount of coil delivered to the treatment location, an identifier of the endovascular coil, an indication of the delivery location of the endovascular coil, a patient identifier, or a timer.

In some embodiments, providing the at least one audible indication may include causing a sound to be emitted by a speaker or another audio output device associated with the at least one processor or other device performing the disclosed operations for monitoring and facilitating endovascular coil delivery. In a non-limiting example, control unit 1900 depicted in FIG. 19 may include at least one processor 1902 configured to determine the length of the second coil section, as discussed herein, and to output a signal to audio output device 1922 to emit a sound indicating the determined length of the second coil section.

In some embodiments, providing the at least one audible indication may include causing a speaker or another audio output device to emit an alert notification sound or a user instruction based at least in part on the determined length of the second coil section. Some non-limiting examples of a user instruction may include an audible instruction to withdraw or remove the second coil section from the catheter, or an audible instruction to replace the second coil section with another endovascular coil.

Consistent with disclosed embodiments, outputting the signal based on the determined length of the second coil section may additionally or alternatively include recording information based on the determined length of the second coil section. In some embodiments, recording the information may include storing the information in a data structure; the data structure may be a component of the disclosed system or a remote computing component (e.g., a cloud-based data structure). Recording the information may include storing the information contiguous or non-contiguous memory. Moreover, the information may be recorded across multiple data structures or servers, which may be owned or operated by the same or different entities. Thus, the term "data structure" as used herein in the singular is inclusive of plural data structures.

By way of a non-limiting example, as illustrated in FIG. 19, processor(s) 1902 may be configured to record the information based on the determined length of the second coil section into data structure(s) 1930. In some embodiments, the determined length of the second coil section may be recorded in data structure(s) 1930; optionally, additional data may also be recorded in data structure(s) 1930 such as data of the original length of the endovascular coil, data of the length of the first coil section, data of the total amount of coil delivered to the treatment location, an identifier or other data of the endovascular coil, imaging data obtained from an imaging device, data of the delivery location, a patient identifier, or timing data. Data structure(s) 1930 may include a Random Access Memory (RAM), a Read-Only Memory (ROM), a hard disk, an optical disk, a magnetic medium, a flash memory, other permanent, fixed, or volatile memory, or any other mechanism capable of storing information or data.

Consistent with disclosed embodiments, outputting the signal based on the determined length of the second coil section may additionally or alternatively include outputting a signal based on the determined length of the second coil section to control a coil advancement mechanism. As used herein, a coil advancement mechanism may include a device configured to move the endovascular device axially and/or rotationally through the catheter. Some non-limiting examples of the coil advancement mechanism may include a driving roller, delivery wire, sheath, a sliding support structure, a torquer, or any other mechanism configured to move the endovascular coil relative to the catheter. In some embodiments, the coil advancement mechanism may be manually operated (e.g., by a doctor or other user). Additionally, or alternatively, the coil advancement mechanism may be semi-automated, or controlled by at least one processor based on user commands received from a user input device such as a button, keyboard, computer mouse, lever, joystick, foot switch or pedal, touch screen, or any other suitable user input device. Additionally, or alternatively, the coil advancement mechanism may be fully automated such that at least one processor may control operations of the coil advancement mechanism based on a pre-programmed coil delivery process, sensor data, imaging data, or any other suitable form of feedback or input data.

In some embodiments, the coil advancement mechanism may be configured to automatically control motion of the second coil section. As used herein, automatic control may refer to processes and operations performed by at least one processor for controlling the coil advancement mechanism, as discussed above, independent of user commands for coil advancement. In some embodiments, the at least one processor may use the determined length of the second coil section to automatically control movement of the second coil section. For example, the at least one processor may use the determined length of the second coil section to determine if a sufficient amount of coil remains in the catheter to complete the operation; based on the determination, the at least one processor may automatically control the coil advancement mechanism to advance the second coil section distally in order to deliver the second coil section to the treatment location, or to move the second coil section proximally in order to remove the second coil section from the catheter and, if needed, to replace the second coil section with a different endovascular coil. Additionally, or alternatively, the at least one processor may use the determined length of the second coil section to automatically control the coil advancement mechanism to move the second coil section to a desired location relative to the coil partitioning mechanism, so that a desired length of the second coil section may be severed by activation of the coil partitioning mechanism.

By way of a non-limiting example, as illustrated in FIG. 19, processor(s) 1902 may be configured to access instructions from memory 1904 for performing operations of an automated process for delivering the endovascular coil 1220 to a treatment location, such as a hollow body structure 2282. The instructions for the automated process may indicate a treatment plan, including a type and amount of endovascular coil to be delivered to the treatment location. Based on the treatment plan, as well as feedback data from sensors 1912 and/or imaging device 1914, processors 1902 may output control signals to coil advancing mechanism 1946 for advancing endovascular coil 1220 through a delivery device, such as endovascular device 1200.

Consistent with disclosed embodiments, methods for monitoring and facilitating endovascular coil delivery may include comparing the determined length of the second coil section with a threshold and outputting at least one output based on a result of the comparison. In some embodiments, the threshold may indicate a desired length of the endovascular coil to be delivered to a treatment location, such as for filling a hollow body structure. In some embodiments, the threshold may be determined from images of the hollow body structure. For example, disclosed embodiments may include obtaining at least one medical image of a hollow body structure associated with the endovascular coil and analyzing the at least one medical image to determine the threshold. As a non-limiting example, imaging device 1914 may be used to generate at least one medical image of hollow body structure 2282, and the threshold may be determined based on analysis of the at least one medical image. In some embodiments, the threshold may be determined based on a current packing density of the hollow body structure determined by analyzing the at least one medical image. Additionally, or alternatively, the threshold may be determined based on a size of the hollow body structure determined by analyzing the at least one medical image. In some embodiments, the threshold may be determined prior to the procedure for delivering the endovascular coil. Additionally, or alternatively, the threshold may be changed during the procedure based on, e.g., sensor data and/or imaging data of the hollow body structure. In some embodiments, the threshold may be based on a type of the endovascular coil to be delivered to the hollow body structure. For example, a parameter of the endovascular coil (e.g., the coil's outer diameter) may affect the length of the coil that is required to treat the hollow body structure; the threshold may therefore be determined based on parameters of the endovascular coil(s) to be used for the procedure.

In some embodiments, methods for monitoring and facilitating endovascular coil delivery may include outputting, based on a result of the comparison between the determined length of the second coil section and the threshold, at least one of a control signal to withdraw the second coil section from the catheter or an instruction to replace the second coil section with another endovascular coil. For example, the at least one of the control signal or the instruction may be outputted when the result of the comparison indicates that the length of the second coil section is smaller than the threshold. In such cases, the second coil section is too short to treat the hollow body structure and should be replaced with a longer coil. Additionally, or alternatively, the at least one of the control signal or the instruction may be outputted when it is determined that a different type of endovascular coil is required in the next stage of treatment. For example, the second coil section may be configured as a filling coil (as discussed herein), but it may be determined (e.g., by at least one processor or a user) that the next type of coil to be delivered should be a finishing coil. In such cases, the at least one of the control signal or the instruction may be outputted so that the second coil section (e.g., a filling coil) may be withdrawn from the catheter and replaced with a suitable finishing coil.

In some embodiments, at least one processor may output the control signal to withdraw the second coil section to a coil advancement mechanism, as discussed herein, to cause the coil advancement mechanism to move the endovascular coil proximally until the coil is removed from the catheter. Optionally, a suitable replacement coil may be introduced into the catheter and advanced distally by the coil advancement mechanism. In a non-limiting example, as illustrated in FIG. 19, processor(s) 1902 may be configured to output the control signal (as discussed above) to the coil advancing mechanism 1946, to cause the coil advancing mechanism 1946 to withdraw endovascular coil 1220 from sheath 1210 (e.g., a delivery catheter).

In some embodiments, at least one processor may output the instruction to replace the second coil section with another endovascular coil to a user via a graphical user interface, a speaker or other audio output device, a haptic output device, or any other suitable notification mechanism. In a non-limiting example, as illustrated in FIG. 19, processor(s) 1902 may be configured to control graphical user interface 1920 and audio output device 1922 to output the instruction to the user. The instruction may include an indication that the second coil section is too short and/or a suggestion to replace the second coil section with another endovascular coil.

Consistent with disclosed embodiments, methods for monitoring and facilitating endovascular coil delivery may include obtaining a third input indicative of a prior activation of the coil partitioning mechanism and determining a length of the first coil section based on at least the first input, the second input, and the third input. For example, at the time of the prior activation of the coil partitioning mechanism, the distal tip of the first coil section may have been located at the coil partitioning mechanism (thus, the prior activation may make the first coil section the distal-most portion of the endovascular coil). Thus, coil displacement detected between the prior activation and the subsequent activation of the coil partitioning mechanism may be equal to the length of the first coil section (which is severed from the remainder of the endovascular coil, including the second coil section, by the subsequent activation of the coil partitioning mechanism). In some embodiments, disclosed methods may include outputting a second signal based on the determined length of the first coil section. Outputting the second signal may include any of the aforementioned embodiments of outputting the first signal.

Consistent with disclosed embodiments, the coil movement sensor may be configured to measure a net distance of movement of the endovascular coil relative to the catheter. As used herein, the net distance of movement may include a difference between a total distance traveled by the endovascular coil in a distal direction and a total distance traveled by the endovascular coil in a proximal direction. That is, the coil movement sensor may be configured to differentiate between distal movement of the coil and proximal movement of the coil in order to accurately detect the final axial location of the coil relative to the catheter. For example, in embodiments in which the coil movement sensor includes an electromagnetic sensor, the electromagnetic sensor may be configured such that movement of the coil in a first direction (e.g., the distal direction) may induce an electric current having first characteristics, while movement of the coil in a second, opposite direction (e.g., the proximal direction) may induce an electric current having second characteristics. Some non-limiting examples of such characteristics may include at least one of amplitude of the electric current being in a particular range of amplitudes, frequency of the electric current being in a particular range of frequencies, net rate of flow of the electric current being in a particular range of rates, and so forth. In this example, the direction of movement of the endovascular coil may be determined based on whether the measured electric current have the first characteristics or the second characteristics. In another example, in embodiments in which the coil movement sensor includes an electromagnetic sensor, the electromagnetic sensor may be configured such that movement of the coil in a first direction (e.g., the distal direction) may cause an electrical resistance of an element to be in a first range of values, while movement of the coil in a second, opposite direction (e.g., the proximal direction) may cause the electrical resistance of the element to be in a second range of values. In this example, the direction of movement of the endovascular coil may be determined based on whether the measured electrical resistance of the element is in the first range of values of in the second range of values.

In yet another example, in embodiments in which the coil movement sensor includes an electromagnetic sensor, the electromagnetic sensor may be configured such that movement of the coil in a first direction (e.g., the distal direction) may cause an electrical capacitance of an element to be in a first range of values, while movement of the coil in a second, opposite direction (e.g., the proximal direction) may cause the electrical capacitance of the element to be in a second range of values. In this example, the direction of movement of the endovascular coil may be determined based on whether the measured electrical capacitance of the element is in the first range of values of in the second range of values. In an additional example, in embodiments in which the coil movement sensor includes an electromagnetic sensor, the electromagnetic sensor may be configured such that movement of the coil in a first direction (e.g., the distal direction) may cause an electromagnetic field in at least one place to be in a first range of values, while movement of the coil in a second, opposite direction (e.g., the proximal direction) may cause the electromagnetic field in the at least one place to be in a second range of values. In this example, the direction of movement of the endovascular coil may be determined based on whether the measured electromagnetic field in the at least one place is in the first range of values of in the second range of values. In another example, in embodiments in which the coil movement sensor includes an electromagnetic sensor, the electromagnetic sensor may be configured such that movement of the coil in a first direction (e.g., the distal direction) may cause a difference of electrical potential between two places to be in a first range of values, while movement of the coil in a second, opposite direction (e.g., the proximal direction) may cause the difference of electrical potential between the two places to be in a second range of values. In this example, the direction of movement of the endovascular coil may be determined based on whether the measured difference of electrical potential between the two places is in the first range of values of in the second range of values. Additionally, or alternatively, in embodiments in which the coil movement sensor includes a mechanical sensor, the movable structure of the mechanical sensor (discussed above) may be configured to move in a first direction when the endovascular coil moves distally and to move in another direction when the coil moves proximally. The coil movement sensor may therefore be configured to determine the direction of movement of the endovascular coil based on the movement of the movable structure of the mechanical sensor.

In some embodiments, the endovascular coil may include at least one marking readable by the coil movement sensor. In some embodiments, the endovascular coil may include multiple markings that are readable by the coil movement sensor. For example, the endovascular coil may include a marking between different regions of the coil having different structural properties (e.g., at a location between a first region of the endovascular coil configured as a framing coil and a second region of the endovascular coil configured as a filling coil). Additionally, or alternatively, the endovascular coil may include a marking at a location between the coil and another device or instrument (e.g., at a location between the coil and a delivery wire). Additionally, or alternatively, the endovascular coil may include a marking at any suitable location along its length, including the distal tip and/or proximal tip of the coil.

In some embodiments, the coil movement sensor may be configured to determine the net distance of movement of the endovascular coil based on readings of the at least one marking. For example, the coil movement sensor may include an imaging device configured to detect the at least one marking of the endovascular coil while the coil and catheter are located within the body of a patient. The imaging device of the coil movement sensor may detect the direction(s) and distance of movement of the at least one marking relative to the patient's body and/or relative to the catheter, in order to determine the net distance of movement of the endovascular coil.

In a non-limiting example, FIGS. 26A and 26B depict an endovascular coil 2620 including at least one marking 2621. In the example shown, the at least one marking 2621 may include a winding of the coil constructed from a detectable material (e.g., a radiopaque material, or any other suitable material configured to be detected by an imaging device). However, endovascular coil 2620 may additionally or alternatively include another embodiment of the at least one marking, as discussed above. In some embodiments, one or both of coil movement sensors 2692 and 2694 may be configured to detect the direction and distance of movement of the at least one marking 2621 relative to the sheath 2610 (e.g., a catheter) and/or relative to any other suitable point of reference. The net distance of movement of endovascular coil 2620 may be determined (e.g., by a coil movement sensor, by at least one processor, etc.) based on the detected direction and distance of movement of the marking 2621.

Consistent with disclosed embodiments, the coil movement sensor may be located at any suitable location along the catheter. The coil movement sensor may be located within the inner lumen of the catheter, on the outer surface of the catheter, or embedded within the side wall of the catheter. In some embodiments, the coil movement sensor may be located within one inch of the coil partitioning mechanism. For example, the coil movement sensor may be incorporated within the coil partitioning mechanism. Alternatively, the coil movement sensor may be located in close proximity to the coil partitioning mechanism; for example, the coil movement sensor may be located immediately adjacent to the coil partitioning mechanism. In alternative embodiments, the coil movement sensor may be located within one inch of a distal tip of the catheter. In a non-limiting example, coil movement sensor 2692 depicted in FIGS. 26A and 26B may be located within one inch of the distal tip 2612 of sheath 2610 (which may be configured as a catheter). Additionally, or alternatively, coil movement sensor 2692 may be located within one inch of the distal end 2602 of endovascular device 2600.

Consistent with disclosed embodiments, the coil movement sensor may be located outside the body and may be configured to capture images of, or otherwise detect, the endovascular coil or a device attached to the coil while the coil is located within the body of a patient. For example, and as discussed above, the coil movement sensor may include an imaging device located outside the body. According to such embodiments, obtaining the first input from the coil movement sensor may include receiving a plurality of images of the endovascular coil captured by the coil movement sensor, specifically by the imaging device. For example, the imaging device may be configured to determine a location of the endovascular coil and/or a marking on the endovascular coil in each of the images. For example, the images may be analyzed using object detection algorithms to determine the location of the endovascular coil and/or of the marking on the endovascular coil. In another example, the images may be analyzed using tracking algorithms to determine changes to the location of the endovascular coil and/or of the marking. The first input may be determined (e.g., by the coil movement sensor, by the imaging device, by at least one processor, etc.) based on a direction and speed of movement of the endovascular coil or marking between the plurality of images, based on the location of the coil, based on the location of the marking, and so forth.

In some embodiments, obtaining the first input from the coil movement sensor may include receiving a plurality of images captured by the coil movement sensor of at least a portion of a device while the portion of the device is located outside the body of the patient. The device may include a structure connected to the endovascular coil and having a portion (e.g., a proximal portion of the device) configured to be positioned outside the body while the endovascular coil and the opposite end of the device are positioned within the body. In some embodiments, the device may be configured to move the endovascular coil through the lumen of the catheter. Some non-limiting examples of the device may include a shaft and a wire. In some embodiments, the plurality of images may be analyzed to determine a movement of the device and/or a movement of a marking on the device, for example using tracking algorithms. The first input may be obtained based on the determined movement of the device and/or the marking on the device.

Figure 27:
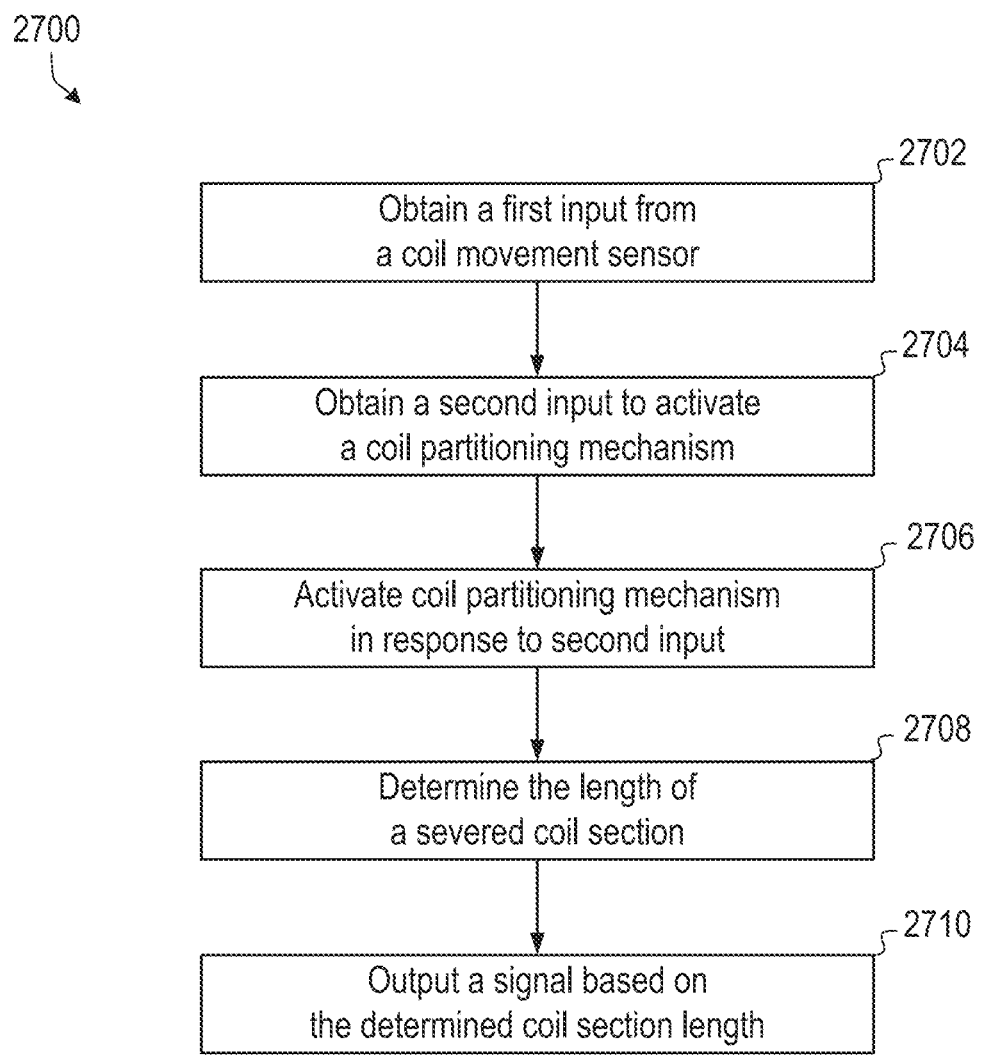
FIG. 27 illustrates a method of monitoring and facilitating endovascular coil delivery, consistent with disclosed embodiments.

FIG. 27 is a flowchart illustrating an example of a method 2700 for monitoring and facilitating endovascular coil delivery, consistent with disclosed embodiments. Method 2700 may be performed by at least one processor, such as one or more microprocessors. Additionally, or alternatively, a non-transitory computer readable medium may be provided containing instructions that when executed by at least one processor, cause the at least one processor to perform some or all of the steps of method 2700. In some embodiments, method 2700 is not necessarily limited to the steps illustrated, and any of the various embodiments described herein may also be included in method 2700.

At step 2702, the method 2700 may include obtaining a first input from a coil movement sensor. As discussed herein, the coil movement sensor may be associated with an endovascular coil within a lumen of a catheter positioned within a body of a patient. The catheter may include a coil partitioning mechanism configured to sever the endovascular coil. In some embodiments, the catheter may additionally include a constrictor configured to narrow the inner lumen of the catheter in order to bring the endovascular coil into contact with the coil partitioning mechanism. At step 2704, the method 2700 may include obtaining, after the first input, a second input to activate the coil partitioning mechanism. As discussed herein, the second input may be received from a user (e.g., via a user input device) and/or from a processor performing an automated process for delivering an endovascular coil. At step 2706, the method 2700 may include activating the coil partitioning mechanism in response to the second input. In some embodiments, activation of the coil partitioning mechanism may sever the endovascular coil into a first coil section for delivery from the catheter and a residual second coil section. At step 2708, the method 2700 may include determining a length of the second coil section severed by the coil partitioning mechanism at step 2706. In some embodiments, the length of the second coil section may be determined based on at least the first input and the second input. At step 2710, the method 2700 may include outputting a signal based on the determined length of the second coil section. As described herein, outputting the signal based on the determined length may include at least one of outputting a user indication, recording information based on the determined length in a data structure, or outputting a signal for controlling a coil advancement mechanism configured to move the endovascular coil relative to the catheter.

Systems and methods disclosed herein involve unconventional improvements over conventional approaches. Descriptions of the disclosed embodiments are not exhaustive and are not limited to the precise forms or embodiments disclosed. Modifications and adaptations of the embodiments will be apparent from consideration of the specification and practice of the disclosed embodiments. Additionally, the disclosed embodiments are not limited to the examples discussed herein.

The foregoing description has been presented for purposes of illustration. It is not exhaustive and is not limited to the precise forms or embodiments disclosed. Modifications and adaptations of the embodiments will be apparent from consideration of the specification and practice of the disclosed embodiments. For example, the described implementations include hardware and software, but systems and methods consistent with the present disclosure may be implemented as hardware alone.

The features and advantages of the disclosure are apparent from the detailed specification, and thus, it is intended that the appended claims cover all systems and methods falling within the true spirit and scope of the disclosure. As used herein, the indefinite articles "a" and "an" mean "one or more." Similarly, the use of a plural term does not necessarily denote a plurality unless it is unambiguous in the given context. Words such as "and" or "or" mean "and/or" unless specifically directed otherwise. Further, since numerous modifications and variations will readily occur from studying the present disclosure, it is not desired to limit the disclosure to the exact construction and operation illustrated and described, and, accordingly, all suitable modifications and equivalents may be resorted to, falling within the scope of the disclosure.

Computer programs based on the written description and methods of this specification are within the skill of a software developer. The various functions, scripts, programs, or modules may be created using a variety of programming techniques. For example, programs, scripts, functions, program sections or program modules may be designed in or by means of languages, including JAVASCRIPT, C, C++, JAVA, PHP, PYTHON, RUBY, PERL, BASH, or other programming or scripting languages. One or more of such software sections or modules may be integrated into a computer system, non-transitory computer readable media, or existing communications software. The programs, modules, or code may also be implemented or replicated as firmware or circuit logic.

Moreover, while illustrative embodiments have been described herein, the scope may include any and all embodiments having equivalent elements, modifications, omissions, combinations (e.g., of aspects across various embodiments), adaptations or alterations based on the present disclosure. The elements in the claims are to be interpreted broadly based on the language employed in the claims and not limited to examples described in the present specification or during the prosecution of the application, which examples are to be construed as non-exclusive. Further, the steps of the disclosed methods may be modified in any manner, including by reordering steps or inserting or deleting steps. It is intended, therefore, that the specification and examples be considered as exemplary only, with a true scope and spirit being indicated by the following claims and their full scope of equivalents.

What is claimed is:

1. An endovascular instrument for filling a hollow body structure, the endovascular instrument comprising:
an elongated member configured to exhibit differing coiling properties along a length of the elongated member, the elongated member having:
a first region configured to bend in a first manner within the hollow body structure to form a stabilizing frame; and
a second region proximal to the first region, wherein the second region is configured to bend, after formation of the frame, in a second manner substantially within the frame, thereby forming a curved mass substantially within the frame,
wherein the first region and the second region are interconnected and wherein at least one structural property differs between the first region and the second region, and
wherein at least a first portion of the second region is configured to be detached from a second portion of the second region within the hollow body structure after detachment of the first region from the second region.

2. The endovascular instrument of claim 1, wherein the second region of the elongated member is configured as at least one of a filling coil or a finishing coil.

3. The endovascular instrument of claim 1, wherein the at least one structural property includes at least one of stiffness, flexibility, material composition, diameter, three-dimensional shape, cross-sectional shape, axial length, and number of turns per unit of length.

4. The endovascular instrument of claim 1, wherein an outer diameter of the first region is larger than an outer diameter of the second region.

5. The endovascular instrument of claim 1, wherein a tertiary structural configuration of the first region differs from a tertiary structural configuration of the second region.

6. The endovascular instrument of claim 1, wherein the first region is configured to assume a predetermined, three-dimensional structural configuration in the presence of body fluid to form the frame within the hollow body structure, and wherein the second region is configured to be delivered into the hollow body structure after the first region and to fill space in the three-dimensional structural configuration of the first region.

7. The endovascular instrument of claim 1, wherein the first region is stiffer than the second region.

8. The endovascular instrument of claim 1, wherein an axial length of the first region is shorter than an axial length of the second region.

9. The endovascular instrument of claim 1, wherein the first region is constructed of a first alloy and the second region is constructed of a second alloy differing from the first alloy.

10. The endovascular instrument of claim 1, wherein the first region is integrally connected to the second region.

11. The endovascular instrument of claim 1, further comprising a third region of the elongated member positioned between the first region and the second region, wherein the at least one structural property of the elongated member differs between the first region, the second region, and the third region.

12. The endovascular instrument of claim 1, wherein the elongated member is configured to block blood flow into the hollow body structure.

13. The endovascular instrument of claim 1, further comprising a support mechanism configured to push the first region in a distal direction, the support mechanism being selectively detachable from the elongated member.

14. The endovascular instrument of claim 13, wherein the support mechanism includes a sleeve configured to engulf at least a portion of the second region, wherein the sleeve is configured to advance in the distal direction together with the second region and to be selectively detached from the elongated member through movement in a proximal direction relative to the second region.

15. The endovascular instrument of claim 1, wherein the first region is configured to be detached from the second region following delivery of the first region to the hollow body structure.

16. The endovascular instrument of claim 1, wherein the second region is configured to connect to a delivery wire.

17. The endovascular instrument of claim 1, further comprising at least one coil detachment mechanism configured to sever the elongated member while the elongated member is within a patient's body.

18. The endovascular instrument of claim 17, wherein the coil detachment mechanism is configured to sever the elongated member in at least one of:
- a first detachment location between the first region and the second region,
- a second detachment location between the second region and a delivery wire, and
- a third detachment location along a length of the second region.

19. The endovascular instrument of claim 1, wherein the elongated member includes an imaging marker in at least one of:
- a first marker location between the first region and the second region,
- a second marker location between the second region and a delivery wire,
- a third marker location at a distal tip of the first region, and
- a fourth marker location at a proximal end of the second region.

* * * * *